(12) United States Patent
Dong et al.

(10) Patent No.: US 8,258,094 B2
(45) Date of Patent: Sep. 4, 2012

(54) ANALOGS OF GHRELIN

(75) Inventors: Zheng Xin Dong, Holliston, MA (US); Michael DeWitt Culler, Hopkinton, MA (US); Yeelana Shen, Franklin, MA (US); Jeanne Mary Comstock, West Boylston, MA (US)

(73) Assignee: IPSEN Pharma S.A.S., Boulogne (FR)

( * ) Notice: Subject to any disclaimer, the term of this patent is extended or adjusted under 35 U.S.C. 154(b) by 541 days.

(21) Appl. No.: 12/079,885

(22) Filed: Mar. 28, 2008

(65) Prior Publication Data

US 2009/0156483 A1 Jun. 18, 2009

Related U.S. Application Data

(63) Continuation-in-part of application No. PCT/US2006/037889, filed on Sep. 27, 2006.

(60) Provisional application No. 60/750,771, filed on Dec. 15, 2005, provisional application No. 60/748,904, filed on Dec. 9, 2005, provisional application No. 60/721,557, filed on Sep. 28, 2005.

(51) Int. Cl.
*A61K 38/22* (2006.01)
*C07K 14/575* (2006.01)

(52) U.S. Cl. .......... 514/4.9; 514/5.3; 514/9.7; 530/324; 530/345

(58) Field of Classification Search .................. None
See application file for complete search history.

(56) References Cited

U.S. PATENT DOCUMENTS

| 7,173,109 B2 * | 2/2007 | Enderle et al. ............. 530/324 |
| 2005/0272648 A1 | 12/2005 | Dong et al. |
| 2006/0105393 A1 * | 5/2006 | Apfel et al. .................. 435/7.1 |
| 2009/0163416 A1 * | 6/2009 | Tulipano et al. ............. 514/12 |
| 2009/0275511 A1 * | 11/2009 | Dong ........................... 514/12 |
| 2009/0304724 A1 * | 12/2009 | Datta et al. ................ 424/185.1 |

FOREIGN PATENT DOCUMENTS

WO   WO 01/92292   12/2001

OTHER PUBLICATIONS

Beevers, A. J. et al., "Conformational flexibility of the peptide hormone ghrelin in solution and lipid membrane bound: a molecular dynamics study", J. Biomolecular Structure and Dymanics, 2006, 23:357-363.

Matsumoto, M. et al., "Structure-activity relationship of ghrelin: pharmacological study of ghrelin peptides", Biochem. Biophys. Res. Comm., 2001, 287:142-146.

* cited by examiner

*Primary Examiner* — Jeffrey E Russel
(74) *Attorney, Agent, or Firm* — Yankwich & Associates; Tony K. Uhm; Pamela C. Ball

(57) ABSTRACT

The invention comprises peptidyl analogs according to formulae (I) or (II) as depicted below:

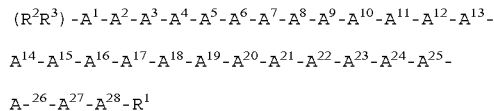

wherein the definitions of $A^1$ to $A^{28}$ and $R^1$ to $R^3$ are provided for in the specification for each of formulae (I) and (II), pharmaceutically acceptable salts thereof and pharmaceutical compositions comprising an effective amount of a compound of formula (I), that possess agonist or antagonist ghrelin activity, along with therapeutic and non-therapeutic uses thereof.

80 Claims, No Drawings

ANALOGS OF GHRELIN

CROSS REFERENCE TO RELATED APPLICATIONS

This application is a continuation-in-part of copending international (PCT) application No. PCT/US2006/037889, filed Sep. 27, 2006, designating the United States, which application claims priority to U.S. provisional application Nos. 60/750,771, filed Dec. 15, 2005; 60/748,904, filed Dec. 9, 2005; and 60/721,557, filed Sep. 28, 2005.

BACKGROUND OF THE INVENTION

1. Field of the Invention

This invention relates to peptidyl analogs that possess agonist or antagonist ghrelin activity and their therapeutic use thereof.

2. Description of the Prior Art

Ghrelin, a recently discovered orexigenic hormone, is produced as a preprohormone that is proteolytically processed to yield a peptide of the following sequence: H-Gly-Ser-Ser-Phe-Leu-Ser-Pro-Glu-His-Gln-Arg-Val-Gln-Gln-Arg-Lys-Glu-Ser-Lys-Lys-Pro-Pro-Ala-Lys-Leu-Gln-Pro-Arg-$NH_2$ (SEQ ID NO:180); Kojima, M. et al., *Nature*, (1999), 402 (6762):656-60). Ghrelin is produced by epithelial cells lining the fundus of the stomach and functions to stimulate appetite; its levels increase prior to a meal and decrease thereafter.

The native structures of ghrelin from several mammalian and non-mammalian species are known (Kaiya, H. et al., *J. Biol. Chem.*, (2001), 276(44):40441-8; and International Patent Application PCT/JP00/04907 [WO 01/07475]). A core region present in ghrelin is responsible for activity observed at the GHS receptor which comprises the four N-terminal amino acids wherein the serine in the third position is normally modified with n-octanoic acid. In addition to acylation by n-octanoic acid, native ghrelin may also be acylated with n-decanoic acid (Kaiya, H. et al., *J. Biol. Chem.*, (2001), 276(44):40441-8).

Ghrelin levels in the plasma of obese individuals are lower than those in leaner individuals and levels of ghrelin increase during the time of the day from midnight to dawn in thinner individuals suggesting a flaw in the circulatory systems of obese individuals (Yildiz, B. O. et al., *Proc. Natl. Acad. Sci. USA*, (2004), 101(28):10434-9). It has been found that individuals suffering from the eating disorder anorexia nervosa and patients who have cancer-induced cachexia have higher plasma levels of ghrelin (Garcia, J. M. et al., *J. Clin. Endocrin. Metab.*, (2005), 90(5):2920-6).

In both animals and in humans, ghrelin powerfully stimulates growth hormone (GH) secretion from the anterior pituitary gland, mainly at the hypothalamic level, through its interaction with the GH secretagogue (GHS) receptor (GHS-R) (Ukkola, O. et al., *Ann. Med.*, (2002), 34(2):102-8; and Kojima, M. et al., *Nature*, (1999), 402(6762):656-60). The GH-releasing activity of ghrelin is mediated by activation of GHS receptors at the pituitary and mainly at the hypothalamic level (Kojima, M. et al., *Nature*, (1999), 402(6762):656-60).

Prior to the discovery that ghrelin is a native ligand for the GHS receptor, it was known that the pulsatile release of GH from the pituitary somatotrops is regulated by two hypothalamic neuropeptides: GH-releasing hormone (GHRH) and somatostatin. GHRH stimulates the release of GH whereas somatostatin inhibits the secretion of GH (Frohman, L. A. et al., *Endocr. Rev.*, (1986), 7(3):223-53; and Strobl, J. S. et al., *Pharmacology Review* (1994) 46:1-34). Ghrelin likely enhances the activity of GHRH-secreting neurons while concomitantly acting as a functional somatostatin antagonist (Ghigo, E. et al., *Eur. J. Endocri.*, (1997), 136(5):445-60).

Release of GH from the pituitary somatotrops can also be controlled by GH-releasing peptides (GHRP). The hexapeptide His-D-Trp-Ala-Trp-D-Phe-Lys-amide (GHRP-6) was found to release GH from the somatotrops in a dose-dependent manner in several species, including man (Bowers, C. Y. et al., *Endocrinology*, (1984), 114(5):1537-45). Subsequent chemical studies on GHRP-6 led to the identification of other potent, synthetic GH secretagogues such as GHRP-1, GHRP-2 and hexarelin (Cheng, K. et al., *Endocrinology*, (1989), 124(6):2791-8; Bowers, C. Y., Novel GH-Releasing Peptides, *Molecular and Clinical Advances in Pituitary Disorders*, Ed: Melmed, S., Endocrine Research and Education, Inc., Los Angeles, Calif., USA, (1993), 153-7; and Deghenghi, R. et al., *Life Sci.*, (1994), 54(18):1321-8). The structures of these three compounds are:

```
GHRP-I     Ala-His-D-(2')-Nal-Ala-Trp-D-Phe-Lys-NH2;
GHRP-2     D-Ala-D-(2')-Nal-Ala-Trp-D-Nal-Lys-NH2;
and
Hexarelin  His-D-2-MeTrp-Ala-Trp-D-Phe-Lys-NH2.
```

A GHS can stimulate secretion of GH by a different mechanism than that of GHRH (Bowers, C. Y. et al., *Endocrinology*, (1984), 114(5):1537-45; Cheng, K. et al., *Endocrinology*, (1989), 124(6):2791-8; Bowers, C. Y., Novel GH-Releasing Peptides, *Molecular and Clinical Advances in Pituitary Disorders*, Ed: Melmed, S., Endocrine Research and Education, Inc., Los Angeles, Calif., USA, (1993), 153-7; and Deghenghi, R. et al., *Life Sci.*, (1994), 54(18):1321-8).

The low oral bioavailability (<1%) of a peptidyl GHS encouraged the search for non-peptide compounds mimicking the action of GHRP-6 in the pituitary. Several benzolactams and spiroindanes have been reported to stimulate GH release in various animal species, including humans (Smith, R. G. et al., *Science*, (1993), 260(5114):1640-3; Patchett, A. A. et al., *Proc. Natl. Acad. Sci. USA*, (1995), 92(15):7001-5; Chen, M.-H. et al., *Bioorg. Mod. Chem. Letts.*, (1996), 6(18): 2163-8). A specific example of a small spiroindane is MK-0677 (Patchett, A. A. et al., *Proc. Natl. Acad. Sci. USA*, (1995), 92(15):7001-5):

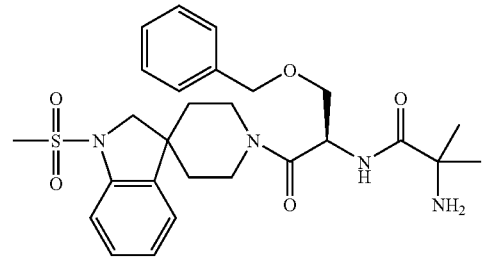

The actions of a GHS (both peptide and non-peptide) appear to be mediated by a specific receptor (Howard, A. D. et al., *Science*, (1996), 273(5277):974-7; and Pong, S. S. et al., *Mol. Endocri.*, (1996), 10(1):57-61). This receptor is present in the pituitary and hypothalamus of various mammalian species (GHSR1a) and is distinct from the GH-releasing hormone receptor. The GHS receptor was also detected in the other areas of the central nervous system and in peripheral tissues, for instance, adrenal, thyroidal, cardiac, pulmonary, renal and muscular (Chen, M.-H. et al., *Bioorg. Med. Chem.*

Letts., (1996), 6(18):2163-9; Howard, A. D. et al., *Science*, (1996), 273(5277):974-7; Pong, S. S. et al., *Mol. Endocri.*, (1996), 10(1):57-61; Guan, X.-M. et al., *Mol. Brain. Res.*, (1997), 48(1):23-9; and McKee, K. K. et al., *Genomics*, (1997), 46(3):426-34). A truncated version of GHSR1a has been reported (Howard, A. D. et al., *Science*, (1996), 273 (5277):974-7).

The GHS receptor is a G-protein coupled-receptor. The effects of GHS receptor activation include depolarization and inhibition of potassium channels, an increase in intercellular concentrations of inositol triphosphate (IP3) and a transient increase in the concentrations of intracellular calcium (Pong, S. S. et al., *Mol. Endocri.*, (1996), 10(1):57-61; Guan, X.-M. et al., *Mol. Brain. Res.*, (1997), 48(1):23-9; and McKee, K. K. et al., *Genomics*, (1997), 46(3):426-34).

GHS molecules such as ghrelin and its analogs have a variety of different therapeutic (U.S. Pat. No. 6,566,337; Inui, A., FASEB J., (2004), 18(3):439-56; Muller, E. E. et al., *Neurobiol. Aging*, (2002), 23(5):907-19; Casanueva, F. F. et al., *Trends Endocrinol. Metab.*, (1999), 10(1):30-8; and Ankerson, M. et al., *Drug Discovery Today*, (1999), 4:497-506) and diagnostic uses. Compounds exhibiting agonist effects at the GHS receptor are indicated for improving a GH-deficient state (U.S. Pat. Nos. 6,861,409 and 6,967,237; and Casanueva, F. F. et al., *Trends Endocrinol. Metab*, (1999), 10(1): 30-8), increasing muscle mass (U.S. Pat. Nos. 6,861,409 and 6,967,237) and/or physical strength (Ankerson, M. et al., *Drug Discovery Today*, (1999), 4:497-506), improving bone density (U.S. Pat. Nos. 6,861,409, 6,967,237 and 6,251,902; and Sibilia, V. et al., *Growth Horm. IGF Res.*, (1999), 9(4): 219-27), treating osteoporosis (International Patent Application Nos. PCT/IB96/01353 [WO 97/24369] and PCT/IB98/00873 [WO 98/58947]; and Casanueva, F. F. et al., *Trends Endocrinol. Metab.*, (1999), 10(1):30-8), overcoming sexual dysfunction (U.S. Pat. No. 6,967,237; and Casanueva, F. F. et al., *Trends Endocrinol. Metab.*, (1999) 10(1):30-8), treating cardiovascular disease (International Patent Application Nos. PCT/IB96/01353 [WO 97/24369] and PCT/IB98/00873 [WO 98/58947]; U.S. Pat. No. 6,251,902; De Gennaro Colonna, V. et al., *Eur. J. Pharmacol.*, (1997), 334(2-3):201-7; and Casanueva, F. F. et al., *Trends Endocrinol. Metab.*, (1999), 10(1):30-8), relieving arthritis pain (Granado, M., *Am. J. Endo. Metab.*, (2005), 288:486-92), preventing or alleviating the onset of Alzheimer's disease (U.S. Pat. Nos. 6,686,359 and 6,566,337) and/or treating systemic lupus erythematosus or inflammatory bowel disease, e.g. Crohn's disease or ulcerative colitis (U.S. Patent Publication No. 2002/0013320).

Agonistic analogs of ghrelin can facilitate a gain in body weight (U.S. Pat. No. 6,967,237; Tschop, M. et al., *Nature*, (2000), 407(6806):908-13; and Tschop, M. et al., *Endocrinology*, (2002), 143(2):558-68) which in turn can be used to maintain a desired body weight (U.S. Pat. Nos. 6,861,409 and 6,967,237) and/or to recover physical function (U.S. Pat. Nos. 6,967,237 and 6,251,902; and International Patent Application No. PCT/IB96/01353 [WO 97/24369]).

Ghrelin also increases appetite (U.S. Pat. No. 6,967,237; and Okada, K. et al., *Endocrinology*, (1996), 137(11):5155-8). As such, ghrelin is often used to treat patients suffering from certain diseases or disorders or undertaking medicinal regimens which are traditionally accompanied with an undesirable weight loss such as: anorexia (U.S. Pat. No. 6,967, 237; and Tschop, M. et al., *Endocrinology*, (2002), 143(2): 558-68), bulimia (U.S. Pat. No. 6,967,237), cachexia (U.S. Pat. Nos. 6,967,237 and 6,251,902), particularly cancer-induced cachexia (U.S. Pat. No. 6,967,237; International Patent Appln. No. PCT/DK2004/000529 [WO 05/014032]; and Tschop, M. et al., *Endocrinology*, (2002), 143:558-68), AIDS (U.S. Pat. Nos. 6,861,409 and 6,967,237; and Tschop, M. et al., *Endocrinology*, (2002), 143(2):558-68), wasting syndrome in the frail and/or elderly (U.S. Pat. Nos. 6,861,409 and 6,967,237; International Patent Application No. PCT/IB96/01353 [WO 97/24369]; and Ankerson, M. et al., *Drug Discovery Today*, (1999) 4:497-506) and chronic renal failure (Casanueva, F. F. et al., *Trends Endocri. Metab.*, (1999), 10(1):30-8). Medicinal treatments traditionally accompanied by a weight loss include chemotherapy, radiation therapy, temporary or permanent immobilization and/or dialysis (U.S. Pat. Nos. 6,967,237 and 6,251,902).

Obesity is a major risk factor for diabetes and a large fraction of non-insulin-dependent diabetes mellitus (otherwise referred to as "NIDDM") patients are obese. Both conditions are characterized by elevated circulating insulin levels and suppressed GH levels. GH treatment of GH-deficient adults (Jorgensen, J. O. et al., *Lancet*, (1989), 1(8649):1221-5), obese women (Richelsen, B. et al., *Am. J. Physiol.*, (1994), 266(2 Pt 1):E211-6) and elderly men (Rudman, D. et al., *Horm. Res.*, (1991), 36 (Suppl 1):73-81) has been shown to produce increases in lean body, hepatic and muscle mass while decreasing fat mass. Accordingly, administration of a ghrelin agonist is an attractive therapy for obesity except for the diabetogenic effects of GH (U.S. Pat. No. 6,251,902; Ankerson, M. et al., *Drug Discovery Today*, (1999) 4:497-506; and Casanueva, F. F. et al., *Trends Endocri. Metab.*, (1999), 10(1):30-8). Complications of diabetes such as retinopathy and/or for treating cardiovascular disorders (U.S. Pat. No. 6,967,237; and U.S. Patent Application Publication No. 2003/0211967) may be indirectly treated by ghrelin as well.

Paradoxically, ghrelin antagonists can be used to facilitate weight loss in an obese individual wherein said obesity is not due to the onset of NIDDM (U.S. Pat. No. 6,967,237; and U.S. Patent Application Publication No. 2003/0211967) as well as several other identified indications. Compounds exhibiting antagonist effects at the GHS receptor to promote the suppression of GH secretion, e.g., antagonist analogs of ghrelin, are indicated to reverse excessive GH secretion (U.S. Patent Application Publication No. 2002/0187938), to facilitate weight loss in the non-obese (U.S. Pat. No. 6,967,237), to maintain an ideal weight and/or to decrease appetite (U.S. Pat. No. 6,967,237). Excessive weight is a contributing factor to many diseases or conditions such as hypertension, dyslipidemia and cardiovascular disease (U.S. Patent Application Publication No. 2003/0211967; and U.S. Pat. No. 6,967,237) as well as gall stones, osteoarthritis (U.S. Pat. No. 6,967,237), certain cancers (U.S. Patent Application Publication Nos. 2003/0211967 and 2004/0157227; and U.S. Pat. No. 6,967, 237) and Prader-Willi syndrome (U.S. Pat. No. 6,950,707; International Patent Application No. PCT/US2004/008385 [WO 04/084943]; Haqq, A. M. et al., *J. Clin. Endocri. Metab.*, (2003), 88(1):174-8; and Cummings, D. E. et al., *Nat. Med.*, (2002), 8(7):643-4). Ghrelin antagonists which facilitate weight loss would therefore reduce the likelihood of such diseases or conditions and/or comprise at least part of a treatment for such diseases or conditions. Antagonists of GHS molecules have also been disclosed to exhibit binding to tumorigenic tissue to result in a decrease in the number of tumorigenic cells in the target tissues, e.g. tumors in the lung, mammary glands, thyroid or pancreas (International Patent Application No. PCT/EP99/08662 [WO 00/29011]).

Analogs of GH secretagogues have also been employed to promote gastrointestinal motility, particularly in patients suffering from decreased gastrointestinal motility resulting from post-operative ileus or from gastroparesis incidental to the onset of diabetes or a chronic diabetic state (U.S. Pat. No. 6,548,501).

In addition, ghrelin has been effective in treating inflammation in a mammalian subject (International Patent Application No. PCT/US2005/016565 [WO 2005/110463]). In particular, the inflammation can be associated with a viral, bacterial, parasitic or fungal infection. Viral infections treatable with ghrelin may include Herpes simplex virus type-1, Herpes simplex virus type-2, Cytomegalovirus, Epstein-Barr virus, Varicella-zoster virus, Human herpesvirus 6, Human herpesvirus 7, Human herpesvirus 8, Variola virus, Vesicular stomatitis virus, Hepatitis A virus, Hepatitis B virus, Hepatitis C virus, Hepatitis D virus, Hepatitis E virus, Rhinovirus, Coronavirus, Influenza virus A, Influenza virus B. Measles virus, Polyomavirus, Human Papilomavirus, Respiratory syncytial virus, Adenovirus, Coxsackie virus, Dengue virus, Mumps virus, Poliovirus, Rabies virus, Rous sarcoma virus, Yellow fever virus, Ebola virus, Marburg virus, Lassa fever virus, Eastern Equine Encephalitis virus, Japanese Encephalitis virus, St. Louis Encephalitis virus, Murray Valley fever virus, West Nile virus, Rift Valley fever virus, Rotavirus A, Rotavirus B, Rotavirus C, Sindbis virus, Simian Immunodeficiency virus, Human T-cell Leukemia virustype-1, Hantavirus, Rubella virus, Simian Immunodeficiency virus, Human Immunodeficiency virus type-1 and Human Immunodeficiency virus type-2. (International Patent Application No. PCT/US2005/016565 [WO 2005/110463]). Bacterial infections that cause inflammation that can be treated with ghrelin (International Patent Application No. PCT/US2005/016565 [WO 2005/110463]) include *M. tuberculosis, M bovis, M. bovis* strain BCG, BCG substrains, *M. avium, M intracellulare, M africanum, M kansasii, M marinum, M ulcerans, M. avium* subspecies *paratuberculosis, Nocardia asteroides*, other *Nocardia* species, *Legionella pneumophila*, other *Legionella* species, *Salmonella typhi*, other *Salmonella* species, *Shigella* species, *Yersinia pestis, Pasteurella haemolytica, Pasteurella multocida*, other *Pasteurella* species, *Actinobacillus pleuropneumoniae, Listeria monocytogenes, Listeria ivanovii, Brucella abortus*, other *Brucella* species, *Cowdria ruminantium, Chlamydia pneumoniae, Chlamydia trachomatis, Chlamydia psittaci, Coxiella burnetti*, other *Rickettsia* species, *Ehrlichia* species, *Staphylococcus aureus, Staphylococcus epidermidis, Streptococcus pyogenes, Streptococcus agalactiae, Bacillus anthracis, Escherichia coli, Vibrio cholerae, Campylobacter* species, *Neiserria meningitidis, Neiserria gonorrhea, Pseudomonas aeruginosa*, other *Pseudomonas* species, *Haemophilus influenzae, Haemophilus ducreyi*, other *Hemophilus* species, *Clostridium tetani*, other *Clostridium* species, *Yersinia enterolitica* and other *Yersinia* species (International Patent Application No. PCT/US2005/016565 [WO 2005/110463]).

Inflammation treatable with ghrelin (International Patent Application No. PCT/US2005/016565 [WO 2005/110463]) can also be caused by parasites including *Toxoplasma gondii, Plasmodium, Trypanosoma brucei, Trypanosoma cruzi, Leishmania, Schistosoma* and *Entamoeba histolytica* or fungi such as *Candida albicans, Cryptococcus neoformans, Histoplama capsulatum, Aspergillus fumigatus, Coccidiodes immitis, Paracoccidiodes brasiliensis, Blastomyces dermitidis, Pneomocystis carnii, Penicillium marneffi* and *Alternaria alternate* (International Patent Application No. PCT/US2005/016565 [WO 2005/110463]).

Inflammation caused by liver toxicity or transplant rejection is also treatable by ghrelin (International Patent Application No. PCT/US2005/016565 [WO 2005/110463]). The liver toxicity may be associated with cancer therapy. In some instances, the cancer therapy, such as chemotherapy, may bring about liver toxicity. Liver toxicity brought about by both chemotherapy and apoptosis may be treatable by administration of ghrelin, ghrelin agonists or ghrelin antagonists (International Patent Application No. PCT/US2005/016565 [WO 2005/110463]).

Inflammation associated with cancer is also treatable with ghrelin (International Patent Application No. PCT/US2005/016565 [WO 2005/110463]). Such cancers include lymphoma, leukemia, mycosis fungoide, carcinoma, adenocarcinoma, sarcoma, glioma, blastoma, neuroblastoma, plasmacytoma, histiocytoma, melanoma, adenoma, hypoxic tumor, myeloma, AIDS-related lymphoma or AIDS-related sarcoma, metastatic cancer, bladder cancer, brain cancer, nervous system cancer, glioblastoma, ovarian cancer (International Patent Application No. PCT/AU02/00582 [WO 02/090387]; and Gaytan, F. et al., *J. Clin. Endocri. Metab.*, (2005), 90(3):1798-804), skin cancer, liver cancer, squamous cell carcinomas of the mouth, throat, larynx, and lung, colon cancer, cervical cancer (International Patent Application No. PCT/AU02/00582 [WO 02/090387]), breast cancer (International Patent Application No. PCT/AU02/00582 [WO 02/090387]; and Cassoni, P. et al., *J. Clin. Endocri. Metab.*, (2001), 86(4):1738-45), epithelial cancer, renal cancer (Jungwirth, A. et al., *Proc. Natl. Acad. Sci. USA*, (1997), 94(11): 5810-3), genitourinary cancer, pulmonary cancer (Ghé, C. et al., *Endocrinology*, (2002), 143(2):484-91), esophageal carcinoma (Nwokolo, C. U. et al., *Gut*, (2003), 52(5):637-40), head and neck carcinoma (Jozkow, P. et al., *Head Neck*, (2005), 27(3):243-7), hematopoietic cancer, testicular cancer (Gaytan, F. et al., *J. Clin. Endocri Metab.*, (2004), 89(1):400-9), colo-rectal cancer (Dagnaes-Hansen, H. et al., *Anticancer Res.*, (2004), 24(6):3735), prostatic cancer (Jeffery, P. L. et al., *Endocrinology*, (2002), 172:R7-11), and pancreatic cancer (Volante, M. et al., *J. Clin. Endocri. Metab.*, (2002), 87(3):1300-8); and International Patent Application No. PCT/US2005/016565 [WO 2005/110463]).

Finally, ghrelin has been shown to treat inflammatory diseases (International Patent Application No. PCT/US2005/016565 [WO 2005/110463]) such as asthma, reactive arthritis, hepatitis (Wallace, J. D. et al., *J. Clin. Endocri. Metab.*, (2002), 87(6):2751-9), spondyarthritis, Sjogren's syndrome, Alzheimer's disease (U.S. Pat. Nos. 6,686,359 and 6,566, 337; and Obermayr, R. P. et al., *Gerontology*, (2003), 49(3): 191-5), and atopic dermatitis or inflammatory diseases associated with an autoimmune disease such as systemic lupus erythematosus, rheumatoid arthritis (Otero, M. et al., *Rheumatology* (Oxford), (2004), 43(3):306-10), systemic vasculitis, insulin dependent diabetes mellitus (Nieves-Riviera, F. et al., *Growth Regul.*, (1993), 3:235-44), multiple sclerosis and muscular dystrophy (U.S. Patent Publication No. 2003/ 0139348), experimental allergic encephalomyelitis (Ikushima, H. et al., *J. Immunol.*, (2003), 171:2769-72), psoriasis (Edmondson, S. R. et al., *Endocri. Rev.*, (2003), 24(6): 737-64), Crohn's disease (Slonim, A. E. et al., *N. Engl. J. Med.*, (2000), 342(22):1633-7), inflammatory bowel disease (Chen, K. et al., *Surgery*, (1997), 121(2):212-8), ulcerative colitis, Addison's disease (Arvat, E. et al., *Neuroendocrinology*, (1999), 70(3):200-6), alopecia aretea, celiac disease (Peracchi, M. et al., Am. J. Gastroenterol., (2003), 98(11): 2474-8); and Capristo, E. et al., *Scand. J. Gastroenterol.*, (2005), 40(4):430-6), thyroid disease (Riis, A. L. et al., *J. Clin. Endocrin. Metab.*, (2003), 88(2):853-7), and scleroderma. Inflammation as a result of a burn may also benefit from treatment with ghrelin as may inflammation of the lung (International Patent Application No. PCT/US2005/016565 [WO 2005/110463]). Inflammation may also cause a subject to lose appetite, particularly when the inflammation is low grade and/or in an aging subject (International Patent Application No. PCT/US2005/016565 [WO 2005/110463]).

Ghrelin antagonists can also be used to achieve a beneficial effect in a patient (U.S. Patent Publication Nos. 2002/187938, 2003/0211967 and 2004/0157227; and U.S. Pat. No. 6,967, 237). For example, a ghrelin antagonist can be used to facilitate weight loss or decrease in appetite, to maintain an ideal body weight, to treat obesity, to manage a diabetic state including complications thereof such as retinopathy, and/or to treat cardiovascular disorders. Excessive weight is a contributing factor of several diverse diseases or conditions including, but not limited to, hypertension, diabetes, dyslipidemia, cardiovascular disease, gall stone formation, osteoarthritis and Prader-Willi syndrome as well as certain forms of cancers. Bringing about a weight loss can be used, for example, to reduce the likelihood of such diseases and as part of a treatment for such diseases.

Given the wide variety of beneficial effects that GHSs have to offer, there is a need in the art for effective agonist or antagonist ghrelin analog molecules.

SUMMARY OF THE INVENTION

It was discovered that ghrelin analogs in which the amino acids at residues $A^{15}$, $A^{16}$, $A^{17}$, $A^{18}$, $A^{19}$ or $A^{20}$ were substituted with either Asp(NH—$R^9$), Asp(O—$R^8$), Cys(S—$R^{14}$), Cys($R^{15}$), hCys(S—$R^{16}$), hCys($R^{17}$), Dab(S(O)$_2$—$R^{11}$), Dap (S(O)$_2$—$R^{11}$), Glu(NH—$R^7$), Glu(O—$R^6$), Gly(myristyl), Ser(C(O)—$R^4$), Thr(C(O)—$R^5$) or HN—CH((CH$_2$)$_n$—N($R^{12}R^{13}$))—C(O), or, in particular, Lys(biotinyl)$^{17}$ or Lys(myristyl)$^{17}$, exhibited higher cell membrane binding affinity and were found to interact more efficiently with membrane bound receptors and thus were more biologically potent compared to native ghrelin.

In light of this finding, the present invention features ghrelin analogs active at the GHS receptor in which amino acids at residues $A^{15}$, $A^{16}$, $A^{17}$, $A^{18}$, $A^{19}$ or $A^{20}$ are substituted with either Asp(NH—$R^9$), Asp(O—$R^8$), Cys(S—$R^{14}$), Cys($R^{15}$), hCys(S—$R^{16}$), hCys($R^{17}$), Dab(S(O)$_2$—$R^{11}$), Dap(S(O)$_2$—$R^{10}$), Glu(NH—$R^7$), Glu(O—$R^6$), Gly(myristyl)$^1$, Lys(biotinyl)$^{17}$, Lys(myristyl)$^{17}$, Ser(C(O)—$R^4$), Thr(C(O)—$R^5$) or HN—CH((CH$_2$)$_n$—N($R^{12}R^{13}$))—C(O).

Thus, a first aspect of the present invention describes a ghrelin analog according to formula (I), wherein the first amino acid listed in the definitions of $A^1$ to $A^{28}$ is the amino acid found at that position in the sequence of native ghrelin, i.e. H-Gly-Ser-Ser-Phe-Leu-Ser-Pro-Glu-His-Gln-Arg-Val-Gln-Gln-Arg-Lys-Glu-Ser-Lys-Lys-Pro-Pro-Ala-Lys-Leu-Gln-Pro-Arg-NH$_2$ (SEQ ID NO:180):

$$(R^2R^3)\text{-}A^1\text{-}A^2\text{-}A^3\text{-}A^4\text{-}A^5\text{-}A^6\text{-}A^7\text{-}A^8\text{-}A^9\text{-}A^{10}\text{-}A^{11}\text{-}A^{12}\text{-}A^{13}\text{-}$$
$$A^{14}\text{-}A^{15}\text{-}A^{16}\text{-}A^{17}\text{-}A^{18}\text{-}A^{19}\text{-}A^{20}\text{-}A^{21}\text{-}A^{22}\text{-}A^{23}\text{-}A^{24}\text{-}A^{25}\text{-}$$
$$A^{26}\text{-}A^{27}\text{-}A^{28}\text{-}R^1 \quad (I)$$

wherein:

$A^1$ is Gly, Acc, Aib, Ala or β-Ala;

$A^2$ is Ser, Abu, Acc, Act, Aib, Ala, Ava, Thr or Val;

$A^3$ is Ser, Asp(NH—$R^9$), Asp(O—$R^8$), Cys(S—$R^{14}$), Dab(S(O)$_2$—$R^{11}$), Dap(S(O)$_2$—$R^{10}$), Glu(NH—$R^7$), Glu(O—$R^6$), Ser(C(O)—$R^4$), Thr(C(O)—$R^5$) or HN—CH((CH$_2$)$_n$—N($R^{12}R^{13}$))—C(O);

$A^4$ is Phe, Acc, Aic, Cha, 2-Fua, 1-Nal, 2-Nal, 2-Pal, 3-Pal, 4-Pal, hPhe, ($X^1,X^2,X^3,X^4,X^5$)Phe, Taz, 2-Thi, 3-Thi, Trp or Tyr;

$A^5$ is Leu, Abu, Acc, Aib, Ala, Cha, Ile, hLeu, Nle, Nva, Phe, Tle or Val;

$A^6$ is Ser, Abu, Acc, Act, Aib, Ala, Gly, Thr or Val;

$A^7$ is Pro, Dhp, Dmt, 3-Hyp, 4-Hyp, Inc, Ktp, Oic, Pip, Thz or Tic;

$A^8$ is Glu, Acc, Aib, Arg, Asn, Asp, Dab, Dap, Gln, Lys, Orn or HN—CH((CH$_2$)$_n$—N($R^{12}R^{13}$))—C(O);

$A^9$ is His, Acc, Apc, Aib, 2-Fua, 2-Pal, 3-Pal, 4-Pal, ($X^1,X^2,X^3,X^4,X^5$—)Phe, Taz, 2-Thi or 3-Thi;

$A^{10}$ is Gln, Acc, Aib, Asn, Asp or Glu;

$A^{11}$ is Arg, Apc, hArg, Dab, Dap, Lys, Orn or HN—CH((CH$_2$)$_n$—N($R^{12}R^{13}$))—C(O);

$A^{12}$ is Val, Abu, Acc, Aib, Ala, Cha, Gly, Ile, Leu, Nle, Nva or Tle;

$A^{13}$ is Gln, Acc, Aib, Asn, Asp or Glu;

$A^{14}$ is Gln, Acc, Aib, Asn, Asp or Glu;

$A^{15}$ is Arg, Acc, Aib, Apc, hArg, Dab, Dap, Lys, Orn, Asp(NH—$R^9$), Asp(O—$R^8$), Cys(S—$R^{14}$), Cys($R^{15}$), hCys(S—$R^{16}$), hCys($R^{17}$), Dab(S(O)$_2$—$R^{11}$), Dap(S(O)$_2$—$R^{10}$), Glu(NH—$R^7$), Glu(O—$R^6$), Ser(C(O)—$R^4$), Thr(C(O)—$R^5$) or HN—CH((CH$_2$)$_n$—N($R^{12}R^{13}$))—C(O);

$A^{16}$ is Lys, Acc, Aib, Apc, Arg, hArg, Dab, Dap, Orn, Asp(NH—$R^9$), Asp(O—$R^8$), Cys(S—$R^{14}$), Cys($R^{15}$), hCys(S—$R^{16}$), hCys($R^{17}$), Dab(S(O)$_2$—$R^7$), Dap(S(O)$_2$—$R^{10}$), Glu(NH—$R^7$), Glu(O—$R^6$), Ser(C(O)—$R^4$), Thr(C(O)—$R^5$), HN—CH((CH$_2$)$_n$—N($R^{12}R^{13}$))—C(O) or deleted;

$A^{17}$ is Glu, Arg, Asn, Asp, Dab, Dap, Gln, Lys, Orn, Asp(NH—$R^9$), Asp(O—$R^8$), Cys(S—$R^{14}$), Cys($R^{15}$), hCys(S—$R^{16}$), hCys($R^{17}$), Dab(S(O)$_2$—$R^{11}$), Dap(S(O)$_2$—$R^{10}$), Glu(NH—$R^7$), Glu(O—$R^6$), Lys(biotinyl), Ser(C(O)—$R^4$), Thr(C(O)—$R^5$), HN—CH((CH$_2$)$_n$—N($R^{12}R^{13}$))—C(O) or deleted;

$A^{18}$ is Ser, Abu, Acc, Act, Aib, Ala, Thr, Val, Asp(NH—$R^9$), Asp(O—$R^8$), Cys(S—$R^{14}$), Cys($R^{15}$), hCys(S—$R^{16}$), hCys($R^{17}$), Dab(S(O)$_2$—$R^{11}$), Dap(S(O)$_2$—$R^{10}$), Glu(NH—$R^7$), Glu(O—$R^6$), Ser(C(O)—$R^4$), Thr(C(O)—$R^5$), HN—CH((CH$_2$)$_n$—N($R^{12}R^{13}$))—C(O) or deleted;

$A^{19}$ is Lys, Acc, Aib, Apc, Arg, hArg, Dab, Dap, Orn, Asp(NH—$R^9$), Asp(O—$R^8$), Cys(S—$R^{14}$), Cys($R^{15}$), hCys(S—$R^{16}$), hCys($R^{17}$), Dab(S(O)$_2$—$R^{11}$), Dap(S(O)$_2$—$R^{10}$), Glu(NH—$R^7$), Glu(O—$R^6$), Ser(C(O)—$R^4$), Thr(C(O)—$R^5$), HN—CH((CH$_2$)$_n$—N($R^{12}R^{13}$))—C(O) or deleted;

$A^{20}$ is Lys, Acc, Aib, Apc, Arg, hArg, Dab, Dap, Orn, Asp(NH—$R^9$), Asp(O—$R^8$), Cys(S—$R^{14}$), Cys($R^{15}$), hCys(S—$R^{16}$), hCys($R^{17}$), Dab(S(O)$_2$—$R^{11}$), Dap(S(O)$_2$—$R^{10}$), Glu(NH—$R^7$), Glu(O—$R^6$), Ser(C(O)—$R^4$), Thr(C(O)—$R^5$), HN—CH((CH$_2$)$_n$—N($R^{12}R^{13}$))—C(O) or deleted;

$A^{21}$ is Pro, Dhp, Dmt, 3-Hyp, 4-Hyp, Inc, Ktp, Oic, Pip, Thz, Tic or deleted;

$A^{22}$ is Pro, Dhp, Dmt, 3-Hyp, 4-Hyp, Inc, Ktp, Oic, Pip, Thz, Tic or deleted;

$A^{23}$ is Abu, Acc, Act, Aib, Ala, Apc, Gly, Nva, Val or deleted;

$A^{24}$ is Lys, Acc, Aib, Apc, Arg, hArg, Dab, Dap, Orn, HN—CH((CH$_2$)$_n$—N($R^{12}R^{13}$))—C(O) or deleted;

$A^{25}$ is Leu, Abu, Acc, Aib, Ala, Cha, Ile, hLeu, Nle, Nva, Phe, Tle, Val or deleted;

$A^{26}$ is Gln, Aib, Asn, Asp, Glu or deleted;

$A^{27}$ is Pro, Dhp, Dmt, 3-Hyp, 4-Hyp, Inc, Ktp, Oic, Pip, Thz, Tic or deleted;

$A^{28}$ is Acc, Aib, Apc, Arg, hArg, Dab, Dap, Lys, Orn, HN—CH((CH$_2$)$_n$—N($R^{12}R^{13}$))—C(O) or deleted;

$R^1$ is —OH, —$NH_2$, —$(C_1$-$C_{30})$alkoxy or NH—$X^6$—$CH_2$—$Z^0$, wherein $X^6$ is a $(C_1$-$C_{12})$alkyl or $(C_2$-$C_{12})$alkenyl and $Z^0$ is —H, —OH, —$CO_2H$ or —C(O)—$NH_2$;

each of $R^2$ and $R^3$ is, independently for each occurrence thereof, selected from the group consisting of H, $(C_1$-$C_{30})$alkyl, $(C_1$-$C_{30})$heteroalkyl, $(C_1$-$C_{30})$acyl, $(C_2$-$C_{30})$alkenyl, $(C_2$-$C_{30})$alkynyl, aryl$(C_1$-$C_{30})$alkyl, aryl$(C_1$-$C_{30})$acyl, substituted $(C_1$-$C_{30})$alkyl, substituted $(C_1$-$C_{30})$heteroalkyl, substituted $(C_2$-$C_{30})$acyl, substituted $(C_2$-$C_{30})$alkenyl, substituted aryl$(C_1$-$C_{30})$alkyl, substituted $(C_2$-$C_{30})$alkynyl and substituted aryl$(C_1$-$C_{30})$acyl;

each of $R^4$, $R^5$, $R^6$, $R^7$, $R^8$, $R^9$, $R^{10}$, $R^{11}$, $R^{14}R^{15}$, $R^{16}$ and $R^{17}$ is, independently for each occurrence thereof, selected from the group consisting of $(C_1$-$C_{40})$alkyl, $(C_2$-$C_{40})$alkenyl, substituted $(C_1$-$C_{40})$alkyl, substituted $(C_2$-$C_{40})$alkenyl, alkylaryl, substituted alkylaryl, aryl and substituted aryl;

each of $R^{12}$ and $R^{13}$ is, independently for each occurrence, selected from the group consisting of H, $(C_1$-$C_{40})$alkyl, $(C_1$-$C_{40})$heteroalkyl, $(C_1$-$C_{40})$acyl, $(C_2$-$C_{40})$alkenyl, $(C_2$-$C_{40})$alkynyl, aryl$(C_1$-$C_{40})$alkyl, aryl$(C_1$-$C_{40})$acyl, substituted $(C_1$-$C_{40})$alkyl, substituted $(C_1$-$C_{40})$heteroalkyl, substituted $(C_1$-$C_{40})$acyl, substituted $(C_2$-$C_{40})$alkenyl, substituted $(C_2$-$C_{40})$alkynyl, substituted aryl$(C_1$-$C_{40})$alkyl, substituted aryl$(C_1$-$C_{40})$acyl, $(C_1$-$C_{40})$alkylsulfonyl, —C(NH)—$NH_2$ and biotinyl;

n is, independently for each occurrence thereof, 1, 2, 3, 4 or 5;

each of $X^1$, $X^2$, $X^3$, $X^4$, and $X^5$ is, independently for each occurrence thereof, selected from the group consisting of H, F, Cl, Br, I, $(C_{1-10})$alkyl, substituted $(C_{1-10})$alkyl, aryl, substituted aryl, OH, $NH_2$, $NO_2$ and CN;

provided that:

(I) when $R^2$ is $(C_1$-$C_{30})$acyl, aryl$(C_1$-$C_{30})$acyl, substituted $(C_2$-$C_{30})$acyl, or substituted aryl$(C_1$-$C_{30})$acyl, then $R^3$ is H, $(C_1$-$C_{30})$alkyl, $(C_1$-$C_{30})$heteroalkyl, $(C_2$-$C_{30})$alkenyl, aryl$(C_1$-$C_{30})$alkyl, substituted $(C_1$-$C_{30})$alkyl, substituted $(C_1$-$C_{30})$heteroalkyl, substituted $(C_2$-$C_{30})$alkenyl, substituted $(C_2$-$C_{30})$alkynyl or substituted aryl$(C_1$-$C_{30})$alkyl;

(II) when $R^{12}$ is $(C_1$-$C_{40})$acyl, aryl$(C_1$-$C_{40})$acyl, substituted $(C_1$-$C_{40})$acyl, substituted aryl$(C_1$-$C_{40})$acyl, $(C_1$-$C_{40})$alkylsulfonyl, or —C(NH)—$NH_2$, then $R^{13}$ is H or $(C_1$-$C_{40})$alkyl, $(C_1$-$C_{40})$heteroalkyl, $(C_2$-$C_{40})$alkenyl, $(C_2$-$C_{40})$alkynyl, aryl$(C_1$-$C_{40})$alkyl, substituted $(C_1$-$C_{40})$alkyl, substituted $(C_1$-$C_{40})$heteroalkyl, substituted $(C_2$-$C_{40})$alkenyl, substituted $(C_2$-$C_{40})$alkynyl, or substituted aryl$(C_1$-$C_{40})$alkyl;

(III) at least one of $A^{15}$, $A^{16}$, $A^{17}$, $A^{18}$, $A^{19}$ or $A^{20}$ of said ghrelin analog is selected from the group consisting of Asp(NH—$R^9$), Asp(O—$R^8$), Cys(S—$R^{14}$), Cys($R^{15}$), hCys(S—$R^{16}$), hCys($R^{17}$), Dab(S(O)$_2$—$R^{11}$), Dap(S(O)$_2$—$R^{10}$), Glu(NH—$R^7$), Glu(O—$R^6$), Ser(C(O)—$R^4$), Thr(C(O)—$R^5$) and HN—CH(($CH_2$)$_n$—N($R^{12}R^{13}$))—C(O); and (IV) when any of the group consisting of $A^{15}$, $A^{16}$, $A^{17}$, $A^{19}$ and $A^{20}$ is HN—CH(($CH_2$)$_n$—N($R^{12}R^{13}$))—C(O), then $R^{12}$ must be biotinyl;

or a pharmaceutically acceptable salt thereof.

A preferred group of compounds of formula (I), termed Group 1 compounds, is where:

$A^1$ is Gly or Aib;
$A^2$ is Ser, Act, Aib, Ava or A5c;
$A^3$ is Dab(S(O)$_2$—$R^{11}$), Dap(S(O)$_2$—$R^{10}$), Glu(NH—$R^7$), Glu(O—$R^6$) or Ser(C(O)—$R^4$);
$A^4$ is Phe;
$A^5$ is Leu, Acc, Aib, Cha or hLeu;
$A^6$ is Ser, Abu, Act, Aib or Thr;
$A^7$ is Pro, Dhp, Dmt, 4Hyp, Ktp, Pip or Thz;
$A^8$ is Glu or Aib;
$A^9$ is His, Aib, Apc, 2-Fua, 2-Pal, 3-Pal, 4-Pal, Taz or 2-Thi;
$A^{10}$ is Gln or Aib;
$A^{11}$ is Arg;
$A^{12}$ is Val or Acc;
$A^{13}$ is Gln;
$A^{14}$ is Gln;
$A^{15}$ is Arg or Orn;
$A^{11}$ is Lys or Apc;
$A^{17}$ is Glu;
$A^{18}$ is Ser;
$A^{19}$ is Lys;
$A^{20}$ is Lys;
$A^{21}$ is Pro;
$A^{22}$ is Pro;
$A^{23}$ is Ala;
$A^{24}$ is Lys;
$A^{25}$ is Leu;
$A^{26}$ is Gln;
$A^{27}$ is Pro; and
$A^{28}$ is Arg;

or a pharmaceutically acceptable salt thereof.

Another preferred group of compounds of formula (I), termed Group 2 compounds, is where:

each of $R^2$ and $R^3$ is, independently for each occurrence thereof, selected from the group consisting of H, acyl, n-butyryl, isobutyryl and n-octanoyl;
$R^4$ is heptyl;
$R^6$ is hexyl;
$R^7$ is hexyl;
$R^{10}$ is octyl;
$R^{11}$ is heptyl; and provided that when Acc is substituted for one of the naturally-occurring residues, it is, independently for each occurrence, A3c, A4c, A5c or A6c;

or pharmaceutically acceptable salts thereof.

Another preferred group of compounds of the immediately preceding group of compounds, termed Group 3 compounds, is where:

$A^3$ is Asp(NH-hexyl), Asp(1-heptanol), Cys(S—($CH_2$)$_9$$CH_3$), Dap(octanesulfonyl), Glu(NH-hexyl) or Glu(1-heptanol);
$A^5$ is Leu;
$A^6$ is Ser;
$A^7$ is Pro, Dhp, 4-Hyp, Pip, Thz or Tic;
$A^9$ is His, 3-Pal, 4-Pal, Taz or 2-Thi;
$A^{12}$ is Val;
$A^{11}$ is Arg, Glu(NH-hexyl) or Ser(n-octanoyl);
$A^{16}$ is Lys, Glu(NH-hexyl) or Ser(n-octanoyl);
$A^{17}$ is Glu, Lys(biotinyl), Asp(NH-hexyl), Asp(1-heptanol), Cys(S—($CH_2$)$_9CH_3$), Dap(octanesulfonyl), Glu(NH-hexyl), Glu(1-heptanol) or Ser(n-octanoyl);
$A^{18}$ is Ser, Glu(NH-hexyl) or Ser(n-octanoyl);
$A^{19}$ is Lys, Glu(NH-hexyl) or Ser(n-octanoyl);
$A^{20}$ is Lys, Glu(NH-hexyl) or Ser(n-octanoyl);

or a pharmaceutically acceptable salt thereof.

A more preferred group of compounds according to formula (I), termed Group 4 compounds, includes compounds according to the formula:

(Ser(n-octanoyl)$^{15}$)hGhrelin(1-28)-$NH_2$;   (SEQ ID NO: 1)

(Glu(NH-hexyl)$^{15}$)hGhrelin(1-28)-$NH_2$;   (SEQ ID NO: 2)

(Glu(NH-hexyl)$^{3,15}$)hGhrelin(1-28)-$NH_2$;   (SEQ ID NO: 3)

-continued

| | |
|---|---|
| (Glu(NH-hexyl)³,Ser(n-octanoyl)¹⁵)hGhrelin(1-28)-NH₂; | (SEQ ID NO: 4) |
| (Aib²,Glu(NH-hexyl)¹⁵)hGhrelin(1-28)-NH²; | (SEQ ID NO: 5) |
| (Aib2,Glu(NH-hexyl)³,¹⁵)hGhrelin(1-28)-NH₂; | (SEQ ID NO: 6) |
| (Aib²,⁸,Glu(NH-hexyl)¹⁵)hGhrelin(1-28)-NH₂; | (SEQ ID NO: 7) |
| (Aib²,⁸,Glu(NH-hexyl)³,¹⁵)hGhrelin(1-28)-NH₂; | (SEQ ID NO: 8) |
| (Aib²,¹⁰,Glu(NH-hexyl)¹⁵)hGhrelin(1-28)-NH₂; | (SEQ ID NO: 9) |
| (Aib²,¹⁰,Glu(NH-hexyl)³,¹⁵)hGhrelin(1-28)-NH₂; | (SEQ ID NO: 10) |
| (Ser(n-octanoyl)¹⁶)hGhrelin(1-28)-NH₂; | (SEQ ID NO: 11) |
| (Glu(NH-hexyl)¹⁶)hGhrelin(1-28)-NH₂; | (SEQ ID NO: 12) |
| (Glu(NH-hexyl)³,¹⁶)hGhrelin(1-28)-NH₂; | (SEQ ID NO: 13) |
| (Glu(NH-hexyl)³,Ser(n-octanoyl)¹⁶)hGhrelin(1-28)-NH₂; | (SEQ ID NO: 14) |
| (Aib²,Glu(NH-hexyl)¹⁶)hGhrelin(1-28)-NH₂; | (SEQ ID NO: 15) |
| (Aib²,Glu(NH-hexyl)³,¹⁶)hGhrelin(1-28)-NH₂; | (SEQ ID NO: 16) |
| (Aib²,⁸,Glu(NH-hexyl)¹⁶)hGhrelin(1-28)-NH₂; | (SEQ ID NO: 17) |
| (Aib²,8,Glu(NH-hexyl)³,¹⁶)hGhrelin(1-28)-NH₂; | (SEQ ID NO: 18) |
| (Aib²,10,Glu(NH-hexyl)¹⁶)hGhrelin(1-28)-NH₂; | (SEQ ID NO: 19) |
| (Aib²,10,Glu(NH-hexyl)³,¹⁶)hGhrelin(1-28)-NH₂; | (SEQ ID NO: 20) |
| (Ser(n-octanoyl)¹⁷)hGhrelin(1-28)-NH₂; | (SEQ ID NO: 21) |
| (Glu(NH-hexyl)¹⁷)hGhrelin(1-28)-NH₂; | (SEQ ID NO: 22) |
| (Glu(NH-hexyl)³,¹⁷)hGhrelin(1-28)-NH₂; | (SEQ ID NO: 23) |
| (Glu(NH-hexyl)³,Ser(n-octanoyl)¹⁷)hGhrelin(1-28)-NH₂; | (SEQ ID NO: 24) |
| (Dap(octanesulfonyl)¹⁷hGhrelin(1-28)-NH₂; | (SEQ ID NO: 25) |
| (Dap(octanesulfonyl)³,¹⁷)hGhrelin(1-28)-NH₂; | (SEQ ID NO: 26) |
| (Dap(octanesulfonyl)³,Glu(NH-hexyl)¹⁷)hGhrelin(1 -28)-NH₂; | (SEQ ID NO: 27) |
| (Dap(octanesulfonyl)³,Ser(n-octanoyl)¹⁷)hGhrelin(1-28)-NH₂; | (SEQ ID NO: 28) |
| (Glu(NH-hexyl)³,Dap(octanesulfonyl)¹⁷)hGhrelin(1-28)-NH₂; | (SEQ ID NO: 29) |
| (Cys(S-(CH₂)₉CH₃)¹⁷)hGhrelin(1-28)-NH₂; | (SEQ ID NO: 30) |
| (Cys(S-(CH₂)₉CH₃)³,¹⁷)hGhrelin(1-28)-NH₂; | (SEQ ID NO: 31) |
| (Glu(NH-hexyl)³,Cys(S-(CH₂)₉CH₃)¹⁷)hGhrelin(1-28)-NH₂; | (SEQ ID NO: 32) |
| (Cys(S-(CH₂)₉CH₃)³,Glu(NH-hexyl)¹⁷)hGhrelin(1-28)-NH₂; | (SEQ ID NO: 33) |
| (Cys(S-(CH₂)₉CH₃)³,Ser(n-octanoyl)¹⁷)hGhrelin(1-28)-NH₂; | (SEQ ID NO: 34) |
| (Aib²,Glu(NH-hexyl)¹⁷)hGhrelin(1-28)-NH₂; | (SEQ ID NO: 35) |
| (Aib²,Glu(NH-hexyl)³,¹⁷)hGhrelin(1-28)-NH₂; | (SEQ ID NO: 36) |
| (Aib²,Thz⁷,Glu(NH-hexyl)¹⁷)hGhrelin(1-28)-NH₂; | (SEQ ID NO: 37) |
| (Aib²,4-Hyp⁷,Glu(NH-hexyl)¹⁷)hGhrelin(1-28)-NH₂; | (SEQ ID NO: 37) |
| (Aib²,Dhp⁷,Glu(NH-hexyl)¹⁷)hGhrelin(1-28)-NH₂; | (SEQ ID NO: 37) |
| (Aib²,Pip⁷,Glu(NH-hexyl)¹⁷)hGhrelin(1-28)-NH₂; | (SEQ ID NO: 37) |
| (Aib²,Tic⁷,Glu(NH-hexyl)¹⁷)hGhrelin(1-28)-NH₂; | (SEQ ID NO: 37) |
| (Aib²,Glu(NH-hexyl)³,¹⁷,Thz⁷)hGhrelin(1-28)-NH₂; | (SEQ ID NO: 38) |
| (Aib²,Glu(NH-hexyl)³,¹⁷,4-HypDhGhrelin(1-28)-NH₂; | (SEQ ID NO: 38) |
| (Aib²,Glu(NH-hexyl)³,¹⁷,Dhp⁷)hGhrelin(1-28)-NH₂; | (SEQ ID NO: 38) |

-continued (Aib², Glu(NH-hexyl)³,¹⁷, Pip⁷)hGhrelin(1-28)-NH₂;   (SEQ ID NO: 38)

(Aib², Glu(NH-hexyl)³,¹⁷, Tic⁷)hGhrelin(1-28)-NH₂;   (SEQ ID NO: 38)

(Aib²,⁸, Glu(NH-hexyl)¹⁷)hGhrelin(1-28)-NH₂;   (SEQ ID NO: 39)

(Aib²,⁸, Glu(NH-hexyl)³,¹⁷)hGhrelin(1-28)-NH₂;   (SEQ ID NO: 40)

(Aib², 3-Pal⁹, Glu(NH-hexyl)¹⁷)hGhrelin(1-28)-NH₂;   (SEQ ID NO: 41)

(Aib², 4-Pal⁹, Glu(NH-hexyl)¹⁷)hGhrelin(1-28)-NH₂;   (SEQ ID NO: 41)

(Aib², Taz⁹, Glu(NH-hexyl)¹⁷)hGhrelin(1-28)-NH₂;   (SEQ ID NO: 41)

(Aib², 2-Thi⁹, Glu(NH-hexyl)¹⁷)hGhrelin(1-28)-NH₂;   (SEQ ID NO: 41)

(Aib², Glu(NH-hexyl)³,¹⁷, 3-Pal⁹)hGhrelin(1-28)-NH₂;   (SEQ ID NO: 42)

(Aib², Glu(NH-hexyl)³,¹⁷, 4-Pal⁹)hGhrelin(1-28)-NH₂;   (SEQ ID NO: 42)

(Aib², Glu(NH-hexyl)³,¹⁷, Taz⁹)hGhrelin(1-28)-NH₂;   (SEQ ID NO: 42)

(Aib², Glu(NH-hexyl)³,¹⁷, 2-Thi⁹)hGhrelin(1-28)-NH₂;   (SEQ ID NO: 42)

(Aib²,¹⁰, Glu(NH-hexyl)¹⁷)hGhrelin(1-28)-NH₂;   (SEQ ID NO: 43)

(Aib²,¹⁰, Glu(NH-hexyl)³,¹⁷)hGhrelin(1-28)-NH₂;   (SEQ ID NO: 44)

(Aib⁸, Glu(NH-hexyl)¹⁷)hGhrelin(1-28)-NH₂;   (SEQ ID NO: 45)

(Taz⁹, Glu(NH-hexyl)¹⁷)hGhrelin(1-28)-NH₂;   (SEQ ID NO: 46)

(3-Pal⁹, Glu(NH-hexyl)¹⁷)hGhrelin(1-28)-NH₂;   (SEQ ID NO: 46)

(4-Pal⁹, Glu(NH-hexyl)¹⁷)hGhrelin(1-28)-NH₂;   (SEQ ID NO: 46)

(2-Thi⁹, Glu(NH-hexyl)¹⁷)hGhrelin(1-28)-NH₂;   (SEQ ID NO: 46)

(Glu(NH-hexyl)³,¹⁷, Aib⁸)hGhrelin(1-28)-NH₂;   (SEQ ID NO: 47)

(Glu(NH-hexyl)³,¹⁷, Taz⁹)hGhrelin(1-28)-NH₂;   (SEQ ID NO: 48)

(Glu(NH-hexyl)³,¹⁷, 3-Pal⁹)hGhrelin(1-28)-NH₂;   (SEQ ID NO: 48)

(Glu(NH-hexyl)³,¹⁷, 4-Pal⁹)hGhrelin(1-28)-NH₂;   (SEQ ID NO: 48)

(Glu(NH-hexyl)³,¹⁷, 2-Thi⁹)hGhrelin(1-28)-NH₂;   (SEQ ID NO: 48)

(Aib¹,²,¹⁰, Glu(NH-hexyl)¹⁷)hGhrelin(1-28)-NH₂;   (SEQ ID NO: 49)

(Aib¹,²,¹⁰, Glu(NH-hexyl)³,¹⁷)hGhrelin(1-28)-NH₂;   (SEQ ID NO: 50)

(A5c², Glu(NH-hexyl)¹⁷)hGhrelin(1-28)-NH₂;   (SEQ ID NO: 51)

(A5c², Glu(NH-hexyl)³,¹⁷)hGhrelin(1-28)-NH₂;   (SEQ ID NO: 52)

(Glu(1-heptanol)³,¹⁷)hGhrelin(1-28)-NH₂;   (SEQ ID NO: 53)

(Asp(1-heptanol)³,¹⁷)hGhrelin(1-28)-NH₂;   (SEQ ID NO: 54)

(Glu(NH-hexyl)³,¹⁷)hGhrelin(1-28)-NH₂;   (SEQ ID NO: 55)

(Asp(NH-hexyl)³,¹⁷)hGhrelin(1-28)-NH₂;   (SEQ ID NO: 56)

(Aib², Glu(NH-hexyl)³,¹⁷)hGhrelin(1-28)-NH₂;   (SEQ ID NO: 57)

(Lys(biotinyl)¹⁷)hGhrelin(1-28)-NH₂;   (SEQ ID NO: 58)

(Ser(n-octanoyl)¹⁸)hGhrelin(1-28)-NH₂;   (SEQ ID NO: 59)

(Glu(NH-hexyl)¹⁸)hGhrelin(1-28)-NH₂;   (SEQ ID NO: 60)

(Glu(NH-hexyl)³,¹⁸)hGhrelin(1-28)-NH₂;   (SEQ ID NO: 61)

(Glu(NH-hexyl)³, Ser(n-octanoyl)¹⁸)hGhrelin(1-28)-NH₂;   (SEQ ID NO: 62)

(Aib², Glu(NH-hexyl)¹⁸)hGhrelin(1-28)-NH₂;   (SEQ ID NO: 63)

(Aib², Glu(NH-hexyl)³,¹⁸)hGhrelin(1-28)-NH₂;   (SEQ ID NO: 64)

-continued

| | |
|---|---|
| (Aib$^{2,8}$,Glu(NH-hexyl)$^{18}$)hGhrelin(1-28)-NH$_2$; | (SEQ ID NO: 65) |
| (Aib$^{2,8}$,Glu(NH-hexyl)$^{3,18}$)hGhrelin(1-28)-NH$_2$; | (SEQ ID NO: 66) |
| (Aib$^{2,10}$,Glu(NH-hexyl)$^{18}$)hGhrelin(1-28)-NH$_2$; | (SEQ ID NO: 67) |
| (Aib$^{2,10}$,Glu(NH-hexyl)$^{3,18}$)hGhrelin(1-28)-NH$_2$; | (SEQ ID NO: 68) |
| (Ser(n-octanoyl)19)hGhrelin(1-28)-NH$_2$; | (SEQ ID NO: 69) |
| (Glu(NH-hexyl)$^{19}$)hGhrelin(1-28)-NH$_2$; | (SEQ ID NO: 70) |
| (Glu(NH-hexyl)$^{3,19}$)hGhrelin(1-28)-NH$_2$; | (SEQ ID NO: 71) |
| (Glu(NH-hexyl)$^{3}$,Ser(n-octanoyl)$^{19}$)hGhrelin(1-28)-NH$_2$; | (SEQ ID NO: 72) |
| (Aib$^{2}$,Glu(NH-hexyl)$^{19}$)hGhrelin(1-28)-NH$_2$; | (SEQ ID NO: 73) |
| (Aib$^{2}$,Glu(NH-hexyl)$^{3,19}$)hGhrelin(1-28)-NH$_2$; | (SEQ ID NO: 74) |
| (Aib$^{2,8}$,Glu(NH-hexyl)$^{19}$)hGhrelin(1-28)-NH$_2$; | (SEQ ID NO: 75) |
| (Aib$^{2,8}$,Glu(NH-hexyl)$^{3,19}$)hGhrelin(1-28)-NH$_2$; | (SEQ ID NO: 76) |
| (Aib$^{2,10}$,Glu(NH-hexyl)$^{19}$)hGhrelin(1-28)-NH$_2$; | (SEQ ID NO: 77) |
| (Aib$^{2,10}$,Glu(NH-hexyl)$^{3,19}$)hGhrelin(1-28)-NH$_2$; | (SEQ ID NO: 78) |
| (Ser(n-octanoyl)$^{20}$)hGhrelin(1-28)-NH$_2$; | (SEQ ID NO: 79) |
| (Glu(NH-hexyl)$^{20}$)hGhrelin(1-28)-NH$_2$; | (SEQ ID NO: 80) |
| (Glu(NH-hexyl)$^{3,20}$)hGhrelin(1-28)-NH$_2$; | (SEQ ID NO: 81) |
| (Glu(NH-hexyl)$^{3}$,Ser(n-octanoyl)$^{20}$)hGhrelin(1-28)-NH$_2$; | (SEQ ID NO: 82) |
| (Aib$^{2}$,Glu(NH-hexyl)$^{20}$)hGhrelin(1-28)-NH$_2$; | (SEQ ID NO: 83) |
| (Aib$^{2}$,Glu(NH-hexyl)$^{3,20}$)hGhrelin(1-28)-NH$_2$; | (SEQ ID NO: 84) |
| (Aib$^{2,8}$,Glu(NH-hexyl)$^{20}$)hGhrelin(1-28)-NH$_2$; | (SEQ ID NO: 85) |
| (Aib$^{2,8}$,Glu(NH-hexyl)$^{3,20}$)hGhrelin(1-28)-NH$_2$; | (SEQ ID NO: 86) |
| (Aib$^{2,10}$,Glu(NH-hexyl)$^{20}$)hGhrelin(1-28)-NH$_2$; | (SEQ ID NO: 87) |
| (Aib$^{2,10}$,Glu(NH-hexyl)$^{3,20}$)hGhrelin(1-28)-NH$_2$; | (SEQ ID NO: 88) |
| (Ac-Gly$^{1}$,Glu(NH-hexyl)$^{17}$)hGhrelin(1-28)-NH$_2$; | (SEQ ID NO: 89) |
| (Ac-Gly$^{1}$,Ser(n-octanoyl)$^{17}$)hGhrelin(1-28)-NH$_2$; | (SEQ ID NO: 90) |
| (Ac-Gly$^{1}$,Glu(NH-hexyl)$^{3,17}$)hGhrelin(1-28)-NH$_2$; | (SEQ ID NO: 91) |
| (Ac-Gly$^{1}$,Glu(NH-hexyl)$^{3}$,Ser(n-octanoyl)$^{17}$)hGhrelin(1-28)-NH$_2$; | (SEQ ID NO: 92) |
| (Ac-Gly$^{1}$,Dap(octanesulfonyl)$^{17}$)hGhrelin(1-28)-NH$_2$; | (SEQ ID NO: 93) |
| (Ac-Gly$^{1}$,Dap(octanesulfonyl)$^{3,17}$)hGhrelin(1-28)-NH$_2$; | (SEQ ID NO: 94) |
| (Ac-Gly$^{1}$,Dap(octanesulfonyl)$^{3}$,Glu(NH-hexyl)$^{17}$)hGhrelin(1-28)-NH$_2$; | (SEQ ID NO: 95) |
| (Ac-Gly$^{1}$,Dap(octanesulfonyl)$^{3}$,Ser(n-octanoyl)$^{17}$)hGhrelin(1-28)-NH$_2$; | (SEQ ID NO: 96) |
| (Ac-Gly$^{1}$,Glu(NH-hexyl)$^{3}$,Dap(octanesulfonyl)$^{17}$)hGhrelin(1-28)-NH$_2$; | (SEQ ID NO: 97) |
| (Ac-Gly$^{1}$,Cys(S-(CH$_2$)$_9$CH$_3$)$^{17}$)hGhrelin(1-28)-NH$_2$; | (SEQ ID NO: 98) |
| (Ac-Gly$^{1}$,Cys(S-(CH$_2$)$_9$CH$_3$)$^{17}$)hGhrelin(1-28)-NH$_2$; | (SEQ ID NO: 99) |
| (Ac-Gly$^{1}$,Glu(NH-hexyl)$^{3}$,Cys(S-(CH$_2$)$_9$CH$_3$)$^{17}$)hGhrelin(1-28)-NH$_2$; | (SEQ ID NO: 100) |
| (Ac-Gly$^{1}$,Cys(S-(CH$_2$)$_9$CH$_3$)$^{3}$,Glu(NH-hexyl)$^{17}$)hGhrelin(1-28)-NH$_2$; | (SEQ ID NO: 101) |
| (Ac-Gly1,Cys(S-(CH$_2$)$_9$CH$_3$)$^{3}$,Ser(n-octanoyl)$^{17}$)hGhrelin(1-28)-NH$_2$; | (SEQ ID NO: 102) |
| (Ac-Gly$^{1}$,Aib$^{2}$,Glu(NH-hexyl)$^{17}$)hGhrelin(1-28)-NH$_2$; | (SEQ ID NO: 103) |
| (Ac-Gly$^{1}$,Aib$^{2}$,Glu(NH-hexyl)$^{3,17}$)hGhrelin(1-28)-NH$_2$; | (SEQ ID NO: 104) |
| (Ac-Gly$^{1}$,Aib$^{2}$,Thz$^{7}$,Glu(NH-hexyl)$^{17}$)hGhrelin(1-28)-NH$_2$; | (SEQ ID NO: 105) |

(Ac-Gly$^1$,Aib$^2$,4-Hyp$^7$,Glu(NH-hexyl)$^{17}$)hGhrelin(1-28)-NH$_2$;            (SEQ ID NO: 105)

(Ac-Gly$^1$,Aib$^2$,Dhp$^7$,Glu(NH-hexyl)$^{17}$)hGhrelin(1-28)-NH$_2$;              (SEQ ID NO: 105)

(Ac-Gly$^1$,Aib$^2$,Pip$^7$,Glu(NH-hexyl)$^{17}$)hGhrelin(1-28)-NH$_2$;              (SEQ ID NO: 105)

(Ac-Gly$^1$,Aib$^2$,Tic$^7$,Glu(NH-hexyl)$^{3,17}$)hGhrelin(1-28)-NH$_2$;            (SEQ ID NO: 105)

(Ac-Gly$^1$,Aib$^2$,Glu(NH-hexyl)$^{3,17}$,Thz$^7$)hGhrelin(1-28)-NH$_2$;            (SEQ ID NO: 106)

(Ac-Gly$^1$,Aib$^2$,Glu(NH-hexyl)$^{3,17}$,4-Hyp$^7$,)hGhrelin(1-28)-NH$_2$;         (SEQ ID NO: 106)

(Ac-Gly$^1$,Aib$^2$,Glu(NH-hexyl)$^{3,17}$,Dhp$^7$hGhrelin(1-28)-NH$_2$;             (SEQ ID NO: 106)

(Ac-Gly$^1$,Aib$^2$,Glu(NH-hexyl)$^{3,17}$,Pip$^7$)hGhrelin(1-28)-NH$_2$;            (SEQ ID NO: 106)

(Ac-Gly$^1$,Aib$^2$,Glu(NH-hexyl)$^{3,17}$,Tic$^7$)hGhrelin(1-28)-NH$_2$;            (SEQ ID NO: 106)

(Ac-Gly$^1$,Aib$^{2,8}$,Glu(NH-hexyl)$^{17}$)hGhrelin(1-28)-NH$_2$;                  (SEQ ID NO: 107)

(Ac-Gly$^1$,Aib$^{2,8}$,Glu(NH-hexyl)$^{3,17}$)hGhrelin(1-28)-NH$_2$;                (SEQ ID NO: 108)

(Ac-Gly$^1$,Aib$^2$,3-Pal$^9$,Glu(NH-hexyl)$^{17}$)hGhrelin(1-28)-NH$_2$;            (SEQ ID NO: 109)

(Ac-Gly$^1$,Aib$^2$,4-Pal$^9$,Glu(NH-hexyl)$^{17}$)hGhrelin(1-28)-NH$_2$;            (SEQ ID NO: 109)

(Ac-Gly$^1$,Aib$^2$,Taz$^9$,Glu(NH-hexyl)$^{17}$)hrelin(1-28)-NH$_2$;                (SEQ ID NO: 109)

(Ac-Gly$^1$,Aib$^2$,2-Thi$^9$,Glu(NH-hexyl)$^{17}$)hGhrelin(1-28)-NH$_2$;            (SEQ ID NO: 109)

(Ac-Gly$^1$,Aib$^2$,Glu(NH-hexyl)$^{3,17}$,3-Pal$^9$)hGhrelin(1-28)-NH$_2$;          (SEQ ID NO: 110)

(Ac-Gly$^1$,Aib$^2$,Glu(NH-hexyl)$^{3,17}$,4-Pal$^9$)hGhrelin(1-28)-NH$_2$;          (SEQ ID NO: 110)

(Ac-Gly$^1$,Aib$^2$,Glu(NH-hexyl)$^{3,17}$,Taz$^9$)hGhrelin(1-28)-NH$_2$;            (SEQ ID NO: 110)

(Ac-Gly$^1$,Aib$^2$,Glu(NH-hexyl)$^{3,17}$,2-Thi$^9$)hGhrelin(1-28)-NH$_2$;          (SEQ ID NO: 110)

(Ac-Gly$^1$,Aib$^{2,10}$,Glu(NH-hexyl)$^{17}$)hGhrelin(1-28)-NH$_2$;                 (SEQ ID NO: 111)

(Ac-Gly$^1$,Aib$^{2,10}$,Glu(NH-hexyl)$^{3,17}$)hGhrelin(1-28)-NH$_2$;               (SEQ ID NO: 112)

(Ac-Gly$^1$,Aib$^8$,Glu(NH-hexyl)$^{17}$)hGhrelin(1-28)-NH$_2$;                      (SEQ ID NO: 113)

(Ac-Gly$^1$,Taz$^9$,Glu(NH-hexyl)$^{17}$)hGhrelin(1-28)-NH$_2$;                      (SEQ ID NO: 114)

(Ac-Gly$^1$,3-Pal$^9$,Glu(NH-hexyl)$^{17}$)hGhrelin(1-28)-NH$_2$;                    (SEQ ID NO: 114)

(Ac-Gly$^1$,4-Pal$^9$,Glu(NH-hexyl)$^{17}$)hGhrelin(1-28)-NH$_2$;                    (SEQ ID NO: 114)

(Ac-Gly$^1$,2-Thi$^9$,Glu(NH-hexyl)$^{17}$)hGhrelin(1-28)-NH$_2$;                    (SEQ ID NO: 114)

(Ac-Gly$^1$,Glu(NH-hexyl)$^{3,17}$,Aib$^8$)hGhrelin(1-28)-NH$_2$;                    (SEQ ID NO: 115)

(Ac-Gly$^1$,Glu(NH-hexyl)$^{3,17}$,Taz$^9$)hGhrelin(1-28)-NH$_2$;                    (SEQ ID NO: 116)

(Ac-Gly$^1$,Glu(NH-hexyl)$^{3,17}$,3-Pal$^9$)hGhrelin(1-28)-NH$_2$;                  (SEQ ID NO: 116)

(Ac-Gly$^1$,Glu(NH-hexyl)$^{3,17}$,4-Pal$^9$)hGhrelin(1-28)-NH$_2$;                  (SEQ ID NO: 116)

(Ac-Gly$^1$,Glu(NH-hexyl)$^{3,17}$,2-Thi$^9$)hGhrelin(1-28)-NH$_2$;                  (SEQ ID NO: 116)

(Ac-Aib$^1$,Aib$^{2,10}$,Glu(NH-hexyl)$^{17}$)hGhrelin(1-28)-NH$_2$;                 (SEQ ID NO: 117)

(Ac-Aib$^1$,Aib$^{2,10}$,Glu(NH-hexyl)$^{3,17}$)hGhrelin(1-28)-NH$_2$;               (SEQ ID NO: 118)

(Ac-Gly$^1$,A5c$^2$,Glu(NH-hexyl$^{17}$)Ghrelin(1-28)-NH$_2$;                        (SEQ ID NO: 119)

(Ac-Gly$^1$,A5c$^2$,Glu(NH-hexyl)$^{3,17}$)hGhrelin(1-28)-NH$_2$;                    (SEQ ID NO: 120)

(Ac-Gly$^1$,Glu(1-heptanol)$^{3,17}$)hGhrelin(1-28)-NH$_2$;                          (SEQ ID NO: 121)

(Ac-Gly$^1$,Asp(1-heptanol)$^{3,17}$)hGhrelin(1-28)-NH$_2$;                          (SEQ ID NO: 122)

(Ac-Gly$^1$,Glu(NH-hexyl)$^{3,17}$)hGhrelin(1-28)-NH$_2$;                            (SEQ ID NO: 123)

(Ac-Gly$^1$,Asp(NH-hexyl)$^{3,17}$)hGhrelin(1-28)-NH$_2$;                            (SEQ ID NO: 124)

(Ac-Gly$^1$,Aib$^2$,Glu(NH-hexyl)$^{3,17}$)hGhrelin(1-28)-NH$_2$;                    (SEQ ID NO: 125)

-continued (Ac-Gly$^1$,Aib$^{2,10}$,Glu(NH-hexyl)$^3$,Lys(biotinyl)$^{17}$)hGhrelin(1-28)-NH$_2$;   (SEQ ID NO: 126)

(Ac-Gly$^1$,Glu(NH-hexyl)$^{15}$)hGhrelin(1-28)-NH$_2$;   (SEQ ID NO: 127)

(Ac-Gly$^1$,Ser(n-octanoyl)$^{15}$)hGhrelin(1-28)-NH$_2$;   (SEQ ID NO: 128)

(Ac-Gly$^1$,Glu(NH-hexyl)$^{3,15}$)hGhrelin(1-28)-NH$_2$;   (SEQ ID NO: 129)

(Ac-Gly$^1$,Glu(NH-hexyl)$^3$,Ser(n-octanoyl)$^{15}$)hGhrelin(1-28)-NH$_2$;   (SEQ ID NO: 130)

(Ac-Gly$^1$,Aib$^2$,Glu(NH-hexyl)$^{15}$)hGhrelin(1-28)-NH$_2$;   (SEQ ID NO: 131)

(Ac-Gly$^1$,Aib$^2$,Glu(NH-hexyl)$^{3,15}$)hGhrelin(1-28)-NH$_2$;   (SEQ ID NO: 132)

(Ac-Gly$^1$,Aib$^{2,8}$,Glu(NH-hexyl)$^{15}$)hGhrelin(1-28)-NH$_2$;   (SEQ ID NO: 133)

(Ac-Gly$^1$,Aib$^{2,8}$,Glu(NH-hexyl)$^{3,15}$)hGhrelin(1-28)-NH$_2$;   (SEQ ID NO: 134)

(Ac-Gly$^1$,Aib$^{2,10}$,Glu(NH-hexyl)$^{15}$)hGhrelin(1-28)-NH$_2$;   (SEQ ID NO: 135)

(Ac-Gly$^1$,Aib$^{2,10}$,Glu(NH-hexyl)$^{3,15}$)hGhrelin(1-28)-NH$_2$;   (SEQ ID NO: 136)

(Ac-Gly$^1$,Glu(NH-hexyl)$^{16}$)hGhrelin(1-28)-NH$_2$;   (SEQ ID NO: 137)

(Ac-Gly$^1$,Ser(n-octanoyl)$^{16}$)hGhrelin(1-28)-NH$_2$;   (SEQ ID NO: 138)

(Ac-Gly$^1$,Glu(NH-hexyl)$^{3,16}$)hGhrelin(1-28)-NH$_2$;   (SEQ ID NO: 139)

(Ac-Gly$^1$,Glu(NH-hexyl)$^3$,Ser(n-octanoyl)$^{16}$)hGhrelin(1-28)-NH$_2$;   (SEQ ID NO: 140)

(Ac-Gly$^1$,Aib$^2$,Glu(NH-hexyl)$^{16}$)hGhrelin(1-28)-NH$_2$;   (SEQ ID NO: 141)

(Ac-Gly$^1$,Aib$^2$,Glu(NH-hexyl)$^{3,16}$)hGhrelin(1-28)-NH$_2$;   (SEQ ID NO: 142)

(Ac-Gly$^1$,Aib$^{2,8}$,Glu(NH-hexyl)$^{16}$)hGhrelin(1-28)-NH$_2$;   (SEQ ID NO: 143)

(Ac-Gly$^1$,Aib$^{2,8}$,Glu(NH-hexyl)$^{3,16}$)hGhrelin(1-28)-NH$_2$;   (SEQ ID NO: 144)

(Ac-Gly$^1$,Aib$^{2,10}$,Glu(NH-hexyl)$^{16}$)hGhrelin(1-28)-NH$_2$;   (SEQ ID NO: 145)

(Ac-Gly$^1$,Aib$^{2,10}$,Glu(NH-hexyl)$^{3,16}$)hGhrelin(1-28)-NH$_2$;   (SEQ ID NO: 146)

(Ac-Gly$^1$,Glu(NH-hexyl)$^{18}$)hGhrelin(1-28)-NH$_2$;   (SEQ ID NO: 147)

(Ac-Gly$^1$,Ser(n-octanoyl)$^{18}$)hGhrelin(1-28)-NH$_2$;   (SEQ ID NO: 148)

(Ac-Gly$^1$,Glu(NH-hexyl)$^{3,18}$)hGhrelin(1-28)-NH$_2$;   (SEQ ID NO: 149)

(Ac-Gly$^1$,Glu(NH-hexyl)$^3$,Ser(n-octanoyl)$^{18}$)hGhrelin(1-28)-NH$_2$;   (SEQ ID NO: 150)

(Ac-Gly$^1$,Aib$^2$,Glu(NH-hexyl)$^{18}$)hGhrelin(1-28)-NH$_2$;   (SEQ ID NO: 151)

(Ac-Gly$^1$,Aib$^2$,Glu(NH-hexyl)$^{3,18}$)hGhrelin(1-28)-NH$_2$;   (SEQ ID NO: 152)

(Ac-Gly$^1$,Aib$^{2,8}$,Glu(NH-hexyl)$^{18}$)hGhrelin(1-28)-NH$_2$;   (SEQ ID NO: 153)

(Ac-Gly$^1$,Aib$^{2,8}$,Glu(NH-hexyl)$^{3,18}$)hGhrelin(1-28)-NH$_2$;   (SEQ ID NO: 154)

(Ac-Gly$^1$,Aib$^{2,10}$,Glu(NH-hexyl)$^{18}$)hGhrelin(1-28)-NH$_2$;   (SEQ ID NO: 155)

(Ac-Gly$^1$,Aib$^{2,10}$,Glu(NH-hexyl)$^{3,18}$)hGhrelin(1-28)-NH$_2$;   (SEQ ID NO: 156)

(Ac-Gly$^1$,Glu(NH-hexyl)$^{19}$)hGhrelin(1-28)-NH$_2$;   (SEQ ID NO: 157)

(Ac-Gly$^1$,Ser(n-octanoyl)$^{19}$)hGhrelin(1-28)-NH$_2$;   (SEQ ID NO: 158)

(Ac-Gly$^1$,Glu(NH-hexyl)$^{3,19}$)hGhrelin(1-28)-NH$_2$;   (SEQ ID NO: 159)

(Ac-Gly$^1$,Glu(NH-hexyl)$^3$,Ser(n-octanoyl)$^{19}$)hGhrelin(1-28)-NH$_2$;   (SEQ ID NO: 160)

(Ac-Gly$^1$,Aib$^2$,Glu(NH-hexyl)$^{19}$)hGhrelin(1-28)-NH$_2$;   (SEQ ID NO: 161)

(Ac-Gly$^1$,Aib$^2$,Glu(NH-hexyl)$^{3,19}$)hGhrelin(1-28)-NH$_2$;   (SEQ ID NO: 162)

(Ac-Gly$^1$,Aib$^{2,8}$,Glu(NH-hexyl)$^{19}$)hGhrelin(1-28)-NH$_2$;   (SEQ ID NO: 163)

(Ac-Gly$^1$,Aib$^{2,8}$,Glu(NH-hexyl)$^{3,19}$)hGhrelin(1-28)-NH$_2$;   (SEQ ID NO: 164)

(Ac-Gly$^1$,Aib$^{2,10}$,Glu(NH-hexyl)$^{19}$)hGhrelin(1-28)-NH$_2$;   (SEQ ID NO: 165)

(Ac-Gly$^1$,Aib$^{2,10}$,Glu(NH-hexyl)$^{3,19}$)hGhrelin(1-28)-NH$_2$;   (SEQ ID NO: 166)

-continued (Ac-Gly[1],Glu(NH-hexyl)[20])hGhrelin(1-28)-NH$_2$;  (SEQ ID NO: 167)

(Ac-Gly[1],Ser(n-octanoyl)[20])hGhrelin(1-28)-NH$_2$;  (SEQ ID NO: 168)

(Ac-Gly[1],Glu(NH-hexyl)[3,20])hGhrelin(1-28)-NH$_2$;  (SEQ ID NO: 169)

(Ac-Gly[1],Glu(NH-hexyl)[3],Ser(n-octanoyl)[20])hGhrelin(1-28)-NH$_2$;  (SEQ ID NO: 170)

(Ac-Gly[1],Aib[2],Glu(NH-hexyl)[20])hGhrelin(1-28)-NH$_2$;  (SEQ ID NO: 171)

(Ac-Gly[1],Aib[2],Glu(NH-hexyl)[3,20])hGhrelin(1-28)-NH$_2$;  (SEQ ID NO: 172)

(Ac-Gly[1],Aib[2,8],Glu(NH-hexyl)[20])hGhrelin(1-28)-NH$_2$;  (SEQ ID NO: 173)

(Ac-Gly[1],Aib[2,8],Glu(NH-hexyl)[3,20])hGhrelin(1-28)-NH$_2$;  (SEQ ID NO: 174)

(Ac-Gly[1],Aib[2,10],Glu(NH-hexyl)[20])hGhrelin(1-28)-NH$_2$; and  (SEQ ID NO: 175)

(Ac-Gly[1],Aib[2,10],Glu(NH-hexyl)[3,20])hGhrelin(1-28)-NH$_2$;  (SEQ ID NO: 176)

or pharmaceutically acceptable salts thereof.

A yet more preferred group of compounds according to formula (I), termed Group 5 compounds, includes compounds according to the formula:

(Ser(n-octanoyl)[17])hGhrelin(1-28)-NH$_2$;  (SEQ ID NO: 21)

(Glu(NH-hexyl)[17])hGhrelin(1-28)-NH$_2$;  (SEQ ID NO: 22)

(Glu(NH-hexyl)[3,17])hGhrelin(1-28)-NH$_2$;  (SEQ ID NO: 23)

(Glu(NH-hexyl)[3],Ser(n-octanoyl)[17])hGhrelin(1-28)-NH$_2$;  (SEQ ID NO: 24)

(Dap(octanesulfonyl)[17])hGhrelin(1-28)-NH$_2$;  (SEQ ID NO: 25)

(Dap(octanesulfonyl)[3,17])hGhrelin(1-28)-NH$_2$;  (SEQ ID NO: 26)

(Dap(octanesulfonyl)[3],Glu(NH-hexyl)[17])hGhrelin(1-28)-NH$_2$;  (SEQ ID NO: 27)

(Dap(octanesulfonyl)[3],Ser(n-octanoyl)[17])hGhrelin(1-28)-NH$_2$;  (SEQ ID NO: 28)

(Glu(NH-hexyl)[3],Dap(octanesulfonyl)[17])hGhrelin(1-28)-NH$_2$;  (SEQ ID NO: 29)

(Cys(S-(CH$_2$)$_9$CH$_3$)[17])hGhrelin(1-28)-NH$_2$;  (SEQ ID NO: 30)

(Cys(S-(CH$_2$)$_9$CH$_3$)[3,17])hGhrelin(1-28)-NH$_2$;  (SEQ ID NO: 31)

(Glu(NH-hexyl)[3],Cys(S-(CH$_2$)$_9$CH$_3$)[17])hGhreliri(1-28)-NH$_2$;  (SEQ ID NO: 32)

(Cys(S-(CH$_2$)$_9$CH$_3$)[3],Glu(NH-hexyl)[17])hGhrelin(1-28)-NH$_2$;  (SEQ ID NO: 33)

(Cys(S-(CH$_2$)$_9$CH$_3$)[3],Ser(n-octanoyl)[17])hGhrelin(1-28)-NH$_2$;  (SEQ ID NO: 34)

(Aib[2],Glu(NH-hexyl)[17])hGhrelin(1-28)-NH$_2$;  (SEQ ID NO: 35)

(Aib[2],Glu(NH-hexyl)[3,17])hGhrelin(1-28)-NH$_2$;  (SEQ ID NO: 36)

(Aib[2],Thz[7],Glu(NH-hexyl)[17])hGhrelin(1-28)-NH$_2$;  (SEQ ID NO: 37)

(Aib[2],4-Hyp[7],Glu(NH-hexyl)[17])hGhrelin(1-28)-NH$_2$;  (SEQ ID NO: 37)

(Aib[2],Dhp[7],Glu(NH-hexyl)[17])hGhrelin(1-28)-NH$_2$;  (SEQ ID NO: 37)

(Aib[2],Pip[7],Glu(NH-hexyl)[17])hGhrelin(1-28)-NH$_2$;  (SEQ ID NO: 37)

(Aib[2],Tic[7],Glu(NH-hexyl)[17])hGhrelin(1-28)-NH$_2$;  (SEQ ID NO: 37)

(Aib[2],Glu(NH-hexyl)[3,17],Thz[7])hGhrelin(1-28)-NH$_2$;  (SEQ ID NO: 38)

(Aib[2],Glu(NH-hexyl)[3,17],4-Hyp[7],)hGhrelin(1-28)-NH$_2$;  (SEQ ID NO: 38)

(Aib[2],Glu(NH-hexyl)[3,17],Dhp[7])hGhrelin(1-28)-NH$_2$;  (SEQ ID NO: 38)

(Aib[2],Glu(NH-hexyl)[3,17],Pip[7])hGhrelin(1-28)-NH$_2$;  (SEQ ID NO: 38)

(Aib[2],Glu(NH-hexyl)[3,17],Tic[7])hGhrelin(1-28)-NH$_2$;  (SEQ ID NO: 38)

(Aib$^{2,8}$,Glu(NH-hexyl)$^{17}$)hGhrelin(1-28)-NH$_2$;   (SEQ ID NO: 39)

(Aib$^{2,8}$,Glu(NH-hexyl)$^{3,17}$)hGhrelin(1-28)-NH$_2$;   (SEQ ID NO: 40)

(Aib$^2$,3-Pal$^9$,Glu(NH-hexyl)$^{17}$)hGhrelin(1-28)-NH$_2$;   (SEQ ID NO: 41)

(Aib$^2$,4-Pal$^9$,Glu(NH-hexyl)$^{17}$)hGhrelin(1-28)-NH$_2$;   (SEQ ID NO: 41)

(Aib$^2$,Taz$^9$,Glu(NH-hexyl)$^{17}$)hGhrelin(1-28)-NH$_2$;   (SEQ ID NO: 41)

(Aib$^2$,2-Thi$^9$,Glu(NH-hexyl)$^{17}$)hGhrelin(1-28)-NH$_2$;   (SEQ ID NO: 41)

(Aib$^2$,Glu(NH-hexyl)$^{3,17}$,3-Pal$^9$)hGhrelin(1-28)-NH$_2$;   (SEQ ID NO: 42)

(Aib$^2$,Glu(NH-hexyl)$^{3,17}$,4-Pal$^9$)hGhrelin(1-28)-NH$_2$;   (SEQ ID NO: 42)

(Aib$^2$,Glu(NH-hexyl)$^{3,17}$,Taz$^9$)hGhrelin(1-28)-NH$_2$;   (SEQ ID NO: 42)

(Aib$^2$,Glu(NH-hexyl)$^{3,17}$,2-Thi$^9$)hGhrelin(1-28)-NH$_2$;   (SEQ ID NO: 42)

(Aib$^{2,10}$,Glu(NH-hexyl)$^{17}$)hGhrelin(1-28)-NH$_2$;   (SEQ ID NO: 43)

(Aib$^{2,10}$,Glu(NH-hexyl)$^{3,17}$)hGhrelin(1-28)-NH$_2$;   (SEQ ID NO: 44)

(Aib$^8$,Glu(NH-hexyl)$^{17}$)hGhrelin(1-28)-NH$_2$;   (SEQ ID NO: 45)

(Taz$^9$,Glu(NH-hexyl)$^{17}$)hGhrelin(1-28)-NH$_2$;   (SEQ ID NO: 46)

(3-Pal$^9$,Glu(NH-hexyl)$^{17}$)hGhrelin(1-28)-NH$_2$;   (SEQ ID NO: 46)

(4-Pal$^9$,Glu(NH-hexyl)$^{17}$)hGhrelin(1-28)-NH$_2$;   (SEQ ID NO: 46)

(2-Thi$^9$,Glu(NH-hexyl)$^{17}$)hGhrelin(1-28)-NH$_2$;   (SEQ ID NO: 46)

(Glu(NH-hexyl)$^{3,17}$,Aib$^8$)hGhrelin(1-28)-NH$_2$;   (SEQ ID NO: 47)

(Glu(NH-hexyl)$^{3,17}$,Taz$^9$)hGhrelin(1-28)-NH$_2$;   (SEQ ID NO: 48)

(Glu(NH-hexyl)$^{3,17}$,3-Pal$^9$)hGhrelin(1-28)-NH$_2$;   (SEQ ID NO: 48)

(Glu(NH-hexyl)$^{3,17}$,4-Pal$^9$)hGhrelin(1-28)-NH$_2$;   (SEQ ID NO: 48)

(Glu(NH-hexyl)$^{3,17}$,2-Thi$^9$)hGhrelin(1-28)-NH$_2$;   (SEQ ID NO: 48)

(Aib$^{1,2,10}$,Glu(NH-hexyl)$^{17}$)hGhrelin(1-28)-NH$_2$;   (SEQ ID NO: 49)

(Aib$^{1,2,10}$,Glu(NH-hexyl)$^{3,17}$)hGhrelin(1-28)-NH$_2$;   (SEQ ID NO: 50)

(A5c$^2$,Glu(NH-hexyl)$^{17}$)hGhrelin(1-28)-NH$_2$;   (SEQ ID NO: 51)

(A5c$^2$,Glu(NH-hexyl)$^{3,17}$)hGhrelin(1-28)-NH$_2$;   (SEQ ID NO: 52)

(Glu(1-heptanol)$^{3,17}$)hGhrelin(1-28)-NH$_2$;   (SEQ ID NO: 53)

(Asp(1-heptanol)$^{3,17}$)hGhrelin(1-28)-NH$_2$;   (SEQ ID NO: 54)

(Glu(NH-hexyl)$^{3,17}$)hGhrelin(1-28)-NH$_2$;   (SEQ ID NO: 55)

(Asp(NH-hexyl)$^{3,17}$)hGhrelin(1-28)-NH$_2$;   (SEQ ID NO: 56)

(Aib$^2$,Glu(NH-hexyl)$^{3,17}$)hGhrelin(1-28)-NH$_2$;   (SEQ ID NO: 57)

(Lys(biotinyl)$^{17}$)hGhrelin(1-28)-NH$_2$;   (SEQ ID NO: 58)

(Ac-Gly$^1$,Glu(NH-hexyl)$^{17}$)hGhrelin(1-28)-NH$_2$;   (SEQ ID NO: 89)

(Ac-Gly$^1$,Ser(n-octanoyl)$^{17}$)hGhrelin(1-28)-NH$_2$;   (SEQ ID NO: 90)

(Ac-Gly$^1$,Glu(NH-hexyl)$^{3,17}$)hGhrelin(1-28)-NH$_2$;   (SEQ ID NO: 91)

(Ac-Gly$^1$,Glu(NH-hexyl)$^3$,Ser(n-octanoyl)$^{17}$)hGhrelin(1-28)-NH$_2$;   (SEQ ID NO: 92)

(Ac-Gly$^1$,Dap(octanesulfonyl)$^{17}$)hGhrelin(1-28)-NH$_2$;   (SEQ ID NO: 93)

(Ac-Gly$^1$,Dap(octanesulfonyl)$^{3,17}$)hGhrelin(1-28)-NH$_2$;   (SEQ ID NO: 94)

(Ac-Gly$^1$,Dap(octanesulfonyl)$^3$,Glu(NH-hexyl)$^{17}$)hGhrelin(1-28)-NH$_2$;   (SEQ ID NO: 95)

(Ac-Gly$^1$,Dap(octanesulfonyl)$^3$,Ser(n-octanoyl)$^{17}$)hGhrelin(1-28)-NH$_2$;   (SEQ ID NO: 96)

-continued (Ac-Gly$^1$,Glu(NH-hexyl)$^3$,Dap(octanesulfonyl)$^{17}$)hGhrelin(1-28)-NH$_2$;  (SEQ ID NO: 97)

(Ac-Gly$^1$,Cys(S-(CH$_2$)$_9$CH$_3$)$^{17}$)hGhrelin(1-28)-NH$_2$;  (SEQ ID NO: 98)

(Ac-Gly$^1$,Cys(S-(CH$_2$)$_9$CH$_3$)$^{3,17}$)hGhrelin(1-28)-NH$_2$;  (SEQ ID NO: 99)

(Ac-Gly$^1$,Glu(NH-hexyl)$^3$,Cys(S-(CH$_2$)$_9$CH$_3$)$^{17}$)hGhrelin(1-28)-NH$_2$;  (SEQ ID NO: 100)

(Ac-Gly$^1$,Cys(S-(CH$_2$)$_9$CH$_3$)$^3$,Glu(NH-hexyl)$^{17}$)hGhrelin(1-28)-NH$_2$;  (SEQ ID NO: 101)

(Ac-Gly$^1$,Cys(S-(CH$_2$)$_9$CH$_3$)$^3$,Ser(n-octanoyl)$^{17}$)hGhrelin(1-28)-NH$_2$;  (SEQ ID NO: 102)

(Ac-Gly$^1$,Aib$^2$,Glu(NH-hexyl)$^{17}$)hGhrelin(1-28)-NH$_2$;  (SEQ ID NO: 103)

(Ac-Gly$^1$,Aib$^2$,Glu(NH-hexyl)$^{3,17}$)hGhrelin(1-28)-NH$_2$;  (SEQ ID NO: 104)

(Ac-Gly$^1$,Aib$^2$,Thz$^7$,Glu(NH-hexyl)$^{17}$)hGhrelin(1-28)-NH$_2$;  (SEQ ID NO: 105)

(Ac-Gly$^1$,Aib$^2$,4-Hyp$^7$,Glu(NH-hexyl)$^{17}$)hGhrelin(1-28)-NH$_2$;  (SEQ ID NO: 105)

(Ac-Gly$^1$,Aib$^2$,Dhp$^7$,Glu(NH-hexyl)$^{17}$)hGhrelin(1-28)-NH$_2$;  (SEQ ID NO: 105)

(Ac-Gly$^1$,Aib$^2$,Pip$^7$,Glu(NH-hexyl)$^{17}$)hGhrelin(1-28)-NH$_2$;  (SEQ ID NO: 105)

(Ac-Gly$^1$,Aib$^2$,Tic$^7$,Glu(NH-hexyl)$^{17}$)hGhrelin(1-28)-NH$_2$;  (SEQ ID NO: 105)

(Ac-Gly$^1$,Aib$^2$,Glu(NH-hexyl)$^{3,17}$,Thz$^7$)hGhrelin(1-28)-NH$_2$;  (SEQ ID NO: 106)

(Ac-Gly$^1$,Aib$^2$,Glu(NH-hexyl)$^{3,17}$,4-Hyp$^7$,)hGhrelin(1-28)-NH$_2$;  (SEQ ID NO: 106)

(Ac-Gly$^1$,Aib$^2$,Glu(NH-hexyl)$^{3,17}$,Dhp$^7$)hGhrelin(1-28)-NH$_2$;  (SEQ ID NO: 106)

(Ac-Gly$^1$,Aib$^2$,Glu(NH-hexyl)$^{3,17}$,Pip$^7$)hGhrelin(1-28)-NH$_2$;  (SEQ ID NO: 106)

(Ac-Gly$^1$,Aib$^2$,Glu(NH-hexyl)$^{3,17}$,Tic$^7$)hGhrelin(1-28)-NH$_2$;  (SEQ ID NO: 106)

(Ac-Gly$^1$,Aib$^{2,8}$,Glu(NH-hexyl)$^{17}$)hGhrelin(1-28)-NH$_2$;  (SEQ ID NO: 107)

(Ac-Gly$^1$,Aib$^{2,8}$,Glu(NH-hexyl)$^{3,17}$)hGhrelin(1-28)-NH$_2$;  (SEQ ID NO: 108)

(Ac-Gly$^1$,Aib$^2$,3-Pal$^9$,Glu(NH-hexyl)$^{17}$)hGhrelin(1-28)-NH$_2$;  (SEQ ID NO: 109)

(Ac-Gly$^1$,Aib$^2$,4-Pal$^9$,Glu(NH-hexyl)$^{17}$)hGhrelin(1-28)-NH$_2$;  (SEQ ID NO: 109)

(Ac-Gly$^1$,Aib$^2$,Taz$^9$,Glu(NH-hexyl)$^{17}$)hGhrelin(1-28)-NH$_2$;  (SEQ ID NO: 109)

(Ac-Gly$^1$,Aib$^2$,2-Thi$^9$,Glu(NH-hexyl)$^{17}$)hGhrelin(1-28)-NH$_2$;  (SEQ ID NO: 109)

(Ac-Gly$^1$,Aib$^2$,Glu(NH-hexyl)$^{3,17}$,3-Pal$^9$)hGhrelin(1-28)-NH$_2$;  (SEQ ID NO: 110)

(Ac-Gly$^1$,Aib$^2$,Glu(NH-hexyl)$^{3,17}$,4-Pal$^9$)hGhrelin(1-28)-NH$_2$;  (SEQ ID NO: 110)

(Ac-Gly$^1$,Aib$^2$,Glu(NH-hexyl)$^{3,17}$,Taz$^9$)hGhrelin(1-28)-NH$_2$;  (SEQ ID NO: 110)

(Ac-Gly$^1$,Aib$^2$,Glu(NH-hexyl)$^{3,17}$,2-Thi$^9$)hGhrelin(1-28)-NH$_2$;  (SEQ ID NO: 110)

(Ac-Gly$^1$,Aib$^{2,10}$,Glu(NH-hexyl)$^{17}$)hGhrelin(1-28)-NH$_2$;  (SEQ ID NO: 111)

(Ac-Gly$^1$,Aib$^{2,10}$,Glu(NH-hexyl)$^{3,17}$)hGhrelin(1-28)-NH$_2$;  (SEQ ID NO: 112)

(Ac-Gly$^1$,Aib$^8$,Glu(NH-hexyl)$^{17}$)hGhrelin(1-28)-NH$_2$;  (SEQ ID NO: 113)

(Ac-Gly$^1$,Taz$^9$,Glu(NH-hexyl)$^{17}$)hGhrelin(1-28)-NH$_2$;  (SEQ ID NO: 114)

(Ac-Gly$^1$,3-Pal$^9$,Glu(NH-hexyl)$^{17}$)hGhrelin(1-28)-NH$_2$;  (SEQ ID NO: 114)

(Ac-Gly$^1$,4-Pal$^9$,Glu(NH-hexyl)$^{17}$)hGhrelin(1-28)-NH$_2$;  (SEQ ID NO: 114)

(Ac-Gly$^1$,2-Thi$^9$,Glu(NH-hexyl)$^{17}$)hGhrelin(1-28)-NH$_2$;  (SEQ ID NO: 114)

(Ac-Gly$^1$,Glu(NH-hexyl)$^{3,17}$,Aib$^8$)hGhrelin(1-28)-NH$_2$;  (SEQ ID NO: 115)

(Ac-Gly$^1$,Glu(NH-hexyl)$^{3,17}$,Taz$^9$)hGhrelin(1-28)-NH$_2$;  (SEQ ID NO: 116)

(Ac-Gly$^1$,Glu(NH-hexyl)$^{3,17}$,3-Pal$^9$)hGhrelin(1-28)-NH$_2$;  (SEQ ID NO: 116)

(Ac-Gly$^1$,Glu(NH-hexyl)$^{3,17}$,4-Pal$^9$)hGhrelin(1-28)-NH$_2$;  (SEQ ID NO: 116)

(Ac-Gly$^1$,Glu(NH-hexyl)$^{3,17}$,2-Thi$^9$)hGhrelin(1-28)-NH$_2$;  (SEQ ID NO: 116)

(Ac-Aib$^1$,Aib$^{2,10}$,Glu(NH-hexyl)$^{17}$)hGhrelin(1-28)-NH$_2$;  (SEQ ID NO: 117)

| | |
|---|---|
| (Ac-Aib$^1$,Aib$^{2,10}$,Glu(NH-hexyl)$^{3,17}$)hGhrelin(1-28)-NH$_2$; | (SEQ ID NO: 118) |
| (Ac-Gly$^1$,A5c$^2$,Glu(NH-hexyl)$^{17}$)hGhrelin(1-28)-NH$_2$; | (SEQ ID NO: 119) |
| (Ac-Gly$^1$,A5c$^2$,Glu(NH-hexyl)$^{3,17}$)hGhrelin(1-28)-NH$_2$; | (SEQ ID NO: 120) |
| (Ac-Gly$^1$,Glu(1-heptanol)$^{3,17}$)hGhrelin(1-28)-NH$_2$; | (SEQ ID NO: 121) |
| (Ac-Gly$^1$,Asp(1-heptanol)$^{3,17}$)hGhrelin(1-28)-NH$_2$; | (SEQ ID NO: 122) |
| (Ac-Gly$^1$,Glu(NH-hexyl)$^{3,17}$)hGhrelin(1-28)-NH$_2$; | (SEQ ID NO: 123) |
| (Ac-Gly$^1$,Asp(NH-hexyl)$^{3,17}$)hGhrelin(1-28)-NH$_2$; | (SEQ ID NO: 124) |
| (Ac-Gly$^1$,Aib$^2$,Glu(NH-hexyl)$^{3,17}$)hGhrelin(1-28)-NH$_2$; and | (SEQ ID NO: 125) |
| (Ac-Gly$^1$,Aib$^{2,10}$,Glu(NH-hexyl)$^3$,Lys(biotinyl)$^{17}$)hGhrelin(1-28)-NH$_2$; | (SEQ ID NO: 126) | or pharmaceutically acceptable salts thereof.

A still more preferred group of compounds according to formula (I), termed Group 6 compounds, includes compounds according to the formula:

| | |
|---|---|
| (Ser(n-octanoyl)$^{17}$)hGhrelin(1-28)-NH$_2$; | (SEQ ID NO: 21) |
| (Glu(NH-hexyl)$^{17}$)hGhrelin(1-28)-NH$_2$; | (SEQ ID NO: 22) |
| (Glu(NH-hexyl)$^{3,17}$)hGhrelin(1-28)-NH$_2$; | (SEQ ID NO: 23) |
| (Glu(NH-hexyl)$^3$,Ser(n-octanoyl)$^{17}$)hGhrelin(1-28)-NH$_2$; | (SEQ ID NO: 24) |
| (Aib$^2$,Glu(NH-hexyl)$^{17}$)hGhrelin(1-28)-NH$_2$; | (SEQ ID NO: 35) |
| (Aib$^2$,Glu(NH-hexyl)$^{3,17}$)hGhrelin(1-28)-NH$_2$; | (SEQ ID NO: 36) |
| (Aib$^{2,8}$,Glu(NH-hexyl)$^{17}$)hGhrelin(1-28)-NH$_2$; | (SEQ ID NO: 39) |
| (Aib$^{2,8}$,Glu(NH-hexyl)$^{3,17}$)hGhrelin(1-28)-NH$_2$; | (SEQ ID NO: 40) |
| (Aib$^{2,10}$,Glu(NH-hexyl)$^{17}$)hGhrelin(1-28)-NH$_2$; | (SEQ ID NO: 43) |
| (Aib$^{2,10}$,Glu(NH-hexyl)$^{3,17}$)hGhrelin(1-28)-NH$_2$; | (SEQ ID NO: 44) |
| (Aib$^{1,2,10}$,Glu(NH-hexyl)$^{17}$)hGhrelin(1-28)-NH$_2$; | (SEQ ID NO: 49) |
| (Aib$^{1,2,10}$,Glu(NH-hexyl)$^{3,17}$)hGhrelin(1-28)-NH$_2$; | (SEQ ID NO: 50) |
| (A5c$^2$,Glu(NH-hexyl)$^{17}$)hGhrelin(1-28)-NH$_2$; | (SEQ ID NO: 51) |
| (A5c$^2$,Glu(NH-hexyl)$^{3,17}$)hGhrelin(1-28)-NH$_2$; | (SEQ ID NO: 52) |
| (Glu(1-heptanol)$^{3,17}$)hGhrelin(1-28)-NH$_2$; | (SEQ ID NO: 53) |
| (Asp(1-heptanol)$^{3,17}$)hGhrelin(1-28)-NH$_2$; | (SEQ ID NO: 54) |
| (Glu(NH-hexyl)$^{3,17}$)hGhrelin(1-28)-NH$_2$; | (SEQ ID NO: 55) |
| (Asp(NH-hexyl)$^{3,17}$)hGhrelin(1-28)-NH$_2$; | (SEQ ID NO: 56) |
| (Aib$^2$,Glu(NH-hexyl)$^{3,17}$)hGhrelin(1-28)-NH$_2$; | (SEQ ID NO: 57) |
| (Lys(biotinyl)$^{17}$)hGhrelin(1-28)-NH$_2$; | (SEQ ID NO: 58) |
| (Ac-Gly$^1$,Glu(NH-hexyl)$^{17}$)hGhrelin(1-28)-NH$_2$; | (SEQ ID NO: 89) |
| (Ac-Gly$^1$,Ser(n-octanoyl)$^{17}$)hGhrelin(1-28)-NH$_2$; | (SEQ ID NO: 90) |
| (Ac-Gly$^1$,Glu(NH-hexyl)$^{3,17}$)hGhrelin(1-28)-NH$_2$; | (SEQ ID NO: 91) |
| (Ac-Gly$^1$,Glu(NH-hexyl)$^3$,Ser(n-octanoyl)$^{17}$)hGhrelin(1-28)-NH$_2$; | (SEQ ID NO: 92) |
| (Ac-Gly$^1$,Aib$^2$,Glu(NH-hexyl)$^{17}$)hGhrelin(1-28)-NH$_2$; | (SEQ ID NO: 103) |
| (Ac-Gly$^1$,Aib$^2$,Glu(NH-hexyl)$^{3,17}$)hGhrelin(1-28)-NH$_2$; | (SEQ ID NO: 104) |
| (Ac-Gly$^1$,Aib$^{2,8}$,Glu(NH-hexyl)$^{17}$)hGhrelin(1-28)-NH$_2$; | (SEQ ID NO: 107) |

(Ac-Gly$^1$,Aib$^{2,8}$,Glu(NH-hexyl)$^{3,17}$)hGhrelin(1-28)-NH$_2$;    (SEQ ID NO: 108)

(Ac-Gly$^1$,Aib$^{2,10}$,Glu(NH-hexyl)$^{17}$)hGhrelin(1-28)-NH$_2$;    (SEQ ID NO: 111)

(Ac-Gly$^1$,Aib$^{2,10}$,Glu(NH-hexyl)$^{3,17}$)hGhrelin(1-28)-NH$_2$;    (SEQ ID NO: 112)

(Ac-Aib$^1$,Aib$^{2,10}$,Glu(NH-hexyl)$^{17}$)hGhrelin(1-28)-NH$_2$;    (SEQ ID NO: 117)

(Ac-Aib$^1$,Aib$^{2,10}$,Glu(NH-hexyl)$^{3,17}$)hGhrelin(1-28)-NH$_2$;    (SEQ ID NO: 118)

(Ac-Gly$^1$,A5c$^2$,Glu(NH-hexyl)$^{17}$)hGhrelin(1-28)-NH$_2$;    (SEQ ID NO: 119)

(Ac-Gly$^1$,A5c$^2$,Glu(NH-hexyl)$^{3,17}$)hGhrelin(1-28)-NH$_2$;    (SEQ ID NO: 120)

(Ac-Gly$^1$,Glu(1-heptanol)$^{3,17}$)hGhrelin(1-28)-NH$_2$;    (SEQ ID NO: 121)

(Ac-Gly$^1$,Asp(1-heptanol)$^{3,17}$)hGhrelin(1-28)-NH$_2$;    (SEQ ID NO: 122)

(Ac-Gly$^1$,Glu(NH-hexyl)$^{3,17}$)hGhrelin(1-28)-NH$_2$;    (SEQ ID NO: 123)

(Ac-Gly$^1$,Asp(NH-hexyl)$^{3,17}$)hGhrelin(1-28)-NH$_2$;    (SEQ ID NO: 124)

(Ac-Gly$^1$,Aib$^2$,Glu(NH-hexyl)$^{3,17}$)hGhrelin(1-28)-NH$_2$;    (SEQ ID NO: 125)
and (Ac-Gly$^1$,Aib$^{2,10}$,Glu(NH-hexyl)$^3$,Lys(biotinyl)$^{17}$)hGhrelin(1-28)-NH$_2$;    (SEQ ID NO: 126)

or pharmaceutically acceptable salts thereof.

A still more preferred group of compounds according to formula (I), termed Group 7 compounds, includes compounds according to the formula:

(Ser(n-octanoyl)$^{17}$)hGhrelin(1-28)-NH$_2$;    (SEQ ID NO: 21)

(Glu(NH-hexyl)$^{17}$)hGhrelin(1-28)-NH$_2$;    (SEQ ID NO: 22)

(Glu(NH-hexyl)$^{3,17}$)hGhrelin(1-28)-NH$_2$;    (SEQ ID NO: 23)

(Glu(NH-hexyl)$^3$,Ser(n-octanoyl)$^{17}$)hGhrelin(1-28)-NH$_2$;    (SEQ ID NO: 24)

(Aib$^2$,Glu(NH-hexyl)$^{17}$)hGhrelin(1-28)-NH$_2$;    (SEQ ID NO: 35)

(Aib$^2$,Glu(NH-hexyl)$^{3,17}$)hGhrelin(1-28)-NH$_2$;    (SEQ ID NO: 36)

(Aib$^{2,8}$,Glu(NH-hexyl)$^{17}$)hGhrelin(1-28)-NH$_2$;    (SEQ ID NO: 39)

(Aib$^{2,8}$,Glu(NH-hexyl)$^{3,17}$)hGhrelin(1-28)-NH$_2$;    (SEQ ID NO: 40)

(Aib$^{2,10}$,Glu(NH-hexyl)$^{17}$)hGhrelin(1-28)-NH$_2$;    (SEQ ID NO: 43)

(Aib$^{2,10}$,Glu(NH-hexyl)$^{3,17}$)hGhrelin(1-28)-NH$_2$;    (SEQ ID NO: 44)

(Aib$^{1,2,10}$,Glu(NH-hexyl)$^{3,17}$)hGhrelin(1-28)-NH$_2$;    (SEQ ID NO: 50)

(A5c$^2$,Glu(NH-hexyl)$^{17}$)hGhrelin(1-28)-NH$_2$;    (SEQ ID NO: 51)

(A5c$^2$,Glu(NH-hexyl)$^{3,17}$)hGhrelin(1-28)-NH$_2$;    (SEQ ID NO: 52)

(Aib$^2$,Glu(NH-hexyl)$^{3,17}$)hGhrelin(1-28)-NH$_2$;    (SEQ ID NO: 36)

(Lys(biotinyl)$^{17}$)hGhrelin(1-28)-NH$_2$;    (SEQ ID NO: 58)

(Ac-Gly$^1$,Glu(NH-hexyl)$^{17}$)hGhrelin(1-28)-NH$_2$;    (SEQ ID NO: 89)

(Ac-Gly$^1$,Ser(n-octanoyl)$^{17}$)hGhrelin(1-28)-NH$_2$;    (SEQ ID NO: 90)

(Ac-Gly$^1$,Glu(NH-hexyl)$^{3,17}$)hGhrelin(1-28)-NH$_2$;    (SEQ ID NO: 91)

(Ac-Gly$^1$,Glu(NH-hexyl)$^3$,Ser(n-octanoyl)$^{17}$)hGhrelin(1-28)-NH$_2$;    (SEQ ID NO: 92)

(Ac-Gly$^1$,Aib$^2$,Glu(NH-hexyl)$^{17}$)hGhrelin(1-28)-NH$_2$;    (SEQ ID NO: 103)

(Ac-Gly$^1$,Aib$^2$,Glu(NH-hexyl)$^{3,17}$)hGhrelin(1-28)-NH$_2$;    (SEQ ID NO: 104)

(Ac-Gly$^1$,Aib$^{2,8}$,Glu(NH-hexyl)$^{17}$)hGhrelin(1-28)-NH$_2$;    (SEQ ID NO: 107)

(Ac-Gly$^1$,Aib$^{2,8}$,Glu(NH-hexyl)$^{3,17}$)hGhrelin(1-28)-NH$_2$;    (SEQ ID NO: 108)

(Ac-Gly$^1$,Aib$^{2,10}$,Glu(NH-hexyl)$^{17}$)hGhrelin(1-28)-NH$_2$;        (SEQ ID NO: 111)

(Ac-Gly$^1$,Aib$^{2,10}$,Glu(NH-hexyl)$^{3,17}$)hGhrelin(1-28)-NH$_2$;      (SEQ ID NO: 112)

(Ac-Aib$^1$,Aib$^{2,10}$,Glu(NH-hexyl)$^{17}$)hGhrelin(1-28)-NH$_2$;        (SEQ ID NO: 117)

(Ac-Aib$^1$,Aib$^{2,10}$,Glu(NH-hexyl)$^{3,17}$)hGhrelin(1-28)-NH$_2$;      (SEQ ID NO: 118)

(Ac-Gly$^1$,A5c$^2$,Glu(NH-hexyl)$^{17}$)hGhrelin(1-28)-NH$_2$;             (SEQ ID NO: 119)

(Ac-Gly$^1$,A5c$^2$,Glu(NH-hexyl)$^{3,17}$)hGhrelin(1-28)-NH$_2$;           (SEQ ID NO: 120)

(Ac-Gly$^1$,Aib$^2$,Glu(NH-hexyl)$^{3,17}$)hGhrelin(1-28)-NH$_2$;           (SEQ ID NO: 125)
or (Ac-Gly$^1$,Aib$^{2,10}$,Glu(NH-hexyl)$^3$,Lys(biotinyl)$^{17}$)hGhrelin(1-28)-NH$_2$;   (SEQ ID NO: 126)

or a pharmaceutically acceptable salt thereof.

A preferred group of compounds according to formula (I), termed Group 8 compounds, includes compounds according to the formula:
A$^1$ is Ac-Gly, Ac-Aib or Aib;
A$^2$ is Aib;
A$^3$ is Glu(NH-hexyl);
A$^8$ is Aib;
A$^{10}$ is Aib; and
A$^{17}$ is Glu(NH-hexyl) or Lys(biotinyl);
or pharmaceutically acceptable salts thereof.

A more preferred group of immediately preceding compounds according to formula (I), termed Group 9 compounds, includes compounds wherein R$^2$ and R$^3$ is, independently for each occurrence thereof, selected from the group consisting of H, acyl, n-butyryl, isobutyryl and n-octanoyl and R$^1$ is NH$_2$;
or pharmaceutically acceptable salts thereof.

An even more preferred group of immediately preceding compounds according to formula (I), termed Group 10 compounds, includes compounds according to the formula:

(Aib$^{2,8}$,Glu(NH-hexyl)$^{3,17}$)hGhrelin(1-28)-NH$_2$;                  (SEQ ID NO: 40)

(Aib$^{1,2,10}$,Glu(NH-hexyl)$^{3,17}$)hGhrelin(1-28)-NH$_2$;               (SEQ ID NO: 50)

(Lys(biotinyl)$^{17}$)hGhrelin(1-28)-NH$_2$;                                 (SEQ ID NO: 58)

(Ac-Gly$^1$,Aib$^2$,Glu(NH-hexyl)$^{3,17}$)hGhrelin(1-28)-NH$_2$;           (SEQ ID NO: 104)

(Ac-Gly$^1$,Aib$^{2,8}$,Glu(NH-hexyl)$^{3,17}$)hGhrelin(1-28)-NH$_2$;       (SEQ ID NO: 108)

(Ac-Gly$^1$,Aib$^{2,10}$,Glu(NH-hexyl)$^{3,17}$)hGhrelin(1-28)-NH$_2$;      (SEQ ID NO: 112)

(Ac-Aib$^1$,Aib$^{2,10}$,Glu(NH-hexyl)$^{3,17}$)hGhrelin(1-28)-NH$_2$;      (SEQ ID NO: 118)
and (Ac-Gly$^1$,Aib$^{2,10}$,Glu(NH-hexyl)$^3$,Lys(biotinyl)$^{17}$)hGhrelin(1-28)-NH$_2$;   (SEQ ID NO: 126)

or pharmaceutically acceptable salts thereof.

And even more preferred to the immediately foregoing group of compounds according to formula (I), termed Group 11 compounds, includes compounds according to the formula:

(Aib$^{2,8}$,Glu(NH-hexyl)$^{3,17}$)hGhrelin(1-28)-NH$_2$;                  (SEQ ID NO: 40)

(Aib$^{1,2,10}$,Glu(NH-hexyl)$^{3,17}$)hGhrelin(1-28)-NH$_2$;               (SEQ ID NO: 50)

(Lys(biotinyl)$^{17}$)hGhrelin(1-28)-NH$_2$;                                 (SEQ ID NO: 58)
and (Ac-Aib$^1$,Aib$^{2,10}$,Glu(NH-hexyl)$^{3,17}$)hGhrelin(1-28)-NH$_2$;      (SEQ ID NO: 118)

or pharmaceutically acceptable salts thereof.

And even more preferred to the immediately foregoing group of compounds according to formula (I), termed a Group 12 compound, includes a compound of the formula:

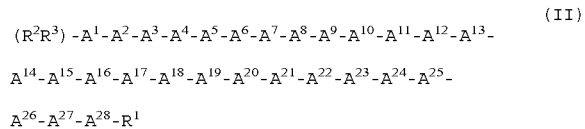
(SEQ ID NO: 58)
(Lys(biotinyl)$^{17}$)hGhrelin(1-28)-NH$_2$;

or a pharmaceutically acceptable salt thereof.

A second aspect of the present invention describes a ghrelin analog according to formula (II):

$$(R^2R^3)-A^1-A^2-A^3-A^4-A^5-A^6-A^7-A^8-A^9-A^{10}-A^{11}-A^{12}-A^{13}- \quad (II)$$
$$A^{14}-A^{15}-A^{16}-A^{17}-A^{18}-A^{19}-A^{20}-A^{21}-A^{22}-A^{23}-A^{24}-A^{25}-$$
$$A^{26}-A^{27}-A^{28}-R^1$$

wherein:

$A^1$ is Gly, Acc, Aib, Ala, β-Ala or Gly(myristyl);

$A^2$ is Ser, Abu, Acc, Act, Aib, Ala, Ava, Thr or Val;

$A^3$ is Ser, Asp(NH—$R^9$), Asp(O—$R^8$), Cys(S—$R^{14}$), Dab (S(O)$_2$—$R^{11}$), Dap(S(O)$_2$—$R^{10}$), Glu(NH—$R^7$), Glu(O—$R^6$), Ser(C(O)—$R^4$), Thr(C(O)—$R^5$) or HN—CH((CH$_2$)$_n$—N($R^{12}R^{13}$))—C(O);

$A^4$ is Phe, Acc, Aic, Cha, 2-Fua, 1-Nal, 2-Nal, 2-Pal, 3-Pal, 4-Pal, hPhe, ($X^1,X^2,X^3,X^4,X^5$)Phe, Taz, 2-Thi, 3-Thi, Trp or Tyr;

$A^5$ is Leu, Abu, Acc, Aib, Ala, Cha, Ile, hLeu, Nle, Nva, Phe, Tle or Val;

$A^6$ is Ser, Abu, Acc, Act, Aib, Ala, Gly, Thr or Val;

$A^7$ is Pro, Dhp, Dmt, 3-Hyp, 4-Hyp, Inc, Ktp, Oic, Pip, Thz or Tic;

$A^8$ is Glu, Acc, Aib, Arg, Asn, Asp, Dab, Dap, Gln, Lys, Orn or HN—CH((CH$_2$)$_n$—N($R^{12}R^{13}$))—C(O);

$A^9$ is His, Acc, Aib, Apc, 2-Fua, 2-Pal, 3-Pal, 4-Pal, ($X^1$, $X^2,X^3,X^4,X^5$—)Phe, Taz, 2-Thi or 3-Thi;

$A^{10}$ is Gln, Acc, Aib, Asn, Asp or Glu;

$A^{11}$ is Arg, Apc, hArg, Dab, Dap, Lys, Orn or HN—CH((CH$_2$)$_n$—N($R^{12}R^{13}$))—C(O);

$A^{12}$ is Val, Abu, Acc, Aib, Ala, Cha, Nva, Gly, Ile, Leu, Nle or Tle;

$A^{13}$ is Gln, Acc, Aib, Asn, Asp or Glu;

$A^{14}$ is Gln, Acc, Aib, Asn, Asp or Glu;

$A^{15}$ is Arg, Acc, Aib, Apc, hArg, Dab, Dap, Lys, Orn, Asp(NH—$R^9$), Asp(O—$R^8$), Cys(S—$R^{14}$), Cys($R^{15}$), hCys (S—$R^{16}$), hCys($R^{17}$), Dab(S(O)$_2$—$R^7$), Dap(S(O)$_2$—$R^{10}$), Glu(NH—$R^7$), Glu(O—$R^6$), Ser(C(O)—$R^4$), Thr(C(O)—$R^5$) or HN—CH((CH$_2$)$_n$—N($R^{12}R^{13}$))—C(O);

$A^{16}$ is Lys, Acc, Aib, Apc, Arg, hArg, Dab, Dap, Orn, Asp(NH—$R^9$), Asp(O—$R^8$), Cys(S—$R^{14}$), Cys($R^{15}$), hCys (S—$R^{16}$), hCys($R^{17}$), Dab(S(O)$_2$—$R^{11}$), Dap(S(O)$_2$—$R^{10}$), Glu(NH—$R^7$), Glu(O—$R^6$), Ser(C(O)—$R^4$), Thr(C(O)—$R^5$), HN—CH((CH$_2$)$_n$—N($R^{12}R^{13}$))—C(O) or deleted;

$A^{17}$ is Glu, Arg, Asn, Asp, Dab, Dap, Gln, Lys, Orn, Asp (NH—$R^9$), Asp(O—$R^8$), Cys(S—$R^{14}$), Cys($R^{15}$), hCys(S—$R^{16}$), hCys($R^{17}$), Dab(S(O)$_2$—$R^{11}$), Dap(S(O)$_2$—$R^{10}$), Glu (NH—$R^7$), Glu(O—$R^6$), Lys(biotinyl), Lys(myristyl), Ser(C (O)—$R^4$), Thr(C(O)—$R^5$), HN—CH((CH$_2$)$_n$—N ($R^{12}R^{13}$))—C(O) or deleted;

$A^{18}$ is Ser, Abu, Acc, Act, Aib, Ala, Thr, Val, Asp(NH—$R^9$), Asp(O—$R^8$), Cys(S—$R^{14}$), Cys($R^{15}$), hCys(S—$R^{16}$), hCys ($R^{17}$), Dab(S(O)$_2$—$R^{11}$), Dap(S(O)$_2$—$R^{10}$), Glu(NH—$R^7$), Glu(O—$R^6$), Ser(C(O)—$R^4$), Thr(C(O)—$R^5$), HN—CH ((CH$_2$)$_n$—N($R^{12}R^{13}$))—C(O) or deleted;

$A^{19}$ is Lys, Acc, Aib, Apc, Arg, hArg, Dab, Dap, Orn, Asp(NH—$R^9$), Asp(O—$R^8$), Cys(S—$R^{14}$), Cys($R^{15}$), hCys (S—$R^{16}$), hCys($R^{17}$), Dab(S(O)$_2$—$R^{11}$), Dap(S(O)$_2$—$R^{10}$), Glu(NH—$R^7$), Glu(O—$R^6$), Ser(C(O)—$R^4$), Thr(C(O)—$R^5$), HN—CH((CH$_2$)$_n$—N($R^{12}R^{13}$))—C(O) or deleted;

$A^{20}$ is Lys, Acc, Aib, Apc, Arg, hArg, Dab, Dap, Orn, Asp(NH—$R^9$), Asp(O—$R^8$), Cys(S—$R^{14}$), Cys($R^{15}$), hCys (S—$R^{16}$), hCys($R^{17}$), Dab(S(O)$_2$—$R^{11}$), Dap(S(O)$_2$—$R^{10}$), Glu(NH—$R^7$), Glu(O—$R^6$), Ser(C(O)—$R^4$), Thr(C(O)—$R^5$), HN—CH((CH$_2$)$_n$—N($R^{12}R^{13}$))—C(O) or deleted;

$A^{21}$ is Pro, Dhp, Dmt, 3-Hyp, 4-Hyp, Inc, Ktp, Oic, Pip, Thz, Tic or deleted;

$A^{22}$ is Pro, Dhp, Dmt, 3-Hyp, 4-Hyp, Inc, Ktp, Oic, Pip, Thz, Tic or deleted;

$A^{23}$ is Abu, Acc, Act, Aib, Ala, Apc, Gly, Nva, Val or deleted;

$A^{24}$ is Lys, Acc, Aib, Apc, Arg, hArg, Dab, Dap, Orn, HN—CH((CH$_2$)$_n$—N($R^{12}R^{13}$))—C(O) or deleted;

$A^{25}$ is Leu, Abu, Acc, Aib, Ala, Cha, Ile, hLeu, Nle, Nva, Phe, Tle, Val or deleted;

$A^{26}$ is Gln, Aib, Asn, Asp, Glu or deleted;

$A^{27}$ is Pro, Dhp, Dmt, 3-Hyp, 4-Hyp, Inc, Ktp, Oic, Pip, Thz, Tic or deleted;

$A^{25}$ is Acc, Aib, Apc, Arg, hArg, Dab, Dap, Lys, Orn, HN—CH((CH$_2$)$_n$—N($R^{12}R^{13}$))—C(O) or deleted;

$R^1$ is —OH, —NH$_2$, —(C$_1$-C$_{30}$)alkoxy or NH—$X^6$—CH$_2$—$Z^0$, wherein $X^6$ is a (C$_1$-C$_{12}$)alkyl or (C$_2$-C$_{12}$)alkenyl and $Z^0$ is —H, —OH, —CO$_2$H or —C(O)—NH$_2$;

each of $R^2$ and $R^3$ is, independently for each occurrence thereof, selected from the group consisting of H, (C$_1$-C$_{30}$) alkyl, (C$_1$-C$_{30}$)heteroalkyl, (C$_1$-C$_{30}$)acyl, (C$_2$-C$_{30}$)alkenyl, (C$_2$-C$_{30}$)alkynyl, aryl(C$_1$-C$_{30}$)alkyl, aryl(C$_1$-C$_{30}$)acyl, substituted (C$_1$-C$_{30}$)alkyl, substituted (C$_1$-C$_{30}$)heteroalkyl, substituted (C$_2$-C$_{30}$)acyl, substituted (C$_2$-C$_{30}$)alkenyl, substituted aryl(C$_1$-C$_{30}$)alkyl, substituted (C$_2$-C$_{30}$)alkynyl and substituted aryl(C$_1$-C$_{30}$)acyl or may be deleted;

each of $R^4$, $R^5$, $R^6$, $R^7$, $R^8$, $R^9$, $R^{10}$, $R^{11}$, $R^{14}$, $R^{15}$, $R^{16}$ and $R^{17}$ is, independently for each occurrence thereof, selected from the group consisting of (C$_1$-C$_{40}$)alkyl, (C$_2$-C$_{40}$)alkenyl, substituted (C$_1$-C$_{40}$)alkyl, substituted (C$_2$-C$_{40}$)alkenyl, alkylaryl, substituted alkylaryl, aryl and substituted aryl;

each of $R^{12}$ and $R^{13}$ is, independently for each occurrence, selected from the group consisting of H, (C$_1$-C$_{40}$)alkyl, (C$_1$-C$_{40}$)heteroalkyl, (C$_1$-C$_{40}$)acyl, (C$_2$-C$_{40}$)alkenyl, (C$_2$-C$_{40}$) alkynyl, aryl(C$_1$-C$_{40}$)alkyl, aryl(C$_1$-C$_{40}$)acyl, substituted (C$_1$-C$_{40}$)alkyl, substituted (C$_1$-C$_{40}$)heteroalkyl, substituted (C$_1$-C$_{40}$)acyl, substituted (C$_2$-C$_{40}$)alkenyl, substituted (C$_2$-C$_{40}$)alkynyl, substituted aryl(C$_1$-C$_{40}$)alkyl, substituted aryl (C$_1$-C$_{40}$)acyl, (C$_1$-C$_{40}$)alkylsulfonyl, —C(NH)—NH$_2$ and biotinyl;

n is, independently for each occurrence thereof, 1, 2, 3, 4 or 5;

each of $X^1$, $X^2$, $X^3$, $X^4$, and $X^1$ is, independently for each occurrence thereof, selected from the group consisting of H, F, Cl, Br, I, (C$_{1-10}$)alkyl, substituted (C$_{1-10}$)alkyl, aryl, substituted aryl, OH, NH$_2$, NO$_2$ and CN;

provided that:

(I) when $R^2$ is (C$_1$-C$_{30}$)acyl, aryl(C$_1$-C$_{30}$)acyl, substituted (C$_2$-C$_{30}$)acyl, or substituted aryl(C$_1$-C$_{30}$)acyl, then $R^3$ is H, (C$_1$-C$_{30}$)alkyl, (C$_1$-C$_{30}$)heteroalkyl, (C$_2$-C$_{30}$)alkenyl, aryl (C$_1$-C$_{30}$)alkyl, substituted (C$_1$-C$_{30}$)alkyl, substituted (C$_1$-C$_{30}$)heteroalkyl, substituted (C$_2$-C$_{30}$)alkenyl, substituted (C$_2$-C$_{30}$)alkynyl or substituted aryl(C$_1$-C$_{30}$)alkyl;

(II) when $R^{12}$ is (C$_1$-C$_{40}$)acyl, aryl(C$_1$-C$_{40}$)acyl, substituted (C$_2$-C$_{40}$)acyl, or substituted aryl(C$_1$-C$_{40}$)acyl, (C$_1$-C$_{40}$) alkylsulfonyl, or —C(NH)—NH$_2$, then $R^{13}$ is H or (C$_1$-C$_{40}$) alkyl, (C$_1$-C$_{40}$)heteroalkyl, (C$_2$-C$_{40}$)alkenyl, (C$_2$-C$_{40}$)

alkynyl, aryl($C_1$-$C_{40}$)alkyl, substituted ($C_1$-$C_{40}$)alkyl, substituted ($C_1$-$C_{40}$)heteroalkyl, substituted ($C_2$-$C_{40}$)alkenyl, substituted ($C_2$-$C_{40}$)alkynyl, or substituted aryl($C_1$-$C_{40}$)alkyl;

(III) at least one of $A^{15}$, $A^{16}$, $A^{17}$, $A^{18}$, $A^{19}$ or $A^{20}$ of said ghrelin analog is selected from the group consisting of Asp(NH—$R^9$), Asp(O—$R^8$), Cys(S—$R^{14}$), Cys($R^{15}$), hCys(S—$R^{16}$), hCys($R^{17}$), Dab(S(O)$_2$—$R^{11}$), Dap(S(O)$_2$—$R^{10}$), Glu(NH—$R^7$), Glu(O—$R^6$), Ser(C(O)—$R^4$), Thr(C(O)—$R^5$) or HN—CH(($CH_2$)$_n$—N($R^{12}R^{13}$))—C(O); and (IV) when any of the group consisting of $A^{15}$, $A^{16}$, $A^{17}$, $A^{19}$ and $A^{20}$ is HN—CH(($CH_2$)$_n$—N($R^{12}R^{13}$))—C(O), then $R^{12}$ must be biotinyl;
or a pharmaceutically acceptable salt thereof.

A preferred group of compounds of formula (II), termed Group 13 compounds, is where:
$A^1$ is Gly or Gly(myristyl;
$A^2$ is Ser or Aib; and
$A^{17}$ is Ser(n-octanoyl) or Lys(myristyl);
or a pharmaceutically acceptable salt thereof.

Yet another preferred group of compounds of formula (II), termed Group 14 compounds, is where:
$A^{17}$ is Lys(myristyl).

A more preferred group of compounds of the preceding group of compounds, termed Group 15 compounds, is where:
$R^2$ selected from the group consisting of H, acyl, n-butyryl, isobutyryl, n-octanoyl and myristyl;
$R^3$ is deleted;
$R^4$ is heptyl;
$R^6$ is hexyl;
$R^7$ is hexyl;
$R^{10}$ is octyl; and
$R^{11}$ is heptyl;
provided that when Acc is substituted for any one of the naturally-occurring residues of the sequence, it is, independently for each occurrence, selected from the group consisting of A3c, A4c, A5c and A6c;
or pharmaceutically acceptable salts thereof.

An even more preferred group of compounds according to formula (II), termed Group 16 compounds, includes compounds according to the formula:
(Aib$^2$, Lys(myristyl)$^{17}$)hGhrelin(1-28)-NH$_2$; (SEQ ID NO:177) and
(Gly(myristyl)$^1$, Aib$^2$, Lys(myristyl)$^{17}$)hGhrelin(1-28)-NH$_2$; (SEQ ID NO:178)
or pharmaceutically acceptable salts thereof.

In another aspect, the present invention provides a pharmaceutical composition comprising an effective amount of a compound of formulae (I) or (II), more preferably a compound according to one or more of Group 1, Group 2, Group 3, Group 4, Group 5, Group 6, Group 7, Group 8, Group 9, Group 10, Group 11, Group 12, Group 13, Group 14, Group 15 and/or Group 16 as defined hereinabove, or a pharmaceutically acceptable salt thereof and a pharmaceutically acceptable carrier or diluent.

Ghrelin analogs described herein are active at the GHS receptor. The analogs can bind to the receptor and stimulate or inhibit the receptor activity. Ghrelin analogs have a variety of different uses including, but not limited to, being employed as a research tool or as a therapeutic agent.

Research tool applications generally involve the use of a ghrelin analog and the presence of a GHS receptor or fragment thereof. The GHS receptor can be present in different environments such as a mammalian subject, a whole cell or a membrane fragment. Examples of research tool applications include, but are not limited to, screening for compounds active at the GHS receptor, determining the presence of the GHS receptor in a sample or preparation and examining the role or effect of ghrelin.

Ghrelin analogs can be used to screen for both ghrelin agonists and ghrelin antagonists. Screening for ghrelin agonists can be performed, for example, by using a ghrelin analog in a competition experiment with test compounds. Screening for ghrelin antagonists can be performed, for example, by using a ghrelin analog to produce GHS receptor activity and then measuring the ability of a compound to alter GHS receptor activity.

Another aspect of the present invention features a method of screening for a compound able to bind to a GHS receptor. The method comprises the step of measuring the ability of a compound to affect binding of a ghrelin analog to the receptor, a fragment of the receptor comprising a ghrelin binding site, a polypeptide comprising the fragment or a derivative of the polypeptide. Compounds useful for screening include compounds encompassed by formulae (I) or (II), more preferably a compound according to one or more of Group 1, Group 2, Group 3, Group 4, Group 5, Group 6, Group 7, Group 8, Group 9, Group 10, Group 11, Group 12, Group 13, Group 14, Group 15 and/or Group 16, as defined hereinabove, or a pharmaceutically acceptable salt thereof and a pharmaceutically acceptable carrier or diluent.

Another aspect of the present invention features a method for achieving a beneficial effect in a subject comprising administering to said subject an effective amount of one or more of a compound according to formulae (I) or (II), more preferably a compound according to one or more of Group 1, Group 2, Group 3, Group 4, Group 5, Group 6, Group 7, Group 8, Group 9, Group 10, Group 11, Group 12, Group 13, Group 14, Group 15 and/or Group 16, or pharmaceutically acceptable salts thereof, wherein said effective amount is effective for producing a beneficial effect in helping to treat (e.g., cure or reduce the severity) or to prevent (e.g., reduce the likelihood of onset or severity) a disease or disorder.

Ghrelin induces GH release from primary-culture pituitary cells in a dose-dependent manner without stimulating the release of the other pituitary hormones. Injected intravenously into anaesthetized rats, ghrelin stimulated the pulsatile release of GH (Kojima, M. et al., *Nature*, (1999), 402(6762): 656-60), thus another aspect of the present invention features a method for stimulating GH secretion in a subject in need thereof, comprising administering an effective amount of one or more of a compound according to formulae (I) or (II), more preferably a compound according to one or more of Group 1, Group 2, Group 3, Group 4, Group 5, Group 6, Group 7, Group 8, Group 9, Group 10, Group 11, Group 12, Group 13, Group 14, Group 15 and/or Group 16, or pharmaceutically acceptable salts thereof, wherein said effective amount is at least an amount sufficient to produce a detectable increase in GH secretion and, preferably, is an amount sufficient to achieve a beneficial effect in a patient.

A preferred method of the immediately preceding method is wherein said stimulation of GH secretion is indicated for treating a GH deficient state, increasing muscle mass and/or bone density, overcoming sexual dysfunction, gaining body weight and/or maintaining an ideal body weight, maintaining and/or regaining physical functioning and/or increasing appetite.

A preferred method of the immediately preceding method is where said weight gain or maintenance thereof or appetite increase is indicated in a patient having a disease or disorder or under going a treatment accompanied by weight loss.

A preferred method of the immediately preceding method is where said disease accompanied by weight loss is associated with the onset of cachexia which include, but are not limited to, anorexia, bulimia, cancer, AIDS and chronic obstructive pulmonary disease (COPD). Another aspect of the immediately preceding method is wherein said weight loss is due to the onset of wasting syndrome, particularly in the frail or elderly. A further preferred method of the preceding method is to facilitate weight gain after an unexplained weight loss in an otherwise healthy elderly patient or to prevent, treat or alleviate the onset of Alzheimer's disease. In yet another preferred method of said immediately preceding method is where said treatments accompanied by weight loss include chemotherapy, radiation therapy, temporary immobilization, permanent immobilization and dialysis.

Another preferred method of the immediately preceding method is where said weight gain or maintenance thereof and/or appetite increase is indicated in an otherwise healthy patient not suffering from a particular disease or disorder or undergoing one of the aforementioned treatments.

Ghrelin analogs described herein may also antagonize the effects of ghrelin in vitro and in vivo, thus another aspect of the present invention features a method for suppressing GH secretion in a subject in need thereof by administering an effective amount of one or more of a compound according to formulae (I) or (II), more preferably a compound according to one or more of Group 1, Group 2, Group 3, Group 4, Group 5, Group 6, Group 7, Group 8, Group 9, Group 10, Group 11, Group 12, Group 13, Group 14, Group 15 and/or Group 16, or pharmaceutically acceptable salts thereof, wherein said effective amount is at least an amount sufficient to produce a detectable decrease in GH secretion and, preferably, is an amount sufficient to achieve a beneficial effect in a patient.

A preferred method of the immediately preceding method is wherein said suppression of GH secretion is indicated for treating excessive GH secretion, losing weight, decreasing appetite, maintaining an ideal weight, overcoming obesity, managing diabetes and its complications such as retinopathy and/or treating a cardiovascular disorder.

The immediately preceding method is preferred when excessive weight gain is a contributing factor of a disease or condition including, but not limited to, hypertension, diabetes, dyslipidemia, cardiovascular disease, gall stones, osteoarthritis and certain cancers, particularly wherein said weight loss reduces the likelihood of such diseases or comprises at least part of a treatment for such diseases or conditions.

Ghrelin agonists or analogs according to formulae (I) or (II), more preferably a compound according to one or more of Group 1, Group 2, Group 3, Group 4, Group 5, Group 6, Group 7, Group 8, Group 9, Group 10, Group 11, Group 12, Group 13, Group 14, Group 15 and/or Group 16, can be used to achieve a beneficial effect in a subject such as one or more of the following: treating a GH deficient state, increasing muscle mass and/or bone density, overcoming sexual dysfunction, facilitating a weight gain, maintaining an ideal weight, recovering and/or restoring normal physical functions and/or increasing appetite. Facilitating a weight gain, maintaining body weight and/or increasing appetite are particularly useful for treating a patient suffering from cachexia or wasting syndrome associated with a disease or disorder or undergoing a medical or therapeutic regimen which is normally accompanied by weight loss. Examples of diseases or disorders accompanied by weight loss due to cachexia include anorexia, bulimia, cancer and AIDS. Gaining body weight, maintaining and ideal body weight or increasing appetite are especially beneficial to patients suffering from wasting syndrome, especially the frail and elderly. Examples of treatments accompanied by weight loss include chemotherapy, radiation therapy, temporary or permanent immobilization and/or dialysis.

Ghrelin agonists or analogs according to formulae (I) or (II), more preferably a compound according to one or more of Group 1, Group 2, Group 3, Group 4, Group 5, Group 6, Group 7, Group 8, Group 9, Group 10, Group 11, Group 12, Group 13, Group 14, Group 15 and/or Group 16, have been successful in treating a subject suffering from post-operative ileus or chronic obstructive pulmonary disease.

In addition, ghrelin has been effective in treating inflammation in a mammalian subject. Thus, in one aspect the invention, the invention provides a method for treating inflammation in a subject in need thereof by administering an effective amount of one or more of a compound according to formulae (I) or (II), more preferably a compound according to one or more of Group 1, Group 2, Group 3, Group 4, Group 5, Group 6, Group 7, Group 8, Group 9, Group 10, Group 11, Group 12, Group 13, Group 14, Group 15 and/or Group 16, or pharmaceutically acceptable salts thereof, wherein said effective amount is at least an amount sufficient to produce a detectable decrease in the inflammation and, preferably, is an amount sufficient to achieve a beneficial effect in a patient.

In one aspect of the immediately foregoing method, the inflammation is associated with a viral, bacterial, parasitic or fungal infection. In one aspect of the foregoing method, the inflammation is associated with a viral infection. Viral infections treatable with ghrelin, ghrelin analogs and/or ghrelin agonists include, but are not limited to, Herpes simplex virus type-1, Herpes simplex virus type-2, Cytomegalovirus, Epstein-Barr virus, Varicella-zoster virus, Human herpesvirus 6, Human herpesvirus 7, Human herpesvirus 8, Variola virus, Vesicular stomatitis virus, Hepatitis A virus, Hepatitis B virus, Hepatitis C virus, Hepatitis D virus, Hepatitis E virus, Rhinovirus, Coronavirus, Influenza virus A, Influenza virus B, Measles virus, Polyomavirus, Human Papilomavirus, Respiratory syncytial virus, Adenovirus, Coxsackie virus, Dengue virus, Mumps virus, Poliovirus, Rabies virus, Rous sarcoma virus, Yellow fever virus, Ebola virus, Marburg virus, Lassa fever virus, Eastern Equine Encephalitis virus, Japanese Encephalitis virus, St. Louis Encephalitis virus, Murray Valley fever virus, West Nile virus, Rift Valley fever virus, Rotavirus A, Rotavirus B, Rotavirus C, Sindbis virus, Simian Immunodeficiency virus, Human T-cell Leukemia virustype-1, Hantavirus, Rubella virus, Simian Immunodeficiency virus, Human Immunodeficiency virus type-1 and/or Human Immunodeficiency virus type-2.

In another aspect of the foregoing method, the inflammation is associated with a bacterial infection. Bacterial infections that cause inflammation that are treatable with ghrelin, one or more ghrelin analog or a ghrelin agonist include, but are not limited to, *M. tuberculosis, M bovis, M. bovis* strain BCG, BCG substrains, *M. avium, M. intracellulare, M. africanum, M. kansasii, M. marinum, M. ulcerans, M. avium* subspecies *paratuberculosis, Nocardia asteroides*, other *Nocardia* species, *Legionella pneumophila*, other *Legionella* species, *Salmonella typhi*, other *Salmonella* species, *Shigella* species, *Yersinia pestis, Pasteurella haemolytica, Pasteurella multocida*, other *Pasteurella* species, *Actinobacillus pleuropneumoniae, Listeria monocytogenes, Listeria ivanovii, Brucella abortus*, other *Brucella* species, *Cowdria ruminantium, Chlamydia pneumoniae, Chlamydia trachomatis, Chlamydia psittaci, Coxiella burnetti*, other *Rickettsia* species, *Ehrlichia* species, *Staphylococcus aureus, Staphylococcus epidermidis, Streptococcus pyogenes, Streptococcus agalactiae, Bacillus anthracis, Escherichia coli, Vibrio cholerae, Campylobacter* species, *Neiserria meningitidis, Neiserria* gonorrhea, *Pseudomonas aeruginosa*, other *Pseudomonas* species, *Haemophilus influenzae, Haemophilus ducreyi*, other *Hemophilus* species, *Clostridium tetani*, other *Clostridium* species, *Yersinia* enterolitica and/or other *Yersinia* species.

In another aspect of the foregoing method, the inflammation is associated with a parasitic or fungal infection. Parasitic infections treatable with ghrelin, one or more ghrelin analog or a ghrelin agonist include, but are not limited to, *Toxoplasma gondii, Plasmodium, Trypanosoma brucei, Trypanosoma cruzi, Leishmania, Schistosoma* and/or *Entamoeba histolytica*. Fungal infections treatable with ghrelin, ghrelin analogs or ghrelin agonists include, but are not limited to, *Candida albicans, Cryptococcus neoformans, Histoplama capsulatum, Aspergillus fumigatus, Coccidiodes immitis, Paracoccidiodes brasiliensis, Blastomyces dermitidis, Pneomocystis carnii, Penicillium marneffi* and/or *Alternaria alternata*.

In another aspect of the invention, inflammation caused by liver toxicity or transplant rejection is also treatable by administering an effective amount of one or more of a compound according to formulae (I) or (II), more preferably a compound according to one or more of Group 1, Group 2, Group 3, Group 4, Group 5, Group 6, Group 7, Group 8, Group 9, Group 10, Group 11, Group 12, Group 13, Group 14, Group 15 and/or Group 16, or pharmaceutically acceptable salts thereof, wherein said effective amount is at least an amount sufficient to produce a detectable decrease in the inflammation and, preferably, is an amount sufficient to achieve a beneficial effect in a patient. The liver toxicity may be associated with cancer therapy. In some instances, the cancer therapy, such as chemotherapy, may bring about liver toxicity. Liver toxicity brought about by both chemotherapy and apoptosis may be treatable by administration of ghrelin, ghrelin agonists and/or ghrelin antagonists.

In yet a further aspect of the invention, inflammation associated with cancers is also treatable by administering an effective amount of one or more of a compound according to formulae (I) or (II), more preferably a compound according to one or more of Group 1, Group 2, Group 3, Group 4, Group 5, Group 6, Group 7, Group 8, Group 9, Group 10, Group 11, Group 12, Group 13, Group 14, Group 15 and/or Group 16, or pharmaceutically acceptable salts thereof, wherein said effective amount is at least an amount sufficient to produce a detectable decrease in the inflammation and, preferably, is an amount sufficient to achieve a beneficial effect in a patient. Such cancers include, but are not limited to, lymphoma, leukemia, mycosis fungoide, carcinoma, adenocarcinoma, sarcoma, glioma, blastoma, neuroblastoma, plasmacytoma, histiocytoma, melanoma, adenoma, hypoxic tumor, myeloma, AIDS-related lymphoma or AIDS-related sarcoma, metastatic cancer, bladder cancer, brain cancer, nervous system cancer, glioblastoma, ovarian cancer, skin cancer, liver cancer, squamous cell carcinomas of the mouth, throat, larynx, and lung, colon cancer, cervical cancer, breast cancer, epithelial cancer, renal cancer, genitourinary cancer, pulmonary cancer, esophageal carcinoma, head and neck carcinoma, hematopoietic cancer, testicular cancer, colo-rectal cancer, prostatic cancer and/or pancreatic cancer.

In yet a further aspect of the invention, inflammatory diseases are also treatable by administering an effective amount of one or more of a compound according to formulae (I) or (II), more preferably a compound according to one or more of Group 1, Group 2, Group 3, Group 4, Group 5, Group 6, Group 7, Group 8, Group 9, Group 10, Group 11, Group 12, Group 13, Group 14, Group 15 and/or Group 16, or pharmaceutically acceptable salts thereof, wherein said effective amount is at least an amount sufficient to produce a detectable decrease in the inflammation and, preferably, is an amount sufficient to achieve a beneficial effect in a patient. Inflammatory diseases treatable by ghrelin, one or more ghrelin agonists and/or ghrelin antagonists of the invention include, but are not limited to, asthma, reactive arthritis, hepatitis, spondyarthritis, Sjogren's syndrome, Alzheimer's disease, and atopic dermatitis or inflammatory diseases associated with an autoimmune disease such as systemic lupus erythematosus, rheumatoid arthritis, systemic vasculitis, insulin dependent diabetes mellitus, multiple sclerosis, muscular dystrophy, experimental allergic encephalomyelitis, psoriasis, Crohn's disease, inflammatory bowel disease, ulcerative colitis, Addison's disease, alopecia aretea, celiac disease, thyroid disease and/or scleroderma. Inflammation as a result of a burn may also benefit from treatment with ghrelin, one or more ghrelin agonist and/or one or more ghrelin antagonist. Inflammation of the lung may also be treated with ghrelin, one or more ghrelin agonist and/or one or more ghrelin antagonist. Inflammation may also cause a subject to lose appetite, particularly when the inflammation is low grade and/or in an aging subject.

Ghrelin antagonists can also be used to achieve a beneficial effect in a patient. For example, a ghrelin antagonist can be used to facilitate weight loss and/or a decrease in appetite, maintain an ideal body weight, reverse obesity, treat diabetes, and complications thereof such as retinopathy and/or improve cardiovascular disorders. Excessive weight is a contributing factor to different diseases including, but not limited to, hypertension, diabetes, dyslipidemia, cardiovascular disease, gall stone formation, osteoarthritis, Prader-Willi syndrome and/or certain forms of cancers. Loss of weight has been proven to reduce the likelihood of such diseases when part of the prescribed treatment for such diseases.

Other features and advantages of the present invention are apparent from the additional descriptions provided herein, including the different examples. The provided examples illustrate different components and methodology useful in practicing the present invention. The examples do not limit the claimed invention. Based on the present disclosure the skilled artisan can identify and employ other components and methodology useful for practicing the present invention.

DETAILED DESCRIPTION OF THE INVENTION

The present invention features ghrelin analogs active at the GHS receptor. Human ghrelin is a 28 amino acid modified peptide wherein a serine hydroxyl group is esterified by n-octanoic acid. (Kojima, M. et al., *Nature*, (1999), 402(6762): 656-60 and Kojima, M. (Abstract), Third International Symposium on Growth Hormone Secretagogues, Keystone, Colo., USA 2000, February 17-19).

As detailed above, the analogs of the instant invention are useful for the treatment of a wide variety of ailments in a subject. A "subject", as used herein and throughout this application, refers to a mammalian or non-mammalian animal including, for example and without limitation, a human, a rat, a mouse or farm animal. Reference to a subject does not necessarily indicate the presence of a disease or disorder. The term "subject" includes, for example, a mammalian or non-mammalian animal being dosed with a ghrelin analog as part of an experiment, a mammalian or non-mammalian animal being treated to help alleviate a disease or disorder, and a mammalian or non-mammalian animal being treated prophylactically to retard or prevent the onset of a disease or disorder.

A "therapeutically acceptable amount" of a compound or composition of the invention, regardless of the formulation or route of administration, is that amount which elicits a desired biological response in a subject. The biological effect of the therapeutic amount may occur at and be measured at many levels in an organism. For example, the biological effect of the therapeutic amount may occur at and be measured at the cellular level by measuring the response at a receptor which binds ghrelin and/or a ghrelin analog, or the biological effect of the therapeutic amount may occur at and be measured at the system level, such as effecting an increase/decrease in the levels of circulating growth hormone. The biological effect of the therapeutic amount may occur at and be measured at the organism level, such as the alleviation of a symptom(s) or progression of a disease or condition in a subject. A therapeutically acceptable amount of a compound or composition of the invention, regardless of the formulation or route of administration, may result in one or more biological responses in a subject. In the event that the compound or composition of the invention is subject to testing in an in vitro system, a therapeutically acceptable amount of the compound or composition may be viewed as that amount which gives a measurable response in the in vitro system of choice.

Unless defined otherwise, all technical and scientific terms used herein have the same meaning as commonly understood by one of ordinary skill in the art to which this invention belongs. Also, all publications, patent applications, patents and other references mentioned herein are incorporated by reference.

Certain amino acids present in compounds of the invention can be and are represented herein as follows:

Nomenclature and Abbreviations

| Symbol | Meaning |
|---|---|
| Abu | α-aminobutyric acid |
| Acc | 1-amino-1-cyclo($C_3$-$C_9$)alkyl carboxylic acid |
| A3c | 1-amino-1-cyclopropanecarboxylic acid |
| A4c | 1-amino-1-cyclobutanecarboxylic acid |
| A5c | 1-amino-1-cyclopentanecarboxylic acid |
| A6c | 1-amino-1-cyclohexanecarboxylic acid |
| Act | denotes the structure 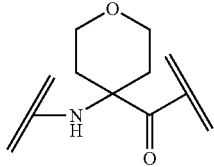 |
| Aib | α-aminoisobutyric acid |
| Aic | 2-aminoindan-2-carboxylic acid |
| Ala or A | alanine |
| β-Ala | beta-alanine |
| Apc | denotes the structure: 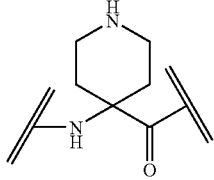 |
| Arg or R | arginine |
| hArg | homoarginine |
| Asn or N | asparagine |
| Asp or D | aspartic acid |
| Ava | 5-amino-n-valeric acid |

Nomenclature and Abbreviations -continued

| Symbol | Meaning |
|---|---|
| Cha | β-cyclohexylalanine |
| Cys or C | cysteine |
| hCys | L-homocysteine |
| Dab | 2,4-diaminobutyric acid |
| Dap | 2,3-diaminopropionic acid |
| Dhp | 3,4-dehydroproline |
| Dmt | 5,5-dimethylthiazolidine-4-carboxylic acid |
| 2-Fua | β-(2-furyl)-alanine |
| Gln or Q | glutamine |
| Glu or E | glutamic acid |
| Gly or G | glycine |
| His or H | histidine |
| 3-Hyp | trans-3-hydroxy-L-proline, i.e., (2S, 3S)-3-hydroxypyrrolidine-2-carboxylic acid |
| 4-Hyp | 4-hydroxyproline, i.e., (2S, 4R)-4-hydroxypyrrolidine-2-carboxylic acid |
| Ile or I | isoleucine |
| Inc | indoline-2-carboxylic acid |
| Inp | isonipecotic acid |
| Ktp | 4-ketoproline |
| Leu or L | leucine |
| hLeu | homoleucine |
| Lys or K | lysine |
| Met or M | methionine |
| 1-Nal | β-(1-naphthyl)-L-alanine |
| 2-Nal | β-(2-naphthyl)-L-alanine |
| Nle | norleucine |
| Nva | norvaline |
| Oic | octahydroindole-2-carboxylic acid |
| Orn | ornithine |
| 2-Pal | β-(2-pyridinyl)alanine |
| 3-Pal | β-(3-pyridinyl)alanine |
| 4-Pal | β-(4-pyridinyl)alanine |
| Phe or F | phenylalanine |
| hPhe | homophenylalanine |
| Pip | pipecolic acid |
| Pro or P | proline |
| Ser or S | serine |
| Taz | β-(4-thiazolyl)alanine, i.e.,  |
| 2-Thi | β-(2-thienyl)alanine |
| 3-Thi | β-(3-thienyl)alanine |
| Thp | 4-amino-4-carboxytetrahydropyran |
| Thr or T | threonine |
| Thz | thiazolidine-4-carboxylic acid |
| Tic | 1,2,3,4-tetrahydroisoquinoline-3-carboxylic acid |
| Tle | tert-leucine |
| Trp or W | tryptophan |
| Tyr or Y | tyrosine |
| Val or V | valine |

Where the amino acid has isomeric forms, it is the L form of the amino acid that is represented unless otherwise explicitly indicated.

The nomenclature used to define the peptides is that typically used in the art wherein the amino group at the N-terminus appears to the left and the carboxyl group at the C-terminus appears to the right, i.e., stand for the structure of —NH—CI(R')—CO—, wherein R and R' each is, independently, hydrogen or the side chain of an amino acid (e.g., R=$CH_3$ and R'=H for Ala), or R and R' may be joined to form a ring system. For the N-terminal amino acid, the abbreviation stands for the structure of:

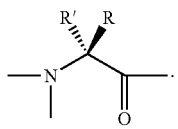

A peptide of this invention is also denoted herein by another format, e.g., (Aib$^2$)hGhrelin(1-28)-NH$_2$ (SEQ ID NO:181), with the substituted amino acid(s) from the natural sequence placed between the first set of parentheses (e.g., Aib$^2$ for Ser$^2$ in hGhrelin). The numbers between the second set of parentheses refer to the number of amino acids present in the peptide (e.g., hGhrelin(1-18) (SEQ ID NO:182) refers to amino acids 1 through 18 of the peptide sequence for human Ghrelin). The designation "NH$_2$" in e.g., (Aib$^2$)hGhrelin(1-28)-NH$_2$ (SEQ ID NO:181), indicates that the C-terminus of the peptide is amidated. (Aib$^2$)hGhrelin(1-28) (SEQ ID NO:183), or, alternatively, (Aib$^2$)hGhrelin(1-28)-OH (SEQ ID NO:183) indicates that the C-terminus is the free acid. A lower case letter is inserted before "Ghrelin" to indicate its source or origin, i.e. "h" indicates that the ghrelin is a homologue of the form of ghrelin found in homo sapiens.

Unless otherwise stated, those amino acids with a chiral center are provided in the L-enantiomer. Reference to "a derivative thereof" refers to a modified amino acid such as the corresponding D-amino acid, N-alkyl-amino acid, β-amino acid or labeled amino acid.

As used herein, Acc encompasses an amino acid selected from the group of 1-amino-1-cyclopropanecarboxylic acid (A3c); 1-amino-1-cyclobutanecarboxylic acid (A4c); 1-amino-1-cyclopentanecarboxylic acid (A5c); 1-amino-1-cyclohexanecarboxylic acid (A6c); 1-amino-1-cycloheptanecarboxylic acid (A7c); 1-amino-1-cyclooctanecarboxylic acid (A8c); and 1-amino-1-cyclononanecarboxylic acid (A9c).

"Acyl" refers to R"—C(O)—, where R" is H, alkyl, substituted alkyl, heteroalkyl, substituted heteroalkyl, alkenyl, substituted alkenyl, aryl, alkylaryl or substituted alkylaryl.

"Alkyl" refers to a hydrocarbon group containing one or more carbon atoms, where multiple carbon atoms if present are joined by single bonds. The alkyl hydrocarbon group may be straight-chain or contain one or more branches or cyclic groups.

"Substituted alkyl" refers to an alkyl wherein one or more hydrogen atoms of the hydrocarbon group are replaced with one or more substituents selected from the group consisting of halogen (i.e., fluorine, chlorine, bromine and iodine), —OH, —CN, —SH, —NH$_2$, —NHCH$_3$, —NO$_2$, —C$_{1-20}$ alkyl substituted with 1 to 6 halogens, —CF$_3$, —OCH$_3$, —OCF$_3$ and —(CH$_2$)$_{0-20}$—COOH. In different embodiments 1, 2, 3 or 4 substituents are present. The presence of —(CH$_2$)$_{0-20}$—COOH results in the production of an alkyl acid. Examples of alkyl acids containing, or consisting of —(CH$_2$)$_{0-20}$—COOH include, but are not limited to, 2-norbornane acetic acid, tert-butyric acid and 3-cyclopentyl propionic acid.

"Heteroalkyl" refers to an alkyl wherein one of more of the carbon atoms in the hydrocarbon group is replaced with one or more of the following groups: amino, amido, —O—, —S— or carbonyl. In different embodiments 1 or 2 heteroatoms are present.

"Substituted heteroalkyl" refers to a heteroalkyl wherein one or more hydrogen atoms of the hydrocarbon group is replaced with one or more substituents selected from the group consisting of halogen (i.e., fluorine, chlorine, bromine and iodine), —OH, —CN, —SH, —NH$_2$, —NHCH$_3$, —NO$_2$, —C$_{1-20}$ alkyl substituted with 1 to 6 halogens, —CF$_3$, —OCH$_3$, —OCF$_3$ and —(CH$_2$)$_{0-20}$—COOH. In different embodiments 1, 2, 3 or 4 substituents are present.

"Alkenyl" refers to a hydrocarbon group made up of two or more carbons where one or more carbon-carbon double bonds are present. The alkenyl hydrocarbon group may be straight-chain or contain one or more branches or cyclic groups.

"Substituted alkenyl" refers to an alkenyl wherein one or more hydrogens are replaced with one or more substituents selected from the group consisting of halogen (i.e., fluorine, chlorine, bromine and iodine), —OH, —CN, —SH, —NH$_2$, —NHCH$_3$, —NO$_2$, —C$_{1-20}$ alkyl substituted with 1 to 6 halogens, —CF$_3$, —OCH$_3$, —OCF$_3$ and —(CH$_2$)$_{0-20}$—COOH. In different embodiments 1, 2, 3 or 4 substituents are present.

"Aryl" refers to an optionally substituted aromatic group with at least one ring having a conjugated π-electron system, containing up to two conjugated or fused ring systems. Aryl includes, but is not limited to, carboxylic aryl, heterocyclic aryl and biaryl groups. Preferably, the aryl is a 5- or 6-membered ring. Preferred atoms for a heterocyclic aryl are one or more sulfur, oxygen and/or nitrogen. Examples of aryl include, but are not limited to, phenyl, 1-naphthyl, 2-naphthyl, indole, quinoline, 2-imidazole and 9-anthracene. Aryl substituents are selected from the group consisting of —C$_{1-20}$ alkyl, —C$_{1-20}$ alkoxy, halogen (i.e., fluorine, chlorine, bromine, and iodine), —OH, —CN, —SH, —NH$_2$, —NO$_2$, —C$_{1-20}$ alkyl substituted with 1 to 5 halogens, —CF$_3$, —OCF$_3$ and —(CH$_2$)$_{0-20}$—COOH. In different embodiments the aryl contains 0, 1, 2, 3 or 4 substituents.

The term "halo" encompasses fluoro, chloro, bromo and iodo.

The term "(C$_1$-C$_{12}$)hydrocarbon moiety" encompasses alkyl, alkenyl and alkynyl and in the case of alkenyl and alkynyl there are C$_2$-C$_{12}$.

"Alkylaryl" refers to an "alkyl" joined to an "aryl".
What is meant by Glu(O-hexyl) is

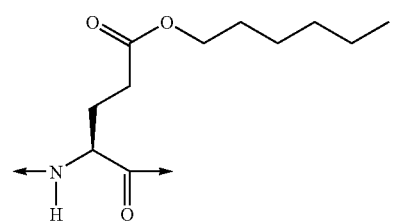

What is meant by Asp(1-heptanol) is

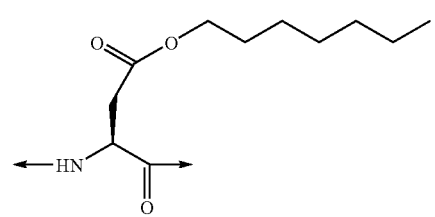

What is meant by Glu(1-heptanol) is
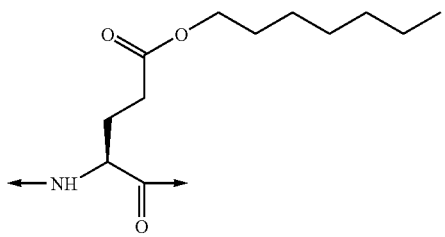
What is meant by Asp(NH-hexyl) is
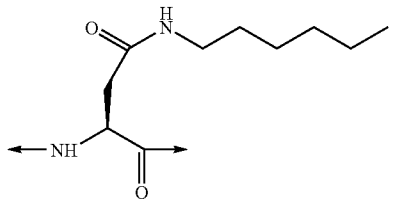
What is meant by Glu(NH-hexyl) is
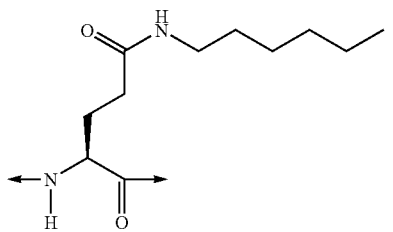
What is meant by Ser(n-octanoyl) or Ser(C(O)-heptyl) is
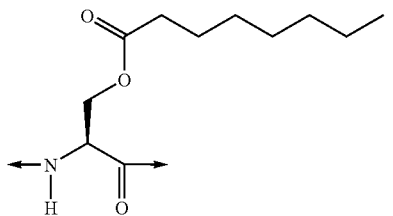
What is meant by Dap(1-octanesulfonyl) is
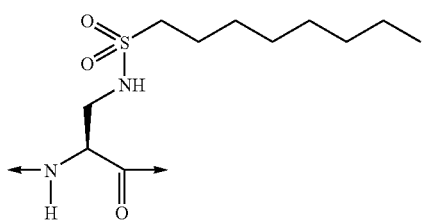
What is meant by Cys(R$^{15}$) is:
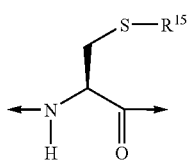
What is meant by Cys(S-heptyl) is
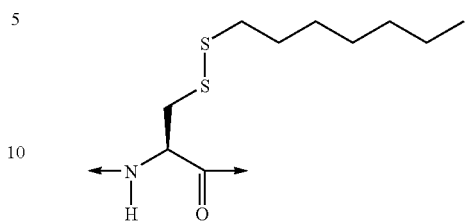
What is meant by Dap(octanoyl) is
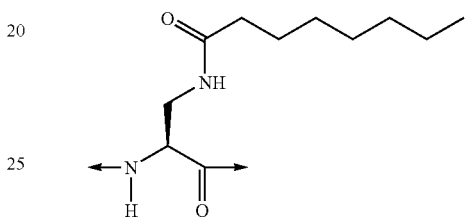
What is meant by biotinyl is
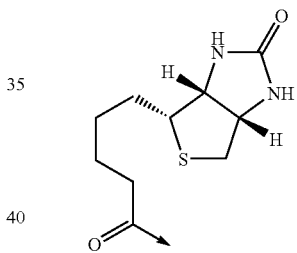
What is meant by myristyl is
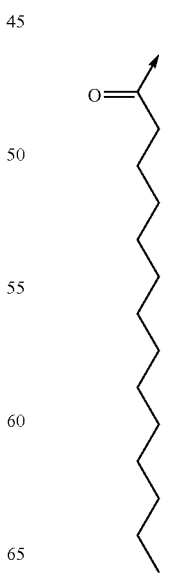

What is meant by Lys(biotinyl) is

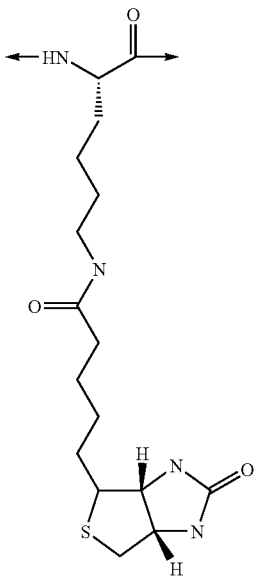

What is meant by Lys(myristyl) is

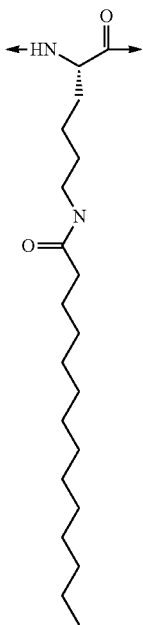

What is meant by Gly(myristyl) is

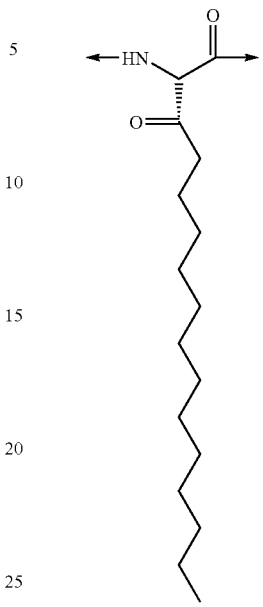

The present invention includes diastereomers as well as their racemic and resolved enantiomerically pure forms. Ghrelin analogs can contain D-amino acids, L-amino acids or a combination thereof. Preferably, amino acids present in a ghrelin analog are the L-enantiomers.

Preferred derivatives of analogs of the invention comprise D-amino acids, N-alkyl-amino acids, β-amino acids and/or one or more labeled amino acids (including a labeled version of a D-amino acid, N-alkyl-amino acids, or a β-amino acid). A labeled derivative indicates the alteration of an amino acid or amino acid derivative with a detectable label. Examples of detectable labels include luminescent, enzymatic and radioactive labels. Both the type of label and the position of the label can affect analog activity. Labels should be selected and positioned so as not to substantially alter the activity of the ghrelin analog at the GHS receptor. The effect of a particular label and position on ghrelin activity can be determined using assays measuring ghrelin activity and/or binding.

A protecting group covalently joined to the C-terminal carboxy group reduces the reactivity of the carboxy terminus under in vivo conditions. The carboxy terminus protecting group is preferably attached to the α-carbonyl group of the last amino acid. Preferred carboxy terminus protecting groups include amide, methylamide and ethylamide.

Certain other abbreviations used herein are defined as follows:

| \multicolumn{2}{l}{Nomenclature and Abbreviations} |
|---|---|
| Symbol | Meaning |
| Boc: | tert-butyloxycarbonyl |
| BSA: | bovine serum albumin |
| Bzl: | benzyl |
| DCM: | dichloromethane |
| DIC: | N,N-diisopropylcarbodiimide |
| DIEA: | diisopropylethyl amine |
| Dmab: | 4-{N-(1-(4,4-dimethyl-2,6-dioxocyclohexylidene)-3-methylbutyl)-amino} benzyl |

-continued

| Nomenclature and Abbreviations | |
|---|---|
| Symbol | Meaning |
| DMAP: | 4-(dimethylamino)pyridine |
| DMF: | dimethylformamide |
| DNP: | 2,4-dinitrophenyl |
| EDTA | ethylenediaminetetracetic acid |
| Fmoc: | fluorenylmethyloxycarbonyl |
| HBTU: | 2-(1H-benzotriazole-1-yl)-1,1,3,3-tetramethyluronium hexafluorophosphate |
| cHex | cyclohexyl |
| HOAT: | O-(7-azabenzotriazol-1-yl)-1,1,3,3-tetramethyluronium hexafluorophosphate |
| HOBt: | 1-hydroxy-benzotriazole |
| HPLC: | high performance liquid chromatography |
| MBHA | 4-methylbenzhydrylamine |
| Mmt: | 4-methoxytrityl |
| NMP: | N-methylpyrrolidone |
| Pbf: | 2,2,4,6,7-pentamethyldihydrobenzofuran-5-sulfonyl |
| PhiPr | γ-2-phenylisopropyl ester |
| PyAOP: | 7-azabenzotriazol-1-yloxytris(pyrrolidino)phosphonium-hexafluorophosphate |
| tBu: | tert-butyl |
| TIS: | triisopropylsilane |
| TOS: | tosyl |
| trt | trityl |
| TFA: | trifluoro acetic acid |
| TFFH: | tetramethylfluoroforamidinium hexafluorophosphate |
| Z: | benzyloxycarbonyl |

Synthetic Methods

The compounds of the invention can be produced using the techniques disclosed in the examples herein as well as techniques that are well known in the art. For example, a polypeptide region of a ghrelin analog can be chemically or biochemically synthesized and modified. Examples of techniques for biochemical synthesis involving the introduction of a nucleic acid into a cell and expression of nucleic acids are provided in Ausubel, *Current Protocols in Molecular Biology*, John Wiley, 1987-1998 and Sambrook et al., in *Molecular Cloning, A Laboratory Manual,* 2nd Edition, Cold Spring Harbor Laboratory Press, 1989. Techniques for chemical synthesis of polypeptides are also well known in the art (Vincent in *Peptide and Protein Drug Delivery*, New York, N.Y., Dekker, 1990). For example, the peptides of this invention can be prepared by standard solid phase peptide synthesis (Stewart, J. M. et al., *Solid Phase Synthesis*, Pierce Chemical Co., 2d ed. 1984).

The substituents $R^2$ and $R^3$ of the above generic formula may be attached to the free amine of the N-terminal amino acid by standard methods known in the art. For example, alkyl groups, e.g., $(C_1-C_{30})$alkyl, may be attached using reductive alkylation. Hydroxyalkyl groups, e.g., $(C_1-C_{30})$hydroxyalkyl, may also be attached using reductive alkylation wherein the free hydroxy group is protected with a t-butyl ester. Acyl groups, e.g., $COE^1$, may be attached by coupling the free acid, e.g., $E^1COOH$, to the free amine of the N-terminal amino acid by mixing the completed resin with 3 molar equivalents of both the free acid and diisopropylcarbodiimide in methylene chloride for 1 hour. If the free acid contains a free hydroxy group, e.g., p-hydroxyphenylpropionic acid, then the coupling should be performed with an additional 3 molar equivalents of HOBT.

When $R^1$ is $NH-X^2-CH_2-CONH_2$, (i.e., $Z^0=CONH_2$), the synthesis of the peptide starts with Fmoc-HN—$X^2$—$CH_2$—COOH coupled to a Rink Amide-MBHA resin (Amide-4-methylbenzhydryl amine obtained from Novabiochem®, San Diego, Calif.). If $R^1$ is NH—$X^2$—$CH_2$—COOH (i.e., $Z^0$—COOH) the synthesis of the peptide starts with Fmoc-HN—$X^2$—$CH_2$—COOH which is coupled to Wang resin.

In the synthesis of a ghrelin analogue of this invention containing A5c, A6c and/or Aib, the coupling time is 2 hours for these residues and the residue immediately following them.

Examples are provided below to further illustrate different features of the present invention. The examples also illustrate useful methodology for practicing the invention. These examples do not limit the claimed invention.

Example 158

(Ac-Aib$^1$,Aib$^{2,10}$,Glu(NH-hexyl)$^{3,17}$)hGhrelin(1-28)-NH$_2$(SEQ ID NO:118)

The title peptide was synthesized on an Applied Biosystems® model 433A peptide synthesizer (obtained from Applied Biosystems®, Foster City, Calif., U.S.A.) using Fluorenylmethyloxycarbonyl (Fmoc) chemistry. A Rink Amide-4-methylbenzylhydrylamine (MBHA) resin (obtained from Novabiochem®, San Diego, Calif.) with substitution of 0.64 mmol/g was employed. The Fmoc amino acids (obtained from AnaSpec®, San Jose, Calif., U.S.A.) used were Fmoc-Ala-OH, Fmoc-Arg(Pbf)-OH, Fmoc-Aib-OH, Fmoc-Gln(Trt)-OH, Fmoc-Glu(tBu)-OH, Fmoc-His(Trt)-OH, Fmoc-Leu-OH, Fmoc-Lys(Boc)-OH, Fmoc-Phe-OH, Fmoc-Pro-OH, Fmoc-Ser(tBu)-OH and Fmoc-Val-OH. In addition, Fmoc-Glu(O-2-PhiPr)—OH (obtained from Novabiochem®, San Diego, Calif.) was used for the amino acids in $3^{rd}$ and $17^{th}$ positions. The synthesis was carried out on a 0.1 mmol scale. The Fmoc groups were removed by treating the resin with a solution of 20% piperidine in N-methylpyrrolidone (NMP) for a period of approximately 30 minutes. In each coupling step, the Fmoc amino acid (3 eq, 0.3 mmol) was first pre-activated in 2 mL solution of 0.45M 2-(1-H-benzotriazole-1-yl)-1,1,2,3-tetramethyluronium-hexafluorophosphate/1-hydroxy-benzotriazole (HBTU/HOBT) in NMP. A solution containing the activated amino acid ester together with 1 mL of diisopropylethylamine (DIEA) and 1 mL of NMP was introduced to the resin. The ABI 433A® peptide synthesizer was programmed to perform the following reaction cycle:
(1) washing with NMP;
(2) removing Fmoc protecting group with 20% piperidine in NMP for 30 minutes;
(3) washing with NMP; and
(4) coupling with pre-activated Fmoc amino acid for approximately 1 or 3 hours.
The resin was coupled successively according to the sequence of the title peptide. After the peptide chain was assembled, the resin was washed completely with N,N-dimethylformamide (DMF) and dichloromethane (DCM).

At the end of the assembly of the peptide chain on the ABI 433A® peptide synthesizer (without the Fmoc-Aib residue in A$^1$), the peptide-resin was transferred to a reaction vessel on a shaker and the Fmoc was removed using 25% piperidine in DMF for 30 minutes. The resin was then washed with DMF. The Fmoc-Aib-OH (0.4 mmole) was coupled using TFFH (Tetramethylfluoroformamidinium Hexafluorophosphate) (obtained from Perceptive Biosystems®, Warrington, U.K.) (0.4 mmole), HOAt (0.4 mmol), DMAP (Dimethylaminopyridine) (0.1 g) and DIEA (1.2 mmole) once for 4 hours and once overnight.

The Fmoc group was removed as above and the peptide was capped using Ac$_2$O (acetic anhydride) (5 mmole) and DIEA (5 mmole) in DMF for approximately 30 minutes. The PhiPr (γ-2-phenylisopropyl ester) groups were removed from the glutamine residues at $A^3$ and $A^{17}$ by washing with a solution of 3% TFA in DCM twice for a period of 10 minutes for each washing. The Boc that was partially removed from the side chain of lysine was replaced by using $Boc_2O$ (0.8 mmole) and DIEA (0.8 mmole) in DCM overnight. The resin was treated with PyAOP (7-Azabenzotriazol-1-yloxytris(pyrrolidino)phosphonium-hexafluorophosphate) (obtained from Applied Biosystems®, Foster City, Calif., U.S.A.) (0.6 mmole), HOAt (0.6 mmole), DMAP (0.1 g) and DIEA (1.8 mmole) for 10 minutes. Hexyl-$NH_2$(Hexylamine) (obtained from Sigma-Aldrich Chemicals®, St. Louis, Mo., U.S.A.) (2.0 mmole) was then added to the resin solution which was then shaken and allowed to stand overnight.

To cleave the title peptide from the resin, the peptide-resin was treated with a mixture of TFA, $H_2O$ and triisopropylsilane (TIS) (9.5 mL/0.85 mL/0.8 mL, respectively) for approximately 4 hours. The cleaved resin was filtered off and the remaining filtrate was poured into 200 mL of ether. A precipitate formed which was then collected by centrifugation. The crude product was dissolved in a mixture of acetonitrile and water which was purified on a reverse-phase preparative HPLC system with a column (4×43 cm) of $C_{18}$ DYNAMAX-100 $A^0$® (obtained from Varian®, Walnut Creek, Calif., U.S.A.). The column was eluted over approximately 1 hour using a linear gradient of 85% A:15% B to 60% A:40% B, where A was 0.1% TFA in water and B was 0.1% TFA in acetonitrile. The fractions were analyzed by HPLC and those fractions found to contain pure product were pooled and lyophilized to dryness. Approximately 27.1 mg (6.3%) of a white solid was recovered which was assayed using HPLC and found to be approximately 97.5% pure. Electro-spray ionization mass spectrometry (ESI-MS) analysis determined the molecular weight to be 3477.4 which was in agreement with the calculated molecular weight of 3477.19.

Example 70

$(Aib^{1,2,10}, Glu(NH-hexyl)^{3,17})hGhrelin(1-28)-NH_2$
(SEQ ID NO:50)

The titled peptide was synthesized according to the procedure described for Example 158, i.e., $(Ac-Aib^1, Aib^{2,10}, Glu(NH-Hexyl)^{3,17})hGhrelin(1-28)-NH_2)$ (SEQ ID NO:118) with the following exception: after coupling the last Fmoc-Aib-OH in the 1$^{st}$ position on a shaker, the PhiPr protecting groups were removed from the glutamine residues at $A^3$ and $A^{17}$ by washing with a 3% TFA in DCM twice for intervals lasting approximately 10 minutes. The Boc that was partially removed from the side chain of lysine was replaced using a solution of $Boc_2O$ (0.8 mmole) and DIEA (0.8 mmole) in DCM. After being shaken and standing overnight, the resin was treated with a solution of PyAOP (7-Azabenzotriazol-1-yloxytris(pyrrolidino)phosphonium-hexafluorophosphate) (obtained from Applied Biosystems®, Foster City, Calif., U.S.A.) (0.6 mmole), HOAt (0.6 mmole), DMAP (0.1 g) and DIEA (1.8 mmole) for 10 minutes after which Hexyl-$NH_2$ (Hexylamine) (obtained from Sigma-Aldrich, St. Louis, Mo., U.S.A.) (2.0 mmole) was then added to the solution which was then shaken and allowed to stand overnight. The Fmoc protecting group was then removed using 25% piperidine in DMF. The peptide was cleaved off from the resin and purified on a HPLC system, as detailed in the discussion of the synthesis of Example 158 above.

Using a HPLC assay, the purity of the resulting produce was found to be approximately 96.5%. Electro-spray ionization mass spectrometry (ESI-MS) analysis determined the molecular weight to 3435.00 which was in agreement with the calculated molecular weight of 3435.16.

The following peptides of the invention can be prepared by a person of ordinary skill in the art using synthetic procedures analogous to those disclosed generally hereinabove:

```
Example 1:   (Ser(n-octanoyl)15)hGhrelin(1-28)-NH2;                       (SEQ ID NO: 1)

Example 2:   (Glu(NH-hexyl)15)hGhrelin(1-28)-NH2;                         (SEQ ID NO: 2)

Example 3:   (Glu(NH-hexyl)3,15)hGhrelin(1-28)-NH2;                       (SEQ ID NO: 3)

Example 4:   (Glu(NH-hexyl)3,Ser(n-octanoyl)15)hGhrelin(1-28)-NH2;        (SEQ ID NO: 4)

Example 5:   (Aib2,Glu(NH-hexyl)15)hGhrelin(1-28)-NH2;                    (SEQ ID NO: 5)

Example 6:   (Aib2,Glu(NH-hexyl)3,15)hGhrelin(1-28)-NH2;                  (SEQ ID NO: 6)

Example 7:   (Aib2,8,Glu(NH-hexyl)15)hGhrelin(1-28)-NH2;                  (SEQ ID NO: 7)

Example 8:   (Aib2,8,Glu(NH-hexyl)3,15)hGhrelin(1-28)-NH2;                (SEQ ID NO: 8)

Example 9:   (Aib2,10,Glu(NH-hexyl)15)hGhrelin(1-28)-NH2;                 (SEQ ID NO: 9)

Example 10:  (Aib2,10,Glu(NH-hexyl)3,15)hGhrelin(1-28)-NH2;               (SEQ ID NO: 10)

Example 11:  (Ser(n-octanoyl)16)hGhrelin(1-28)-NH2;                       (SEQ ID NO: 11)

Example 12:  (Glu(NH-hexyl)16)hGhrelin(1-28)-NH2;                         (SEQ ID NO: 12)

Example 13:  (Glu(NH-hexyl)3,16)hGhrelin(1-28)-NH2;                       (SEQ ID NO: 13)

Example 14:  (Glu(NH-hexyl)3,Ser(n-octanoyl)16)hGhrelin(1-28)-NH2;        (SEQ ID NO: 14)

Example 15:  (Aib2,Glu(NH-hexyl)16)hGhrelin(1-28)-NH2;                    (SEQ ID NO: 15)

Example 16:  (Aib2,Glu(NH-hexyl)3,16)hGhrelin(1-28)-NH2;                  (SEQ ID NO: 16)

Example 17:  (Aib2,8,Glu(NH-hexyl)16)hGhrelin(1-28)-NH2;                  (SEQ ID NO: 17)

Example 18:  (Aib2,8,Glu(NH-hexyl)3,16)hGhrelin(1-28)-NH2;                (SEQ ID NO: 18)
```

-continued

| | | |
|---|---|---|
| Example 19: | (Aib$^{2,10}$,Glu(NH-hexyl)$^{16}$)hGhrelin(1-28)-NH$_2$; | (SEQ ID NO: 19) |
| Example 20: | (Aib$^{2,10}$,Glu(NH-hexyl)$^{3,16}$)hGhrelin(1-28)-NH$_2$; | (SEQ ID NO: 20) |
| Example 21: | (Ser(n-octanoyl)$^{17}$)hGhrelin(1-28)-NH$_2$; | (SEQ ID NO: 21) |
| Example 22: | (Glu(NH-hexyl)$^{17}$)hGhrelin(1-28)-NH$_2$; | (SEQ ID NO: 22) |
| Example 23: | (Glu(NH-hexyl)$^{3,17}$)hGhrelin(1-28)-NH$_2$; | (SEQ ID NO: 23) |
| Example 24: | (Glu(NH-hexyl)$^3$,Ser(n-octanoyl)$^{17}$)hGhrelin(1-28)-NH$_2$; | (SEQ ID NO: 24) |
| Example 25: | (Dap(octanesulfonyl)$^{17}$hGhrelin(1-28)-NH$_2$; | (SEQ ID NO: 25) |
| Example 26: | (Dap(octanesulfonyl)$^{3,17}$hGhrelin(1-28)-NH$_2$; | (SEQ ID NO: 26) |
| Example 27: | (Dap(octanesulfonyl)$^3$,Glu(NH-hexyl)$^{17}$)hGhrelin(1-28)-NH$_2$; | (SEQ ID NO: 27) |
| Example 28: | (Dap(octanesulfonyl)$^3$,Ser(n-octanoyl)$^{17}$)hGhrelin(1-28)-NH$_2$; | (SEQ ID NO: 28) |
| Example 29: | (Glu(NH-hexyl)$^3$,Dap(octanesulfonyl)$^{17}$)hGhrelin(1-28)-NH$_2$; | (SEQ ID NO: 29) |
| Example 30: | (Cys(S-(CH$_2$)$_9$CH$_3$)$^{17}$)hGhrelin(1-28)-NH$_2$; | (SEQ ID NO: 30) |
| Example 31: | (Cys(S-(CH$_2$)$_9$CH$_3$)$^{3,17}$)hGhrelin(1-28)-NH$_2$; | (SEQ ID NO: 31) |
| Example 32: | (Glu(NH-hexyl)$^3$,Cys(S-(CH$_2$)$_9$CH$_3$)$^{17}$)hGhrelin(1-28)-NH$_2$; | (SEQ ID NO: 32) |
| Example 33: | (Cys(S-(CH$_2$)$_9$CH$_3$)$^3$,Glu(NH-hexyl)$^{17}$)hGhrelin(1-28)-NH$_2$; | (SEQ ID NO: 33) |
| Example 34: | (Cys(S-(CH$_2$)$_9$CH$_3$)$^3$,Ser(n-octanoyl)$^{17}$)hGhrelin(1-28)-NH$_2$; | (SEQ ID NO: 34) |
| Example 35: | (Aib$^2$,Glu(NH-hexyl)$^{17}$)hGhrelin(1-28)-NH$_2$; | (SEQ ID NO: 35) |
| Example 36: | (Aib$^2$,Glu(NH-hexyl)$^{3,17}$)hGhrelin(1-28)-NH$_2$; | (SEQ ID NO: 36) |
| Example 37: | (Aib$^2$,Thz$^7$,Glu(NH-hexyl)$^{17}$)hGhrelin(1-28)-NH$_2$; | (SEQ ID NO: 37) |
| Example 38: | (Aib$^2$,4-Hyp$^7$,Glu(NH-hexyl)$^{17}$)hGhrelin(1-28)-NH$_2$; | (SEQ ID NO: 37) |
| Example 39: | (Aib$^2$,Dhp$^7$,Glu(NH-hexyl)$^{17}$)hGhrelin(1-28)-NH$_2$; | (SEQ ID NO: 37) |
| Example 40: | (Aib$^2$,Pip$^7$,Glu(NH-hexyl)$^{17}$)hGhrelin(1-28)-NH$_2$; | (SEQ ID NO: 37) |
| Example 41: | (Aib$^2$,Tic$^7$,Glu(NH-hexyl)$^{17}$)hGhrelin(1-28)-NH$_2$; | (SEQ ID NO: 37) |
| Example 42: | (Aib$^2$,Glu(NH-hexyl)$^{3,17}$,Thz$^7$)hGhrelin(1-28)-NH$_2$; | (SEQ ID NO: 38) |
| Example 43: | (Aib$^2$,Glu(NH-hexyl)$^{3,17}$,4-Hyp$^7$,)hGhrelin(1-28)-NH$_2$; | (SEQ ID NO: 38) |
| Example 44: | (Aib$^2$,Glu(NH-hexyl)$^{3,17}$,Dhp$^7$)hGhrelin(1-28)-NH$_2$; | (SEQ ID NO: 38) |
| Example 45: | (Aib$^2$,Glu(NH-hexyl)$^{3,17}$,Pip$^7$)hGhrelin(1-28)-NH$_2$; | (SEQ ID NO: 38) |
| Example 46: | (Aib$^2$,Glu(NH-hexyl)$^{3,17}$,Tic$^7$)hGhrelin(1-28)-NH$_2$; | (SEQ ID NO: 38) |
| Example 47: | (Aib$^{2,8}$,Glu(NH-hexyl)$^{17}$)hGhrelin(1-28)-NH$_2$; | (SEQ ID NO: 39) |
| Example 48: | (Aib$^{2,8}$,Glu(NH-hexyl)$^{3,17}$)hGhrelin(1-28)-NH$_2$; | (SEQ ID NO: 40) |
| Example 49: | (Aib$^2$,3-Pal$^9$,Glu(NH-hexyl)$^{17}$)hGhrelin(1-28)-NH$_2$; | (SEQ ID NO: 41) |
| Example 50: | (Aib$^2$,4-Pal$^9$,Glu(NH-hexyl)$^{17}$)hGhrelin(1-28)-NH$_2$; | (SEQ ID NO: 41) |
| Example 51: | (Aib$^2$,Taz$^9$,Glu(NH-hexyl)$^{17}$)hGhrelin(1-28)-NH$_2$; | (SEQ ID NO: 41) |
| Example 52: | (Aib$^2$,2-Thi$^9$,Glu(NH-hexyl)$^{17}$)hGhrelin(1-28)-NI-L; | (SEQ ID NO: 41) |
| Example 53: | (Aib$^2$,Glu(NH-hexyl)$^{3,17}$,3-Pal$^9$)hGhrelin(1-28)-NH$_2$; | (SEQ ID NO: 42) |
| Example 54: | (Aib$^2$,Glu(NH-hexyl)$^{3,17}$,4-Pal$^9$)hGhrelin(1-28)-NH$_2$; | (SEQ ID NO: 42) |
| Example 55: | (Aib$^2$,Glu(NH-hexyl)$^{3,17}$,Taz$^9$)hGhrelin(1-28)-NH$_2$; | (SEQ ID NO: 42) |
| Example 56: | (Aib$^2$,Glu(NH-hexyl)$^{3,17}$,2-Thi$^9$)hGhrelin(1-28)-NH$_2$; | (SEQ ID NO: 42) |
| Example 57: | (Aib$^{2,10}$,Glu(NH-hexyl)$^{17}$)hGhrelin(1-28)-NH$_2$; | (SEQ ID NO: 43) |
| Example 58: | (Aib$^{2,10}$,Glu(NH-hexyl)$^{3,17}$)hGhrelin(1-28)-NH$_2$; | (SEQ ID NO: 44) |

-continued

| | | |
|---|---|---|
| Example 59: | (Aib$^8$,Glu(NH-hexyl)$^{17}$)hGhrelin(1-28)-NH$_2$; | (SEQ ID NO: 45) |
| Example 60: | (Taz$^9$,Glu(NH-hexyl)$^{17}$)hGhrelin(1-28)-NH$_2$; | (SEQ ID NO: 46) |
| Example 61: | (3-Pal$^9$,Glu(NH-hexyl)$^{17}$)hGhrelin(1-28)-NH$_2$; | (SEQ ID NO: 46) |
| Example 62: | (4-Pal$^9$,Glu(NH-hexyl)$^{17}$)hGhrelin(1-28)-NH$_2$; | (SEQ ID NO: 46) |
| Example 63: | (2-Thi$^9$,Glu(NH-hexyl)$^{17}$)hGhrelin(1-28)-NH$_2$; | (SEQ ID NO: 46) |
| Example 64: | (Glu(NH-hexyl)$^{3,17}$,Aib$^8$)hGhrelin(1-28)-NH$_2$; | (SEQ ID NO: 47) |
| Example 65: | (Glu(NH-hexyl)$^{3,17}$,Taz$^9$)hGhrelin(1-28)-NH$_2$; | (SEQ ID NO: 48) |
| Example 66: | (Glu(NH-hexyl)$^{3,17}$,3-Pal$^9$)hGhrelin(1-28)-NH$_2$; | (SEQ ID NO: 48) |
| Example 67: | (Glu(NH-hexyl)$^{3,17}$,4-Pal$^9$)hGhrelin(1-28)-NH$_2$; | (SEQ ID NO: 48) |
| Example 68: | (Glu(NH-hexyl)$^{3,17}$,2-Thi$^9$)hGhrelin(1-28)-NH$_2$; | (SEQ ID NO: 48) |
| Example 69: | (Aib$^{1,2,10}$,Glu(NH-hexyl)$^{17}$)hGhrelin(1-28)-NH$_2$; | (SEQ ID NO: 49) |
| Example 71: | (A5c$^2$,Glu(NH-hexyl)$^{17}$)hGhrelin(1-28)-NH$_2$; | (SEQ ID NO: 51) |
| Example 72: | (A5c$^2$,Glu(NH-hexyl)$^{3,17}$)hGhrelin(1-28)-NH$_2$; | (SEQ ID NO: 52) |
| Example 73: | (Glu(1-heptanol)$^{3,17}$)hGhrelin(1-28)-NH$_2$; | (SEQ ID NO: 53) |
| Example 74: | (Asp(1-heptanol)$^{3,17}$)hGhrelin(1-28)-NH$_2$; | (SEQ ID NO: 54) |
| Example 75: | (Glu(NH-hexyl)$^{3,17}$)hGhrelin(1-28)-NH$_2$; | (SEQ ID NO: 55) |
| Example 76: | (Asp(NH-hexyl)$^{3,17}$)hGhrelin(1-28)-NH$_2$; | (SEQ ID NO: 56) |
| Example 77: | (Aib$^2$,Glu(NH-hexyl)$^{3,17}$)hGhrelin(1-28)-NH$_2$; | (SEQ ID NO: 57) |
| Example 78: | (Lys(biotinyl)$^{17}$)hGhrelin(1-28)-NH$_2$; | (SEQ ID NO: 58) |
| Example 79: | (Ser(n-octanoyl)$^{18}$)hGhrelin(1-28)-NH$_2$; | (SEQ ID NO: 59) |
| Example 80: | (Glu(NH-hexyl)$^{18}$)hGhrelin(1-28)-NH$_2$; | (SEQ ID NO: 60) |
| Example 81: | (Glu(NH-hexyl)$^{3,18}$)hGhrelin(1-28)-NH$_2$; | (SEQ ID NO: 61) |
| Example 82: | (Glu(NH-hexyl)$^3$,(n-octanoyl)$^{18}$)hGhrelin(1-28)-NH$_2$; | (SEQ ID NO: 62) |
| Example 83: | (Aib$^2$,Glu(NH-hexyl)$^{18}$)hGhrelin(1-28)-NH$_2$; | (SEQ ID NO: 63) |
| Example 84: | (Aib$^2$,Glu(NH-hexyl)$^{3,18}$)hGhrelin(1-28)-NH$_2$; | (SEQ ID NO: 64) |
| Example 85: | (Aib$^{2,8}$,Glu(NH-hexyl)$^{18}$)hGhrelin(1-28)-NH$_2$; | (SEQ ID NO: 65) |
| Example 86: | (Aib$^{2,8}$,Glu(NH-hexyl)$^{3,18}$)hGhrelin(1-28)-NH$_2$; | (SEQ ID NO: 66) |
| Example 87: | (Aib$^{2,10}$,Glu(NH-hexyl)$^{18}$)hGhrelin(1-28)-NH$_2$; | (SEQ ID NO: 67) |
| Example 88: | (Aib$^{2,10}$,Glu(NH-hexyl)$^{3,18}$)hGhrelin(1-28)-NH$_2$; | (SEQ ID NO: 68) |
| Example 89: | (Ser(n-octanoyl)$^{19}$)hGhrelin(1-28)-NH$_2$; | (SEQ ID NO: 69) |
| Example 90: | (Glu(NH-hexyl)$^{19}$)hGhrelin(1-28)-NH$_2$; | (SEQ ID NO: 70) |
| Example 91: | (Glu(NH-hexyl)$^{3,19}$)hGhrelin(1-28)-NH$_2$; | (SEQ ID NO: 71) |
| Example 92: | (Glu(NH-hexyl)$^3$,Ser(n-octanoyl)$^{19}$)hGhrelin(1-28)-NH$_2$; | (SEQ ID NO: 72) |
| Example 93: | (Aib$^2$,Glu(NH-hexyl)$^{19}$)hGhrelin(1-28)-NH$_2$; | (SEQ ID NO: 73) |
| Example 94: | (Aib$^2$,Glu(NH-hexyl)$^{3,19}$)hGhrelin(1-28)-NH$_2$; | (SEQ ID NO: 74) |
| Example 95: | (Aib$^{2,8}$,Glu(NH-hexyl)$^{19}$)hGhrelin(1-28)-NH$_2$; | (SEQ ID NO: 75) |
| Example 96: | (Aib$^{2,8}$,Glu(NH-hexyl)$^{3,19}$)hGhrelin(1-28)-NH$_2$; | (SEQ ID NO: 76) |
| Example 97: | (Aib$^{2,10}$,Glu(NH-hexyl)$^{19}$)hGhrelin(1-28)-NH$_2$; | (SEQ ID NO: 77) |
| Example 98: | (Aib$^{2,10}$,Glu(NH-hexyl)$^{3,19}$)hGhrelin(1-28)-NH$_2$; | (SEQ ID NO: 78) |
| Example 99: | (Ser(n-octanoyl)$^{20}$)hGhrelin(1-28)-NH$_2$; | (SEQ ID NO: 79) |
| Example 100: | (Glu(NH-hexyl)$^{20}$)hGhrelin(1-28)-NH$_2$; | (SEQ ID NO: 80) |

-continued

| | | |
|---|---|---|
| Example 101: | (Glu(NH-hexyl)³,²⁰)hGhrelin(1-28)-NH₂; | (SEQ ID NO: 81) |
| Example 102: | (Glu(NH-hexyl)³,Ser(n-octanoyl)²⁰)hGhrelin(1-28)-NH₂; | (SEQ ID NO: 82) |
| Example 103: | (Aib²,Glu(NH-hexyl)²⁰)hGhrelin(1-28)-NH₂; | (SEQ ID NO: 83) |
| Example 104: | (Aib²,Glu(NH-hexyl)³,²⁰)hGhrelin(1-28)-NH₂; | (SEQ ID NO: 84) |
| Example 105: | (Aib²,⁸,Glu(NH-hexyl)²⁰)hGhrelin(1-28)-NH₂; | (SEQ ID NO: 85) |
| Example 106: | (Aib²,⁸,Glu(NH-hexyl)³,²⁰)hGhrelin(1-28)-NH₂; | (SEQ ID NO: 86) |
| Example 107: | (Aib²,¹⁰,Glu(NH-hexyl)²⁰)hGhrelin(1-28)-NH₂; | (SEQ ID NO: 87) |
| Example 108: | (Aib²,¹⁰,Glu(NH-hexyl)³,²⁰)hGhrelin(1-28)-NH₂; | (SEQ ID NO: 88) |
| Example 109: | (Ac-Gly¹,Glu(NH-hexyl)¹⁷)hGhrelin(1-28)-NH₂; | (SEQ ID NO: 89) |
| Example 110: | (Ac-Gly¹,Ser(n-octanoyl)¹⁷)hGhrelin(1-28)-NH₂; | (SEQ ID NO: 90) |
| Example 111: | (Ac-Gly¹,Glu(NH-hexyl)³,¹⁷)hGhrelin(1-28)-NH₂; | (SEQ ID NO: 91) |
| Example 112: | (Ac-Gly¹,Glu(NH-hexyl)³,Ser(n-octanoyl)¹⁷)hGhrelin(1-28)-NH₂; | (SEQ ID NO: 92) |
| Example 113: | (Ac-Gly¹,Dap(octanesulfonyl)¹⁷)hGhrelin(1-28)-NH₂; | (SEQ ID NO: 93) |
| Example 114: | (Ac-Gly¹,Dap(octanesulfonyl)³,¹⁷)hGhrelin(1-28)-NH₂; | (SEQ ID NO: 94) |
| Example 115: | (Ac-Gly¹,Dap(octanesulfonyl)³,Glu(NH-Hexyl)¹⁷)hGhrelin(1-28)-NH₂; | (SEQ ID NO: 95) |
| Example 116: | (Ac-Gly¹,Dap(octanesulfonyl)³,Ser(n-octanoyl)¹⁷)hGhrelin(1-28)-NH₂; | (SEQ ID NO: 96) |
| Example 117: | (Ac-Gly¹,Glu(NH-hexyl)³,Dap(octanesulfonyl)¹⁷)hGhrelin(1-28)-NH₂; | (SEQ ID NO: 97) |
| Example 118: | (Ac-Gly¹,(Cys(S-(CH₂)₉CH₃)¹⁷)hGhrelin(1-28)-NH₂; | (SEQ ID NO: 98) |
| Example 119: | (Ac-Gly¹,(Cys(S-(CH₂)₉CH₃)³,¹⁷)hGhrelin(1-28)-NH₂; | (SEQ ID NO: 99) |
| Example 120: | (Ac-Gly¹,Glu(NH-hexyl)³,(Cys(S-(CH₂)₉CH₃)¹⁷)hGhrelin(1-28)-NH₂; | (SEQ ID NO: 100) |
| Example 121: | (Ac-Gly¹,(Cys(S-(CH₂)₉CH₃)³,Glu(NH-hexyl)¹⁷)hGhrelin(1-28)-NH₂; | (SEQ ID NO: 101) |
| Example 122: | (Ac-Gly¹,(Cys(S-(CH₂)₉CH₃)³,Ser(n-octanoyl)¹⁷)hGhrelin(1-28)-NH₂; | (SEQ ID NO: 102) |
| Example 123: | (Ac-Gly¹,Aib²,Glu(NH-hexyl)hGhrelin(1-28)-NH₂; | (SEQ ID NO: 103) |
| Example 124: | (Ac-Gly¹,Aib²,Glu(NH-hexyl)³,¹⁷)hGhrelin(1-28)-NH₂; | (SEQ ID NO: 104) |
| Example 125: | (Ac-Gly¹,Aib²,Thz⁷,Glu(NH-hexyl)¹⁷)hGhrelin(1-28)-NH₂; | (SEQ ID NO: 105) |
| Example 126: | (Ac-Gly¹,Aib²,4-Hyp⁷,Glu(NH-hexyl)¹⁷)hGhrelin(1-28)-NH₂; | (SEQ ID NO: 105) |
| Example 127: | (Ac-Gly¹,Aib²,Dhp⁷,Glu(NH-hexyl)¹⁷)hGhrelin(1-28)-NH₂; | (SEQ ID NO: 105) |
| Example 128: | (Ac-Gly¹,Aib²,Pip⁷,Glu(NH-hexyl)¹⁷)hGhrelin(1-28)-NH₂; | (SEQ ID NO: 105) |
| Example 129: | (Ac-Gly¹,Aib²,Tic⁷,Glu(NH-hexyl)¹⁷)hGhrelin(1-28)-NH₂; | (SEQ ID NO: 105) |
| Example 130: | (Ac-Gly¹,Aib²,Glu(NH-hexyl)3,17,Thz-hGhrelin(1-28)-NH₂; | (SEQ ID NO: 106) |
| Example 131: | (Ac-Gly¹,Aib²,Glu(NH-hexyl)³,¹⁷,4-Hyp-hGhrelin(1-28)-NH₂; | (SEQ ID NO: 106) |
| Example 132: | (Ac-Gly¹,Aib²,Glu(NH-hexyl)³,¹⁷,Dhp⁷)hGhrelin(1-28)-NH₂; | (SEQ ID NO: 106) |
| Example 133: | (Ac-Gly¹,Aib²,Glu(NH-hexyl)³,¹⁷,Pip⁷)hGhrelin(1-28)-NH₂; | (SEQ ID NO: 106) |
| Example 134: | (Ac-Gly¹,Aib²,Glu(NH-hexyl)³,¹⁷,Tic⁷)hGhrelin(1-28)-NH₂; | (SEQ ID NO: 106) |
| Example 135: | (Ac-Gly¹,Aib²,⁸,Glu(NH-hexyl)¹⁷)hGhrelin(1-28)-NH₂; | (SEQ ID NO: 107) |
| Example 136: | (Ac-Gly¹,Aib²,⁸,Glu(NH-hexyl)³,¹⁷)hGhrelin(1-28)-NH₂; | (SEQ ID NO: 108) |
| Example 137: | (Ac-Gly¹,Aib²,3-Pal⁹,Glu(NH-hexyl)¹⁷)hGhrelin(1-28)-NH₂; | (SEQ ID NO: 109) |
| Example 138: | (Ac-Gly¹,Aib²,4-Pal⁹,Glu(NH-hexyl)¹⁷)hGhrelin(1-28)-NH₂; | (SEQ ID NO: 109) |
| Example 139: | (Ac-Gly¹,Aib²,Taz⁹,Glu(NH-hexyl)¹⁷)hGhrelin(1-28)-NH₂; | (SEQ ID NO: 109) |
| Example 140: | (Ac-Gly¹,Aib²,2-Thi⁹,Glu(NH-hexyl)¹⁷)hGhrelin(1-28)-NH₂; | (SEQ ID NO: 109) |

-continued

| | | |
|---|---|---|
| Example 141: | (Ac-Gly$^1$,Aib$^2$,Glu(NH-hexyl)$^{3,17}$,3-Pal$^9$)hGhrelin(1-28)-NH$_2$; | (SEQ ID NO: 110) |
| Example 142: | (Ac-Gly$^1$,Aib$^2$,Glu(NH-hexyl)$^{3,17}$,4-Pal$^9$)hGhrelin(1-28)-NH$_2$; | (SEQ ID NO: 110) |
| Example 143: | (Ac-Gly$^1$,Aib$^2$,Glu(NH-hexyl)$^{3,17}$,Taz$^9$)hGhrelin(1-28)-NH$_2$; | (SEQ ID NO: 110) |
| Example 144: | (Ac-Gly$^1$,Aib$^2$,Glu(NH-hexyl)$^{3,17}$,2-Thi$^9$)hGhrelin(1-28)-NH$_2$; | (SEQ ID NO: 110) |
| Example 145: | (Ac-Gly$^1$,Aib$^{2,10}$,Glu(NH-hexyl)$^{17}$)hGhrelin(1-28)-NH$_2$; | (SEQ ID NO: 111) |
| Example 146: | (Ac-Gly$^1$,Aib$^{2,10}$,Glu(NH-hexyl)$^{3,17}$)hGhrelin(1-28)-NH$_2$; | (SEQ ID NO: 112) |
| Example 147: | (Ac-Gly$^1$,Aib$^8$,Glu(NH-hexyl)$^{17}$)hGhrelin(1-28)-NH$_2$; | (SEQ ID NO: 113) |
| Example 148: | (Ac-Gly$^1$,Taz$^9$,Glu(NH-hexyl)$^{17}$)hGhrelin(1-28)-NH$_2$; | (SEQ ID NO: 114) |
| Example 149: | (Ac-Gly$^1$,3-Pal$^9$,Glu(NH-hexyl)$^{17}$)hGhrelin(1-28)-NH$_2$; | (SEQ ID NO: 114) |
| Example 150: | (Ac-Gly$^1$,4-Pal$^9$,Glu(NH-hexyl)$^{17}$)hGhrelin(1-28)-NH$_2$; | (SEQ ID NO: 114) |
| Example 151: | (Ac-Gly$^1$,2-Thi$^9$,Glu(NH-hexyl)$^{17}$)hGhrelin(1-28)-NH$_2$; | (SEQ ID NO: 114) |
| Example 152: | (Ac-Gly$^1$,Glu(NH-hexyl)$^{3,17}$,Aib$^8$)hGhrelin(1-28)-NH$_2$; | (SEQ ID NO: 115) |
| Example 153: | (Ac-Gly$^1$,Glu(NH-hexyl)$^{3,17}$,Taz$^9$)hGhrelin(1-28)-NH$_2$; | (SEQ ID NO: 116) |
| Example 154: | (Ac-Gly$^1$,Glu(NH-hexyl)$^{3,17}$,3-Pal$^9$)hGhrelin(1-28)-NH$_2$; | (SEQ ID NO: 116) |
| Example 155: | (Ac-Gly$^1$,Glu(NH-hexyl)$^{3,17}$,4-Pal$^9$)hGhrelin(1-28)-NH$_2$; | (SEQ ID NO: 116) |
| Example 156: | (Ac-Gly$^1$,Glu(NH-hexyl)$^{3,17}$,2-Thi$^9$)hGhrelin(1-28)-NH$_2$; | (SEQ ID NO: 116) |
| Example 157: | (Ac-Aib$^1$,Aib$^{2,10}$,Glu(NH-hexyl)$^{17}$)hGhrelin(1-28)-NH$_2$; | (SEQ ID NO: 117) |
| Example 159: | (Ac-Gly$^1$,A5c$^2$,Glu(NH-hexyl)1-hGhrelin(1-28)-NH$_2$; | (SEQ ID NO: 119) |
| Example 160: | (Ac-Gly$^1$,A5c$^2$,Glu(NH-hexyl)$^{3,17}$)hGhrelin(1-28)-NH$_2$; | (SEQ ID NO: 120) |
| Example 161: | (Ac-Gly$^1$,Glu(1-heptanol)$^{3,17}$)hGhrelin(1-28)-NH$_2$; | (SEQ ID NO: 121) |
| Example 162: | (Ac-Gly$^1$,Asp(1-heptanol)$^{3,17}$)hGhrelin(1-28)-NH$_2$; | (SEQ ID NO: 122) |
| Example 163: | (Ac-Gly$^1$,Glu(NH-hexyl)$^{3,17}$)hGhrelin(1-28)-NH$_2$; | (SEQ ID NO: 123) |
| Example 164: | (Ac-Gly$^1$,Asp(NH-hexyl)3$^{3,17}$)hGhrelin(1-28)-NH$_2$; | (SEQ ID NO: 124) |
| Example 165: | (Ac-Gly$^1$,Aib$^2$,Glu(NH-hexyl)$^{3,17}$)hGhrelin(1-28)-NH$_2$; | (SEQ ID NO: 125) |
| Example 166: | (Ac-Gly$^1$,Aib$^{2,10}$,Glu(NH-hexyl)$^3$,Lys(biotinyl)$^{17}$)hGhrelin(1-28)-NH$_2$; | (SEQ ID NO: 126) |
| Example 167: | (Ac-Gly$^1$,Glu(NH-hexyl)$^{15}$)hGhrelin(1-28)-NH$_2$; | (SEQ ID NO: 127) |
| Example 168: | (Ac-Gly$^1$,Ser(n-octanoyl)$^{15}$)hGhrelin(1-28)-NH$_2$; | (SEQ ID NO: 128) |
| Example 169: | (Ac-Gly$^1$,Glu(NH-hexyl)$^{3,15}$)hGhrelin(1-28)-NH$_2$; | (SEQ ID NO: 129) |
| Example 170: | (Ac-Gly$^1$,Glu(NH-hexyl)$^3$,Ser(n-octanoyl)$^{15}$)hGhrelin(1-28)-NH$_2$; | (SEQ ID NO: 130) |
| Example 171: | (Ac-Gly$^1$,Aib$^2$,Glu(NH-hexyl)$^{15}$)hGhrelin(1-28)-NH$_2$; | (SEQ ID NO: 131) |
| Example 172: | (Ac-Gly$^1$,Aib$^2$,Glu(NH-hexyl)$^{3,15}$)hGhrelin(1-28)-NH$_2$; | (SEQ ID NO: 132) |
| Example 173: | (Ac-Gly$^1$,Aib$^{2,8}$,Glu(NH-hexyl)$^{15}$)hGhrelin(1-28)-NH$_2$; | (SEQ ID NO: 133) |
| Example 174: | (Ac-Gly$^1$,Aib$^{2,8}$,Glu(NH-hexyl)$^{3,15}$)hGhrelin(1-28)-NH$_2$; | (SEQ ID NO: 134) |
| Example 175: | (Ac-Gly$^1$,Aib$^{2,10}$,Glu(NH-hexyl)$^{15}$)hGhrelin(1-28)-NH$_2$; | (SEQ ID NO: 135) |
| Example 176: | (Ac-Gly$^1$,Aib$^{2,10}$,Glu(NH-hexyl)$^{3,15}$)hGhrelin(1-28)-NH$_2$; | (SEQ ID NO: 136) |
| Example 177: | (Ac-Gly$^1$,Glu(NH-hexyl)$^{16}$)hGhrelin(1-28)-NH$_2$; | (SEQ ID NO: 137) |
| Example 178: | (Ac-Gly$^1$,Ser(n-octanoyl)$^{16}$)hGhrelin(1-28)-NH$_2$; | (SEQ ID NO: 138) |
| Example 179: | (Ac-Gly$^1$,Glu(NH-hexyl)$^{3,16}$)hGhrelin(1-28)-NH$_2$; | (SEQ ID NO: 139) |
| Example 180: | (Ac-Gly$^1$,Glu(NH-hexyl)$^3$,Ser(n-octanoyl)$^{16}$)hGhrelin(1-28)-NH$_2$; | (SEQ ID NO: 140) |
| Example 181: | (Ac-Gly$^1$,Aib$^2$,Glu(NH-hexyl)$^{16}$)hGhrelin(1-28)-NH$_2$; | (SEQ ID NO: 141) |
| Example 182: | (Ac-Gly$^1$,Aib$^2$,Glu(NH-hexyl)$^{3,16}$)hGhrelin(1-28)-NH$_2$; | (SEQ ID NO: 142) |

-continued

| | | |
|---|---|---|
| Example 183: | (Ac-Gly$^1$,Aib$^{2,8}$,Glu(NH-hexyl)$^{16}$)hGhrelin(1-28)-NH$_2$; | (SEQ ID NO: 143) |
| Example 184: | (Ac-Gly$^1$,Aib$^{2,8}$,Glu(NH-hexyl)$^{3,16}$)hGhrelin(1-28)-NH$_2$; | (SEQ ID NO: 144) |
| Example 185: | (Ac-Gly$^1$,Aib$^{2,10}$,Glu(NH-hexyl)$^{16}$)hGhrelin(1-28)-NH$_2$; | (SEQ ID NO: 145) |
| Example 186: | (Ac-Gly$^1$,Aib$^{2,10}$,Glu(NH-hexyl)$^{3,16}$)hGhrelin(1-28)-NH$_2$; | (SEQ ID NO: 146) |
| Example 187: | (Ac-Gly$^1$,Glu(NH-hexyl)$^{18}$)hGhrelin(1-28)-NH$_2$; | (SEQ ID NO: 147) |
| Example 188: | (Ac-Gly$^1$,Ser(n-octanoyl)$^{18}$)hGhrelin(1-28)-NH$_2$; | (SEQ ID NO: 148) |
| Example 189: | (Ac-Gly$^1$,Glu(NH-hexyl)$^{3,18}$)hGhrelin(1-28)-NH$_2$; | (SEQ ID NO: 149) |
| Example 190: | (Ac-Gly$^1$,Glu(NH-hexyl)$^3$,Ser(n-octanoyl)$^{18}$)hGhrelin(1-28)-NH$_2$; | (SEQ ID NO: 150) |
| Example 191: | (Ac-Gly$^1$,Aib$^2$,Glu(NH-hexyl)$^{18}$)hGhrelin(1-28)-NH$_2$; | (SEQ ID NO: 151) |
| Example 192: | (Ac-Gly$^1$,Aib$^2$,Glu(NH-hexyl)$^{3,18}$)hGhrelin(1-28)-NH$_2$; | (SEQ ID NO: 152) |
| Example 193: | (Ac-Gly$^1$,Aib$^{2,8}$,Glu(NH-hexyl)$^{18}$)hGhrelin(1-28)-NH$_2$; | (SEQ ID NO: 153) |
| Example 194: | (Ac-Gly$^1$,Aib$^{2,8}$,Glu(NH-hexyl)$^{3,18}$)hGhrelin(1-28)-NH$_2$; | (SEQ ID NO: 154) |
| Example 195: | (Ac-Gly$^1$,Aib$^{2,10}$,Glu(NH-hexyl)$^{18}$)hGhrelin(1-28)-NH$_2$; | (SEQ ID NO: 155) |
| Example 196: | (Ac-Gly$^1$,Aib$^{2,10}$,Glu(NH-hexyl)$^{3,18}$)hGhrelin(1-28)-NH$_2$; | (SEQ ID NO: 156) |
| Example 197: | (Ac-Gly$^1$,Glu(NH-hexyl)$^{19}$)hGhrelin(1-28)-NH$_2$; | (SEQ ID NO: 157) |
| Example 198: | (Ac-Gly$^1$,Ser(n-octanoyl)$^{19}$)hGhrelin(1-28)-NH$_2$; | (SEQ ID NO: 158) |
| Example 199: | (Ac-Gly$^1$,Glu(NH-hexyl)$^{3,19}$)hGhrelin(1-28)-NH$_2$; | (SEQ ID NO: 159) |
| Example 200: | (Ac-Gly$^1$,Glu(NH-hexyl)$^3$,Ser(n-octanoyl)$^{19}$)hGhrelin(1-28)-NH$_2$; | (SEQ ID NO: 160) |
| Example 201: | (Ac-Gly$^1$,Aib$^2$,Glu(NH-hexyl)$^{19}$)hGhrelin(1-28)-NH$_2$; | (SEQ ID NO: 161) |
| Example 202: | (Ac-Gly$^1$,Aib$^2$,Glu(NH-hexyl)$^{3,19}$)hGhrelin(1-28)-NH$_2$; | (SEQ ID NO: 162) |
| Example 203: | (Ac-Gly$^1$,Aib$^{2,8}$,Glu(NH-hexyl)$^{19}$)hGhrelin(1-28)-NH$_2$; | (SEQ ID NO: 163) |
| Example 204: | (Ac-Gly$^1$,Aib$^{2,8}$,Glu(NH-hexyl)$^{3,19}$)hGhrelin(1-28)-NH$_2$; | (SEQ ID NO: 164) |
| Example 205: | (Ac-Gly$^1$,Aib$^{2,10}$,Glu(NH-hexyl)$^{19}$)hGhrelin(1-28)-NH$_2$; | (SEQ ID NO: 165) |
| Example 206: | (Ac-Gly$^1$,Aib$^{2,10}$,Glu(NH-hexyl)$^{3,19}$)hGhrelin(1-28)-NH$_2$; | (SEQ ID NO: 166) |
| Example 207: | (Ac-Gly$^1$,Glu(NH-hexyl)$^{20}$)hGhrelin(1-28)-NH$_2$; | (SEQ ID NO: 167) |
| Example 208: | (Ac-Gly$^1$,Ser(n-octanoyl)$^{20}$)hGhrelin(1-28)-NH$_2$; | (SEQ ID NO: 168) |
| Example 209: | (Ac-Gly$^1$,Glu(NH-hexyl)$^{3,20}$)hGhrelin(1-28)-NH$_2$; | (SEQ ID NO: 169) |
| Example 210: | (Ac-Gly$^1$,Glu(NH-hexyl)$^3$,Ser(n-octanoyl)$^{20}$)hGhrelin(1-28)-NH$_2$; | (SEQ ID NO: 170) |
| Example 211: | (Ac-Gly$^1$,Aib$^2$,Glu(NH-hexyl)$^{20}$)hGhrelin(1-28)-NH$_2$; | (SEQ ID NO: 171) |
| Example 212: | (Ac-Gly$^1$,Aib$^2$,Glu(NH-hexyl)$^{3,20}$)hGhrelin(1-28)-NH$_2$; | (SEQ ID NO: 172) |
| Example 213: | (Ac-Gly$^1$,Aib$^{2,8}$,Glu(NH-hexyl)$^{20}$)hGhrelin(1-28)-NH$_2$; | (SEQ ID NO: 173) |
| Example 214: | (Ac-Gly$^1$,Aib$^{2,8}$,Glu(NH-hexyl)$^{3,20}$)hGhrelin(1-28)-NH$_2$; | (SEQ ID NO: 174) |
| Example 215: and | (Ac-Gly$^1$,Aib$^{2,10}$,Glu(NH-hexyl)$^{20}$)hGhrelin(1-28)-NH$_2$; | (SEQ ID NO: 175) |
| Example 216: | (Ac-Gly$^1$,Aib$^{2,10}$,Glu(NH-hexyl)$^{3,20}$)hGhrelin(1-28)-NH$_2$; | (SEQ ID NO: 176) |
| Example 217: and | (Aib$^2$,Lys(myristyl)$^{17}$)hGhrelin(1-28)-NH$_2$; | (SEQ ID NO: 177) |
| Example 218: | (Gly(myristyl)$^1$,Aib$^2$,Lys(myristyl)$^{17}$)hGhrelin(1-28)-NH$_2$. | (SEQ ID NO: 178) |
| Example 219: | (Aib$^{2,8}$,Ser$^3$,Glu(NH-hexyl)$^{17}$)hGrehlin(1-28)-NH$_2$ | (SEQ ID NO: 179) |

A selection of the preferred embodiments listed above was analyzed by electro-spray ionization mass spectrometry (ESI-MS) to determine molecular weight. Table 1 presented below reports the data compiled during this testing. The purity of each of the selected compounds, assayed using HPLC, is also provided in Tables 1A, 1B, 1C, and 1D.

TABLE 1A

Molecular Weight and Purity of Selected Compounds

| Example # | COMPOUND | Molecular Weight (Calculated) | Molecular Weight (MS-ES) | Purity (%) |
|---|---|---|---|---|
| #48 (SEQ ID NO: 40) | (Aib$^{2,8}$,Glu(NH-hexyl)$^{3,17}$)hGhrelin(1-28)-NH$_2$ | 3406.12 | 3405.70 | 99.9% |
| #136 (SEQ ID NO: 108) | (Ac-Gly$^1$,Aib$^{2,8}$,Glu(NH-hexyl)$^{3,17}$)hGhrelin(1-28)-NH$_2$ | 3448.16 | 3447.98 | 98.0% |
| #124 (SEQ ID NO: 104) | (Ac-Gly$^1$,Aib$^2$,Glu(NH-hexyl)$^{3,17}$)hGhrelin(1-28)-NH$_2$ | 3492.17 | 3492.00 | 99.0% |
| #166 (SEQ ID NO: 126) | (Ac-Gly$^1$,Aib$^{2,10}$,Glu(NH-hexyl)$^3$,Lys(biotinyl)$^{17}$)hGhrelin(1-28)-NH$_2$ | 3591.32 | 3591.50 | 98.4% |
| #70 (SEQ ID NO: 50) | (Aib$^{1,2,10}$,Glu(NH-hexyl)$^{3,17}$)hGhrelin(1-28)-NH$_2$ | 3435.16 | 3435.00 | 96.5% |
| #158 (SEQ ID NO: 118) | (Ac-Aib$^1$,Aib$^{2,10}$,Glu(NH-hexyl)$^{3,17}$)hGhrelin(1-28)-NH$_2$ | 3477.19 | 3477.40 | 97.5% |
| #146 (SEQ ID NO: 112) | (Ac-Gly$^1$,Aib$^{2,10}$,Glu(NH-hexyl)$^{3,17}$)hGhrelin(1-28)-NH$_2$ | 3449.14 | 3449.20 | 99.0% |
| #78 (SEQ ID NO: 58) | (Lys(biotinyl)$^{17}$)hGhrelin(1-28)-NH$_2$ | 3595.27 | 3594.90 | 97.7% |

TABLE 1B

Molecular Weight and Purity of Selected Compounds

| Example # | COMPOUND | Molecular Weight (Calculated) | Molecular Weight (MS-ES) | Purity (%) |
|---|---|---|---|---|
| #217 (SEQ ID NO: 177) | (Aib$^2$,Lys(myristyl)$^{17}$)hGhrelin(1-28)-NH$_2$ | 3577.35 | 3577.2 | 99.2% |
| #218 (SEQ ID NO: 178) | (Gly(myristyl)$^1$,Aib$^2$,Lys(myristyl)$^{17}$)hGhrelin(1-28)-NH$_2$ | 3787.71 | 3788.2 | 98.6% |

TABLE 1C

Molecular Weight and Purity of Selected Compounds

| Example # | COMPOUND | Molecular Weight (Calculated) | Molecular Weight (MS-ES) | Purity (%) |
|---|---|---|---|---|
| #58 (SEQ ID NO: 44) | (Aib$^{2,10}$,Glu(NH-hexyl)$^{3,17}$)hGhrelin(1-28)-NH$_2$ | 3407.10 | 3407.20 | 100% |

TABLE 1D

Molecular Weight and Purity of Selected Compounds

| Example # | COMPOUND | Molecular Weight (Calculated) | Molecular Weight (MS-ES) | Purity (%) |
|---|---|---|---|---|
| #219 (SEQ ID NO: 179) | (Aib$^{2,8}$,Ser$^3$,Glu(NH-hexyl)$^{17}$)hGhrelin(1-28)-NH$_2$ | 3280.91 | 3281.60 | 99.0% |

Determination of Biological Activity
GHS Receptor Binding Determination Assay

The activity of the compounds of the invention at the GHS receptor can be and were determined using techniques such as those described in the examples provided below. In different embodiments, a ghrelin analog has at least about 50%, at least about 60%, at least about 70%, at least about 80% at least about 90%, at least about 95%, at least about 98% or more, functional activity relative to ghrelin as determined using one or more of the functional activity assays described below; and/or has an $IC_{50}$ greater than about 1,000 nM, greater than about 100 nM, or greater than about 50 nM, using the receptor binding assay described below. With respect to $IC_{50}$, greater refers to potency and thus indicates a lesser amount is needed to achieve binding inhibition.

Assays measuring the ability of a compound to bind a GHS receptor employ a GHS receptor, a fragment of the receptor comprising a ghrelin binding site, a polypeptide comprising such a fragment, or a derivative of the polypeptide. Preferably, the assay uses the GHS receptor or a fragment thereof.

A polypeptide comprising a GHS receptor fragment that binds ghrelin can also contain one or more polypeptide regions not found in a GHS receptor. A derivative of such a polypeptide comprises a GHS receptor fragment that binds ghrelin along with one or more non-peptide components.

The GHS receptor amino acid sequence involved in ghrelin binding can be readily identified using labeled ghrelin or ghrelin analogs and different receptor fragments. Different strategies can be employed to select fragments to be tested to narrow down the binding region. Examples of such strategies include, but are not limited to, testing consecutive fragments about 15 amino acids in length starting at the N-terminus and testing longer length fragments. If longer length fragments are tested, a fragment binding ghrelin can be subdivided to further locate the ghrelin binding region. Fragments used for binding studies can be generated using recombinant nucleic acid techniques.

Binding assays can be performed using individual compounds or preparations containing different numbers of compounds. A preparation containing different numbers of compounds having the ability to bind to the GHS receptor can be divided into smaller groups of compounds that can be tested to identify the compound(s) binding to the GHS receptor. In an embodiment of the present invention, a test preparation containing at least 10 compounds is used in a binding assay.

Binding assays can be performed using recombinantly produced GHS receptor polypeptides present in different environments. Such environments include, for example, cell extracts and purified cell extracts containing the GHS receptor polypeptide expressed from recombinant nucleic acid or naturally occurring nucleic acid; and also include, for example, the use of a purified GHS receptor polypeptide produced by recombinant means or from naturally occurring nucleic acid which is introduced into a different environment.

Screening for GHS Receptor Active Compounds

Screening for GHS receptor active compounds is facilitated using a recombinantly expressed receptor. A recombinantly expressed GHS receptor offers several advantages such as the ability to express the receptor in a defined cell system so that a response to a compound at the GHS receptor can more readily be differentiated from responses at other receptors. For example, the GHS receptor can be expressed in a cell line such as HEK 293, COS 7 and CHO not normally expressing the receptor by an expression vector wherein the same cell line without the expression vector can act as a control.

Screening for compounds reducing GHS receptor activity is facilitated using a ghrelin analog in the assay which provides for GHS receptor activity. The effect of test compounds on such activity can be measured to identify, for example, allosteric modulators and antagonists.

GHS receptor activity can be measured using different techniques such as detecting a change in the intracellular conformation of the GHS receptor, in the G-protein coupled activities and/or in the intracellular messengers. Preferably, GHS receptor activity is measured using techniques such as those measuring intracellular $Ca^{2+}$. Examples of techniques well known in the art that can be employed to measure $Ca^{2+}$ include the use of dyes such as Fura-2 and the use of $Ca^{2+}$-bioluminescent sensitive reporter proteins such as aequorin. An example of a cell line employing aequorin to measure G-protein activity is HEK293/aeq17 (Button, D. et al., *Cell Calcium*, (1993), 14(9):663-71; and Feighner, S. D. et al., *Science*, (1999), 284(5423):2184-8).

Chimeric receptors containing a ghrelin binding region functionally coupled to a different G-protein can also be used to measure GHS receptor activity. A chimeric GHS receptor contains an N-terminal extracellular domain, a transmembrane domain made up of transmembrane regions, extracellular loop regions and intracellular loop regions and an intracellular carboxy terminus. Techniques for producing chimeric receptors and measuring G-protein coupled responses are provided in, for example, International Patent Application No. PCT/US96/12336 [WO 97/05252] and U.S. Pat. No. 5,264,565 incorporated herein by reference.

Stimulation of GHS Receptor Activity

Ghrelin analogs can be used to stimulate GHS receptor activity which can be used, for example, to study the effects of GHS receptor modulation and/or GH secretion, to identify ghrelin antagonists and/or to benefit a subject suffering from a disease or condition such as a GH-deficient state, diminished muscle mass and/or bone density, sexual dysfunction, unhealthy body weight, loss of motor skills and/or physical functioning and/or a lack of normal appetite.

Increasing weight or appetite is crucial in maintaining an ideal, healthy body weight in an individual susceptible to weight loss, such as the sick or elderly. Loss of weight or appetite in an under weight subject can lead to serious health problems. In a patient suffering from a disease or undergoing a medical treatment which causes weight loss and/or a lack of normal appetite, the effectiveness of the treatment of said disease or condition is contingent upon the patient's ability to maintain a consistent weight. Underweight subjects include those having a body weight about 10% or less, 20% or less, or 30% or less, than the lower end of a "normal" weight range or Body Mass Index ("BMI") which is determined by calculating weight in kilograms divided by the square of height in meters. The BMI "normal" range, which is well known in the art, is 19-22. Individuals whose body-mass index falls below the "normal" range are more susceptible to disease and certain beneficial medical treatments such as chemotherapy, are less effective in individuals having a subnormal BMI.

Biological Assays—Examples
1. Receptor Binding Assay
A. Preparation of CHO-K1 Cells Expressing the Human Recombinant GHS Receptor The cDNA for human GH secretagogue receptor (hGHS-R or ghrelin receptor) was cloned using Polymerase Chain Reaction (PCR) techniques well known to those skilled in the art wherein human brain RNA was employed as a template (obtained from Clontech®, Palo Alto, Calif., U.S.A.), gene specific primers flanking the full-length coding sequence of hGHS-R(S: 5'-ATGTGGAACGCGACGCCCAGCGAA-GAG-3'(SEQ ID NO:184) and AS: 5'-TCATGTATTAATAC-TAGATTCTGTCCA-3'(SEQ ID NO:185)) and Advantage 2 PCR Kit® (available from Clontech®, Palo Alto, Calif., U.S.A.). The PCR product was cloned into the pCR2.1 vector using Original TA Cloning Kit® (obtained from Invitrogen®, Carlsbad, Calif., U.S.A.). The full length human GHS-R was subcloned into the mammalian expression vector pcDNA 3.1 (available from Invitrogen®, Carlsbad, Calif., U.S.A.). The plasmid was transfected into the Chinese hamster ovary cell line, CHO-K1 (provided by American Type Culture Collection®, Rockville, Md., U.S.A.) using known calcium phosphate methods as described in Wigler, M. et al., Cell, (1977), 11(1):223-32. Single cell clones stably expressing the hGHS-R were obtained by selecting transfected cells grown in cloning rings in RPMI 1640 media supplemented with 10% fetal bovine serum and 1 mM sodium pyruvate containing 0.8 mg/ml G418 (purchased from Gibco®, Grand Island, N.Y., U.S.A.).

B. GHS-R Binding Assay:

Membranes for radioligand binding studies can be and were prepared by homogenization of the foregoing CHO-K1 cells expressing the human recombinant GHS receptor in about 20 ml of ice-cold 50 mM Tris-HCl with a Brinkman Polytron® (Brinkman®, Westbury, N.Y., U.S.A.) at setting 6 for about 15 seconds. The homogenates were washed twice by centrifugation (39,000 g/10 minutes) and the final pellets were resuspended in about 50 mM Tris-HCl containing 2.5 mM MgCl$_2$ and 0.1% bovine serum albumin (BSA). For the selected assay, aliquots of approximately 0.4 ml were incubated with 0.05 nM ($^{125}$I)ghrelin (~2000 Ci/mmol; Perkin Elmer Life Sciences®, Boston, Mass., U.S.A.) with and without 0.05 ml of unlabeled competing test peptide. After approximately 60 minutes at 4° C., the bound ($^{125}$I)ghrelin was separated from the free ghrelin by rapid filtration through GF/C filters (available from Brandel®, Gaithersburg, Md., U.S.A.) which were pre-soaked in 0.5% polyethyleneimine/0.1% BSA. The filters were then washed 3 times with 5-ml aliquots of ice-cold 50 mM Tris-HCl and 0.1% BSA. The bound radioactivity trapped on the filters was counted by gamma spectrometry (using a spectrometer from Wallace LKB®, Gaithersburg, Md., U.S.A.). Specific binding was determined by subtracting ($^{125}$I)ghrelin bound in the presence of 1000 nM ghrelin (available from Bachem®, Torrence, Calif., U.S.A.) from the total ($^{125}$I)ghrelin bound.

A selection of the preferred embodiments was tested using the receptor binding assay discussed above and the results are reported in Table 2 presented below.

TABLE 2

Receptor Binding Ki Values for Selected Compounds

| Example # | COMPOUND | Ki(nM) |
|---|---|---|
| #48 (SEQ ID NO: 40) | (Aib$^{2,8}$,Glu(NH-hexyl)$^{3,17}$)hGhrelin(1-28)-NH$_2$ | 0.45 |
| #136 (SEQ ID NO: 108) | (Ac-Gly$^1$,Aib$^{2,8}$,Glu(NH-hexyl)$^{3,17}$)hGhrelin(1-28)-NH$_2$ | 2.94 |
| #124 (SEQ ID NO: 104) | (Ac-Gly$^1$,Aib$^2$,Glu(NH-hexyl)$^{3,17}$)hGhrelin(1-28)-NH$_2$ | 1.68 |
| #166 (SEQ ID NO: 126) | (Ac-Gly$^1$,Aib$^{2,10}$,Glu(NH-hexyl)$^3$,Lys(biotinyl)$^{17}$)hGhrelin(1-28)-NH$_2$ | 1.28 |
| #70 (SEQ ID NO: 50) | (Aib$^{1,2,10}$,Glu(NH-hexyl)$^{3,17}$)hGhrelin(1-28)-NH$_2$ | 0.63 |
| #158 (SEQ ID NO: 118) | (Ac-Aib$^1$,Aib$^{2,10}$,Glu(NH-hexyl)$^{3,17}$)hGhrelin(1-28)-NH$_2$ | 24.44 |
| #146 (SEQ ID NO: 112) | (Ac-Gly$^1$,Aib$^{2,10}$,Glu(NH-hexyl)$^{3,17}$)hGhrelin(1-28)-NH$_2$ | 0.99 |
| #78 (SEQ ID NO: 58) | (Lys(biotinyl)$^{17}$)hGhrelin(1-28)-NH$_2$ | 0.07 |
| #58 (SEQ ID NO: 44) | (Aib$^{2,10}$,Glu(NH-hexyl)$^{3,17}$)hGhrelin(1-28)-NH$_2$ | 0.40 |
| #217 (SEQ ID NO: 177) | (Aib$^2$,Lys(myristyl)$^{17}$)hGhrelin(1-28)-NH$_2$ | 0.16 |
| #219 (SEQ ID NO: 179) | (Aib$^{2,8}$,Ser$^3$,Glu(NH-hexyl)$^{17}$)hGrehlin(1-28)-NH$_2$ | 214 |

2. GHS-R Functional Activity Assays

A. In vitro GSH Receptor Mediated Intracellular iCa$^{2+}$ Mobilization

The foregoing CHO-K1 cells expressing the human GSH receptor were harvested by incubating in a 0.3% EDTA/phosphate buffered saline solution at 25° C.; the cells were then washed 2 times by centrifugation. The washed cells were resuspended in Hank's buffered saline solution (HBSS) for loading of the fluorescent Ca$^{2+}$ indicator Fura-2AM. Cell suspensions of approximately 10$^6$ cells/ml were incubated with 2 µM Fura-2AM for about 30 minutes at about 25° C. Unloaded Fura-2AM was removed by centrifugation twice in HBSS and the final suspensions were transferred to a spectrofluorometer (model Hitachi F-2000® Tokyo, Japan) equipped with a magnetic stirring mechanism and a temperature-regulated cuvette holder. After equilibration to 37° C., the ghrelin analogs were added for measurement of intracellular Ca$^{2+}$ mobilization. The excitation and emission wavelengths were 340 and 510 nm, respectively. Using this analysis method, compounds of Examples 124 and 136 were found to exhibit antagonistic activity at the ghrelin receptor.

B. In Vivo GH Release/Suppression

As is well known in the art, compounds may be tested for their ability to stimulate or suppress release of GH in vivo.

(Deghenghi, R. et al., *Life Sciences*, (1994), 54(18):1321-8; and International Patent Application No. PCT/EP01/07929 [WO 02/08250]). In order to ascertain a compound's ability to stimulate GH release in vivo, the selected compound at a dosage of approximately 300 mg/kg is injected subcutaneously in 10-day old rats. The circulating GH is measured approximately 15 minutes after injection and compared to GH levels in rats injected with a solvent control.

Similarly, selected compounds may be tested for their ability to antagonize ghrelin-induced GH secretion in vivo. A 300 mg/kg dose of a compound of the instant application should be injected subcutaneously in 10-day old rats along with ghrelin. The circulating GH is then measure approximately 15 minutes after injection and compared to GH levels in rats injected with ghrelin alone.

Administration

Ghrelin analogs can be formulated and administered to a subject using the guidance provided herein along with techniques well known in the art. The preferred route of administration ensures that an effective amount of compound reaches the target. Guidelines for pharmaceutical administration in general are provided in, for example, *Remington's Pharmaceutical Sciences* 18th Edition, Ed. Gennaro, Mack Publishing, 1990, and *Modem Pharmaceutics 2nd Edition*, Eds. Banker and Rhodes, Marcel Dekker, Inc., 1990, both of which are hereby incorporated by reference.

Ghrelin analogs can be prepared as acidic or basic salts. Pharmaceutically acceptable salts (in the form of water- or oil-soluble or dispersible products) include conventional non-toxic salts or the quaternary ammonium salts formed from inorganic or organic acids or bases. Examples of such salts include, but are not limited to, acid addition salts such as acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate; and base salts such as ammonium salts, alkali metal salts such as sodium and potassium salts, alkaline earth metal salts such as calcium and magnesium salts, salts with organic bases such as dicyclohexylamine salts, N-methyl-D-glucamine and salts with amino acids such as arginine and lysine.

Ghrelin analogs can be administered using different routes including oral and nasal ingestion or by transdermal and transmucosal injection. Active ingredients administered orally as a suspension can be prepared according to techniques well known in the art of pharmaceutical formulation and may contain microcrystalline cellulose for imparting bulk, alginic acid or sodium alginate as a suspending agent, methylcellulose as a viscosity enhancer and sweeteners/flavoring agents. As immediate release tablets, pharmaceutical formulations may contain microcrystalline cellulose, dicalcium phosphate, starch, magnesium stearate and lactose and/or other excipients, binders, extenders, disintegrants, diluents and lubricants.

Administered by nasal aerosol or inhalation formulations may be prepared, for example, as solutions in saline, employing benzyl alcohol or other suitable preservatives, absorption promoters to enhance bioavailability, employing fluorocarbons and/or employing other solubilizing or dispersing agents.

Ghrelin analogs may also be administered in intravenously (both bolus and infusion), intraperitoneally, subcutaneously, topically, with or without occlusion, or intramuscularly. When administered by injection, the injectable solution or suspension may be formulated using suitable non-toxic, parenterally-acceptable diluents or solvents, such as Ringer's solution or isotonic sodium chloride solution, or suitable dispersing or wetting and suspending agents, such as sterile, bland, fixed oils, including synthetic mono- or diglycerides and fatty acids, including oleic acid.

Suitable dosing regimens are preferably determined taking into account factors well known in the art including type of subject being dosed; age, weight, sex and medical condition of the subject; the route of administration; the renal and hepatic function of the subject; the desired effect; and the particular compound employed.

Optimal precision in achieving concentrations of drug within the range that yields efficacy without toxicity requires a regimen based on the kinetics of the drug's availability to target sites. This involves a consideration of the distribution, equilibrium, and elimination of a drug. The daily dose for a subject is expected to be between 0.01 and 1,000 mg per subject per day.

Ghrelin analogs can be provided in a kit. Such a kit typically contains an active compound in dosage forms for administration. A dosage form contains a sufficient amount of active compound such that a desirable effect can be obtained when administered to a subject during regular intervals, such as 1 to 6 times a day, during the course of 1 or more days. Preferably, a kit contains instructions indicating the use of the dosage form to achieve a desirable affect and the amount of dosage form to be taken over a specified time period.

The invention has been described in an illustrative manner, and it is to be understood that the terminology which has been used is intended to be in the nature of words of description rather than of limitation. Obviously, many modifications and variations of the present invention are possible in light of the above teachings. It is, therefore, to be understood that within the scope of the appended claims the invention may be practiced otherwise than as specifically described.

The patent and scientific literature referred to herein represents knowledge that is available to those with skill in the art. All patents, patent publications and other publications cited herein are hereby incorporated by reference in their entirety.

The invention claimed is:

1. A compound according to formula (I):

$$(R^2R^3)-A^1-A^2-A^3-A^4-A^5-A^6-A^7-A^8-A^9-A^{10}-A^{11}-A^{12}-A^{13}-A^{14}-A^{15}-A^{16}-A^{17}-A^{18}-A^{19}-A^{20}-A^{21}-A^{22}-A^{23}-A^{24}-A^{25}-A^{26}-A^{27}-A^{28}-R^1 \quad (I)$$

wherein:

$A^1$ is Gly, Aib, Ala, β-Ala or Acc;

$A^2$ is Ser, Aib, Ala, Acc, Abu, Act, Ava, Thr or Val;

$A^3$ is Asp(NH—$R^9$), Asp(O—$R^8$), Cys(S—$R^{14}$), Dab(S(O)$_2$—$R^{11}$), Dap(S(O)$_2$—$R^{10}$), Glu(NH—$R^7$), Glu(O—$R^6$), Ser(C(O)—$R^4$), Thr(C(O)—$R^5$) or HN—CH((CH$_2$)$_n$—N($R^{12}R^{13}$))—C(O);

$A^4$ is Phe, Acc, Aic, Cha, 2-Fua, 1-Nal, 2-Nal, 2-Pal, 3-Pal, 4-Pal, hPhe, $(X^1,X^2,X^3,X^4,X^5)$Phe, Taz, 2-Thi, 3-Thi, Trp or Tyr;

$A^5$ is Leu, Abu, Acc, Aib, Ala, Cha, Ile, hLeu, Nle, Nva, Phe, Tle or Val;

$A^6$ is Ser, Abu, Acc, Act, Aib, Ala, Gly, Thr or Val;

$A^7$ is Pro, Dhp, Dmt, 3-Hyp, 4-Hyp, Inc, Ktp, Oic, Pip, Thz or Tic;

$A^8$ is Glu, Acc, Aib, Arg, Asn, Asp, Dab, Dap, Gln, Lys, Orn or HN—CH$((CH_2)_n$—N$(R^{12}R^{13}))$—C(O);

$A^9$ is His, Apc, Aib, Acc, 2-Fua, 2-Pal, 3-Pal, 4-Pal, $(X^1, X^2,X^3,X^4,X^5$—)Phe, Taz, 2-Thi or 3-Thi;

$A^{10}$ is Gln, Acc, Aib, Asn, Asp or Glu;

$A^{11}$ is Arg, Apc, hArg, Dab, Dap, Lys, Orn or HN—CH$((CH_2)_n$—N$(R^{12}R^{13}))$—C(O);

$A^{12}$ is Val, Abu, Acc, Aib, Ala, Cha, Nva, Gly, Ile, Leu, Nle or Tle;

$A^{13}$ is Gln, Acc, Aib, Asn, Asp or Glu;

$A^{14}$ is Gln, Acc, Aib, Asn, Asp or Glu;

$A^{15}$ is Arg, hArg, Acc, Aib, Apc, Dab, Dap, Lys, Orn, Asp(NH—$R^9$), Asp(O—$R^8$), Cys(S—$R^{14}$), Cys($R^{15}$), hCys(S—$R^{16}$), hCys($R^{17}$), Dab(S(O)$_2$—$R^{11}$), Dap(S(O)$_2$—$R^{10}$), Glu(NH—$R^7$), Glu(O—$R^6$), Ser(C(O)—$R^4$), Thr(C(O)—$R^5$) or HN—CH$((CH_2)_n$—N$(R^{12}R^{13}))$—C(O);

$A^{16}$ is Lys, Acc, Aib, Apc, Arg, hArg, Dab, Dap, Orn, Asp(NH—$R^9$), Asp(O—$R^8$), Cys(S—$R^{14}$), Cys($R^{15}$), hCys(S—$R^{16}$), hCys($R^{17}$), Dab(S(O)$_2$—$R^{11}$), Dap(S(O)$_2$—$R^{10}$), Glu(NH—$R^7$), Glu(O—$R^6$), Ser(C(O)—$R^4$), Thr(C(O)—$R^5$), HN—CH$((CH_2)_n$—N$(R^{12}R^{13}))$—C(O) or deleted;

$A^{17}$ is Glu, Arg, Asn, Asp, Dab, Dap, Gln, Lys, Orn, Asp(NH—$R^9$), Asp(O—$R^8$), Cys(S—$R^{14}$), Cys($R^{15}$), hCys(S—$R^{16}$), hCys($R^{17}$), Dab(S(O)$_2$—$R^{11}$), Dap(S(O)$_2$—$R^{10}$), Glu(NH—$R^7$), Glu(O—$R^6$), Lys(biotinyl), Ser(C(O)—$R^4$), Thr(C(O)—$R^5$), HN—CH$((CH_2)_n$—N$(R^{12}R^{13}))$—C(O) or deleted;

$A^{18}$ is Ser, Abu, Acc, Act, Aib, Ala, Thr, Val, Asp(NH—$R^9$), Asp(O—$R^8$), Cys(S—$R^{14}$), Cys($R^{15}$), hCys(S—$R^{16}$), hCys($R^{17}$), Dab(S(O)$_2$—$R^{11}$), Dap(S(O)$_2$—$R^{10}$), Glu(NH—$R^7$), Glu(O—$R^6$), Ser(C(O)—$R^4$), Thr(C(O)—$R^5$), HN—CH$((CH_2)_n$—N$(R^{12}R^{13}))$—C(O) or deleted;

$A^{19}$ is Lys, Acc, Aib, Apc, Arg, hArg, Dab, Dap, Orn, Asp(NH—$R^9$), Asp(O—$R^8$), Cys(S—$R^{14}$), Cys($R^{15}$), hCys(S—$R^{16}$), hCys($R^{17}$), Dab(S(O)$_2$—$R^{11}$), Dap(S(O)$_2$—$R^{10}$), Glu(NH—$R^7$), Glu(O—$R^6$), Ser(C(O)—$R^4$), Thr(C(O)—$R^5$), HN—CH$((CH_2)_n$—N$(R^{12}R^{13}))$—C(O) or deleted;

$A^{20}$ is Lys, Acc, Aib, Apc, Arg, hArg, Dab, Dap, Orn, Asp(NH—$R^9$), Asp(O—$R^8$), Cys(S—$R^{14}$), Cys($R^{15}$), hCys(S—$R^{16}$), hCys($R^{17}$), Dab(S(O)$_2$—$R^{11}$), Dap(S(O)$_2$—$R^{10}$), Glu(NH—$R^7$), Glu(O—$R^6$), Ser(C(O)—$R^4$), Thr(C(O)—$R^5$), HN—CH$((CH_2)_n$—N$(R^{12}R^{13}))$—C(O) or deleted;

$A^{21}$ is Pro, Dhp, Dmt, 3-Hyp, 4-Hyp, Inc, Ktp, Oic, Pip, Thz, Tic or deleted;

$A^{22}$ is Pro, Dhp, Dmt, 3-Hyp, 4-Hyp, Inc, Ktp, Oic, Pip, Thz, Tic or deleted;

$A^{23}$ is Ala, Abu, Acc, Act, Aib, Apc, Gly, Nva, Val or deleted;

$A^{24}$ is Lys, Acc, Aib, Apc, Arg, hArg, Dab, Dap, Orn, HN—CH$((CH_2)_n$—N$(R^{12}R^{13}))$—C(O) or deleted;

$A^{25}$ is Leu, Abu, Acc, Aib, Ala, Cha, Ile, hLeu, Nle, Nva, Phe, Tle, Val or deleted;

$A^{26}$ is Gln, Aib, Asn, Asp, Glu or deleted;

$A^{27}$ is Pro, Dhp, Dmt, 3-Hyp, 4-Hyp, Inc, Ktp, Oic, Pip, Thz, Tic or deleted;

$A^{28}$ is Arg, Acc, Aib, Apc, hArg, Dab, Dap, Lys, Orn, HN—CH$((CH_2)_n$—N$(R^{12}R^{13}))$—C(O) or deleted;

$R^1$ is —OH, —NH$_2$, —$(C_1-C_{30})$alkoxy or NH—$X^6$—CH$_2$—$Z^0$, wherein $X^6$ is a $(C_1-C_{12})$alkyl or $(C_2-C_{12})$alkenyl and $Z^0$ is —H, —OH, —CO$_2$H or —C(O)—NH$_2$;

$R^2$ and $R^3$ is, independently for each occurrence thereof, selected from the group consisting of H, $(C_1-C_{30})$alkyl, $(C_1-C_{30})$heteroalkyl, $(C_1-C_{30})$acyl, $(C_2-C_{30})$alkenyl, $(C_2-C_{30})$alkynyl, aryl$(C_1-C_{30})$alkyl, aryl$(C_1-C_{30})$acyl, substituted $(C_1-C_{30})$alkyl, substituted $(C_1-C_{30})$heteroalkyl, substituted $(C_2-C_{30})$acyl, substituted $(C_2-C_{30})$alkenyl, substituted aryl$(C_1-C_{30})$alkyl and substituted aryl$(C_1-C_{30})$acyl;

$R^4, R^5, R^6, R^7, R^8, R^9, R^{10}, R^{11}, R^{14}, R^{15}, R^{16}$ and $R^{17}$ is, independently for each occurrence thereof, selected from the group consisting of $(C_1-C_{40})$alkyl, $(C_2-C_{40})$alkenyl, substituted $(C_1-C_{40})$alkyl, substituted $(C_2-C_{40})$alkenyl, alkylaryl, substituted alkylaryl, aryl and substituted aryl;

$R^{12}$ and $R^{13}$ is, independently for each occurrence thereof, selected from the group consisting of H, $(C_1-C_{40})$alkyl, $(C_1-C_{40})$acyl, $(C_1-C_{30})$alkylsulfonyl, biotinyl and —C(NH)—NH$_2$;

$X^1, X^2, X^3, X^4$, and $X^5$ is, independently for each occurrence thereof, selected from the group consisting of H, F, Cl, Br, I, $(C_{1-10})$alkyl, substituted $(C_{1-10})$alkyl, aryl, substituted aryl, OH, NH$_2$, NO$_2$ and CN; and n is, independently for each occurrence thereof, 1, 2, 3, 4 or 5; provided that:

(I) if $R^2$ is $(C_1-C_{30})$acyl, aryl$(C_1-C_{30})$acyl, substituted $(C_2-C_{30})$acyl, or substituted aryl$(C_1-C_{30})$acyl, then $R^3$ is H, $(C_1-C_{30})$alkyl, $(C_1-C_{30})$heteroalkyl, $(C_2-C_{30})$alkenyl, aryl$(C_1-C_{30})$alkyl, substituted $(C_1-C_{30})$alkyl, substituted $(C_1-C_{30})$heteroalkyl, substituted $(C_2-C_{30})$alkenyl or substituted aryl$(C_1-C_{30})$alkyl;

(II) if $R^{12}$ is $(C_1-C_{40})$acyl, $(C_1-C_{30})$alkylsulfonyl, biotinyl or —C(NH)—NH$_2$, then $R^{13}$ is H or $(C_1-C_{40})$alkyl;

(III) at least one of $A^{15}, A^{16}, A^{17}, A^{18}, A^{19}$ or $A^{20}$ must be selected from the group consisting of Asp(NH—$R^9$), Asp(O—$R^8$), Cys(S—$R^{14}$), Cys($R^{15}$), hCys(S—$R^{16}$), hCys($R^{17}$), Dab(S(O)$_2$—$R^{11}$) Dap(S(O)$_2$—$R^{10}$), Glu(NH—$R^7$), Glu(O—$R^6$), Ser(C(O)—$R^4$), Thr(C(O)—$R^5$) and HN—CH$((CH_2)_n$—N$(R^{12}R^{13}))$—C(O); and (IV) if any member of the group consisting of $A^{15}, A^{16}, A^{17}, A^{19}$ and $A^{20}$ is HN—CH$((CH_2)_n$—N$(R^{12}R^{13}))$—C(O), then $R^{12}$ must be biotinyl;

or a pharmaceutically acceptable salt thereof.

2. A compound according to claim 1, wherein:

$A^1$ is Gly or Aib;

$A^2$ is Ser, Act, Aib, Ava or A5c;

$A^3$ is Asp(NH—$R^9$), Asp(O—$R^8$), Cys(S—$R^{14}$), Dap(S(O)$_2$—$R^{10}$, Glu(NH—$R^7$), Glu(O—$R^6$) or Ser(C(O)—$R^4$);

$A^4$ is Phe;

$A^5$ is Leu, Acc, Aib, Cha or hLeu;

$A^6$ is Ser, Abu, Act, Aib or Thr;

$A^7$ is Pro, Dhp, Dmt, 4-Hyp, Ktp, Pip, Thz or Tic;

$A^8$ is Glu or Aib;

$A^9$ is His, Aib, Apc, 2-Fua, 2-Pal, 3-Pal, 4-Pal, Taz or 2-Thi;

$A^{10}$ is Gln or Aib;

$A^{11}$ is Arg;

$A^{12}$ is Val or Acc;

$A^{13}$ is Gln;

$A^{14}$ is Gln;

$A^{15}$ is Arg, Orn, Glu(NH—$R^7$) or Ser(C(O)—$R^4$);

$A^{16}$ is Lys, Apc, Glu(NH—$R^7$) or Ser(C(O)—$R^4$);

A$^{17}$ is Glu, Lys(biotinyl), Asp(NH—R$^9$), Asp(O—R$^8$), Cys(S—R$^{14}$), Dap(S(O)$_2$—R$^{10}$), Glu(NH—R$^7$), Glu (O—R$^6$), Ser(C(O)—R$^4$) or HN—CH((CH$_2$)$_n$—N (R$^{12}$R$^{13}$))—C(O);
A$^{18}$ is Ser, Glu(NH—R$^7$) or Ser(C(O)—R$^4$);
A$^{19}$ is Lys, Glu(NH—R$^7$) or Ser(C(O)—R$^4$);
A$^{20}$ is Lys, Glu(NH—R$^7$) or Ser(C(O)—R$^4$);
A$^{21}$ is Pro;
A$^{22}$ is Pro;
A$^{23}$ is Ala;
A$^{24}$ is Lys;
A$^{25}$ is Leu;
A$^{26}$ is Gln;
A$^{27}$ is Pro; and
A$^{28}$ is Arg;
or a pharmaceutically acceptable salt thereof.

3. A compound according to claim 2, wherein:
R$^2$ and R$^3$ is, independently for each occurrence thereof, selected from the group consisting of H, (C$_1$-C$_6$)acyl, n-butyryl, isobutyryl and n-octanoyl;
R$^4$ is heptyl;
R$^6$ is hexyl;
R$^7$ is hexyl;
R$^{10}$ is octyl;
and
Acc is, independently for each occurrence thereof, selected from the group consisting of A3c, A4c, A5c and A6c;
or a pharmaceutically acceptable salt thereof.

4. A compound according to claim 3, wherein:
A$^3$ is Asp(NH-hexyl), Asp(1-heptanol), Cys(S—(CH$_2$)$_9$CH$_3$), Dap(octanesulfonyl), Glu(NH-hexyl) or Glu(1-heptanol);
A$^5$ is Leu;
A$^6$ is Ser;
A$^7$ is Pro, Dhp, 4-Hyp, Pip, Thz or Tic;
A$^9$ is His, 3-Pal, 4-Pal, Taz or 2-Thi;
A$^{12}$ is Val;
A$^{15}$ is Arg, Glu(NH-hexyl) or Ser(n-octanoyl);
A$^{16}$ is Lys, Glu(NH-hexyl) or Ser(n-octanoyl);
A$^{17}$ is Glu, Lys(biotinyl), Asp(NH-hexyl), Asp(1-heptanol), Cys(S—(CH$_2$)$_9$CH$_3$), Dap(octanesulfonyl), Glu(NH-hexyl), Glu(1-heptanol) or Ser(n-octanoyl);
A$^{18}$ is Ser, Glu(NH-hexyl) or Ser(n-octanoyl);
A$^{19}$ is Lys, Glu(NH-hexyl) or Ser(n-octanoyl);
A$^{20}$ is Lys, Glu(NH-hexyl) or Ser(n-octanoyl);
or a pharmaceutically acceptable salt thereof.

5. A compound according to claim 4, wherein said compound is:

| | |
|---|---|
| (Glu(NH-hexyl)$^{3,15}$)hGhrelin(1-28)-NH$_2$; | (SEQ ID NO: 3) |
| (Glu(NH-hexyl)$^3$,Ser(n-Octanoyl)$^{15}$)hGhrelin(1-28)-NH$_2$; | (SEQ ID NO: 4) |
| (Aib$^2$,Glu(NH-hexyl)$^{3,15}$)hGhrelin(1-28)-NH$_2$; | (SEQ ID NO: 6) |
| (Aib$^{2,8}$,Glu(NH-hexyl)$^{3,15}$)hGhrelin(1-28)-NH$_2$; | (SEQ ID NO: 8) |
| (Aib$^{2,10}$,Glu(NH-hexyl)$^{3,15}$)hGhrelin(1-28)-NH$_2$; | (SEQ ID NO: 10) |
| (Glu(NH-hexyl)$^{3,16}$)hGhrelin(1-28)-NH$_2$; | (SEQ ID NO: 13) |
| (Glu(NH-hexyl)$^3$,Ser(n-octanoyl)$^{16}$)hGhrelin(1-28)-NH$_2$; | (SEQ ID NO: 14) |
| (Aib$^2$,Glu(NH-hexyl)$^{3,16}$)hGhrelin(1-28)-NH$_2$; | (SEQ ID NO: 16) |
| (Aib$^{2,8}$,Glu(NH-hexyl)$^{3,16}$)hGhrelin(1-28)-NH$_2$; | (SEQ ID NO: 18) |
| (Aib$^{2,10}$,Glu(NH-hexyl)$^{3,16}$)hGhrelin(1-28)-NH$_2$; | (SEQ ID NO: 20) |
| (Glu(NH-hexyl)$^{3,17}$)hGhrelin(1-28)-NH$_2$; | (SEQ ID NO: 23) |
| (Glu(NH-hexyl)$^3$,Ser(n-octanoyl)$^{17}$)hGhrelin(1-28)-NH$_2$; | (SEQ ID NO: 24) |
| (Dap(octanesulfonyl)$^{3,17}$)hGhrelin(1-28)-NH$_2$; | (SEQ ID NO: 26) |
| (Dap(octanesulfonyl)$^3$,Glu(NH-hexyl)$^{17}$)hGhrelin(1-28)-NH$_2$; | (SEQ ID NO: 27) |
| (Dap(octanesulfonyl)$^3$,Ser(n-octanoyl)$^{17}$)hGhrelin(1-28)-NH$_2$; | (SEQ ID NO: 28) |
| (Glu(NH-hexyl)$^3$,Dap(octanesulfonyl)$^{17}$)hGhrelin(1-28)-NH$_2$; | (SEQ ID NO: 29) |
| (Cys(S-(CH$_2$)$_9$CH$_3$)$^{3,17}$)hGhrelin(1-28)-NH$_2$; | (SEQ ID NO: 31) |
| (Glu(NH-hexyl)$^3$,(Cys(S-(CH$_2$)$_9$CH$_3$)$^{17}$)hGhrelin(1-28)-NH$_2$; | (SEQ ID NO: 32) |
| (Cys(S-(CH$_2$)$_9$CH$_3$)$^3$,Glu(NH-hexyl)$^{17}$)hGhrelin(1-28)-NH$_2$; | (SEQ ID NO: 33) |
| (Cys(S-(CH$_2$)$_9$CH$_3$)$^3$,Ser(n-octanoyl)$^{17}$)hGhrelin(1-28)-NH$_2$; | (SEQ ID NO: 34) |
| (Aib$^2$,Glu(NH-hexyl)$^{3,17}$)hGhrelin(1-28)-NH$_2$; | (SEQ ID NO: 36) |
| (Aib$^2$,Glu(NH-hexyl)$^{3,17}$,Thz$^7$)hGhrelin(1-28)-NH$_2$; | (SEQ ID NO: 38) |
| (Aib$^2$,Glu(NH-hexyl)$^{3,17}$,4-Hyp$^7$)hGhrelin(1-28)-NH$_2$; | (SEQ ID NO: 38) |
| (Aib$^2$,Glu(NH-hexyl)$^{3,17}$,Dhp$^7$)hGhrelin(1-28)-NH$_2$; | (SEQ ID NO: 38) |
| (Aib$^2$,Glu(NH-hexyl)$^{3,17}$,Pip$^7$)hGhrelin(1-28)-NH$_2$; | (SEQ ID NO: 38) |

-continued

| | |
|---|---|
| (Aib$^2$,Glu(NH-hexyl)$^{3,17}$,Tic$^7$)hGhrelin(1-28)-NH$_2$; | (SEQ ID NO: 38) |
| (Aib$^{2,8}$,Glu(NH-hexyl)$^{3,17}$)hGhrelin(1-28)-NH$_2$; | (SEQ ID NO: 40) |
| (Aib$^2$,Glu(NH-hexyl)$^{3,17}$,3-Pal$^9$)hGhrelin(1-28)-NH$_2$; | (SEQ ID NO: 42) |
| (Aib$^2$,Glu(NH-hexyl)$^{3,17}$,4-Pal$^9$)hGhrelin(1-28)-NH$_2$; | (SEQ ID NO: 42) |
| (Aib$^2$,Glu(NH-hexyl)$^{3,17}$,Taz$^9$)hGhrelin(1-28)-NH$_2$; | (SEQ ID NO: 42) |
| (Aib$^2$,Glu(NH-hexyl)$^{3,17}$,2-Thi$^9$)hGhrelin(1-28)-NH$_2$; | (SEQ ID NO: 42) |
| (Aib$^{2,10}$,Glu(NH-hexyl)$^{3,17}$)hGhrelin(1-28)-NH$_2$; | (SEQ ID NO: 44) |
| (Glu(NH-hexyl)$^{3,17}$,Aib$^8$)hGhrelin(1-28)-NH$_2$; | (SEQ ID NO: 47) |
| (Glu(NH-hexyl)$^{3,17}$,Taz$^9$)hGhrelin(1-28)-NH$_2$; | (SEQ ID NO: 48) |
| (Glu(NH-hexyl)$^{3,17}$,3-Pal$^9$)hGhrelin(1-28)-NH$_2$; | (SEQ ID NO: 48) |
| (Glu(NH-hexyl)$^{3,17}$,4-Pal$^9$)hGhrelin(1-28)-NH$_2$; | (SEQ ID NO: 48) |
| (Glu(NH-hexyl)$^{3,17}$,2-Thi$^9$)hGhrelin(1-28)-NH$_2$; | (SEQ ID NO: 48) |
| (Aib$^{1,2,10}$,Glu(NH-hexyl)$^{3,17}$)hGhrelin(1-28)-NH$_2$; | (SEQ ID NO: 50) |
| (A5c$^2$,Glu(NH-hexyl)$^{3,17}$)hGhrelin(1-28)-NH$_2$; | (SEQ ID NO: 52) |
| (Glu(1-heptanol)$^{3,17}$)hGhrelin(1-28)-NH$_2$; | (SEQ ID NO: 53) |
| (Asp(1-heptanol)$^{3,17}$)hGhrelin(1-28)-NH$_2$; | (SEQ ID NO: 54) |
| (Glu(NH-hexyl)$^{3,17}$)hGhrelin(1-28)-NH$_2$; | (SEQ ID NO: 55) |
| (Asp(NH-hexyl)$^{3,17}$)hGhrelin(1-28)-NH$_2$; | (SEQ ID NO: 56) |
| (Aib$^2$,Glu(NH-hexyl)$^{3,17}$)hGhrelin(1-28)-NH$_2$; | (SEQ ID NO: 57) |
| (Glu(NH-hexyl)$^{3,18}$)hGhrelin(1-28)-NH$_2$; | (SEQ ID NO: 61) |
| (Glu(NH-hexyl)$^3$,Ser(n-octanoyl)$^{18}$)hGhrelin(1-28)-NH$_2$; | (SEQ ID NO: 62) |
| (Aib$^2$,Glu(NH-hexyl)$^{3,18}$)hGhrelin(1-28)-NH$_2$; | (SEQ ID NO: 64) |
| (Aib$^{2,18}$,Glu(NH-hexyl)$^{3,18}$)hGhrelin(1-28)-NH$_2$; | (SEQ ID NO: 66) |
| (Aib$^{2,10}$,Glu(NH-hexyl)$^{3,18}$)hGhrelin(1-28)-NH$_2$; | (SEQ ID NO: 68) |
| (Glu(NH-hexyl)$^{3,19}$)hGhrelin(1-28)-NH$_2$; | (SEQ ID NO: 71) |
| (Glu(NH-hexyl)$^3$,Ser(n-octanoyl)$^{19}$)hGhrelin(1-28)-NH$_2$; | (SEQ ID NO: 72) |
| (Aib$^2$,Glu(NH-hexyl)$^{3,19}$)hGhrelin(1-28)-NH$_2$; | (SEQ ID NO: 74) |
| (Aib$^{2,8}$,Glu(NH-hexyl)$^{3,19}$)hGhrelin(1-28)-NH$_2$; | (SEQ ID NO: 76) |
| (Aib$^{2,10}$,Glu(NH-hexyl)$^{3,19}$)hGhrelin(1-28)-NH$_2$; | (SEQ ID NO: 78) |
| (Glu(NH-hexyl)$^{3,20}$)hGhrelin(1-28)-NH$_2$; | (SEQ ID NO: 81) |
| (Glu(NH-hexyl)$^3$,Ser(n-octanoyl)$^{20}$)hGhrelin(1-28)-NH$_2$; | (SEQ ID NO: 82) |
| (Aib$^2$,Glu(NH-hexyl)$^{3,20}$)hGhrelin(1-28)-NH$_2$; | (SEQ ID NO: 84) |
| (Aib$^{2,8}$,Glu(NH-hexyl)$^{3,20}$)hGhrelin(1-28)-NH$_2$; | (SEQ ID NO: 86) |
| (Aib$^{2,10}$,Glu(NH-hexyl)$^{3,20}$)hGhrelin(1-28)-NH$_2$; | (SEQ ID NO: 88) |
| (Ac-Gly$^1$,Glu(NH-hexyl)$^{3,17}$)hGhrelin(1-28)-NH$_2$; | (SEQ ID NO: 91) |
| (Ac-Gly$^1$,Glu(NH-hexyl)$^3$,Ser(n-octanoyl)$^{17}$)hGhrelin(1-28)-NH$_2$; | (SEQ ID NO: 92) |
| (Ac-Gly$^1$,Dap(octanesulfonyl)$^{3,17}$)hGhrelin(1-28)-NH$_2$; | (SEQ ID NO: 94) |
| (Ac-Gly$^1$,Dap(octanesulfonyl)$^3$,Glu(NH-hexyl)$^{17}$)hGhrelin(1-28)-NH$_2$; | (SEQ ID NO: 95) |
| (Ac-Gly$^1$,Dap(octanesulfonyl)$^3$,Ser(n-octanoyl)$^{17}$)hGhrelin(1-28)-NH$_2$; | (SEQ ID NO: 96) |
| (Ac-Gly$^1$,Glu(NH-hexyl)$^3$, Dap(octanesulfonyl)$^{17}$)hGhrelin(1-28)-NH$_2$; | (SEQ ID NO: 97) |
| (Ac-Gly$^1$,(Cys(S-(CH$_2$)$_9$CH$_3$)$^{3,17}$)hGhrelin(1-28)-NH$_2$; | (SEQ ID NO: 99) |

-continued

| | |
|---|---|
| (Ac-Gly¹,Glu(NH-hexyl)³, (Cys(S-(CH₂)₉CH₃)¹⁷)hGhrelin(1-28)-NH₂; | (SEQ ID NO: 100) |
| (Ac-Gly¹, (Cys(S-(CH₂)₉CH₃)³,Glu(NH-hexyl)¹⁷)hGhrelin(1-28)-NH₂; | (SEQ ID NO: 101) |
| (Ac-Gly¹, (Cys(S-(CH₂)₉CH₃)³, Ser(n-octanoyl)¹⁷)hGhrelin(1-28)-NH₂; | (SEQ ID NO: 102) |
| (Ac-Gly¹,Aib²,Glu(NH-hexyl)³,¹⁷)hGhrelin(1-28)-NH₂; | (SEQ ID NO: 104) |
| (Ac-Gly¹,Aib²,Glu(NH-hexyl)³,¹⁷,Thz⁷)hGhrelin(1-28)-NH₂; | (SEQ ID NO: 106) |
| (Ac-Gly¹,Aib²,Glu(NH-hexyl)³,¹⁷,4-Hyp⁷)hGhrelin(1-28)-NH₂; | (SEQ ID NO: 106) |
| (Ac-Gly¹,Aib²,Glu(NH-hexyl)³,¹⁷,Dhp⁷)hGhrelin(1-28)-NH₂; | (SEQ ID NO: 106) |
| (Ac-Gly¹,Aib²,Glu(NH-hexyl)³,¹⁷,Pip⁷)hGhrelin(1-28)-NH₂; | (SEQ ID NO: 106) |
| (Ac-Gly¹,Aib²,Glu(NH-hexyl)³,¹⁷,Tic⁷)hGhrelin(1-28)-NH₂; | (SEQ ID NO: 106) |
| (Ac-Gly¹,Aib²,⁸,Glu(NH-hexyl)³,¹⁷)hGhrelin(1-28)-NH₂; | (SEQ ID NO: 108) |
| (Ac-Gly¹,Aib²,Glu(NH-hexyl)³,¹⁷,3-Pal⁹)hGhrelin(1-28)-NH₂; | (SEQ ID NO: 110) |
| (Ac-Gly¹,Aib²,Glu(NH-hexyl)³,¹⁷,4-Pal⁹)hGhrelin(1-28)-NH₂; | (SEQ ID NO: 110) |
| (Ac-Gly¹,Aib²,Glu(NH-hexyl)³,¹⁷,Taz⁹)hGhrelin(1-28)-NH₂; | (SEQ ID NO: 110) |
| (Ac-Gly¹,Aib²,Glu(NH-hexyl)³,¹⁷,2-Thi⁹)hGhrelin(1-28)-NH₂; | (SEQ ID NO: 110) |
| (Ac-Gly¹,Aib²,¹⁰,Glu(NH-hexyl)³,¹⁷)hGhrelin(1-28)-NH₂; | (SEQ ID NO: 112) |
| (Ac-Gly¹,Glu(NH-hexyl)³,¹⁷,Aib⁸)hGhrelin(1-28)-NH₂; | (SEQ ID NO: 115) |
| (Ac-Gly¹,Glu(NH-hexyl)³,¹⁷,Taz⁹)hGhrelin(1-28)-NH₂; | (SEQ ID NO: 116) |
| (Ac-Gly¹,Glu(NH-hexyl)³,¹⁷,3-Pal⁹)hGhrelin(1-28)-NH₂; | (SEQ ID NO: 116) |
| (Ac-Gly¹,Glu(NH-hexyl)³,¹⁷,4-Pal⁹)hGhrelin(1-28)-NH₂; | (SEQ ID NO: 116) |
| (Ac-Gly¹,Glu(NH-hexyl)³,¹⁷,2-Thi⁹)hGhrelin(1-28)-NH₂; | (SEQ ID NO: 116) |
| (Ac-Aib¹,Aib²,¹⁰,Glu(NH-hexyl)³,¹⁷)hGhrelin(1-28)-NH₂; | (SEQ ID NO: 118) |
| (Ac-Gly¹,A5c²,Glu(NH-hexyl)³,¹⁷)hGhrelin(1-28)-NH₂; | (SEQ ID NO: 120) |
| (Ac-Gly¹,Glu(1-heptanol)³,¹⁷)hGhrelin(1-28)-NH₂; | (SEQ ID NO: 121) |
| (Ac-Gly¹,Asp(1-heptanol)³,¹⁷)hGhrelin(1-28)-NH₂; | (SEQ ID NO: 122) |
| (Ac-Gly¹,Glu(NH-hexyl)³,¹⁷)hGhrelin(1-28)-NH₂; | (SEQ ID NO: 123) |
| (Ac-Gly¹,Asp(NH-hexyl)³,¹⁷)hGhrelin(1-28)-NH₂; | (SEQ ID NO: 124) |
| (Ac-Gly¹,Aib²,Glu(NH-hexyl)³,¹⁷)hGhrelin(1-28)-NH₂; | (SEQ ID NO: 125) |
| (Ac-Gly¹,Aib²,¹⁰,Glu(NH-hexyl)³,Lys(biotinyl)¹⁷)hGhrelin(1-28)-NH₂; | (SEQ ID NO: 126) |
| (Ac-Gly¹,Glu(NH-hexyl)³,¹⁵)hGhrelin(1-28)-NH₂; | (SEQ ID NO: 129) |
| (Ac-Gly¹,Glu(NH-hexyl)³,Ser(n-octanoyl)¹⁵)hGhrelin(1-28)-NH₂; | (SEQ ID NO: 130) |
| (Ac-Gly¹,Aib²,Glu(NH-hexyl)hu 3,15)hGhrelin(1-28)-NH₂; | (SEQ ID NO: 132) |
| (Ac-Gly¹,Aib²,⁸,Glu(NH-hexyl)³,¹⁵)hGhrelin(1-28)-NH₂; | (SEQ ID NO: 134) |
| (Ac-Gly¹,Aib²,¹⁰,Glu(NH-hexyl)³,¹⁵)hGhrelin(1-28)-NH₂; | (SEQ ID NO: 136) |
| (Ac-Gly¹,Glu(NH-hexyl)³,¹⁶)hGhrelin(1-28)-NH₂; | (SEQ ID NO: 139) |
| (Ac-Gly¹,Glu(NH-hexyl)³,Ser(n-octanoyl)¹⁶)hGhrelin(1-28)-NH₂; | (SEQ ID NO: 140) |
| (Ac-Gly¹,Aib²,Glu(NH-hexyl)³,¹⁶)hGhrelin(1-28)-NH₂; | (SEQ ID NO: 142) |
| (Ac-Gly¹,Aib²,⁸,Glu(NH-hexyl)³,¹⁶)hGhrelin(1-28)-NH₂; | (SEQ ID NO: 144) |
| (Ac-Gly¹,Aib²,¹⁰,Glu(NH-hexyl)³,¹⁶)hGhrelin(1-28)-NH₂; | (SEQ ID NO: 146) |
| (Ac-Gly¹,Glu(NH-hexyl)³,¹⁸)hGhrelin(1-28)-NH₂; | (SEQ ID NO: 149) |
| (Ac-Gly¹,Glu(NH-hexyl)³,Ser(n-octanoyl)¹⁸)hGhrelin(1-28)-NH₂; | (SEQ ID NO: 150) |

-continued

| | |
|---|---|
| (Ac-Gly$^1$,Aib$^2$,Glu(NH-hexyl)$^{3,18}$)hGhrelin(1-28):NH$_2$; | (SEQ ID NO: 152) |
| (Ac-Gly$^1$,Aib$^{2,18}$,Glu(NH-hexyl)$^{3,18}$)hGhrelin(1-28)-NH$_2$; | (SEQ ID NO: 154) |
| (Ac-Gly$^1$,Aib$^{2,10}$,Glu(NH-hexyl)$^{3,18}$)hGhrelin(1-28)-NH$_2$; | (SEQ ID NO: 156) |
| (Ac-Gly$^1$,Glu(NH-hexyl)$^{3,9}$)hGhrelin(1-28)-NH$_2$; | (SEQ ID NO: 159) |
| (Ac-Gly$^1$,Glu(NH-hexyl)$^3$,Ser(n-octanoyl)$^{19}$)hGhrelin(1-28)-NH$_2$; | (SEQ ID NO: 160) |
| (Ac-Gly$^1$,Aib$^2$,Glu(NH-hexyl)$^{3,19}$)hGhrelin(1-28)-NH$_2$; | (SEQ ID NO: 162) |
| (Ac-Gly$^1$,Aib$^{2,18}$,Glu(NH-hexyl)$^{3,19}$)hGhrelin(1-28)-NH$_2$; | (SEQ ID NO: 164) |
| (Ac-Gly$^1$,Aib$^{2,10}$,Glu(NH-hexyl)$^{3,19}$)hGhrelin(1-28)-NH$_2$; | (SEQ ID NO: 166) |
| (Ac-Gly$^1$,Glu(NH-hexyl)$^{3,20}$)hGhrelin(1-28)-NH$_2$; | (SEQ ID NO: 169) |
| (Ac-Gly$^1$,Glu(NH-hexyl)$^3$,Ser(n-octanoyl)$^{20}$)hGhrelin(1-28)-NH$_2$; | (SEQ ID NO: 170) |
| (Ac-Gly$^1$,Aib$^2$,Glu(NH-hexyl)$^{3,20}$)hGhrelin(1-28)-NH$_2$; | (SEQ ID NO: 172) |
| (Ac-Gly$^1$,Aib$^{2,18}$,Glu(NH-hexyl)$^{3,20}$)hGhrelin(1-28)-NH$_2$; or | (SEQ ID NO: 174) |
| (Ac-Gly$^1$,Aib$^{2,10}$,Glu(NH-hexyl)$^{3,20}$)hGhrelin(1-28)-NH$_2$; | (SEQ ID NO: 176) | or a pharmaceutically acceptable salt thereof.

6. A compound according to claim 5, wherein said compound is:

| | |
|---|---|
| (Glu(NH-hexyl)$^{3,17}$)hGhrelin(1-28)-NH$_2$; | (SEQ ID NO: 23) |
| (Glu(NH-hexyl)$^3$,Ser(n-octanoyl)$^{17}$)hGhrelin(1-28)-NH$_2$; | (SEQ ID NO: 24) |
| (Dap(octanesulfonyl)$^{3,17}$)hGhrelin(1-28)-NH$_2$; | (SEQ ID NO: 26) |
| (Dap(octanesulfonyl)$^3$,Glu(NH-hexyl)$^{17}$)hGhrelin(1-28)-NH$_2$; | (SEQ ID NO: 27) |
| (Dap(octanesulfonyl)$^3$,Ser(n-octanoyl)$^{17}$)hGhrelin(1-28)-NH$_2$; | (SEQ ID NO: 28) |
| (Glu(NH-hexyl)$^3$,Dap(octanesulfonyl)$^{17}$)hGhrelin(1-28)-NH$_2$; | (SEQ ID NO: 29) |
| (Cys(S-(CH$_2$)$_9$CH$_3$)$^{3,17}$)hGhrelin(1-28)-NH$_2$; | (SEQ ID NO: 31) |
| (Glu(NH-hexyl)$^3$,(Cys(S-(CH$_2$)$_9$CH$_3$)$^{17}$)hGhrelin(1-28)-NH$_2$; | (SEQ ID NO: 32) |
| (Cys(S-(CH$_2$)$_9$CH$_3$)$^3$,Glu(NH-hexyl)$^{17}$)hGhrelin(1-28)-NH$_2$; | (SEQ ID NO: 33) |
| (Cys(S-(CH$_2$)$_9$CH$_3$)$^3$,Ser(n-octanoyl)$^{17}$)hGhrelin(1-28)-NH$_2$; | (SEQ ID NO: 34) |
| (Aib$^2$,Glu(NH-hexyl)$^{3,17}$)hGhrelin(1-28)-NH$_2$; | (SEQ ID NO: 36) |
| (Aib$^2$,Glu(NH-hexyl)$^{3,7}$,Thz$^7$)hGhrelin(1-28)-NH$_2$; | (SEQ ID NO: 38) |
| (Aib$^2$,Glu(NH-hexyl)$^{3,17}$,4-Hyp$^7$)hGhrelin(1-28)-NH$_2$; | (SEQ ID NO: 38) |
| (Aib$^2$,Glu(NH-hexyl)$^{3,17}$,Dhp$^7$)hGhrelin(1-28)-NH$_2$; | (SEQ ID NO: 38) |
| (Aib$^2$,Glu(NH-hexyl)$^{3,17}$,Pip$^7$)hGhrelin(1-28)-NH$_2$; | (SEQ ID NO: 38) |
| (Aib$^2$,Glu(NH-hexyl)$^{3,17}$,Tic$^7$)hGhrelin(1-28)-NH$_2$; | (SEQ ID NO: 38) |
| (Aib$^{2,8}$,Glu(NH-hexyl)$^{3,17}$)hGhrelin(1-28)-NH$_2$; | (SEQ ID NO: 40) |
| (Aib$^2$,Glu(NH-hexyl)$^{3,17}$,3-Pal$^9$)hGhrelin(1-28)-NH$_2$; | (SEQ ID NO: 42) |
| (Aib$^2$,Glu(NH-hexyl)$^{3,17}$,4-Pal$^9$)hGhrelin(1-28)-NH$_2$; | (SEQ ID NO: 42) |
| (Aib$^2$,Glu(NH-hexyl)$^{3,17}$,Taz$^9$)hGhrelin(1-28)-NH$_2$; | (SEQ ID NO: 42) |
| (Aib$^2$,Glu(NH-hexyl)$^{3,17}$,2-Thi$^9$)hGhrelin(1-28)-NH$_2$; | (SEQ ID NO: 42) |
| (Aib$^{2,10}$,Glu(NH-hexyl)$^{3,17}$)hGhrelin(1-28)-NH$_2$; | (SEQ ID NO: 44) |
| (Glu(NH-hexyl)$^{3,17}$,Aib$^8$)hGhrelin(1-28)-NH$_2$; | (SEQ ID NO: 47) |
| (Glu(NH-hexyl)$^{3,17}$,Taz$^9$)hGhrelin(1-28)-NH$_2$; | (SEQ ID NO: 48) |

-continued

| | |
|---|---|
| (Glu(NH-hexyl)$^{3,17}$,3-Pal$^9$)hGhrelin(1-28)-NH$_2$; | (SEQ ID NO: 48) |
| (Glu(NH-hexyl)$^{3,17}$,4-Pal$^9$)hGhrelin(1-28)-NH$_2$; | (SEQ ID NO: 48) |
| (Glu(NH-hexyl)$^{3,17}$,2-Thi$^9$)hGhrelin(1-28)-NH$_2$; | (SEQ ID NO: 48) |
| (Aib$^{1,2,10}$,Glu(NH-hexyl)$^{3,17}$)hGhrelin(1-28)-NH$_2$; | (SEQ ID NO: 50) |
| (A5c$^2$,Glu(NH-hexyl)$^{3,17}$)hGhrelin(1-28)-NH$_2$; | (SEQ ID NO: 52) |
| (Glu(1-heptanol)$^{3,17}$)hGhrelin(1-28)-NH$_2$; | (SEQ ID NO: 53) |
| (Asp(1-heptanol)$^{3,17}$)hGhrelin(1-28)-NH$_2$; | (SEQ ID NO: 54) |
| (Glu(NH-hexyl)$^{3,17}$)hGhrelin(1-28)-NH$_2$; | (SEQ ID NO: 55) |
| (Asp(NH-hexyl)$^{3,17}$)hGhrelin(1-28)-NH$_2$; | (SEQ ID NO: 56) |
| (Aib$^2$,Glu(NH-hexyl)$^{3,17}$)hGhrelin(1-28)-NH$_2$; | (SEQ ID NO: 57) |
| (Ac-Gly$^1$,Glu(NH-hexyl)$^{3,17}$)hGhrelin(1-28)-NH$_2$; | (SEQ ID NO: 91) |
| (Ac-Gly$^1$,Glu(NH-hexyl)$^3$, Ser(n-octanoyl)$^{17}$)hGhrelin(1-28)-NH$_2$; | (SEQ ID NO: 92) |
| (Ac-Gly$^1$,Dap(octanesulfonyl)$^{3,17}$)hGhrelin(1-28)-NH$_2$; | (SEQ ID NO: 94) |
| (Ac-Gly$^1$,Dap(octanesulfonyl)$^3$,Glu(NH-hexyl)$^{17}$)hGhrelin(1-28)-NH$_2$; | (SEQ ID NO: 95) |
| (Ac-Gly$^1$,Dap(octanesulfonyl)$^3$,Ser(n-octanoyl)$^{17}$)hGhrelin(1-28)-NH$_2$; | (SEQ ID NO: 96) |
| (Ac-Gly$^1$,Glu(NH-hexyl)$^3$, Dap(octanesulfonyl)$^{17}$)hGhrelin(1-28)-NH$_2$; | (SEQ ID NO: 97) |
| (Ac-Gly$^1$,(Cys(S-(CH$_2$)$_9$CH$_3$)$^{3,17}$)hGhrelin(1-28)-NH$_2$; | (SEQ ID NO: 99) |
| (Ac-Gly$^1$,Glu(NH-hexyl)$^3$,(Cys(S-(CH$_2$)$_9$CH$_3$)$^{17}$)hGhrelin(1-28)-NH$_2$; | (SEQ ID NO: 100) |
| (Ac-Gly$^1$,(Cys(S-(CH$_2$)$_9$CH$_3$)$^3$,Glu(NH-hexyl)$^{17}$)hGhrelin(1-28)-NH$_2$; | (SEQ ID NO: 101) |
| (Ac-Gly$^1$,(Cys(S-(CH$_2$)$_9$CH$_3$)$^3$,Ser(n-octanoyl)$^{17}$)hGhrelin(1-28)-NH$_2$; | (SEQ ID NO: 102) |
| (Ac-Gly$^1$,Aib$^2$,Glu(NH-hexyl)$^{3,17}$)hGhrelin(1-28)-NH$_2$; | (SEQ ID NO: 104) |
| (Ac-Gly$^1$,Aib$^2$,Glu(NH-hexyl)$^{3,17}$,Thz$^7$)hGhrelin(1-28)-NH$_2$; | (SEQ ID NO: 106) |
| (Ac-Gly$^1$,Aib$^2$,Glu(NH-hexyl)$^{3,17}$,4-Hyp$^7$)hGhrelin(1-28)-NH$_2$; | (SEQ ID NO: 106) |
| (Ac-Gly$^1$,Aib$^2$,Glu(NH-hexyl)$^{3,17}$,Dhp$^7$)hGhrelin(1-28)-NH$_2$; | (SEQ ID NO: 106) |
| (Ac-Gly$^1$,Aib$^2$,Glu(NH-hexyl)$^{3,17}$,Pip$^7$)hGhrelin(1-28)-NH$_2$; | (SEQ ID NO: 106) |
| (Ac-Gly$^1$,Aib$^2$,Glu(NH-hexyl)$^{3,17}$,Tic$^7$)hGhrelin(1-28)-NH$_2$; | (SEQ ID NO: 106) |
| (Ac-Gly$^1$,Aib$^{2,8}$,Glu(NH-hexyl)$^{3,17}$)hGhrelin(1-28)-NH$_2$; | (SEQ ID NO: 108) |
| (Ac-Gly$^1$,Aib$^2$,3-Pal$^9$,Glu(NH-hexyl)$^{17}$)hGhrelin(1-28)-NH$_2$; | (SEQ ID NO: 109) |
| (Ac-Gly$^1$,Aib$^2$,Glu(NH-hexyl)$^{3,17}$,3-Pal$^9$)hGhrelin(1-28)-NH$_2$; | (SEQ ID NO: 110) |
| (Ac-Gly$^1$,Aib$^2$,Glu(NH-hexyl)$^{3,17}$,4-Pal$^9$)hGhrelin(1-28)-NH$_2$; | (SEQ ID NO: 110) |
| (Ac-Gly$^1$,Aib$^2$,Glu(NH-hexyl)$^{3,17}$,Taz$^9$)hGhrelin(1-28)-NH$_2$; | (SEQ ID NO: 110) |
| (Ac-Gly$^1$,Aib$^2$,Glu(NH-hexyl)$^{3,17}$,2-Thi$^9$)hGhrelin(1-28)-NH$_2$; | (SEQ ID NO: 110) |
| (Ac-Gly$^1$,Aib$^{2,10}$,Glu(NH-hexyl)$^{3,17}$)hGhrelin(1-28)-NH$_2$; | (SEQ ID NO: 112) |
| (Ac-Gly$^1$,Glu(NH-hexyl)$^{3,17}$,Aib$^8$)hGhrelin(1-28)-NH$_2$; | (SEQ ID NO: 115) |
| (Ac-Gly$^1$,Glu(NH-hexyl)$^{3,17}$,Taz$^9$)hGhrelin(1-28)-NH$_2$; | (SEQ ID NO: 116) |
| (Ac-Gly$^1$,Glu(NH-hexyl)$^{3,17}$,3-Pal$^9$)hGhrelin(1-28)-NH$_2$; | (SEQ ID NO: 116) |
| (Ac-Gly$^1$,Glu(NH-hexyl)$^{3,17}$,4-Pal$^9$)hGhrelin(1-28)-NH$_2$; | (SEQ ID NO: 116) |
| (Ac-Gly$^1$,Glu(NH-hexyl)$^{3,17}$,2-Thi$^9$)hGhrelin(1-28)-NH$_2$; | (SEQ ID NO: 116) |
| (Ac-Aib$^1$,Aib$^{2,10}$,Glu(NH-hexyl)$^{3,17}$)hGhrelin(1-28)-NH$_2$; | (SEQ ID NO: 118) |
| (Ac-Gly$^1$,A5c$^2$,Glu(NH-hexyl)$^{3,17}$)hGhrelin(1-28)-NH$_2$; | (SEQ ID NO: 120) |

-continued

| | |
|---|---|
| (Ac-Gly¹,Glu(1-heptanol)³,¹⁷)hGhrelin(1-28)-NH₂; | (SEQ ID NO: 121) |
| (Ac-Gly¹,Asp(1-heptanol)³,¹⁷)hGhrelin(1-28)-NH₂; | (SEQ ID NO: 122) |
| (Ac-Gly¹,Glu(NH-hexyl)³,¹⁷)hGhrelin(1-28)-NH₂; | (SEQ ID NO: 123) |
| (Ac-Gly¹,Asp(NH-hexyl)³,¹⁷)hGhrelin(1-28)-NH₂; | (SEQ ID NO: 124) |
| (Ac-Gly¹,Aib²,Glu(NH-hexyl)³,¹⁷)hGhrelin(1-28)-NH₂; or | (SEQ ID NO: 125) |
| (Ac-Gly¹,Aib²,¹⁰,Glu(NH-hexyl)³,Lys(biotinyl)¹⁷)hGhrelin(1-28)-NH₂; | (SEQ ID NO: 126); | or a pharmaceutically acceptable salt thereof.

7. A compound according to claim 6, wherein said compound is:

| | |
|---|---|
| (Glu(NH-hexyl)³,¹⁷)hGhrelin(1-28)-NH₂; | (SEQ ID NO: 23) |
| (Glu(NH-hexyl)³,Ser(n-octanoyl)¹⁷)hGhrelin(1-28)-NH₂; | (SEQ ID NO: 24) |
| (Aib²,Glu(NH-hexyl)³,¹⁷)hGhrelin(1-28)-NH₂; | (SEQ ID NO: 36) |
| (Aib²,⁸,Glu(NH-hexyl)³,¹⁷)hGhrelin(1-28)-NH₂; | (SEQ ID NO: 40) |
| (Aib²,¹⁰,Glu(NH-hexyl)³,¹⁷)hGhrelin(1-28)-NH₂; | (SEQ ID NO: 44) |
| (Aib¹,²,¹⁰,Glu(NH-hexyl)³,¹⁷)hGhrelin(1-28)-NH₂; | (SEQ ID NO: 50) |
| (A5c²,Glu(NH-hexyl)³,¹⁷)hGhrelin(1-28)-NH₂; | (SEQ ID NO: 52) |
| (Glu(1-heptanol)³,¹⁷)hGhrelin(1-28)-NH₂; | (SEQ ID NO: 53) |
| (Asp(1-heptanol)³,¹⁷)hGhrelin(1-28)-NH₂; | (SEQ ID NO: 54) |
| (Glu(NH-hexyl)³,¹⁷)hGhrelin(1-28)-NH₂; | (SEQ ID NO: 55) |
| (Asp(NH-hexyl)³,¹⁷)hGhrelin(1-28)-NH₂; | (SEQ ID NO: 56) |
| (Aib²,Glu(NH-hexyl)³,¹⁷)hGhrelin(1-28)-NH₂; | (SEQ ID NO: 57) |
| (Ac-Gly¹,Glu(NH-hexyl)³,¹⁷)hGhrelin(1-28)-NH₂; | (SEQ ID NO: 91) |
| (Ac-Gly¹,Glu(NH-hexyl)³,Ser(n-octanoyl)¹⁷)hGhrelin(1-28)-NH₂; | (SEQ ID NO: 92); |
| (Ac-Gly¹,Aib²,Glu(NH-hexyl)³,¹⁷)hGhrelin(1-28)-NH₂; | (SEQ ID NO: 104) |
| (Ac-Gly¹,Aib²,⁸,Glu(NH-hexyl)³,¹⁷)hGhrelin(1-28)-NH₂; | (SEQ ID NO: 108) |
| (Ac-Gly¹,Aib²,¹⁰,Glu(NH-hexyl)³,¹⁷)hGhrelin(1-28)-NH₂; | (SEQ ID NO: 112) |
| (Ac-Aib¹,Aib²,¹⁰,Glu(NH-hexyl)³,¹⁷)hGhrelin(1-28)-NH₂; | (SEQ ID NO: 118) |
| (Ac-Gly¹,A5c²,Glu(NH-hexyl)³,¹⁷)hGhrelin(1-28)-NH₂; | (SEQ ID NO: 120) |
| (Ac-Gly¹,Glu(1-heptanol)³,¹⁷)hGhrelin(1-28)-NH₂; | (SEQ ID NO: 121) |
| (Ac-Gly¹,Asp(1-heptanol)³,¹⁷)hGhrelin(1-28)-NH₂; | (SEQ ID NO: 122) |
| (Ac-Gly¹,Glu(NH-hexyl)³,¹⁷)hGhrelin(1-28)-NH₂; | (SEQ ID NO: 123) |
| (Ac-Gly¹,Asp(NH-hexyl)³,¹⁷)hGhrelin(1-28)-NH₂; | (SEQ ID NO: 124) |
| (Ac-Gly¹,Aib²,Glu(NH-hexyl)³,¹⁷)hGhrelin(1-28)-NH₂; or | (SEQ ID NO: 125) |
| (Ac-Gly¹,Aib²,¹⁰,Glu(NH-hexyl)³,Lys(biotinyl)¹⁷)hGhrelin(1-28)-NH₂; | (SEQ ID NO: 126) | or a pharmaceutically acceptable salt thereof.

8. A compound according to claim 7, wherein said compound is:

| | |
|---|---|
| (Glu(NH-hexyl)³,¹⁷)hGhrelin(1-28)-NH₂; | (SEQ ID NO: 23) |
| (Glu(NH-hexyl)³,Ser(n-octanoyl)¹⁷)hGhrelin(1-28)-NH₂; | (SEQ ID NO: 24) |

| | |
|---|---|
| (Aib², Glu(NH-hexyl)³,¹⁷)hGhrelin(1-28)-NH₂; | (SEQ ID NO: 36) |
| (Aib²,⁸, Glu(NH-hexyl)³,¹⁷)hGhrelin(1-28)-NH₂; | (SEQ ID NO: 40) |
| (Aib²,¹⁰, Glu(NH-hexyl)³,¹⁷)hGhrelin(1-28)-NH₂; | (SEQ ID NO: 44) |
| (Aib¹,²,¹⁰, Glu(NH-hexyl)³,¹⁷)hGhrelin(1-28)-NH₂; | (SEQ ID NO: 50) |
| (A5c², Glu(NH-hexyl)³,¹⁷)hGhrelin(1-28)-NH₂; | (SEQ ID NO: 52) |
| (Aib², Glu(NH-hexyl)³,¹⁷)hGhrelin(1-28)-NH₂; | (SEQ ID NO: 36) |
| (Ac-Gly¹, Glu(NH-hexyl)³,¹⁷)hGhrelin(1-28)-NH₂; | (SEQ ID NO: 91) |
| (Ac-Gly¹, Glu(NH-hexyl)³, Ser(n-octanoyl)¹⁷)hGhrelin(1-28)-NH₂; | (SEQ ID NO: 92) |
| (Ac-Gly¹, Aib², Glu(NH-hexyl)³,¹⁷)hGhrelin(1-28)-NH₂; | (SEQ ID NO: 104) |
| (Ac-Gly¹, Aib²,⁸, Glu(NH-hexyl)³,¹⁷)hGhrelin(1-28)-NH₂; | (SEQ ID NO: 108) |
| (Ac-Gly¹, Aib²,¹⁰, Glu(NH-hexyl)³,¹⁷)hGhrelin(1-28)-NH₂; | (SEQ ID NO: 112) |
| (Ac-Aib¹, Aib²,¹⁰, Glu(NH-hexyl)³,¹⁷)hGhrelin(1-28)-NH₂; | (SEQ ID NO: 118) |
| (Ac-Gly¹, A5c², Glu(NH-hexyl)³,¹⁷)hGhrelin(1-28)-NH₂; | (SEQ ID NO: 120) |
| (Ac-Gly¹, Aib², Glu(NH-hexyl)³,¹⁷)hGhrelin(1-28)-NH₂; or | (SEQ ID NO: 125) |
| (Ac-Gly¹, Aib²,¹⁰, Glu(NH-hexyl)³, Lys(biotinyl)¹⁷)hGhrelin(1-28)-NH₂; | (SEQ ID NO: 126) | or a pharmaceutically acceptable salt thereof.

9. A compound according to claim 1, wherein:
$A^1$ is Gly or Aib;
$A^2$ is Ser or Aib;
$A^3$ is Glu(NH-hexyl);
$A^8$ is Glu or Aib;
$A^{10}$ is Gln or Aib; and
$A^{17}$ is Glu(NH-hexyl) or Lys(biotinyl);
or a pharmaceutically acceptable salt thereof.

10. A compound according to claim 9, wherein:
$R^1$ is $NH_2$;
each of $R^2$ and $R^3$ is, independently for each occurrence thereof, selected from the group consisting of H, ($C_1$-$C_{30}$)acyl, n-butyryl, isobutyryl and n-octanoyl;
or pharmaceutically acceptable salts thereof.

11. A compound according to claim 10, wherein said compound is:

| | |
|---|---|
| (Aib²,⁸, Glu(NH-hexyl)³,¹⁷)hGhrelin(1-28)-NH₂; | (SEQ ID NO: 40) |
| (Aib¹,²,¹⁰, Glu(NH-hexyl)³,¹⁷)hGhrelin(1-28)-NH₂; | (SEQ ID NO: 50) |
| (Ac-Gly¹, Aib², Glu(NH-hexyl)³,¹⁷)hGhrelin(1-28)-NH₂; | (SEQ ID NO: 104) |
| (Ac-Gly¹, Aib²,⁸, Glu(NH-hexyl)³,¹⁷)hGhrelin(1-28)-NH₂; | (SEQ ID NO: 108) |
| (Ac-Gly¹, Aib²,¹⁰, Glu(NH-hexyl)³,¹⁷)hGhrelin(1-28)-NH₂; | (SEQ ID NO: 112) |
| (Ac-Aib¹, Aib²,¹⁰, Glu(NH-hexyl)³,¹⁷)hGhrelin(1-28)-NH₂; | (SEQ ID NO: 118) |
| (Ac-Gly¹, Aib²,¹⁰, Glu(NH-hexyl)³, Lys(biotinyl)¹⁷)hGhrelin(1-28)-NH₂; | (SEQ ID NO: 126) | or pharmaceutically acceptable salts thereof.

12. A compound according to claim 11, wherein said compound is:

| | |
|---|---|
| (Aib²,⁸, Glu(NH-hexyl)³,¹⁷)hGhrelin(1-28)-NH₂; | (SEQ ID NO: 40) |
| (Aib¹,²,¹⁰, Glu(NH-hexyl)³,¹⁷)hGhrelin(1-28)-NH₂; and | (SEQ ID NO: 50) |
| (Ac-Aib¹, Aib²,¹⁰, Glu(NH-hexyl)³,¹⁷)hGhrelin(1-28)-NH₂; | (SEQ ID NO: 118) | or pharmaceutically acceptable salts thereof.

13. A pharmaceutical composition comprising an effective amount of a compound according to claim 1, or a pharmaceutically acceptable salt thereof, and a pharmaceutically acceptable carrier or diluent.

14. A method of screening for a compound able to bind to a GHS receptor, said method comprising the step of measuring the ability of a compound to affect binding of a compound according claim 1 to said receptor, to a fragment of said receptor, to a polypeptide comprising said fragment of said receptor, or to a derivative of said polypeptide.

15. A method for stimulating growth hormone secretion in a subject in need of such stimulation, comprising the step of administering to the subject an effective amount of a ghrelin analog agonist according to claim 1, or a pharmaceutically acceptable salt thereof, wherein said effective amount is at least an amount sufficient to produce a detectable increase in growth hormone secretion.

16. A method according to claim 15 wherein said stimulation of growth hormone secretion is indicated for treatment of a growth hormone deficient state, for increasing muscle mass, for increasing bone density, for sexual dysfunction in males or females, for facilitating a weight gain, for facilitating maintenance of weight, for facilitating maintenance of physical functioning, for facilitating recovery of physical function and/or facilitating appetite increase.

17. A method according to claim 16 wherein said facilitating weight gain, facilitating maintenance of weight, and/or facilitating appetite increase is indicated in a patient having a disease or disorder or undergoing a treatment accompanied by weight loss.

18. A method according to claim 17 wherein said weight loss is due to onset of cachexia.

19. A method according to claim 18 wherein said cachexia is incidental to said subject suffering from anorexia, bulimia, cancer, AIDS or chronic obstructive pulmonary disease.

20. A method according to claim 17 wherein said weight loss is due to the onset of wasting syndrome.

21. A method according to claim 20 wherein said subject in need thereof suffering from wasting syndrome is frail and elderly.

22. A method according to claim 17 wherein said weight loss is unexplained and wherein said subject is a healthy elder.

23. A method according to claim 17 wherein said weight loss is a precursor to the onset of Alzheimer's disease.

24. A method according to claim 17 wherein said treatment accompanied by weight loss is selected from the group consisting of chemotherapy, radiation therapy, temporary immobilization, permanent immobilization and dialysis.

25. A method of according to claim 15 wherein said subject in need thereof is not suffering from a disease or disorder and is not undergoing a treatment accompanied by weight loss and is otherwise healthy.

26. A method for achieving a beneficial effect in a subject comprising, said method comprising the step of administering to said subject an effective amount of a compound according to claim 1, or a pharmaceutically acceptable salt thereof, wherein said effective amount is effective for producing a beneficial effect in helping to treat or prevent chronic obstructive pulmonary disease.

27. A method for suppressing growth hormone secretion in a subject in need of such suppression, comprising the step of administering to the subject an effective amount of a ghrelin analog according to claim 1, or a pharmaceutically acceptable salt thereof, wherein said effective amount is at least an amount sufficient to produce a detectable decrease in growth hormone secretion.

28. A method according to claim 27 wherein said suppression of growth hormone secretion is indicated for the treatment of a disease or condition characterized by excessive growth hormone secretion, for facilitation of loss of excessive body weight, for facilitation of appetite decrease, for facilitation of weight maintenance, for treating obesity, for treating diabetes, for treating complications of diabetes and/or for treating cardiovascular disorders.

29. A method according to claim 28 wherein said excessive weight is a contributing factor to hypertension, diabetes, dyslipidemia, cardiovascular disease, gall stones, osteoarthritis or cancers.

30. A method according to claim 28 wherein said facilitation of loss of excessive body weight reduces the likelihood of such diseases or conditions.

31. A method according to claim 28 wherein said facilitation of loss of excessive body weight comprises at least part of a treatment for such diseases or conditions.

32. A method according to claim 28 wherein said excessive weight is due to Prader-Willi syndrome.

33. A compound according to formula (II):

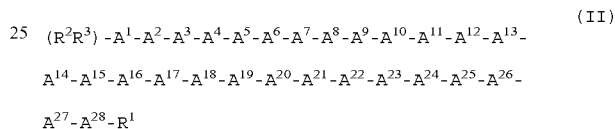

$(R^2R^3)$-$A^1$-$A^2$-$A^3$-$A^4$-$A^5$-$A^6$-$A^7$-$A^8$-$A^9$-$A^{10}$-$A^{11}$-$A^{12}$-$A^{13}$-$A^{14}$-$A^{15}$-$A^{16}$-$A^{17}$-$A^{18}$-$A^{19}$-$A^{20}$-$A^{21}$-$A^{22}$-$A^{23}$-$A^{24}$-$A^{25}$-$A^{26}$-$A^{27}$-$A^{28}$-$R^1$ wherein:
$A^1$ is Gly;
$A^2$ is Ser or Aib;
$A^3$ is Asp(NH—$R^9$), Asp(O—$R^8$), Cys(S—$R^{14}$), Dab(S(O)$_2$—$R^{11}$), Dap(S(O)$_2$—$R^{10}$), Glu(NH—$R^7$), Glu(O—$R^6$), Ser(C(O)—$R^4$), Thr(C(O)—$R^5$) or HN—CH((CH$_2$)$_n$—N($R^{12}R^{13}$))—C(O);
$A^4$ is Phe, Acc, Aic, Cha, 2-Fua, 1-Nal, 2-Nal, 2-Pal, 3-Pal, 4-Pal, hPhe, ($X^1$,$X^2$,$X^3$,$X^4$,$X^5$)Phe, Taz, 2-Thi, 3-Thi, Trp or Tyr;
$A^5$ is Leu, Abu, Acc, Aib, Ala, Cha, Ile, hLeu, Nle, Nva, Phe, Tle or Val;
$A^6$ is Ser, Abu, Acc, Act, Aib, Ala, Gly, Thr or Val;
$A^7$ is Pro, Dhp, Dmt, 3-Hyp, 4-Hyp, Inc, Ktp, Oic, Pip, Thz or Tic;
$A^8$ is Glu or Aib;
$A^9$ is His, Acc, Aib, Apc, 2-Fua, 2-Pal, 3-Pal, 4-Pal, ($X^1$,$X^2$,$X^3$,$X^4$,$X^5$—)Phe, Taz, 2-Thi or 3-Thi;
$A^{10}$ is Gln, Acc, Aib, Asn, Asp or Glu;
$A^{11}$ is Arg, Apc, hArg, Dab, Dap, Lys, Orn or HN—CH((CH$_2$)$_n$—N($R^{12}R^{13}$))—C(O);
$A^{12}$ is Val, Abu, Acc, Aib, Ala, Cha, Nva, Gly, Ile, Leu, Nle or Tle;
$A^{13}$ is Gln, Acc, Aib, Asn, Asp or Glu;
$A^{14}$ is Gln, Acc, Aib, Asn, Asp or Glu;
$A^{15}$ is Arg, Acc, Aib, Apc, hArg, Dab, Dap, Lys, Orn, Asp(NH—$R^9$), Asp(O—$R^8$), Cys(S—$R^{14}$), Cys($R^{15}$), hCys(S—$R^{16}$), hCys($R^{17}$), Dab(S(O)$_2$—$R^{11}$), Dap(S(O)$_2$—$R^{10}$), Glu(NH—$R^7$), Glu(O—$R^6$), Ser(C(O)—$R^4$), Thr(C(O)—$R^5$) or HN—CH((CH$_2$)$_n$—N($R^{12}R^{13}$))—C(O);
$A^{16}$ is Lys, Acc, Aib, Apc, Arg, hArg, Dab, Dap, Orn, Asp(NH—$R^9$), Asp(O—$R^8$), Cys(S—$R^{14}$), Cys($R^{15}$), hCys(S—$R^{16}$), hCys($R^{17}$), Dab(S(O)$_2$—$R^{11}$), Dap(S(O)$_2$—$R^{10}$), Glu(NH—$R^7$), Glu(O—$R^6$), Ser(C(O)—$R^4$), Thr(C(O)—$R^5$), HN—CH((CH$_2$)$_n$—N($R^{12}R^{13}$))—C(O) or deleted;
$A^{17}$ is Lys(myristyl);

A$^{18}$ is Ser, Abu, Acc, Act, Aib, Ala, Thr, Val, Asp(NH—R$^9$), Asp(O—R$^8$), Cys(S—R$^{14}$), Cys(R$^{15}$), hCys(S—R$^{16}$), hCys(R$^{17}$), Dab(S(O)$_2$—R$^{11}$), Dap(S(O)$_2$—R$^{10}$), Glu(NH—R$^7$), Glu(O—R$^6$), Ser(C(O)—R$^4$), Thr(C(O)—R$^5$), HN—CH((CH$_2$)$_n$—N(R$^{12}$R$^{13}$))—C(O) or deleted;

A$^{19}$ is Lys, Acc, Aib, Apc, Arg, hArg, Dab, Dap, Orn, Asp(NH—R$^9$), Asp(O—R$^8$), Cys(S—R$^{14}$), Cys(R$^{15}$), hCys(S—R$^{16}$), hCys(R$^{17}$), Dab(S(O)$_2$—R$^{11}$), Dap(S(O)$_2$—R$^{10}$), Glu(NH—R$^7$), Glu(O—R$^6$), Ser(C(O)—R$^4$), Thr(C(O)—R$^5$), HN—CH((CH$_2$)$_n$—N(R$^{12}$R$^{13}$))—C(O) or deleted;

A$^{20}$ is Lys, Acc, Aib, Apc, Arg, hArg, Dab, Dap, Orn, Asp(NH—R$^9$), Asp(O—R$^8$), Cys(S—R$^{14}$), Cys(R$^{15}$), hCys(S—R$^{16}$), hCys(R$^{17}$), Dab(S(O)$_2$—R$^{11}$), Dap(S(O)$_2$—R$^{10}$), Glu(NH—R$^7$), Glu(O—R$^6$), Ser(C(O)—R$^4$), Thr(C(O)—R$^5$), HN—CH((CH$_2$)$_n$—N(R$^{12}$R$^{13}$))—C(O) or deleted;

A$^{21}$ is Pro, Dhp, Dmt, 3-Hyp, 4-Hyp, Inc, Ktp, Oic, Pip, Thz, Tic or deleted;

A$^{22}$ is Pro, Dhp, Dmt, 3-Hyp, 4-Hyp, Inc, Ktp, Oic, Pip, Thz, Tic or deleted;

A$^{23}$ is Abu, Acc, Act, Aib, Ala, Apc, Gly, Nva, Val or deleted;

A$^{24}$ is Lys, Acc, Aib, Apc, Arg, hArg, Dab, Dap, Orn, HN—CH((CH$_2$)$_n$—N(R$^{12}$R$^{13}$))—C(O) or deleted;

A$^{25}$ is Leu, Abu, Acc, Aib, Ala, Cha, Ile, hLeu, Nle, Nva, Phe, Tle, Val or deleted;

A$^{26}$ is Gln, Aib, Asn, Asp, Glu or deleted;

A$^{27}$ is Pro, Dhp, Dmt, 3-Hyp, 4-Hyp, Inc, Ktp, Oic, Pip, Thz, Tic or deleted;

A$^{28}$ is Acc, Aib, Apc, Arg, hArg, Dab, Dap, Lys, Orn, HN—CH((CH$_2$)$_n$—N(R$^{12}$R$^{13}$))—C(O) or deleted;

R$^1$ is —OH, —NH$_2$, —(C$_1$-C$_{30}$)alkoxy or NH—X$^6$—CH$_2$—Z$^0$, wherein X$^6$ is a (C$_1$-C$_{12}$)alkyl or (C$_2$-C$_{12}$)alkenyl and Z$^0$ is —H, —OH, —CO$_2$H or —C(O)—NH$_2$;

each of R$^2$ and R$^3$ is, independently for each occurrence thereof, selected from the group consisting of H, (C$_1$-C$_{30}$)alkyl, (C$_1$-C$_{30}$)heteroalkyl, (C$_1$-C$_{30}$)acyl, (C$_2$-C$_{30}$)alkenyl, (C$_2$-C$_{30}$)alkynyl, aryl(C$_1$-C$_{30}$)alkyl, aryl(C$_1$-C$_{30}$)acyl, substituted (C$_1$-C$_{30}$)alkyl, substituted (C$_1$-C$_{30}$)heteroalkyl, substituted (C$_2$-C$_{30}$)acyl, substituted (C$_2$-C$_{30}$)alkenyl, substituted aryl(C$_1$-C$_{30}$)alkyl, substituted (C$_2$-C$_{30}$)alkynyl and substituted aryl(C$_1$-C$_{30}$)acyl;

each of R$^4$, R$^5$, R$^6$, R$^7$, R$^8$, R$^9$, R$^{10}$, R$^{11}$, R$^{14}$, R$^{15}$, R$^{16}$ and R$^{17}$ is, independently for each occurrence thereof, selected from the group consisting of (C$_1$-C$_{40}$)alkyl, (C$_2$-C$_{40}$)alkenyl, substituted (C$_1$-C$_{40}$)alkyl, substituted (C$_2$-C$_{40}$)alkenyl, alkylaryl, substituted alkylaryl, aryl and substituted aryl;

each of R$^{12}$ and R$^{13}$ is, independently for each occurrence, selected from the group consisting of H, (C$_1$-C$_{40}$)alkyl, (C$_1$-C$_{40}$)heteroalkyl, (C$_1$-C$_{40}$)acyl, (C$_2$-C$_{40}$)alkenyl, (C$_2$-C$_{40}$)alkynyl, aryl(C$_1$-C$_{40}$)alkyl, aryl(C$_1$-C$_{40}$)acyl, substituted (C$_1$-C$_{40}$)alkyl, substituted (C$_1$-C$_{40}$)heteroalkyl, substituted (C$_1$-C$_{40}$)acyl, substituted (C$_2$-C$_{40}$)alkenyl, substituted (C$_2$-C$_{40}$)alkynyl, substituted aryl(C$_1$-C$_{40}$)alkyl, substituted aryl(C$_1$-C$_{40}$)acyl, (C$_1$-C$_{40}$)alkylsulfonyl, —C(NH)—NH$_2$ and biotinyl;

n is, independently for each occurrence thereof, 1, 2, 3, 4 or 5;

each of X$^1$, X$^2$, X$^3$, X$^4$, and X$^5$ is, independently for each occurrence thereof, selected from the group consisting of H, F, Cl, Br, I, (C$_{1-10}$)alkyl, substituted (C$_{1-10}$)alkyl, aryl, substituted aryl, OH, NH$_2$, NO$_2$ and CN;

provided that:

(I) when R$^2$ is (C$_1$-C$_{30}$)acyl, aryl(C$_1$-C$_{30}$)acyl, substituted (C$_2$-C$_{30}$)acyl, or substituted aryl(C$_1$-C$_{30}$)acyl, then R$^3$ is H, (C$_1$-C$_{30}$)alkyl, (C$_1$-C$_{30}$)heteroalkyl, (C$_2$-C$_{30}$)alkenyl, aryl(C$_1$-C$_{30}$)alkyl, substituted (C$_1$-C$_{30}$)alkyl, substituted (C$_1$-C$_{30}$)heteroalkyl, substituted (C$_2$-C$_{30}$)alkenyl, substituted (C$_2$-C$_{30}$)alkynyl or substituted aryl(C$_1$-C$_{30}$)alkyl;

(II) when R$^{12}$ is (C$_1$-C$_{40}$)acyl, aryl(C$_1$-C$_{40}$)acyl, substituted (C$_1$-C$_{40}$)acyl, substituted aryl(C$_1$-C$_{40}$)acyl, (C$_1$-C$_{40}$)alkylsulfonyl, or —C(NH)—NH$_2$, then R$^{13}$ is H, (C$_1$-C$_{40}$)alkyl, (C$_1$-C$_{40}$)heteroalkyl, (C$_2$-C$_{40}$)alkenyl, (C$_2$-C$_{40}$)alkynyl, aryl(C$_1$-C$_{40}$)alkyl, substituted (C$_1$-C$_{40}$)alkyl, substituted (C$_1$-C$_{40}$)heteroalkyl, substituted (C$_2$-C$_{40}$)alkenyl, substituted (C$_2$-C$_{40}$)alkynyl, or substituted aryl(C$_1$-C$_{40}$)alkyl;

(III) at least one of A$^{15}$, A$^{16}$, A17, A$^{18}$, A$^{19}$ or A$^{20}$ is selected from the group consisting of Asp(NH—R$^9$), Asp(O—R$^8$), Cys(S—R$^{14}$), Cys(R$^{15}$), hCys(S—R$^{16}$), hCys(R$^{17}$), Dab(S(O)$_2$—R$^{11}$), Dap(S(O)$_2$—R$^{10}$), Glu(NH—R$^7$), Glu(O—R$^6$), Ser(C(O)—R$^4$), Thr(C(O)—R$^5$) and HN—CH((CH$_2$)$_n$—N(R$^{12}$R$^{13}$))—C(O); and (IV) when any of the group consisting of A$^{15}$, A$^{16}$, A$^{19}$ and A$^{20}$ is HN—CH((CH$_2$)$_n$—N(R$^{12}$R$^{13}$))—C(O), then R$^{12}$ must be biotinyl;

or a pharmaceutically acceptable salt thereof.

34. A compound according to claim 33, wherein:

R$^2$ and R$^3$ is, independently for each occurrence thereof, selected from the group consisting of H, (C$_1$-C$_{30}$)acyl, n-butyryl, isobutyryl, n-octanoyl and myristyl;

R$^4$ is heptyl;
R$^6$ is hexyl;
R$^7$ is hexyl;
R$^{10}$ is octyl; and
Acc is, independently for each occurrence thereof, selected from the group consisting of A3c, A4c, A5c and A6c;

or a pharmaceutically acceptable salt thereof.

35. A compound of the formula:

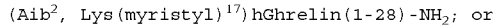
(Aib$^2$, Lys(myristyl)$^{17}$)hGhrelin(1-28)-NH$_2$; or    (SEQ ID NO: 177)

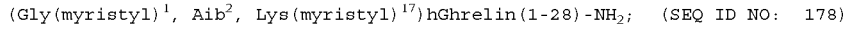
(Gly(myristyl)$^1$, Aib$^2$, Lys(myristyl)$^{17}$)hGhrelin(1-28)-NH$_2$;    (SEQ ID NO: 178)

or a pharmaceutically acceptable salt thereof.

36. A pharmaceutical composition comprising an effective amount of a compound of according to claim 33, or a pharmaceutically acceptable salt thereof, and a pharmaceutically acceptable carrier or diluent.

37. A method of screening for a compound able to bind to a GHS receptor, said method comprising the step of measuring the ability of a compound to affect binding of a compound according to claim 33 to said receptor, to a fragment of said receptor, to a polypeptide comprising said fragment of said receptor or to a derivative of said polypeptide.

38. A method for achieving a beneficial effect in a subject comprising, said method comprising the step of administering to said subject an effective amount of a compound according to claim 37, or a pharmaceutically acceptable salt thereof, wherein said effective amount is effective for producing a beneficial effect in helping to treat or prevent a disease or disorder.

39. A method for stimulating growth hormone secretion in a subject in need of such stimulation, comprising the step of administering to the subject an effective amount of a ghrelin analog agonist according to claim 33, or a pharmaceutically acceptable salt thereof, wherein said effective amount is at least an amount sufficient to produce a detectable increase in growth hormone secretion.

40. A method according to claim 39 wherein said stimulation of growth hormone secretion is indicated for treatment of a growth hormone deficient state, for increasing muscle mass, for increasing bone density, for sexual dysfunction in males or females, for facilitating a weight gain, for facilitating maintenance of weight, for facilitating maintenance of physical functioning, for facilitating recovery of physical function and/or facilitating appetite increase.

41. A method according to claim 40 wherein said facilitating weight gain, facilitating maintenance of weight and/or facilitating appetite increase is indicated in a patient having a disease or disorder or undergoing a treatment which is accompanied by weight loss.

42. A method according to claim 41 wherein said weight loss is due to the onset of cachexia.

43. A method according to claim 42 wherein said cachexia is incidental to said subject suffering from anorexia, bulimia, cancer, AIDS or chronic obstructive pulmonary disease.

44. A method according to claim 41 wherein said weight loss is due to the onset of wasting syndrome.

45. A method according to claim 44 wherein said subject in need thereof suffering from wasting syndrome is frail and elderly.

46. A method according to claim 41 wherein said weight loss is unexplained and wherein said subject is a healthy elder.

47. A method according to claim 41 wherein said weight loss is a precursor to the onset of Alzheimer's disease.

48. A method according to claim 41 wherein said treatment accompanied by weight loss is selected from the group consisting of chemotherapy, radiation therapy, temporary immobilization, permanent immobilization and dialysis.

49. A method of according to claim 39 wherein said subject in need thereof is not suffering from a disease or disorder and is not undergoing a treatment accompanied by weight loss and is otherwise healthy.

50. A method for achieving a beneficial effect in a subject comprising, said method comprising the step of administering to said subject an effective amount of a compound according to claim 33, or a pharmaceutically acceptable salt thereof, wherein said effective amount is effective for producing a beneficial effect in helping to treat or prevent chronic obstructive pulmonary disease.

51. A method for suppressing growth hormone secretion in a subject in need of such suppression, comprising the step of administering to the subject an effective amount of a ghrelin analog according to claim 33, or a pharmaceutically acceptable salt thereof, wherein said effective amount is at least an amount sufficient to produce a detectable decrease in growth hormone secretion.

52. A method according to claim 51 wherein said suppression of growth hormone secretion is indicated for the treatment of a disease or condition characterized by excessive growth hormone secretion, for facilitation of loss of excessive body weight, for facilitation of appetite decrease, for facilitation of weight maintenance, for treating obesity, for treating diabetes, for treating complications of diabetes and/or for treating cardiovascular disorders.

53. A method according to claim 51 wherein said excessive weight is a contributing factor to hypertension, diabetes, dyslipidemia, cardiovascular disease, gall stones, osteoarthritis or cancers.

54. A method according to claim 51 wherein said facilitation of loss of body weight reduces the likelihood of such diseases or conditions.

55. A method according to claim 52 wherein said facilitation of loss of body weight comprises at least part of a treatment for such diseases or conditions.

56. A method according to claim 52 wherein said excessive weight is due to Prader-Willi syndrome.

57. The method of treating inflammation in a subject comprising administering to the subject an effective amount of a compound according to claim 1, wherein the inflammation is associated with an infectious process.

58. The method of claim 57, wherein the infectious process is a viral infection selected from the group consisting of Herpes simplex virus type-1, Herpes simplex virus type-2, Cytomegalovirus, Epstein-Barr virus, Varicella-zoster virus, Human herpes virus 6, Human herpesvirus 7, Human herpesvirus 8, Variola virus, Vesicular stomatitis virus, Hepatitis A virus, Hepatitis B virus, Hepatitis C virus, Hepatitis D virus, Hepatitis E virus, Rhinovirus, Coronavirus, Influenza virus A, Influenza virus B, Measles virus, Polyomavirus, Human Papilomavirus, Respiratory syncytial virus, Adenovirus, Coxsackie virus, Dengue virus, Mumps virus, Poliovirus, Rabies virus, Rous sarcoma virus, Yellow fever virus, Ebola virus, Marburg virus, Lassa fever virus, Eastern Equine Encephalitis virus, Japanese Encephalitis virus, St. Louis Encephalitis virus, Murray Valley fever virus, West Nile virus, Rift Valley fever virus, Rotavirus A, Rotavirus B, Rotavirus C, Sindbis virus, Simian Immunodeficiency virus, Human T-cell Leukemia virustype-1, Hantavirus, Rubella virus, Simian Immunodeficiency virus, Human Immunodeficiency virus type-1 and Human Immunodeficiency virus type-2.

59. The method of claim 57, wherein the infectious process is a bacterial infection selected from the group consisting of *M. tuberculosis*, *M. bovis*, *M. bovis* strain BCG, BCG substrains, *M. avium*, *M. intracellulare*, *M. africanum*, *M. kansasii*, *M. marinum*, *M. ulcerans*, *M. avium* subspecies *paratuberculosis*, *Nocardia asteroides*, other *Nocardia* species, *Legionella pneumophila*, other *Legionella* species, *Salmonella typhi*, other *Salmonella* species, *Shigella* species, *Yersinia pestis*, *Pasteurella haemolytica*, *Pasteurella multocida*, other *Pasteurella* species, *Actinobacillus pleuropneumoniae*, *Listeria monocytogenes*, *Listeria ivanovii*, *Brucella abortus*, other *Brucella* species, *Cowdria ruminantium*, *Chlamydia pneumoniae*, *Chlamydia trachomatis*, *Chlamydia psittaci*, *Coxiella burnetti*, other *Rickettsia* species, *Ehrlichia* species, *Staphylococcus aureus*, *Staphylococcus epidermidis*, *Streptococcus pyogenes*, *Streptococcus agalactiae*, *Bacillus anthracis*, *Escherichia coli*, *Vibrio cholerae*, *Campylobacter* species, *Neiserria meningitidis*, *Neiserria gonorrhea*, *Pseudomonas aeruginosa*, other *Pseudomonas* species, *Haemophilus influenzae*, *Haemophilus ducreyi*, other *Hemophilus* species, *Clostridium tetani*, other *Clostridium* species, *Yersinia enterolitica* and other *Yersinia* species.

60. The method of claim 57, wherein the infectious process is a parasitic infection selected from the group consisting of *Toxoplasma gondii*, *Plasmodium*, *Trypanosoma brucei*, *Trypanosoma cruzi*, *Leishmania*, *Schistosoma* and *Entamoeba histolytica*.

61. The method of claim 57, wherein the infectious process is a fungal infection selected from the group consisting of *Candida albicans*, *Cryptococcus neoformans*, *Histoplama capsulatum*, *Aspergillus fumigatus*, *Coccidiodes immitis*, *Paracoccidiodes brasiliensis*, *Blastomyces dermitidis*, *Pneomocystis carnii*, *Penicillium marneffi* and *Alternaria alternata*.

62. The method of treating inflammation in a subject comprising administering to the subject an effective amount of a compound according to claim 1, wherein said inflammation is associated with liver toxicity.

63. The method of claim 62, wherein said liver toxicity is associated with cancer therapy.

64. The method of claim 63, wherein said cancer therapy is apoptosis induction.

65. The method of claim 63, wherein said cancer therapy is chemotherapy.

66. The method of claim 63, wherein said cancer therapy is a combination of chemotherapy and apoptosis induction.

67. The method of treating an inflammatory disease in a subject comprising administering to the subject an effective amount of a compound according to claim 1, wherein the inflammatory disease is selected from the group consisting of asthma, reactive arthritis, hepatitis, spondyarthritis, Sjogren's syndrome, Alzheimer's disease and atopic dermatitis.

68. The method of treating an inflammatory disease in a subject comprising administering to the subject an effective amount of a compound according to claim 1, wherein the inflammatory disease is associated with an autoimmune disease.

69. The method of claim 68, wherein the autoimmune disease is systemic lupus erythematosus, rheumatoid arthritis, systemic vasculitis, insulin dependent diabetes mellitus, multiple sclerosis, muscular dystrophy, experimental allergic encephalomyelitis, psoriasis, Crohn's disease, inflammatory bowel disease, ulcerative colitis, Addison's disease, alopecia aretea, celiac disease, thyroid disease and scleroderma.

70. The method of treating inflammation in a subject comprising administering to the subject an effective amount of a compound according to claim 1, wherein the inflammation is associated with a burn.

71. The method of treating inflammation in a subject comprising administering to the subject an effective amount of a compound according to claim 1, wherein the inflammation is associated with lung inflammation.

72. The method of treating inflammation in a subject comprising administering to the subject an effective amount of a compound according to claim 1, wherein the inflammation is associated with cancer.

73. The method of claim 72, wherein the cancer is selected from the group consisting of lymphoma, leukemia, mycosis fungoide, carcinoma, adenocarcinoma, sarcoma, glioma, blastoma, neuroblastoma, plasmacytoma, histiocytoma, melanoma, adenoma, hypoxic tumor, myeloma, AIDS-related lymphoma, AIDS-related sarcoma, metastatic cancer, bladder cancer, brain cancer, nervous system cancer, glioblastoma, ovarian cancer, skin cancer, liver cancer, squamous cell carcinomas of the mouth, throat, larynx, and lung, colon cancer, cervical cancer, breast cancer, epithelial cancer, renal cancer, genitourinary cancer, pulmonary cancer, esophageal carcinoma, head and neck carcinoma, hematopoietic cancer, testicular cancer, colo-rectal cancer, prostatic cancer and pancreatic cancer.

74. The method of treating inflammation in a subject comprising administering to the subject an effective amount of a compound according to claim 1, wherein the inflammation is associated with transplant rejection.

75. A method of treating loss of appetite caused by an inflammation in a subject by administering to the subject an effective amount of a compound according to claim 1.

76. The method of claim 75 wherein the inflammation is low grade inflammation.

77. The method of claim 76 wherein the low grade inflammation is caused by aging.

78. A method according to claim 28 wherein said complication of diabetes is retinopathy.

79. A method according to claim 52 wherein said complication of diabetes is retinopathy.

80. A compound, wherein said compound is:

| | |
|---|---|
| $(Ser(n\text{-}octanoyl)^{15})hGhrelin(1\text{-}28)\text{-}NH_2;$ | (SEQ ID NO: 1) |
| $(Glu(NH\text{-}hexyl)^{15})hGhrelin(1\text{-}28)\text{-}NH_2;$ | (SEQ ID NO: 2) |
| $(Aib^2, Glu(NH\text{-}hexyl)^{15})hGhrelin(1\text{-}28)\text{-}NH_2;$ | (SEQ ID NO: 5) |
| $(Aib^{2,8}, Glu(NH\text{-}hexyl)^{15})hGhrelin(1\text{-}28)\text{-}NH_2;$ | (SEQ ID NO: 7) |
| $(Aib^{2,10}, Glu(NH\text{-}hexyl)^{15})hGhrelin(1\text{-}28)\text{-}NH_2;$ | (SEQ ID NO: 9) |
| $(Ser(n\text{-}octanoyl)^{16})hGhrelin(1\text{-}28)\text{-}NH_2;$ | (SEQ ID NO: 11) |
| $(Glu(NH\text{-}hexyl)^{16})hGhrelin(1\text{-}28)\text{-}NH_2;$ | (SEQ ID NO: 12) |
| $(Aib^2, Glu(NH\text{-}hexyl)^{16})hGhrelin(1\text{-}28)\text{-}NH_2;$ | (SEQ ID NO: 15) |
| $(Aib^{2,8}, Glu(NH\text{-}hexyl)^{16})hGhrelin(1\text{-}28)\text{-}NH_2;$ | (SEQ ID NO: 17) |
| $(Aib^{2,10}, Glu(NH\text{-}hexyl)^{16})hGhrelin(1\text{-}28)\text{-}NH_2;$ | (SEQ ID NO: 19) |
| $(Ser(n\text{-}octanoyl)^{17})hGhrelin(1\text{-}28)\text{-}NH_2;$ | (SEQ ID NO: 21) |
| $(Glu(NH\text{-}hexyl)^{17})hGhrelin(1\text{-}28)\text{-}NH_2;$ | (SEQ ID NO: 22) |
| $(Dap(octanesulfonyl)^{17})hGhrelin(1\text{-}28)\text{-}NH_2;$ | (SEQ ID NO: 25) |
| $(Cys(S\text{-}(CH_2)_9CH_3)^{17})hGhrelin(1\text{-}28)\text{-}NH_2;$ | (SEQ ID NO: 30) |
| $(Aib^2, Glu(NH\text{-}hexyl)^{17})hGhrelin(1\text{-}28)\text{-}NH_2;$ | (SEQ ID NO: 35) |
| $(Aib^2, Thz^7, Glu(NH\text{-}hexyl)^{17})hGhrelin(1\text{-}28)\text{-}NH_2;$ | (SEQ ID NO: 37) |
| $(Aib^2, 4\text{-}Hyp^7, Glu(NH\text{-}hexyl)^{17})hGhrelin(1\text{-}28)\text{-}NH_2;$ | (SEQ ID NO: 37) |
| $(Aib^2, Dhp^7, Glu(NH\text{-}hexyl)^{17})hGhrelin(1\text{-}28)\text{-}NH_2;$ | (SEQ ID NO: 37) |

-continued

| | |
|---|---|
| (Aib², Pip⁷, Glu(NH-hexyl)¹⁷)hGhrelin(1-28)-NH₂; | (SEQ ID NO: 37) |
| (Aib², Tic⁷, Glu(NH-hexyl)¹⁷)hGhrelin(1-28)-NH₂; | (SEQ ID NO: 37) |
| (Aib²,⁸, Glu(NH-hexyl)¹⁷)hGhrelin(1-28)-NH₂; | (SEQ ID NO: 39) |
| (Aib², 3-Pal⁹, Glu(NH-hexyl)¹⁷)hGhrelin(1-28)-NH₂; | (SEQ ID NO: 41) |
| (Aib², 4-Pal⁹, Glu(NH-hexyl)¹⁷)hGhrelin(1-28)-NH₂; | (SEQ ID NO: 41) |
| (Aib², Taz⁹, Glu(NH-hexyl)¹⁷)hGhrelin(1-28)-NH₂; | (SEQ ID NO: 41) |
| (Aib², 2-Thi⁹, Glu(NH-hexyl)¹⁷)hGhrelin(1-28)-NH₂; | (SEQ ID NO: 41) |
| (Aib²,¹⁰, Glu(NH-hexyl)¹⁷)hGhrelin(1-28)-NH₂; | (SEQ ID NO: 43) |
| (Aib⁸, Glu(NH-hexyl)¹⁷)hGhrelin(1-28)-NH₂; | (SEQ ID NO: 45) |
| (Taz⁹, Glu(NH-hexyl)¹⁷)hGhrelin(1-28)-NH₂; | (SEQ ID NO: 46) |
| (3-Pal⁹, Glu(NH-hexyl)¹⁷)hGhrelin(1-28)-NH₂; | (SEQ ID NO: 46) |
| (4-Pal⁹, Glu(NH-hexyl)¹⁷)hGhrelin(1-28)-NH₂; | (SEQ ID NO: 46) |
| (2-Thi⁹, Glu(NH-hexyl)¹⁷)hGhrelin(1-28)-NH₂; | (SEQ ID NO: 46) |
| (Aib¹,²,¹⁰, Glu(NH-hexyl)¹⁷)hGhrelin(1-28)-NH₂; | (SEQ ID NO: 49) |
| (A5c², Glu(NH-hexyl)¹⁷)hGhrelin(1-28)-NH₂; | (SEQ ID NO: 51) |
| (Lys(biotinyl)¹⁷)hGhrelin(1-28)-NH₂; | (SEQ ID NO: 58) |
| (Ser(n-octanoyl)¹⁸)hGhrelin(1-28)-NH₂; | (SEQ ID NO: 59) |
| (Glu(NH-hexyl)¹⁸)hGhrelin(1-28)-NH₂; | (SEQ ID NO: 60) |
| (Aib², Glu(NH-hexyl)¹⁸)hGhrelin(1-28)-NH₂; | (SEQ ID NO: 63) |
| (Aib²,⁸, Glu(NH-hexyl)¹⁸)hGhrelin(1-28)-NH₂; | (SEQ ID NO: 65) |
| (Aib²,¹⁰, Glu(NH-hexyl)¹⁸)hGhrelin(1-28)-NH₂; | (SEQ ID NO: 67) |
| (Ser(n-octanoyl)¹⁹)hGhrelin(1-28)-NH₂; | (SEQ ID NO: 69) |
| (Glu(NH-hexyl)¹⁹)hGhrelin(1-28)-NH₂; | (SEQ ID NO: 70) |
| (Aib², Glu(NH-hexyl)¹⁹)hGhrelin(1-28)-NH₂; | (SEQ ID NO: 73) |
| (Aib²,⁸, Glu(NH-hexyl)¹⁹)hGhrelin(1-28)-NH₂; | (SEQ ID NO: 75) |
| (Aib²,¹⁰, Glu(NH-hexyl)¹⁹)hGhrelin(1-28)-NH₂; | (SEQ ID NO: 77) |
| (Ser(n-octanoyl)²⁰)hGhrelin(1-28)-NH₂; | (SEQ ID NO: 79) |
| (Glu(NH-hexyl)²⁰)hGhrelin(1-28)-NH₂; | (SEQ ID NO: 80) |
| (Aib², Glu(NH-hexyl)²⁰)hGhrelin(1-28)-NH₂; | (SEQ ID NO: 83) |
| (Aib²,⁸, Glu(NH-hexyl)²⁰)hGhrelin(1-28)-NH₂; | (SEQ ID NO: 85) |
| (Aib²,¹⁰, Glu(NH-hexyl)²⁰)hGhrelin(1-28)-NH₂; | (SEQ ID NO: 87) |
| (Ac-Gly¹, Glu(NH-hexyl)¹⁷)hGhrelin(1-28)-NH₂; | (SEQ ID NO: 89) |
| (Ac-Gly¹, Ser(n-octanoyl)¹⁷)hGhrelin(1-28)-NH₂; | (SEQ ID NO: 90) |
| (Ac-Gly¹, Dap(octanesulfonyl)¹⁷)hGhrelin(1-28)-NH₂; | (SEQ ID NO: 93) |
| (Ac-Gly¹, (Cys(S-(CH₂)₉CH₃)¹⁷)hGhrelin(1-28)-NH₂; | (SEQ ID NO: 98) |
| (Ac-Gly¹, Aib², Glu(NH-hexyl)¹⁷)hGhrelin(1-28)-NH₂; | (SEQ ID NO: 103) |
| (Ac-Gly¹, Aib², Thz⁷, Glu(NH-hexyl)¹⁷)hGhrelin(1-28)-NH₂; | (SEQ ID NO: 105) |
| (Ac-Gly¹, Aib², 4-Hyp⁷, Glu(NH-hexyl)¹⁷)hGhrelin(1-28)-NH₂; | (SEQ ID NO: 105) |
| (Ac-Gly¹, Aib², Dhp⁷, Glu(NH-hexyl)¹⁷)hGhrelin(1-28)-NH₂; | (SEQ ID NO: 105) |
| (Ac-Gly¹, Aib², Pip⁷, Glu(NH-hexyl)¹⁷)hGhrelin(1-28)-NH₂; | (SEQ ID NO: 105) |
| (Ac-Gly¹, Aib², Tic⁷, Glu(NH-hexyl)¹⁷)hGhrelin(1-28)-NH₂; | (SEQ ID NO: 105) |

-continued (Ac-Gly$^1$, Aib$^{2,8}$, Glu(NH-hexyl)$^{17}$)hGhrelin(1-28)-NH$_2$; (SEQ ID NO: 107)

(Ac-Gly$^1$, Aib$^2$, 3-Pal$^9$, Glu(NH-hexyl)$^{17}$)hGhrelin(1-28)-NH$_2$; (SEQ ID NO: 109)

(Ac-Gly$^1$, Aib$^2$, 4-Pal$^9$, Glu(NH-hexyl)$^{17}$)hGhrelin(1-28)-NH$_2$; (SEQ ID NO: 109)

(Ac-Gly$^1$, Aib$^2$, Taz$^9$, Glu(NH-hexyl)$^{17}$)hGhrelin(1-28)-NH$_2$; (SEQ ID NO: 109)

(Ac-Gly$^1$, Aib$^2$, 2-Thi$^9$, Glu(NH-hexyl)$^{17}$)hGhrelin(1-28)-NH$_2$; (SEQ ID NO: 109)

(Ac-Gly$^1$, Aib$^{2,10}$, Glu(NH-hexyl)$^{17}$)hGhrelin(1-28)-NH$_2$; (SEQ ID NO: 111)

(Ac-Gly$^1$, Aib$^8$, Glu(NH-hexyl)$^{17}$)hChrelin(1-28)-NH$_2$; (SEQ ID NO: 113)

(Ac-Gly$^1$, Taz$^9$, Glu(NH-hexyl)$^{17}$)hGhrelin(1-28)-NH$_2$; (SEQ ID NO: 114)

(Ac-Gly$^1$, 3-Pal$^9$, Glu(NH-hexyl)$^{17}$)hGhrelin(1-28)-NH$_2$; (SEQ ID NO: 114)

(Ac-Gly$^1$, 4-Pal$^9$, Glu(NH-hexyl)$^{17}$)hGhrelin(1-28)-NH$_2$; (SEQ ID NO: 114)

(Ac-Gly$^1$, 2-Thi$^9$, Glu(NH-hexyl)$^{17}$)hGhrelin(1-28)-NH$_2$; (SEQ ID NO: 114)

(Ac-Aib$^1$, Aib$^{2,10}$, Glu(NH-hexyl)$^{17}$)hGhrelin(1-28)-NH$_2$; (SEQ ID NO: 117)

(Ac-Gly$^1$, A5c$^2$, Glu(NH-hexyl)$^{17}$)hGhrelin(1-28)-NH$_2$; (SEQ ID NO: 119)

(Ac-Gly$^1$, Glu(NH-hexyl)$^{15}$)hGhrelin(1-28)-NH$_2$; (SEQ ID NO: 127)

(Ac-Gly$^1$, Ser(n-octanoyl)$^{15}$)hGhrelin(1-28)-NH$_2$; (SEQ ID NO: 128)

(Ac-Gly$^1$, Aib$^2$, Glu(NH-hexyl)$^{15}$)hGhrelin(1-28)-NH$_2$; (SEQ ID NO: 131)

(Ac-Gly$^1$, Aib$^{2,8}$, Glu(NH-hexyl)$^{15}$)hGhrelin(1-28)-NH$_2$; (SEQ ID NO: 133)

(Ac-Gly$^1$, Aib$^{2,10}$, Glu(NH-hexyl)$^{15}$)hGhrelin(1-28)-NH$_2$; (SEQ ID NO: 135)

(Ac-Gly$^1$, Glu(NH-hexyl)$^{16}$)hGhrelin(1-28)-NH$_2$; (SEQ ID NO: 137)

(Ac-Gly$^1$, Ser(n-octanoyl)$^{16}$)hGhrelin(1-28)-NH$_2$; (SEQ ID NO: 138)

(Ac-Gly$^1$, Aib$^2$, Glu(NH-hexyl)$^{16}$)hGhrelin(1-28)-NH$_2$; (SEQ ID NO: 141)

(Ac-Gly$^1$, Aib$^{2,8}$, Glu(NH-hexyl)$^{16}$)hGhrelin(1-28)-NH$_2$; (SEQ ID NO: 143)

(Ac-Gly$^1$, Aib$^{2,10}$, Glu(NH-hexyl)$^{16}$)hGhrelin(1-28)-NH$_2$; (SEQ ID NO: 145)

(Ac-Gly$^1$, Glu(NH-hexyl)$^{18}$)hGhrelin(1-28)-NH$_2$; (SEQ ID NO: 147)

(Ac-Gly$^1$, Ser(n-octanoyl)$^{18}$)hGhrelin(1-28)-NH$_2$; (SEQ ID NO: 148)

(Ac-Gly$^1$, Aib$^2$, Glu(NH-hexyl)$^{18}$)hGhrelin(1-28)-NH$_2$; (SEQ ID NO: 151)

(Ac-Gly$^1$, Aib$^{2,8}$, Glu(NH-hexyl)$^{18}$)hGhrelin(1-28)-NH$_2$; (SEQ ID NO: 153)

(Ac-Gly$^1$, Aib$^{2,10}$, Glu(NH-hexyl)$^{18}$)hGhrelin(1-28)-NH$_2$; (SEQ ID NO: 155)

(Ac-Gly$^1$, Glu(NH-hexyl)$^{19}$)hGhrelin(1-28)-NH$_2$; (SEQ ID NO: 157)

(Ac-Gly$^1$, Ser(n-octanoyl)$^{19}$)hGhrelin(1-28)-NH$_2$; (SEQ ID NO: 158)

(Ac-Gly$^1$, Aib$^2$, Glu(NH-hexyl)$^{19}$)hGhrelin(1-28)-NH$_2$; (SEQ ID NO: 161)

(Ac-Gly$^1$, Aib$^{2,8}$, Glu(NH-hexyl)$^{19}$)hGhrelin(1-28)-NH$_2$; (SEQ ID NO: 163)

(Ac-Gly$^1$, Aib$^{2,10}$, Glu(NH-hexyl)$^{19}$)hGhrelin(1-28)-NH2; (SEQ ID NO: 165)

(Ac-Gly$^1$, Glu(NH-hexyl)$^{20}$)hGhrelin(1-28)-NH$_2$; (SEQ ID NO: 167)

(Ac-Gly$^1$, Ser(n-octanoyl)$^{20}$)hGhrelin(1-28)-NH$_2$; (SEQ ID NO: 168)

(Ac-Gly$^1$, Aib$^2$, Glu(NH-hexyl)$^{20}$)hGhrelin(1-28)-NH$_2$; (SEQ ID NO: 171)

(Ac-Gly$^1$, Aib$^{2,8}$, Glu(NH-hexyl)$^{20}$)hGhrelin(1-28)-NH$_2$; or (SEQ ID NO: 173)

(Ac-Gly$^1$, Aib$^{2,10}$, Glu(NH-hexyl)$^{20}$)hGhrelin(1-28)-NH$_2$; (SEQ ID NO: 175)

or a pharmaceutically acceptable salt thereof.

* * * * *

SEQUENCE LISTING

```
<160> NUMBER OF SEQ ID NOS: 185

<210> SEQ ID NO 1
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
```

```
<222> LOCATION: (15)..(15)
<223> OTHER INFORMATION: modified with n-octanoyl
<220> FEATURE:
<221> NAME/KEY: MOD_RES
<222> LOCATION: (28)..(28)
<223> OTHER INFORMATION: AMIDATION

<400> SEQUENCE: 1

Gly Ser Ser Phe Leu Ser Pro Glu His Gln Arg Val Gln Gln Ser Lys
1               5                   10                  15

Glu Ser Lys Lys Pro Pro Ala Lys Leu Gln Pro Arg
            20                  25

<210> SEQ ID NO 2
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (15)..(15)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 2

Gly Ser Ser Phe Leu Ser Pro Glu His Gln Arg Val Gln Gln Glu Lys
1               5                   10                  15

Glu Ser Lys Lys Pro Pro Ala Lys Leu Gln Pro Arg
            20                  25

<210> SEQ ID NO 3
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (15)..(15)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 3

Gly Ser Glu Phe Leu Ser Pro Glu His Gln Arg Val Gln Gln Glu Lys
1               5                   10                  15

Glu Ser Lys Lys Pro Pro Ala Lys Leu Gln Pro Arg
            20                  25

<210> SEQ ID NO 4
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
```

```
<222> LOCATION: (15)..(15)
<223> OTHER INFORMATION: modified with n-octanoyl
<220> FEATURE:
<221> NAME/KEY: MOD_RES
<222> LOCATION: (28)..(28)
<223> OTHER INFORMATION: AMIDATION

<400> SEQUENCE: 4

Gly Ser Glu Phe Leu Ser Pro Glu His Gln Arg Val Gln Gln Ser Lys
1               5                   10                  15

Glu Ser Lys Lys Pro Pro Ala Lys Leu Gln Pro Arg
            20                  25

<210> SEQ ID NO 5
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MOD_RES
<222> LOCATION: (15)..(15)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 5

Gly Xaa Ser Phe Leu Ser Pro Glu His Gln Arg Val Gln Gln Glu Lys
1               5                   10                  15

Glu Ser Lys Lys Pro Pro Ala Lys Leu Gln Pro Arg
            20                  25

<210> SEQ ID NO 6
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (15)..(15)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 6

Gly Xaa Glu Phe Leu Ser Pro Glu His Gln Arg Val Gln Gln Glu Lys
1               5                   10                  15

Glu Ser Lys Lys Pro Pro Ala Lys Leu Gln Pro Arg
            20                  25

<210> SEQ ID NO 7
<211> LENGTH: 28
<212> TYPE: PRT
<213> ORGANISM: Artificial Sequence
```

```
<220> FEATURE:
<223> OTHER INFORMATION: Ghrelin Analog
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MISC_FEATURE
<222> LOCATION: (8)..(8)
<223> OTHER INFORMATION: Xaa = alpha-aminoisobutyric acid
<220> FEATURE:
<221> NAME/KEY: MOD_RES
<222> LOCATION: (15)..(15)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 7

Gly Xaa Ser Phe Leu Ser Pro Xaa His Gln Arg Val Gln Gln Glu Lys
1               5                   10                  15

Glu Ser Lys Lys Pro Pro Ala Lys Leu Gln Pro Arg
            20                  25

<210> SEQ ID NO 8
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (8)..(8)
<223> OTHER INFORMATION: Xaa = alpha-aminoisobutyric acid
<220> FEATURE:
<221> NAME/KEY: MOD_RES
<222> LOCATION: (15)..(15)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 8

Gly Xaa Glu Phe Leu Ser Pro Xaa His Gln Arg Val Gln Gln Glu Lys
1               5                   10                  15

Glu Ser Lys Lys Pro Pro Ala Lys Leu Gln Pro Arg
            20                  25

<210> SEQ ID NO 9
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MISC_FEATURE
<222> LOCATION: (10)..(10)
<223> OTHER INFORMATION: Xaa = alpha-aminoisobutyric acid
<220> FEATURE:
<221> NAME/KEY: MOD_RES
```

```
<222> LOCATION: (15)..(15)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 9

Gly Xaa Ser Phe Leu Ser Pro Glu His Xaa Arg Val Gln Gln Glu Lys
1               5                   10                  15

Glu Ser Lys Lys Pro Pro Ala Lys Leu Gln Pro Arg
            20                  25

<210> SEQ ID NO 10
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (10)..(10)
<223> OTHER INFORMATION: Xaa = alpha-aminoisobutyric acid
<220> FEATURE:
<221> NAME/KEY: MOD_RES
<222> LOCATION: (15)..(15)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 10

Gly Xaa Glu Phe Leu Ser Pro Glu His Xaa Arg Val Gln Gln Glu Lys
1               5                   10                  15

Glu Ser Lys Lys Pro Pro Ala Lys Leu Gln Pro Arg
            20                  25

<210> SEQ ID NO 11
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (16)..(16)
<223> OTHER INFORMATION: modified with n-octanoyl
<220> FEATURE:
<221> NAME/KEY: MOD_RES
<222> LOCATION: (28)..(28)
<223> OTHER INFORMATION: AMIDATION

<400> SEQUENCE: 11

Gly Ser Ser Phe Leu Ser Pro Glu His Gln Arg Val Gln Gln Arg Ser
1               5                   10                  15

Glu Ser Lys Lys Pro Pro Ala Lys Leu Gln Pro Arg
            20                  25

<210> SEQ ID NO 12
<211> LENGTH: 28
<212> TYPE: PRT
<213> ORGANISM: Artificial Sequence
```

```
<220> FEATURE:
<223> OTHER INFORMATION: Ghrelin Analog
<220> FEATURE:
<221> NAME/KEY: MOD_RES
<222> LOCATION: (16)..(16)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 12

Gly Ser Ser Phe Leu Ser Pro Glu His Gln Arg Val Gln Gln Arg Glu
1               5                   10                  15

Glu Ser Lys Lys Pro Pro Ala Lys Leu Gln Pro Arg
            20                  25

<210> SEQ ID NO 13
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (16)..(16)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 13

Gly Ser Glu Phe Leu Ser Pro Glu His Gln Arg Val Gln Gln Arg Glu
1               5                   10                  15

Glu Ser Lys Lys Pro Pro Ala Lys Leu Gln Pro Arg
            20                  25

<210> SEQ ID NO 14
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (16)..(16)
<223> OTHER INFORMATION: modified with n-octanoyl
<220> FEATURE:
<221> NAME/KEY: MOD_RES
<222> LOCATION: (28)..(28)
<223> OTHER INFORMATION: AMIDATION

<400> SEQUENCE: 14

Gly Ser Glu Phe Leu Ser Pro Glu His Gln Arg Val Gln Gln Arg Ser
1               5                   10                  15

Glu Ser Lys Lys Pro Pro Ala Lys Leu Gln Pro Arg
            20                  25

<210> SEQ ID NO 15
<211> LENGTH: 28
<212> TYPE: PRT
<213> ORGANISM: Artificial Sequence
```

-continued

```
<220> FEATURE:
<223> OTHER INFORMATION: Ghrelin Analog
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MOD_RES
<222> LOCATION: (16)..(16)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 15

Gly Xaa Ser Phe Leu Ser Pro Glu His Gln Arg Val Gln Gln Arg Glu
 1               5                  10                  15
Glu Ser Lys Lys Pro Pro Ala Lys Leu Gln Pro Arg
             20                  25

<210> SEQ ID NO 16
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (16)..(16)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 16

Gly Xaa Glu Phe Leu Ser Pro Glu His Gln Arg Val Gln Gln Arg Glu
 1               5                  10                  15
Glu Ser Lys Lys Pro Pro Ala Lys Leu Gln Pro Arg
             20                  25

<210> SEQ ID NO 17
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MISC_FEATURE
<222> LOCATION: (8)..(8)
<223> OTHER INFORMATION: Xaa = alpha-aminoisobutyric acid
<220> FEATURE:
<221> NAME/KEY: MOD_RES
<222> LOCATION: (16)..(16)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 17
```

```
Gly Xaa Ser Phe Leu Ser Pro Xaa His Gln Arg Val Gln Gln Arg Glu
1               5                   10                  15

Glu Ser Lys Lys Pro Pro Ala Lys Leu Gln Pro Arg
            20                  25
```

<210> SEQ ID NO 18
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (8)..(8)
<223> OTHER INFORMATION: Xaa = alpha-aminoisobutyric acid
<220> FEATURE:
<221> NAME/KEY: MOD_RES
<222> LOCATION: (16)..(16)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 18

```
Gly Xaa Glu Phe Leu Ser Pro Xaa His Gln Arg Val Gln Gln Arg Glu
1               5                   10                  15

Glu Ser Lys Lys Pro Pro Ala Lys Leu Gln Pro Arg
            20                  25
```

<210> SEQ ID NO 19
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MISC_FEATURE
<222> LOCATION: (10)..(10)
<223> OTHER INFORMATION: Xaa = alpha-aminoisobutyric acid
<220> FEATURE:
<221> NAME/KEY: MOD_RES
<222> LOCATION: (16)..(16)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 19

```
Gly Xaa Ser Phe Leu Ser Pro Glu His Xaa Arg Val Gln Gln Arg Glu
1               5                   10                  15

Glu Ser Lys Lys Pro Pro Ala Lys Leu Gln Pro Arg
            20                  25
```

<210> SEQ ID NO 20
<211> LENGTH: 28
<212> TYPE: PRT
<213> ORGANISM: Artificial Sequence

```
<220> FEATURE:
<223> OTHER INFORMATION: Ghrelin Analog
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (10)..(10)
<223> OTHER INFORMATION: Xaa = alpha-aminoisobutyric acid
<220> FEATURE:
<221> NAME/KEY: MOD_RES
<222> LOCATION: (16)..(16)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 20

Gly Xaa Glu Phe Leu Ser Pro Glu His Xaa Arg Val Gln Gln Arg Glu
1               5                   10                  15

Glu Ser Lys Lys Pro Pro Ala Lys Leu Gln Pro Arg
            20                  25

<210> SEQ ID NO 21
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (17)..(17)
<223> OTHER INFORMATION: modified with n-octanoyl
<220> FEATURE:
<221> NAME/KEY: MOD_RES
<222> LOCATION: (28)..(28)
<223> OTHER INFORMATION: AMIDATION

<400> SEQUENCE: 21

Gly Ser Ser Phe Leu Ser Pro Glu His Gln Arg Val Gln Gln Arg Lys
1               5                   10                  15

Ser Ser Lys Lys Pro Pro Ala Lys Leu Gln Pro Arg
            20                  25

<210> SEQ ID NO 22
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 22

Gly Ser Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25
```

```
<210> SEQ ID NO 23
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 23

Gly Ser Glu Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 24
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (17)..(17)
<223> OTHER INFORMATION: modified with n-octanoyl
<220> FEATURE:
<221> NAME/KEY: MOD_RES
<222> LOCATION: (28)..(28)
<223> OTHER INFORMATION: AMIDATION

<400> SEQUENCE: 24

Gly Ser Glu Phe Leu Ser Pro Glu His Gln Arg Val Gln Gln Arg Lys
1               5                   10                  15

Ser Ser Lys Lys Pro Pro Ala Lys Leu Gln Pro Arg
            20                  25

<210> SEQ ID NO 25
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MISC_FEATURE
<222> LOCATION: (17)..(17)
<223> OTHER INFORMATION: Xaa = 2,3-diaminopropionic acid modified with
      octanesulfonyl
<220> FEATURE:
<221> NAME/KEY: MOD_RES
<222> LOCATION: (28)..(28)
<223> OTHER INFORMATION: AMIDATION

<400> SEQUENCE: 25

Gly Ser Ser Phe Leu Ser Pro Glu His Gln Arg Val Gln Gln Arg Lys
1               5                   10                  15

Xaa Ser Lys Lys Pro Pro Ala Lys Leu Gln Pro Arg
            20                  25
```

```
<210> SEQ ID NO 26
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MISC_FEATURE
<222> LOCATION: (3)..(3)
<223> OTHER INFORMATION: Xaa = 2,3-diaminopropionic acid modified with
      octanesulfonyl
<220> FEATURE:
<221> NAME/KEY: MISC_FEATURE
<222> LOCATION: (17)..(17)
<223> OTHER INFORMATION: Xaa = 2,3-diaminopropionic acid modified with
      octanesulfonyl
<220> FEATURE:
<221> NAME/KEY: MOD_RES
<222> LOCATION: (28)..(28)
<223> OTHER INFORMATION: AMIDATION

<400> SEQUENCE: 26

Gly Ser Xaa Phe Leu Ser Pro Glu His Gln Arg Val Gln Gln Arg Lys
1               5                   10                  15

Xaa Ser Lys Lys Pro Pro Ala Lys Leu Gln Pro Arg
            20                  25

<210> SEQ ID NO 27
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MISC_FEATURE
<222> LOCATION: (3)..(3)
<223> OTHER INFORMATION: Xaa = 2,3-diaminopropionic acid modified with
      octanesulfonyl
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 27

Gly Ser Xaa Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 28
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MISC_FEATURE
<222> LOCATION: (3)..(3)
<223> OTHER INFORMATION: Xaa = 2,3-diaminopropionic acid modified with
      octanesulfonyl
<220> FEATURE:
<221> NAME/KEY: MOD_RES
<222> LOCATION: (17)..(17)
<223> OTHER INFORMATION: modified with n-octanoyl
<220> FEATURE:
<221> NAME/KEY: MOD_RES
<222> LOCATION: (28)..(28)
<223> OTHER INFORMATION: AMIDATION
```

```
<400> SEQUENCE: 28

Gly Ser Xaa Phe Leu Ser Pro Glu His Gln Arg Val Gln Gln Arg Lys
1               5                   10                  15

Ser Ser Lys Lys Pro Pro Ala Lys Leu Gln Pro Arg
            20                  25

<210> SEQ ID NO 29
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (17)..(17)
<223> OTHER INFORMATION: Xaa = 2,3-diaminopropionic acid modified with
      octanesulfonyl
<220> FEATURE:
<221> NAME/KEY: MOD_RES
<222> LOCATION: (28)..(28)
<223> OTHER INFORMATION: AMIDATION

<400> SEQUENCE: 29

Gly Ser Glu Phe Leu Ser Pro Glu His Gln Arg Val Gln Gln Arg Lys
1               5                   10                  15

Xaa Ser Lys Lys Pro Pro Ala Lys Leu Gln Pro Arg
            20                  25

<210> SEQ ID NO 30
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (17)..(17)
<223> OTHER INFORMATION: modified with S-(CH2)9CH3
<220> FEATURE:
<221> NAME/KEY: MOD_RES
<222> LOCATION: (28)..(28)
<223> OTHER INFORMATION: AMIDATION

<400> SEQUENCE: 30

Gly Ser Ser Phe Leu Ser Pro Glu His Gln Arg Val Gln Gln Arg Lys
1               5                   10                  15

Cys Ser Lys Lys Pro Pro Ala Lys Leu Gln Pro Arg
            20                  25

<210> SEQ ID NO 31
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (3)..(3)
<223> OTHER INFORMATION: modified with S-(CH2)9CH3
<220> FEATURE:
<221> NAME/KEY: MOD_RES
<222> LOCATION: (17)..(17)
<223> OTHER INFORMATION: modified with S-(CH2)9CH3
<220> FEATURE:
<221> NAME/KEY: MOD_RES
<222> LOCATION: (28)..(28)
<223> OTHER INFORMATION: AMIDATION
```

```
<400> SEQUENCE: 31

Gly Ser Cys Phe Leu Ser Pro Glu His Gln Arg Val Gln Gln Arg Lys
1               5                   10                  15

Cys Ser Lys Lys Pro Pro Ala Lys Leu Gln Pro Arg
            20                  25

<210> SEQ ID NO 32
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (17)..(17)
<223> OTHER INFORMATION: modified with S-(CH2)9CH3
<220> FEATURE:
<221> NAME/KEY: MOD_RES
<222> LOCATION: (28)..(28)
<223> OTHER INFORMATION: AMIDATION

<400> SEQUENCE: 32

Gly Ser Glu Phe Leu Ser Pro Glu His Gln Arg Val Gln Gln Arg Lys
1               5                   10                  15

Cys Ser Lys Lys Pro Pro Ala Lys Leu Gln Pro Arg
            20                  25

<210> SEQ ID NO 33
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (3)..(3)
<223> OTHER INFORMATION: modified with S-(CH2)9CH3
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 33

Gly Ser Cys Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 34
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (3)..(3)
<223> OTHER INFORMATION: modified with S-(CH2)9CH3
<220> FEATURE:
<221> NAME/KEY: MOD_RES
<222> LOCATION: (17)..(17)
<223> OTHER INFORMATION: modified with n-octanoyl
```

```
<220> FEATURE:
<221> NAME/KEY: MOD_RES
<222> LOCATION: (28)..(28)
<223> OTHER INFORMATION: AMIDATION

<400> SEQUENCE: 34

Gly Ser Cys Phe Leu Ser Pro Glu His Gln Arg Val Gln Gln Arg Lys
1               5                   10                  15

Ser Ser Lys Lys Pro Pro Ala Lys Leu Gln Pro Arg
            20                  25

<210> SEQ ID NO 35
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 35

Gly Xaa Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 36
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 36

Gly Xaa Glu Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 37
<211> LENGTH: 28
<212> TYPE: PRT
<213> ORGANISM: Artificial Sequence
<220> FEATURE:
<223> OTHER INFORMATION: Ghrelin Analog
```

```
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MISC_FEATURE
<222> LOCATION: (7)..(7)
<223> OTHER INFORMATION: Xaa = thiazolidine-4-carboxylic acid, 4-
      hydroxyproline, i.e., (2S, 4R)-4-hydroxypyrrolidine-2-carboxylic
      acid, 3,4-dehydroproline, pipecolic acid or
      1,2,3,4-tetrahydroisoquinoline-3-carboxylic acid
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 37

Gly Xaa Ser Phe Leu Ser Xaa Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 38
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (7)..(7)
<223> OTHER INFORMATION: Xaa = thiazolidine-4-carboxylic acid, 4-
      hydroxyproline, i.e., (2S, 4R)-4-hydroxypyrrolidine-2-carboxylic
      acid, 3,4-dehydroproline, pipecolic acid or
      1,2,3,4-tetrahydroisoquinoline-3-carboxylic acid
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 38

Gly Xaa Glu Phe Leu Ser Xaa Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 39
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MISC_FEATURE
```

```
<222> LOCATION: (8)..(8)
<223> OTHER INFORMATION: Xaa = alpha-aminoisobutyric acid
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 39

Gly Xaa Ser Phe Leu Ser Pro Xaa His Gln Arg Val Gln Gln Arg Lys
1               5                   10                  15

Glu Ser Lys Lys Pro Pro Ala Lys Leu Gln Pro Arg
            20                  25

<210> SEQ ID NO 40
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MOD_RES
<222> LOCATION: (3)..(3)
<223> OTHER INFORMATION: modfied with NH-hexyl
<220> FEATURE:
<221> NAME/KEY: MISC_FEATURE
<222> LOCATION: (8)..(8)
<223> OTHER INFORMATION: Xaa = alpha-aminoisobutyric acid
<220> FEATURE:
<221> NAME/KEY: MOD_RES
<222> LOCATION: (17)..(17)
<223> OTHER INFORMATION: modfied with NH-hexyl
<220> FEATURE:
<221> NAME/KEY: MOD_RES
<222> LOCATION: (28)..(28)
<223> OTHER INFORMATION: AMIDATION

<400> SEQUENCE: 40

Gly Xaa Glu Phe Leu Ser Pro Xaa His Gln Arg Val Gln Gln Arg Lys
1               5                   10                  15

Glu Ser Lys Lys Pro Pro Ala Lys Leu Gln Pro Arg
            20                  25

<210> SEQ ID NO 41
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MISC_FEATURE
<222> LOCATION: (9)..(9)
<223> OTHER INFORMATION: Xaa = beta-(3-pyridinyl)alanine, beta-(4-
      pyridinyl)alanine, beta-(4-thiazolyl)alanine or beta-(2-thienyl)
      alanine
<220> FEATURE:
<221> NAME/KEY: MOD_RES
<222> LOCATION: (17)..(17)
<223> OTHER INFORMATION: modified by NH-hexyl
<220> FEATURE:
<221> NAME/KEY: MOD_RES
<222> LOCATION: (28)..(28)
<223> OTHER INFORMATION: AMIDATION
```

```
<400> SEQUENCE: 41

Gly Xaa Ser Phe Leu Ser Pro Glu Xaa Gln Arg Val Gln Gln Arg Lys
1               5                   10                  15

Glu Ser Lys Lys Pro Pro Ala Lys Leu Gln Pro Arg
            20                  25

<210> SEQ ID NO 42
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MOD_RES
<222> LOCATION: (3)..(3)
<223> OTHER INFORMATION: modified by NH-hexyl
<220> FEATURE:
<221> NAME/KEY: MISC_FEATURE
<222> LOCATION: (9)..(9)
<223> OTHER INFORMATION: Xaa = beta-(3-pyridinyl)alanine, beta-(4-
      pyridinyl)alanine, beta-(4-thiazolyl)alanine or beta-(2-thienyl)
      alanine
<220> FEATURE:
<221> NAME/KEY: MOD_RES
<222> LOCATION: (17)..(17)
<223> OTHER INFORMATION: modified by NH-hexyl
<220> FEATURE:
<221> NAME/KEY: MOD_RES
<222> LOCATION: (28)..(28)
<223> OTHER INFORMATION: AMIDATION

<400> SEQUENCE: 42

Gly Xaa Glu Phe Leu Ser Pro Glu Xaa Gln Arg Val Gln Gln Arg Lys
1               5                   10                  15

Glu Ser Lys Lys Pro Pro Ala Lys Leu Gln Pro Arg
            20                  25

<210> SEQ ID NO 43
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MISC_FEATURE
<222> LOCATION: (10)..(10)
<223> OTHER INFORMATION: Xaa = alpha-aminoisobutyric acid
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 43

Gly Xaa Ser Phe Leu Ser Pro Glu His Xaa Arg Val Gln Gln Arg Lys
1               5                   10                  15

Glu Ser Lys Lys Pro Pro Ala Lys Leu Gln Pro Arg
            20                  25
```

```
<210> SEQ ID NO 44
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (10)..(10)
<223> OTHER INFORMATION: Xaa = alpha-aminoisobutyric acid
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 44

Gly Xaa Glu Phe Leu Ser Pro Glu His Xaa Arg Val Gln Gln Arg Lys
 1               5                  10                  15

Glu Ser Lys Lys Pro Pro Ala Lys Leu Gln Pro Arg
            20                  25

<210> SEQ ID NO 45
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MISC_FEATURE
<222> LOCATION: (8)..(8)
<223> OTHER INFORMATION: Xaa = alpha-aminoisobutyric acid
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 45

Gly Ser Ser Phe Leu Ser Pro Xaa His Gln Arg Val Gln Gln Arg Lys
 1               5                  10                  15

Glu Ser Lys Lys Pro Pro Ala Lys Leu Gln Pro Arg
            20                  25

<210> SEQ ID NO 46
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MISC_FEATURE
<222> LOCATION: (9)..(9)
<223> OTHER INFORMATION: Xaa = beta-(4-thiazolyl)alanine, beta-(3-
      pyridinyl)alanine, beta-(4-pyridinyl)alanine or beta-(2-
      thienyl)alanine
<220> FEATURE:
<221> NAME/KEY: MOD_RES
<222> LOCATION: (17)..(17)
<223> OTHER INFORMATION: modified with NH-hexyl
```

```
<220> FEATURE:
<221> NAME/KEY: MOD_RES
<222> LOCATION: (28)..(28)
<223> OTHER INFORMATION: AMIDATION

<400> SEQUENCE: 46

Gly Ser Ser Phe Leu Ser Pro Glu Xaa Gln Arg Val Gln Gln Arg Lys
1               5                   10                  15

Glu Ser Lys Lys Pro Pro Ala Lys Leu Gln Pro Arg
            20                  25

<210> SEQ ID NO 47
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (8)..(8)
<223> OTHER INFORMATION: Xaa = alpha-aminoisobutyric acid
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 47

Gly Ser Glu Phe Leu Ser Pro Xaa His Gln Arg Val Gln Gln Arg Lys
1               5                   10                  15

Glu Ser Lys Lys Pro Pro Ala Lys Leu Gln Pro Arg
            20                  25

<210> SEQ ID NO 48
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (9)..(9)
<223> OTHER INFORMATION: Xaa = beta-(4-thiazolyl)alanine, beta-(3-
      pyridinyl)alanine, beta-(4-pyridinyl)alanine or beta-(2-thienyl)
      alanine
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 48

Gly Ser Glu Phe Leu Ser Pro Glu Xaa Gln Arg Val Gln Gln Arg Lys
1               5                   10                  15

Glu Ser Lys Lys Pro Pro Ala Lys Leu Gln Pro Arg
            20                  25
```

```
<210> SEQ ID NO 49
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MISC_FEATURE
<222> LOCATION: (1)..(2)
<223> OTHER INFORMATION: Xaa = alpha-aminoisobutyric acid
<220> FEATURE:
<221> NAME/KEY: MISC_FEATURE
<222> LOCATION: (10)..(10)
<223> OTHER INFORMATION: Xaa = alpha-aminoisobutyric acid
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 49

Xaa Xaa Ser Phe Leu Ser Pro Glu His Xaa Arg Val Gln Gln Arg Lys
 1               5                  10                  15

Glu Ser Lys Lys Pro Pro Ala Lys Leu Gln Pro Arg
             20                  25

<210> SEQ ID NO 50
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MISC_FEATURE
<222> LOCATION: (1)..(2)
<223> OTHER INFORMATION: Xaa = alpha-aminoisobutyric acid
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (10)..(10)
<223> OTHER INFORMATION: Xaa = alpha-aminoisobutyric acid
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 50

Xaa Xaa Glu Phe Leu Ser Pro Glu His Xaa Arg Val Gln Gln Arg Lys
 1               5                  10                  15

Glu Ser Lys Lys Pro Pro Ala Lys Leu Gln Pro Arg
             20                  25

<210> SEQ ID NO 51
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MISC_FEATURE
<222> LOCATION: (2)..(2)
<223> OTHER INFORMATION: Xaa = 1-amino-1-cyclopentanecarboxylic acid
<220> FEATURE:
<221> NAME/KEY: MOD_RES
```

```
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 51

Gly Xaa Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 52
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MISC_FEATURE
<222> LOCATION: (2)..(2)
<223> OTHER INFORMATION: Xaa = 1-amino-1-cyclopentanecarboxylic acid
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 52

Gly Xaa Glu Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 53
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (3)..(3)
<223> OTHER INFORMATION: modified with 1-heptanol
<220> FEATURE:
<221> NAME/KEY: MOD_RES
<222> LOCATION: (17)..(17)
<223> OTHER INFORMATION: modified with 1-heptanol
<220> FEATURE:
<221> NAME/KEY: MOD_RES
<222> LOCATION: (28)..(28)
<223> OTHER INFORMATION: AMIDATION

<400> SEQUENCE: 53

Gly Ser Glu Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 54
<211> LENGTH: 28
<212> TYPE: PRT
<213> ORGANISM: Artificial Sequence
```

```
<220> FEATURE:
<223> OTHER INFORMATION: Ghrelin Analog
<220> FEATURE:
<221> NAME/KEY: MOD_RES
<222> LOCATION: (3)..(3)
<223> OTHER INFORMATION: modified with 1-heptanol
<220> FEATURE:
<221> NAME/KEY: MOD_RES
<222> LOCATION: (17)..(17)
<223> OTHER INFORMATION: modified with 1-heptanol
<220> FEATURE:
<221> NAME/KEY: MOD_RES
<222> LOCATION: (28)..(28)
<223> OTHER INFORMATION: AMIDATION

<400> SEQUENCE: 54

Gly Ser Asp Phe Leu Ser Pro Glu His Gln Arg Val Gln Gln Arg Lys
1               5                   10                  15

Asp Ser Lys Lys Pro Pro Ala Lys Leu Gln Pro Arg
            20                  25

<210> SEQ ID NO 55
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 55

Gly Ser Glu Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 56
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 56

Gly Ser Asp Phe Leu Ser Pro Glu His Gln Arg Val Gln Gln Arg Lys
1               5                   10                  15

Asp Ser Lys Lys Pro Pro Ala Lys Leu Gln Pro Arg
            20                  25
```

```
<210> SEQ ID NO 57
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 57

Gly Xaa Glu Phe Leu Ser Pro Glu His Gln Arg Val Gln Gln Arg Lys
 1               5                  10                  15

Glu Ser Lys Lys Pro Pro Ala Lys Leu Gln Pro Arg
            20                  25

<210> SEQ ID NO 58
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (17)..(17)
<223> OTHER INFORMATION: modified with biotinyl
<220> FEATURE:
<221> NAME/KEY: MOD_RES
<222> LOCATION: (28)..(28)
<223> OTHER INFORMATION: AMIDATION

<400> SEQUENCE: 58

Gly Ser Ser Phe Leu Ser Pro Glu His Gln Arg Val Gln Gln Arg Lys
 1               5                  10                  15

Lys Ser Lys Lys Pro Pro Ala Lys Leu Gln Pro Arg
            20                  25

<210> SEQ ID NO 59
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (18)..(18)
<223> OTHER INFORMATION: modified with n-octanoyl
<220> FEATURE:
<221> NAME/KEY: MOD_RES
<222> LOCATION: (28)..(28)
<223> OTHER INFORMATION: AMIDATION

<400> SEQUENCE: 59

Gly Ser Ser Phe Leu Ser Pro Glu His Gln Arg Val Gln Gln Arg Lys
 1               5                  10                  15

Glu Ser Lys Lys Pro Pro Ala Lys Leu Gln Pro Arg
            20                  25
```

```
<210> SEQ ID NO 60
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (18)..(18)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 60

Gly Ser Ser Phe Leu Ser Pro Glu His Gln Arg Val Gln Gln Arg Lys
1               5                   10                  15

Glu Glu Lys Lys Pro Pro Ala Lys Leu Gln Pro Arg
            20                  25

<210> SEQ ID NO 61
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (18)..(18)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 61

Gly Ser Glu Phe Leu Ser Pro Glu His Gln Arg Val Gln Gln Arg Lys
1               5                   10                  15

Glu Glu Lys Lys Pro Pro Ala Lys Leu Gln Pro Arg
            20                  25

<210> SEQ ID NO 62
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (18)..(18)
<223> OTHER INFORMATION: modified with n-octanoyl
<220> FEATURE:
<221> NAME/KEY: MOD_RES
<222> LOCATION: (28)..(28)
<223> OTHER INFORMATION: AMIDATION

<400> SEQUENCE: 62

Gly Ser Glu Phe Leu Ser Pro Glu His Gln Arg Val Gln Gln Arg Lys
1               5                   10                  15

Glu Ser Lys Lys Pro Pro Ala Lys Leu Gln Pro Arg
            20                  25
```

```
<210> SEQ ID NO 63
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MOD_RES
<222> LOCATION: (18)..(18)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 63

Gly Xaa Ser Phe Leu Ser Pro Glu His Gln Arg Val Gln Gln Arg Lys
1               5                   10                  15
Glu Glu Lys Lys Pro Pro Ala Lys Leu Gln Pro Arg
            20                  25

<210> SEQ ID NO 64
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (18)..(18)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 64

Gly Xaa Glu Phe Leu Ser Pro Glu His Gln Arg Val Gln Gln Arg Lys
1               5                   10                  15
Glu Glu Lys Lys Pro Pro Ala Lys Leu Gln Pro Arg
            20                  25

<210> SEQ ID NO 65
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MISC_FEATURE
<222> LOCATION: (8)..(8)
<223> OTHER INFORMATION: Xaa = alpha-aminoisobutyric acid
<220> FEATURE:
<221> NAME/KEY: MOD_RES
<222> LOCATION: (18)..(18)
<223> OTHER INFORMATION: modified with NH-hexyl
<220> FEATURE:
<221> NAME/KEY: MOD_RES
```

```
<222> LOCATION: (28)..(28)
<223> OTHER INFORMATION: AMIDATION

<400> SEQUENCE: 65

Gly Xaa Ser Phe Leu Ser Pro Xaa His Gln Arg Val Gln Gln Arg Lys
 1               5                  10                  15

Glu Glu Lys Lys Pro Pro Ala Lys Leu Gln Pro Arg
            20                  25

<210> SEQ ID NO 66
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (8)..(8)
<223> OTHER INFORMATION: Xaa = alpha-aminoisobutyric acid
<220> FEATURE:
<221> NAME/KEY: MOD_RES
<222> LOCATION: (18)..(18)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 66

Gly Xaa Glu Phe Leu Ser Pro Xaa His Gln Arg Val Gln Gln Arg Lys
 1               5                  10                  15

Glu Glu Lys Lys Pro Pro Ala Lys Leu Gln Pro Arg
            20                  25

<210> SEQ ID NO 67
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MISC_FEATURE
<222> LOCATION: (10)..(10)
<223> OTHER INFORMATION: Xaa = alpha-aminoisobutyric acid
<220> FEATURE:
<221> NAME/KEY: MOD_RES
<222> LOCATION: (18)..(18)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 67

Gly Xaa Ser Phe Leu Ser Pro Glu His Xaa Arg Val Gln Gln Arg Lys
 1               5                  10                  15

Glu Glu Lys Lys Pro Pro Ala Lys Leu Gln Pro Arg
            20                  25
```

```
<210> SEQ ID NO 68
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (10)..(10)
<223> OTHER INFORMATION: Xaa = alpha-aminoisobutyric acid
<220> FEATURE:
<221> NAME/KEY: MOD_RES
<222> LOCATION: (18)..(18)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 68

Gly Xaa Glu Phe Leu Ser Pro Glu His Xaa Arg Val Gln Gln Arg Lys
1               5                   10                  15

Glu Glu Lys Lys Pro Pro Ala Lys Leu Gln Pro Arg
            20                  25

<210> SEQ ID NO 69
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (19)..(19)
<223> OTHER INFORMATION: modified with n-octanoyl
<220> FEATURE:
<221> NAME/KEY: MOD_RES
<222> LOCATION: (28)..(28)
<223> OTHER INFORMATION: AMIDATION

<400> SEQUENCE: 69

Gly Ser Ser Phe Leu Ser Pro Glu His Gln Arg Val Gln Gln Arg Lys
1               5                   10                  15

Glu Ser Ser Lys Pro Pro Ala Lys Leu Gln Pro Arg
            20                  25

<210> SEQ ID NO 70
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (19)..(19)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 70

Gly Ser Ser Phe Leu Ser Pro Glu His Gln Arg Val Gln Gln Arg Lys
1               5                   10                  15
```

```
Glu Ser Glu Lys Pro Pro Ala Lys Leu Gln Pro Arg
            20                  25

<210> SEQ ID NO 71
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (19)..(19)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 71

Gly Ser Glu Phe Leu Ser Pro Glu His Gln Arg Val Gln Gln Arg Lys
1               5                   10                  15

Glu Ser Glu Lys Pro Pro Ala Lys Leu Gln Pro Arg
            20                  25

<210> SEQ ID NO 72
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (19)..(19)
<223> OTHER INFORMATION: modified with n-octanoyl
<220> FEATURE:
<221> NAME/KEY: MOD_RES
<222> LOCATION: (28)..(28)
<223> OTHER INFORMATION: AMIDATION

<400> SEQUENCE: 72

Gly Ser Glu Phe Leu Ser Pro Glu His Gln Arg Val Gln Gln Arg Lys
1               5                   10                  15

Glu Ser Ser Lys Pro Pro Ala Lys Leu Gln Pro Arg
            20                  25

<210> SEQ ID NO 73
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MOD_RES
<222> LOCATION: (19)..(19)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 73
```

-continued

```
Gly Xaa Ser Phe Leu Ser Pro Glu His Gln Arg Val Gln Gln Arg Lys
1               5                   10                  15

Glu Ser Glu Lys Pro Pro Ala Lys Leu Gln Pro Arg
            20                  25

<210> SEQ ID NO 74
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (19)..(19)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 74

Gly Xaa Glu Phe Leu Ser Pro Glu His Gln Arg Val Gln Gln Arg Lys
1               5                   10                  15

Glu Ser Glu Lys Pro Pro Ala Lys Leu Gln Pro Arg
            20                  25

<210> SEQ ID NO 75
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MISC_FEATURE
<222> LOCATION: (8)..(8)
<223> OTHER INFORMATION: Xaa = alpha-aminoisobutyric acid
<220> FEATURE:
<221> NAME/KEY: MOD_RES
<222> LOCATION: (19)..(19)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 75

Gly Xaa Ser Phe Leu Ser Pro Xaa His Gln Arg Val Gln Gln Arg Lys
1               5                   10                  15

Glu Ser Glu Lys Pro Pro Ala Lys Leu Gln Pro Arg
            20                  25

<210> SEQ ID NO 76
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MISC_FEATURE
```

```
<222> LOCATION: (2)..(2)
<223> OTHER INFORMATION: Xaa = alpha-aminoisobutyric acid
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (8)..(8)
<223> OTHER INFORMATION: Xaa = alpha-aminoisobutyric acid
<220> FEATURE:
<221> NAME/KEY: MOD_RES
<222> LOCATION: (19)..(19)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 76

Gly Xaa Glu Phe Leu Ser Pro Xaa His Gln Arg Val Gln Gln Arg Lys
1               5                   10                  15

Glu Ser Glu Lys Pro Pro Ala Lys Leu Gln Pro Arg
            20                  25

<210> SEQ ID NO 77
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MISC_FEATURE
<222> LOCATION: (10)..(10)
<223> OTHER INFORMATION: Xaa = alpha-aminoisobutyric acid
<220> FEATURE:
<221> NAME/KEY: MOD_RES
<222> LOCATION: (19)..(19)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 77

Gly Xaa Ser Phe Leu Ser Pro Glu His Xaa Arg Val Gln Gln Arg Lys
1               5                   10                  15

Glu Ser Glu Lys Pro Pro Ala Lys Leu Gln Pro Arg
            20                  25

<210> SEQ ID NO 78
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (10)..(10)
<223> OTHER INFORMATION: Xaa = alpha-aminoisobutyric acid
<220> FEATURE:
<221> NAME/KEY: MOD_RES
```

```
<222> LOCATION: (19)..(19)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 78

Gly Xaa Glu Phe Leu Ser Pro Glu His Xaa Arg Val Gln Gln Arg Lys
1               5                   10                  15

Glu Ser Glu Lys Pro Pro Ala Lys Leu Gln Pro Arg
            20                  25

<210> SEQ ID NO 79
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (20)..(20)
<223> OTHER INFORMATION: modified with n-octanoyl
<220> FEATURE:
<221> NAME/KEY: MOD_RES
<222> LOCATION: (28)..(28)
<223> OTHER INFORMATION: AMIDATION

<400> SEQUENCE: 79

Gly Ser Ser Phe Leu Ser Pro Glu His Gln Arg Val Gln Gln Arg Lys
1               5                   10                  15

Glu Ser Lys Ser Pro Pro Ala Lys Leu Gln Pro Arg
            20                  25

<210> SEQ ID NO 80
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (20)..(20)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 80

Gly Ser Ser Phe Leu Ser Pro Glu His Gln Arg Val Gln Gln Arg Lys
1               5                   10                  15

Glu Ser Lys Glu Pro Pro Ala Lys Leu Gln Pro Arg
            20                  25

<210> SEQ ID NO 81
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (20)..(20)
<223> OTHER INFORMATION: modified with NH-hexyl
<220> FEATURE:
<221> NAME/KEY: MOD_RES
```

```
<222> LOCATION: (28)..(28)
<223> OTHER INFORMATION: AMIDATION

<400> SEQUENCE: 81

Gly Ser Glu Phe Leu Ser Pro Glu His Gln Arg Val Gln Gln Arg Lys
1               5                  10                  15

Glu Ser Lys Glu Pro Pro Ala Lys Leu Gln Pro Arg
            20                  25

<210> SEQ ID NO 82
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (20)..(20)
<223> OTHER INFORMATION: modified with n-octanoyl
<220> FEATURE:
<221> NAME/KEY: MOD_RES
<222> LOCATION: (28)..(28)
<223> OTHER INFORMATION: AMIDATION

<400> SEQUENCE: 82

Gly Ser Glu Phe Leu Ser Pro Glu His Gln Arg Val Gln Gln Arg Lys
1               5                  10                  15

Glu Ser Lys Ser Pro Pro Ala Lys Leu Gln Pro Arg
            20                  25

<210> SEQ ID NO 83
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MOD_RES
<222> LOCATION: (20)..(20)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 83

Gly Xaa Ser Phe Leu Ser Pro Glu His Gln Arg Val Gln Gln Arg Lys
1               5                  10                  15

Glu Ser Lys Glu Pro Pro Ala Lys Leu Gln Pro Arg
            20                  25

<210> SEQ ID NO 84
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MOD_RES
```

```
<222> LOCATION: (3)..(3)
<223> OTHER INFORMATION: modified with NH-hexyl
<220> FEATURE:
<221> NAME/KEY: MOD_RES
<222> LOCATION: (20)..(20)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 84

Gly Xaa Glu Phe Leu Ser Pro Glu His Gln Arg Val Gln Gln Arg Lys
1               5                   10                  15
Glu Ser Lys Glu Pro Pro Ala Lys Leu Gln Pro Arg
            20                  25

<210> SEQ ID NO 85
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MISC_FEATURE
<222> LOCATION: (8)..(8)
<223> OTHER INFORMATION: Xaa = alpha-aminoisobutyric acid
<220> FEATURE:
<221> NAME/KEY: MOD_RES
<222> LOCATION: (20)..(20)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 85

Gly Xaa Ser Phe Leu Ser Pro Xaa His Gln Arg Val Gln Gln Arg Lys
1               5                   10                  15
Glu Ser Lys Glu Pro Pro Ala Lys Leu Gln Pro Arg
            20                  25

<210> SEQ ID NO 86
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (8)..(8)
<223> OTHER INFORMATION: Xaa = alpha-aminoisobutyric acid
<220> FEATURE:
<221> NAME/KEY: MOD_RES
<222> LOCATION: (20)..(20)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 86
```

```
Gly Xaa Glu Phe Leu Ser Pro Xaa His Gln Arg Val Gln Gln Arg Lys
1               5                   10                  15

Glu Ser Lys Glu Pro Pro Ala Lys Leu Gln Pro Arg
            20                  25
```

<210> SEQ ID NO 87
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MISC_FEATURE
<222> LOCATION: (10)..(10)
<223> OTHER INFORMATION: Xaa = alpha-aminoisobutyric acid
<220> FEATURE:
<221> NAME/KEY: MOD_RES
<222> LOCATION: (20)..(20)
<223> OTHER INFORMATION: modified by NH-hexyl
<220> FEATURE:
<221> NAME/KEY: MOD_RES
<222> LOCATION: (28)..(28)
<223> OTHER INFORMATION: AMIDATION

<400> SEQUENCE: 87

```
Gly Xaa Ser Phe Leu Ser Pro Glu His Xaa Arg Val Gln Gln Arg Lys
1               5                   10                  15

Glu Ser Lys Glu Pro Pro Ala Lys Leu Gln Pro Arg
            20                  25
```

<210> SEQ ID NO 88
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (10)..(10)
<223> OTHER INFORMATION: Xaa = alpha-aminoisobutyric acid
<220> FEATURE:
<221> NAME/KEY: MOD_RES
<222> LOCATION: (20)..(20)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 88

```
Gly Xaa Glu Phe Leu Ser Pro Glu His Xaa Arg Val Gln Gln Arg Lys
1               5                   10                  15

Glu Ser Lys Glu Pro Pro Ala Lys Leu Gln Pro Arg
            20                  25
```

<210> SEQ ID NO 89
<211> LENGTH: 28
<212> TYPE: PRT
<213> ORGANISM: Artificial Sequence

```
<220> FEATURE:
<223> OTHER INFORMATION: Ghrelin Analog
<220> FEATURE:
<221> NAME/KEY: MOD_RES
<222> LOCATION: (1)..(1)
<223> OTHER INFORMATION: modified with acyl
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 89

Gly Ser Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 90
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (1)..(1)
<223> OTHER INFORMATION: modified with acyl
<220> FEATURE:
<221> NAME/KEY: MOD_RES
<222> LOCATION: (17)..(17)
<223> OTHER INFORMATION: modified with n-octanoyl
<220> FEATURE:
<221> NAME/KEY: MOD_RES
<222> LOCATION: (28)..(28)
<223> OTHER INFORMATION: AMIDATION

<400> SEQUENCE: 90

Gly Ser Ser Phe Leu Ser Pro Glu His Gln Arg Val Gln Gln Arg Lys
1               5                   10                  15

Ser Ser Lys Lys Pro Pro Ala Lys Leu Gln Pro Arg
            20                  25

<210> SEQ ID NO 91
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (1)..(1)
<223> OTHER INFORMATION: modified with acyl
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 91

Gly Ser Glu Phe Leu Ser Pro Glu His Gln Arg Val Gln Gln Arg Lys
1               5                   10                  15
```

Glu Ser Lys Lys Pro Pro Ala Lys Leu Gln Pro Arg
            20                  25

<210> SEQ ID NO 92
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (1)..(1)
<223> OTHER INFORMATION: modified with acyl
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (17)..(17)
<223> OTHER INFORMATION: modified with n-octanoyl
<220> FEATURE:
<221> NAME/KEY: MOD_RES
<222> LOCATION: (28)..(28)
<223> OTHER INFORMATION: AMIDATION

<400> SEQUENCE: 92

Gly Ser Glu Phe Leu Ser Pro Glu His Gln Arg Val Gln Gln Arg Lys
1               5                   10                  15

Ser Ser Lys Lys Pro Pro Ala Lys Leu Gln Pro Arg
            20                  25

<210> SEQ ID NO 93
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (1)..(1)
<223> OTHER INFORMATION: modified with acyl
<220> FEATURE:
<221> NAME/KEY: MISC_FEATURE
<222> LOCATION: (17)..(17)
<223> OTHER INFORMATION: Xaa = 2,3-diaminopropionic acid modified with
      octanesulfonyl
<220> FEATURE:
<221> NAME/KEY: MOD_RES
<222> LOCATION: (28)..(28)
<223> OTHER INFORMATION: AMIDATION

<400> SEQUENCE: 93

Gly Ser Ser Phe Leu Ser Pro Glu His Gln Arg Val Gln Gln Arg Lys
1               5                   10                  15

Xaa Ser Lys Lys Pro Pro Ala Lys Leu Gln Pro Arg
            20                  25

<210> SEQ ID NO 94
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (1)..(1)
<223> OTHER INFORMATION: modified with acyl
<220> FEATURE:
<221> NAME/KEY: MISC_FEATURE
<222> LOCATION: (3)..(3)
<223> OTHER INFORMATION: Xaa = 2,3-diaminopropionic acid modified with
      octanesulfonyl

```
<220> FEATURE:
<221> NAME/KEY: MISC_FEATURE
<222> LOCATION: (17)..(17)
<223> OTHER INFORMATION: Xaa = 2,3-diaminopropionic acid modified with
      octanesulfonyl
<220> FEATURE:
<221> NAME/KEY: MOD_RES
<222> LOCATION: (28)..(28)
<223> OTHER INFORMATION: AMIDATION

<400> SEQUENCE: 94

Gly Ser Xaa Phe Leu Ser Pro Glu His Gln Arg Val Gln Gln Arg Lys
1               5                   10                  15

Xaa Ser Lys Lys Pro Pro Ala Lys Leu Gln Pro Arg
            20                  25

<210> SEQ ID NO 95
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (1)..(1)
<223> OTHER INFORMATION: modified with acyl
<220> FEATURE:
<221> NAME/KEY: MISC_FEATURE
<222> LOCATION: (3)..(3)
<223> OTHER INFORMATION: Xaa = 2,3-diaminopropionic acid modified with
      octanesulfonyl
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 95

Gly Ser Xaa Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 96
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (1)..(1)
<223> OTHER INFORMATION: modified with acyl
<220> FEATURE:
<221> NAME/KEY: MISC_FEATURE
<222> LOCATION: (3)..(3)
<223> OTHER INFORMATION: Xaa = 2,3-diaminopropionic acid modified with
      octanesulfonyl
<220> FEATURE:
<221> NAME/KEY: MOD_RES
<222> LOCATION: (17)..(17)
<223> OTHER INFORMATION: modified with n-octanoyl
<220> FEATURE:
<221> NAME/KEY: MOD_RES
<222> LOCATION: (28)..(28)
<223> OTHER INFORMATION: AMIDATION

<400> SEQUENCE: 96

Gly Ser Xaa Phe Leu Ser Pro Glu His Gln Arg Val Gln Gln Arg Lys
1               5                   10                  15
```

```
Ser Ser Lys Lys Pro Pro Ala Lys Leu Gln Pro Arg
            20                  25

<210> SEQ ID NO 97
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (1)..(1)
<223> OTHER INFORMATION: modified with acyl
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (17)..(17)
<223> OTHER INFORMATION: Xaa = 2,3-diaminopropionic acid modified with
      octanesulfonyl
<220> FEATURE:
<221> NAME/KEY: MOD_RES
<222> LOCATION: (28)..(28)
<223> OTHER INFORMATION: AMIDATION

<400> SEQUENCE: 97

Gly Ser Glu Phe Leu Ser Pro Glu His Gln Arg Val Gln Gln Arg Lys
1               5                   10                  15

Xaa Ser Lys Lys Pro Pro Ala Lys Leu Gln Pro Arg
            20                  25

<210> SEQ ID NO 98
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (1)..(1)
<223> OTHER INFORMATION: modified with acyl
<220> FEATURE:
<221> NAME/KEY: MOD_RES
<222> LOCATION: (17)..(17)
<223> OTHER INFORMATION: modified with S-(CH2)9CH3
<220> FEATURE:
<221> NAME/KEY: MOD_RES
<222> LOCATION: (28)..(28)
<223> OTHER INFORMATION: AMIDATION

<400> SEQUENCE: 98

Gly Ser Ser Phe Leu Ser Pro Glu His Gln Arg Val Gln Gln Arg Lys
1               5                   10                  15

Cys Ser Lys Lys Pro Pro Ala Lys Leu Gln Pro Arg
            20                  25

<210> SEQ ID NO 99
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (1)..(1)
<223> OTHER INFORMATION: modified with acyl
<220> FEATURE:
<221> NAME/KEY: MOD_RES
<222> LOCATION: (3)..(3)
<223> OTHER INFORMATION: modified with S-(CH2)9CH3
```

```
<220> FEATURE:
<221> NAME/KEY: MOD_RES
<222> LOCATION: (17)..(17)
<223> OTHER INFORMATION: modified with S-(CH2)9CH3
<220> FEATURE:
<221> NAME/KEY: MOD_RES
<222> LOCATION: (28)..(28)
<223> OTHER INFORMATION: AMIDATION

<400> SEQUENCE: 99

Gly Ser Cys Phe Leu Ser Pro Glu His Gln Arg Val Gln Gln Arg Lys
 1               5                  10                  15

Cys Ser Lys Lys Pro Pro Ala Lys Leu Gln Pro Arg
            20                  25

<210> SEQ ID NO 100
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (1)..(1)
<223> OTHER INFORMATION: modified with acyl
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (17)..(17)
<223> OTHER INFORMATION: modified with S-(CH2)9CH3
<220> FEATURE:
<221> NAME/KEY: MOD_RES
<222> LOCATION: (28)..(28)
<223> OTHER INFORMATION: AMIDATION

<400> SEQUENCE: 100

Gly Ser Glu Phe Leu Ser Pro Glu His Gln Arg Val Gln Gln Arg Lys
 1               5                  10                  15

Cys Ser Lys Lys Pro Pro Ala Lys Leu Gln Pro Arg
            20                  25

<210> SEQ ID NO 101
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (1)..(1)
<223> OTHER INFORMATION: modfed with acyl
<220> FEATURE:
<221> NAME/KEY: MOD_RES
<222> LOCATION: (3)..(3)
<223> OTHER INFORMATION: modified with S-(CH2)9CH3
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 101

Gly Ser Cys Phe Leu Ser Pro Glu His Gln Arg Val Gln Gln Arg Lys
 1               5                  10                  15

Glu Ser Lys Lys Pro Pro Ala Lys Leu Gln Pro Arg
            20                  25
```

```
<210> SEQ ID NO 102
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (1)..(1)
<223> OTHER INFORMATION: modified with acyl
<220> FEATURE:
<221> NAME/KEY: MOD_RES
<222> LOCATION: (3)..(3)
<223> OTHER INFORMATION: modified with S-(CH2)9CH3
<220> FEATURE:
<221> NAME/KEY: MOD_RES
<222> LOCATION: (17)..(17)
<223> OTHER INFORMATION: modified with n-octanoyl
<220> FEATURE:
<221> NAME/KEY: MOD_RES
<222> LOCATION: (28)..(28)
<223> OTHER INFORMATION: AMIDATION

<400> SEQUENCE: 102

Gly Ser Cys Phe Leu Ser Pro Glu His Gln Arg Val Gln Gln Arg Lys
1               5                   10                  15

Ser Ser Lys Lys Pro Pro Ala Lys Leu Gln Pro Arg
            20                  25

<210> SEQ ID NO 103
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (1)..(1)
<223> OTHER INFORMATION: modified with acyl
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 103

Gly Xaa Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 104
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (1)..(1)
<223> OTHER INFORMATION: modified with acyl
<220> FEATURE:
<221> NAME/KEY: MISC_FEATURE
<222> LOCATION: (2)..(2)
<223> OTHER INFORMATION: Xaa = alpha-aminoisobutyric acid
```

```
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 104

Gly Xaa Glu Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 105
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (1)..(1)
<223> OTHER INFORMATION: modified with acyl
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MISC_FEATURE
<222> LOCATION: (7)..(7)
<223> OTHER INFORMATION: Xaa = thiazolidine-4-carboxylic acid, 4-
      hydroxyproline, i.e., (2S, 4R)-4-hydroxypyrrolidine-2-carboxylic
      acid, 3,4-dehydroproline, pipecolic acid, or
      1,2,3,4-tetrahydroisoquinoline-3-carboxylic acid
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 105

Gly Xaa Ser Phe Leu Ser Xaa Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 106
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (1)..(1)
<223> OTHER INFORMATION: modified with acyl
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MOD_RES
<222> LOCATION: (3)..(3)
<223> OTHER INFORMATION: modified with NH-hexyl
<220> FEATURE:
```

```
<221> NAME/KEY: MISC_FEATURE
<222> LOCATION: (7)..(7)
<223> OTHER INFORMATION: Xaa = thiazolidine-4-carboxylic acid, 4-
      hydroxyproline, i.e., (2S, 4R)-4-hydroxypyrrolidine-2-
      carboxylic acid, 3,4-dehydroproline, pipecolic acid or
      1,2,3,4-tetrahydroisoquinoline-3-carboxylic acid
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 106

Gly Xaa Glu Phe Leu Ser Xaa Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 107
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (1)..(1)
<223> OTHER INFORMATION: modified with acyl
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MISC_FEATURE
<222> LOCATION: (8)..(8)
<223> OTHER INFORMATION: Xaa = alpha-aminoisobutyric acid
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 107

Gly Xaa Ser Phe Leu Ser Pro Xaa His Gln Arg Val Gln Gln Arg Lys
1               5                   10                  15

Glu Ser Lys Lys Pro Pro Ala Lys Leu Gln Pro Arg
            20                  25

<210> SEQ ID NO 108
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (1)..(1)
<223> OTHER INFORMATION: modified with acyl
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
```

```
<222> LOCATION: (8)..(8)
<223> OTHER INFORMATION: Xaa = alpha-aminoisobutyric acid
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 108

Gly Xaa Glu Phe Leu Ser Pro Xaa His Gln Arg Val Gln Gln Arg Lys
1               5                   10                  15

Glu Ser Lys Lys Pro Pro Ala Lys Leu Gln Pro Arg
            20                  25

<210> SEQ ID NO 109
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (1)..(1)
<223> OTHER INFORMATION: modified with acyl
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MISC_FEATURE
<222> LOCATION: (9)..(9)
<223> OTHER INFORMATION: Xaa = beta-(3-pyridinyl)alanine, beta-(4-
      pyridinyl)alanine, beta-(4-thiazolyl)alanine or beta-(2-thienyl)
      alanine
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 109

Gly Xaa Ser Phe Leu Ser Pro Glu Xaa Gln Arg Val Gln Gln Arg Lys
1               5                   10                  15

Glu Ser Lys Lys Pro Pro Ala Lys Leu Gln Pro Arg
            20                  25

<210> SEQ ID NO 110
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (1)..(1)
<223> OTHER INFORMATION: modified with acyl
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (9)..(9)
<223> OTHER INFORMATION: Xaa = beta-(3-pyridinyl)alanine, beta-(4-
``` pyridinyl)alanine, beta-(4-thiazolyl)alanine or beta-(2-thienyl)
    alanine
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 110

Gly Xaa Glu Phe Leu Ser Pro Glu Xaa Gln Arg Val Gln Gln Arg Lys
1               5                   10                  15

Glu Ser Lys Lys Pro Pro Ala Lys Leu Gln Pro Arg
            20                  25

<210> SEQ ID NO 111
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (1)..(1)
<223> OTHER INFORMATION: modified with acyl
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MISC_FEATURE
<222> LOCATION: (10)..(10)
<223> OTHER INFORMATION: Xaa = alpha-aminoisobutyric acid
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 111

Gly Xaa Ser Phe Leu Ser Pro Glu His Xaa Arg Val Gln Gln Arg Lys
1               5                   10                  15

Glu Ser Lys Lys Pro Pro Ala Lys Leu Gln Pro Arg
            20                  25

<210> SEQ ID NO 112
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (1)..(1)
<223> OTHER INFORMATION: modified with acyl
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (10)..(10)
<223> OTHER INFORMATION: Xaa = alpha-aminoisobutyric acid
<220> FEATURE:
<221> NAME/KEY: MOD_RES

```
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 112

Gly Xaa Glu Phe Leu Ser Pro Glu His Xaa Arg Val Gln Gln Arg Lys
1               5                  10                  15

Glu Ser Lys Lys Pro Pro Ala Lys Leu Gln Pro Arg
            20                  25

<210> SEQ ID NO 113
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (1)..(1)
<223> OTHER INFORMATION: modified with acyl
<220> FEATURE:
<221> NAME/KEY: MISC_FEATURE
<222> LOCATION: (8)..(8)
<223> OTHER INFORMATION: Xaa = alpha-aminoisobutyric acid
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 113

Gly Ser Ser Phe Leu Ser Pro Xaa His Gln Arg Val Gln Gln Arg Lys
1               5                  10                  15

Glu Ser Lys Lys Pro Pro Ala Lys Leu Gln Pro Arg
            20                  25

<210> SEQ ID NO 114
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (1)..(1)
<223> OTHER INFORMATION: modified with acyl
<220> FEATURE:
<221> NAME/KEY: MISC_FEATURE
<222> LOCATION: (9)..(9)
<223> OTHER INFORMATION: Xaa = beta-(4-thiazolyl)alanine, beta-(3-
     pyridinyl)alanine, beta-(4-pyridinyl)alanine or beta-(2-thienyl)
     alanine
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 114

Gly Ser Ser Phe Leu Ser Pro Glu Xaa Gln Arg Val Gln Gln Arg Lys
1               5                  10                  15

Glu Ser Lys Lys Pro Pro Ala Lys Leu Gln Pro Arg
            20                  25
```

```
<210> SEQ ID NO 115
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (1)..(1)
<223> OTHER INFORMATION: modified with acyl
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (8)..(8)
<223> OTHER INFORMATION: Xaa = alpha-aminoisobutyric acid
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 115

Gly Ser Glu Phe Leu Ser Pro Xaa His Gln Arg Val Gln Gln Arg Lys
1               5                   10                  15

Glu Ser Lys Lys Pro Pro Ala Lys Leu Gln Pro Arg
            20                  25

<210> SEQ ID NO 116
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (1)..(1)
<223> OTHER INFORMATION: modified with acyl
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (9)..(9)
<223> OTHER INFORMATION: Xaa = beta-(4-thiazolyl)alanine, beta-(3-
      pyridinyl)alanine, beta-(4-pyridinyl)alanine or beta-(2-thienyl)
      alanine
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 116

Gly Ser Glu Phe Leu Ser Pro Glu Xaa Gln Arg Val Gln Gln Arg Lys
1               5                   10                  15

Glu Ser Lys Lys Pro Pro Ala Lys Leu Gln Pro Arg
            20                  25

<210> SEQ ID NO 117
<211> LENGTH: 28
<212> TYPE: PRT
<213> ORGANISM: Artificial Sequence
```

```
<220> FEATURE:
<223> OTHER INFORMATION: Ghrelin Analog
<220> FEATURE:
<221> NAME/KEY: MISC_FEATURE
<222> LOCATION: (1)..(1)
<223> OTHER INFORMATION: Xaa = alpha-aminoisobutyric acid modified
      with acyl group
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MISC_FEATURE
<222> LOCATION: (10)..(10)
<223> OTHER INFORMATION: Xaa = alpha-aminoisobutyric acid
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 117

Xaa Xaa Ser Phe Leu Ser Pro Glu His Xaa Arg Val Gln Gln Arg Lys
1               5                   10                  15

Glu Ser Lys Lys Pro Pro Ala Lys Leu Gln Pro Arg
            20                  25

<210> SEQ ID NO 118
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MISC_FEATURE
<222> LOCATION: (1)..(1)
<223> OTHER INFORMATION: Xaa = alpha-aminoisobutyric acid modified with
      acyl group
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (10)..(10)
<223> OTHER INFORMATION: Xaa = alpha-aminoisobutyric acid
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 118

Xaa Xaa Glu Phe Leu Ser Pro Glu His Xaa Arg Val Gln Gln Arg Lys
1               5                   10                  15

Glu Ser Lys Lys Pro Pro Ala Lys Leu Gln Pro Arg
            20                  25

<210> SEQ ID NO 119
<211> LENGTH: 28
<212> TYPE: PRT
<213> ORGANISM: Artificial Sequence
<220> FEATURE:
<223> OTHER INFORMATION: Ghrelin Analog
```

```
<220> FEATURE:
<221> NAME/KEY: MOD_RES
<222> LOCATION: (1)..(1)
<223> OTHER INFORMATION: modified with acyl group
<220> FEATURE:
<221> NAME/KEY: MISC_FEATURE
<222> LOCATION: (2)..(2)
<223> OTHER INFORMATION: Xaa = 1-amino-1-cyclopentanecarboxylic acid
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 119

Gly Xaa Ser Phe Leu Ser Pro Glu His Gln Arg Val Gln Gln Arg Lys
 1               5                  10                  15

Glu Ser Lys Lys Pro Pro Ala Lys Leu Gln Pro Arg
            20                  25

<210> SEQ ID NO 120
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (1)..(1)
<223> OTHER INFORMATION: modified with acyl group
<220> FEATURE:
<221> NAME/KEY: MISC_FEATURE
<222> LOCATION: (2)..(2)
<223> OTHER INFORMATION: Xaa = 1-amino-1-cyclopentanecarboxylic acid
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 120

Gly Xaa Glu Phe Leu Ser Pro Glu His Gln Arg Val Gln Gln Arg Lys
 1               5                  10                  15

Glu Ser Lys Lys Pro Pro Ala Lys Leu Gln Pro Arg
            20                  25

<210> SEQ ID NO 121
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (1)..(1)
<223> OTHER INFORMATION: modified with acyl
<220> FEATURE:
<221> NAME/KEY: MOD_RES
<222> LOCATION: (3)..(3)
<223> OTHER INFORMATION: modified with 1-heptanol
<220> FEATURE:
<221> NAME/KEY: MOD_RES
<222> LOCATION: (17)..(17)
<223> OTHER INFORMATION: modified with 1-heptanol
```

```
<220> FEATURE:
<221> NAME/KEY: MOD_RES
<222> LOCATION: (28)..(28)
<223> OTHER INFORMATION: AMIDATION

<400> SEQUENCE: 121

Gly Ser Glu Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 122
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (1)..(1)
<223> OTHER INFORMATION: modified with acyl
<220> FEATURE:
<221> NAME/KEY: MOD_RES
<222> LOCATION: (3)..(3)
<223> OTHER INFORMATION: modified with 1-heptanol
<220> FEATURE:
<221> NAME/KEY: MOD_RES
<222> LOCATION: (17)..(17)
<223> OTHER INFORMATION: modified with 1-heptanol
<220> FEATURE:
<221> NAME/KEY: MOD_RES
<222> LOCATION: (28)..(28)
<223> OTHER INFORMATION: AMIDATION

<400> SEQUENCE: 122

Gly Ser Asp Phe Leu Ser Pro Glu His Gln Arg Val Gln Gln Arg Lys
1               5                   10                  15

Asp Ser Lys Lys Pro Pro Ala Lys Leu Gln Pro Arg
            20                  25

<210> SEQ ID NO 123
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (1)..(1)
<223> OTHER INFORMATION: modified with acyl
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 123

Gly Ser Glu Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 124
<211> LENGTH: 28
```

```
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (1)..(1)
<223> OTHER INFORMATION: modified with acyl
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 124

Gly Ser Asp Phe Leu Ser Pro Glu His Gln Arg Val Gln Gln Arg Lys
1               5                   10                  15

Asp Ser Lys Lys Pro Pro Ala Lys Leu Gln Pro Arg
            20                  25

<210> SEQ ID NO 125
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (1)..(1)
<223> OTHER INFORMATION: modified with acyl
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (17)..(17)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 125

Gly Xaa Glu Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 126
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (1)..(1)
<223> OTHER INFORMATION: modified with acyl
<220> FEATURE:
<221> NAME/KEY: MISC_FEATURE
<222> LOCATION: (2)..(2)
<223> OTHER INFORMATION: Xaa = alpha-aminoisobutyric acid
```

```
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (10)..(10)
<223> OTHER INFORMATION: Xaa = alpha-aminoisobutyric acid
<220> FEATURE:
<221> NAME/KEY: MOD_RES
<222> LOCATION: (17)..(17)
<223> OTHER INFORMATION: modified with biotinyl
<220> FEATURE:
<221> NAME/KEY: MOD_RES
<222> LOCATION: (28)..(28)
<223> OTHER INFORMATION: AMIDATION

<400> SEQUENCE: 126

Gly Xaa Glu Phe Leu Ser Pro Glu His Xaa Arg Val Gln Gln Arg Lys
1               5                   10                  15

Lys Ser Lys Lys Pro Pro Ala Lys Leu Gln Pro Arg
            20                  25

<210> SEQ ID NO 127
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (1)..(1)
<223> OTHER INFORMATION: is modified with acyl
<220> FEATURE:
<221> NAME/KEY: MOD_RES
<222> LOCATION: (15)..(15)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 127

Gly Ser Ser Phe Leu Ser Pro Glu His Gln Arg Val Gln Gln Glu Lys
1               5                   10                  15

Glu Ser Lys Lys Pro Pro Ala Lys Leu Gln Pro Arg
            20                  25

<210> SEQ ID NO 128
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (1)..(1)
<223> OTHER INFORMATION: modified with acyl
<220> FEATURE:
<221> NAME/KEY: MOD_RES
<222> LOCATION: (15)..(15)
<223> OTHER INFORMATION: modified with n-octanoyl
<220> FEATURE:
<221> NAME/KEY: MOD_RES
<222> LOCATION: (28)..(28)
<223> OTHER INFORMATION: AMIDATION

<400> SEQUENCE: 128

Gly Ser Ser Phe Leu Ser Pro Glu His Gln Arg Val Gln Gln Ser Lys
1               5                   10                  15

Glu Ser Lys Lys Pro Pro Ala Lys Leu Gln Pro Arg
            20                  25
```

```
<210> SEQ ID NO 129
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (1)..(1)
<223> OTHER INFORMATION: modified with acyl
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (15)..(15)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 129

Gly Ser Glu Phe Leu Ser Pro Glu His Gln Arg Val Gln Gln Glu Lys
1               5                   10                  15

Glu Ser Lys Lys Pro Pro Ala Lys Leu Gln Pro Arg
            20                  25

<210> SEQ ID NO 130
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (1)..(1)
<223> OTHER INFORMATION: modified with acyl
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (15)..(15)
<223> OTHER INFORMATION: modified with n-octanoyl
<220> FEATURE:
<221> NAME/KEY: MOD_RES
<222> LOCATION: (28)..(28)
<223> OTHER INFORMATION: AMIDATION

<400> SEQUENCE: 130

Gly Ser Glu Phe Leu Ser Pro Glu His Gln Arg Val Gln Gln Ser Lys
1               5                   10                  15

Glu Ser Lys Lys Pro Pro Ala Lys Leu Gln Pro Arg
            20                  25

<210> SEQ ID NO 131
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (1)..(1)
<223> OTHER INFORMATION: modified with acyl
<220> FEATURE:
<221> NAME/KEY: MISC_FEATURE
<222> LOCATION: (2)..(2)
<223> OTHER INFORMATION: Xaa = alpha-aminoisobutyric acid
```

```
<220> FEATURE:
<221> NAME/KEY: MOD_RES
<222> LOCATION: (15)..(15)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 131

Gly Xaa Ser Phe Leu Ser Pro Glu His Gln Arg Val Gln Gln Glu Lys
1               5                   10                  15

Glu Ser Lys Lys Pro Pro Ala Lys Leu Gln Pro Arg
            20                  25

<210> SEQ ID NO 132
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (1)..(1)
<223> OTHER INFORMATION: modified with acyl
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (15)..(15)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 132

Gly Xaa Glu Phe Leu Ser Pro Glu His Gln Arg Val Gln Gln Glu Lys
1               5                   10                  15

Glu Ser Lys Lys Pro Pro Ala Lys Leu Gln Pro Arg
            20                  25

<210> SEQ ID NO 133
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (1)..(1)
<223> OTHER INFORMATION: modified with acyl
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MISC_FEATURE
<222> LOCATION: (8)..(8)
<223> OTHER INFORMATION: Xaa = alpha-aminoisobutyric acid
<220> FEATURE:
<221> NAME/KEY: MOD_RES
<222> LOCATION: (15)..(15)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION
```

```
<400> SEQUENCE: 133

Gly Xaa Ser Phe Leu Ser Pro Xaa His Gln Arg Val Gln Gln Glu Lys
1               5                   10                  15

Glu Ser Lys Lys Pro Pro Ala Lys Leu Gln Pro Arg
            20                  25

<210> SEQ ID NO 134
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (1)..(1)
<223> OTHER INFORMATION: modified with acyl
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (8)..(8)
<223> OTHER INFORMATION: Xaa = alpha-aminoisobutyric acid
<220> FEATURE:
<221> NAME/KEY: MOD_RES
<222> LOCATION: (15)..(15)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 134

Gly Xaa Glu Phe Leu Ser Pro Xaa His Gln Arg Val Gln Gln Glu Lys
1               5                   10                  15

Glu Ser Lys Lys Pro Pro Ala Lys Leu Gln Pro Arg
            20                  25

<210> SEQ ID NO 135
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (1)..(1)
<223> OTHER INFORMATION: modified with acyl
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MISC_FEATURE
<222> LOCATION: (10)..(10)
<223> OTHER INFORMATION: Xaa = alpha-aminoisobutyric acid
<220> FEATURE:
<221> NAME/KEY: MOD_RES
<222> LOCATION: (15)..(15)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 135

Gly Xaa Ser Phe Leu Ser Pro Glu His Xaa Arg Val Gln Gln Glu Lys
```

```
                1               5                  10                  15
Glu Ser Lys Lys Pro Pro Ala Lys Leu Gln Pro Arg
            20                  25

<210> SEQ ID NO 136
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (1)..(1)
<223> OTHER INFORMATION: modified with acyl
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (10)..(10)
<223> OTHER INFORMATION: Xaa = alpha-aminoisobutyric acid
<220> FEATURE:
<221> NAME/KEY: MOD_RES
<222> LOCATION: (15)..(15)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 136

Gly Xaa Glu Phe Leu Ser Pro Glu His Xaa Arg Val Gln Gln Glu Lys
1               5                  10                  15

Glu Ser Lys Lys Pro Pro Ala Lys Leu Gln Pro Arg
            20                  25

<210> SEQ ID NO 137
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (1)..(1)
<223> OTHER INFORMATION: modified with acyl
<220> FEATURE:
<221> NAME/KEY: MOD_RES
<222> LOCATION: (16)..(16)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 137

Gly Ser Ser Phe Leu Ser Pro Glu His Gln Arg Val Gln Gln Arg Glu
1               5                  10                  15

Glu Ser Lys Lys Pro Pro Ala Lys Leu Gln Pro Arg
            20                  25

<210> SEQ ID NO 138
<211> LENGTH: 28
<212> TYPE: PRT
<213> ORGANISM: Artificial Sequence
<220> FEATURE:
<223> OTHER INFORMATION: Ghrelin Analog
```

```
<220> FEATURE:
<221> NAME/KEY: MOD_RES
<222> LOCATION: (1)..(1)
<223> OTHER INFORMATION: modified with acyl
<220> FEATURE:
<221> NAME/KEY: MOD_RES
<222> LOCATION: (16)..(16)
<223> OTHER INFORMATION: modified with n-octanoyl
<220> FEATURE:
<221> NAME/KEY: MOD_RES
<222> LOCATION: (28)..(28)
<223> OTHER INFORMATION: AMIDATION

<400> SEQUENCE: 138

Gly Ser Ser Phe Leu Ser Pro Glu His Gln Arg Val Gln Gln Arg Ser
1               5                   10                  15

Glu Ser Lys Lys Pro Pro Ala Lys Leu Gln Pro Arg
            20                  25

<210> SEQ ID NO 139
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (1)..(1)
<223> OTHER INFORMATION: modified with acyl
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (16)..(16)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 139

Gly Ser Glu Phe Leu Ser Pro Glu His Gln Arg Val Gln Gln Arg Glu
1               5                   10                  15

Glu Ser Lys Lys Pro Pro Ala Lys Leu Gln Pro Arg
            20                  25

<210> SEQ ID NO 140
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (1)..(1)
<223> OTHER INFORMATION: modified with acyl
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (16)..(16)
<223> OTHER INFORMATION: modified with n-octanoyl
<220> FEATURE:
<221> NAME/KEY: MOD_RES
<222> LOCATION: (28)..(28)
<223> OTHER INFORMATION: AMIDATION

<400> SEQUENCE: 140

Gly Ser Glu Phe Leu Ser Pro Glu His Gln Arg Val Gln Gln Arg Ser
```

```
                1               5                  10                  15
Glu Ser Lys Lys Pro Pro Ala Lys Leu Gln Pro Arg
            20                  25

<210> SEQ ID NO 141
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (1)..(1)
<223> OTHER INFORMATION: modified with acyl
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MOD_RES
<222> LOCATION: (16)..(16)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 141

Gly Xaa Ser Phe Leu Ser Pro Glu His Gln Arg Val Gln Gln Arg Glu
1               5                  10                  15

Glu Ser Lys Lys Pro Pro Ala Lys Leu Gln Pro Arg
            20                  25

<210> SEQ ID NO 142
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (1)..(1)
<223> OTHER INFORMATION: modified with acyl
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (16)..(16)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 142

Gly Xaa Glu Phe Leu Ser Pro Glu His Gln Arg Val Gln Gln Arg Glu
1               5                  10                  15

Glu Ser Lys Lys Pro Pro Ala Lys Leu Gln Pro Arg
            20                  25

<210> SEQ ID NO 143
<211> LENGTH: 28
<212> TYPE: PRT
<213> ORGANISM: Artificial Sequence
<220> FEATURE:
<223> OTHER INFORMATION: Ghrelin Analog
```

-continued

```
<220> FEATURE:
<221> NAME/KEY: MOD_RES
<222> LOCATION: (1)..(1)
<223> OTHER INFORMATION: modified with acyl
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MISC_FEATURE
<222> LOCATION: (8)..(8)
<223> OTHER INFORMATION: Xaa = alpha-aminoisobutyric acid
<220> FEATURE:
<221> NAME/KEY: MOD_RES
<222> LOCATION: (16)..(16)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 143

Gly Xaa Ser Phe Leu Ser Pro Xaa His Gln Arg Val Gln Gln Arg Glu
 1               5                  10                  15

Glu Ser Lys Lys Pro Pro Ala Lys Leu Gln Pro Arg
            20                  25

<210> SEQ ID NO 144
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (1)..(1)
<223> OTHER INFORMATION: modified with acyl
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (8)..(8)
<223> OTHER INFORMATION: Xaa = alpha-aminoisobutyric acid
<220> FEATURE:
<221> NAME/KEY: MOD_RES
<222> LOCATION: (16)..(16)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 144

Gly Xaa Glu Phe Leu Ser Pro Xaa His Gln Arg Val Gln Gln Arg Glu
 1               5                  10                  15

Glu Ser Lys Lys Pro Pro Ala Lys Leu Gln Pro Arg
            20                  25

<210> SEQ ID NO 145
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (1)..(1)
<223> OTHER INFORMATION: modified with acyl
```

```
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MISC_FEATURE
<222> LOCATION: (10)..(10)
<223> OTHER INFORMATION: Xaa = alpha-aminoisobutyric acid
<220> FEATURE:
<221> NAME/KEY: MOD_RES
<222> LOCATION: (16)..(16)
<223> OTHER INFORMATION: modified by NH-hexyl
<220> FEATURE:
<221> NAME/KEY: MOD_RES
<222> LOCATION: (28)..(28)
<223> OTHER INFORMATION: AMIDATION

<400> SEQUENCE: 145

Gly Xaa Ser Phe Leu Ser Pro Glu His Xaa Arg Val Gln Gln Arg Glu
1               5                   10                  15

Glu Ser Lys Lys Pro Pro Ala Lys Leu Gln Pro Arg
            20                  25

<210> SEQ ID NO 146
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (1)..(1)
<223> OTHER INFORMATION: modified by acyl
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MOD_RES
<222> LOCATION: (3)..(3)
<223> OTHER INFORMATION: modified by NH-hexyl
<220> FEATURE:
<221> NAME/KEY: MISC_FEATURE
<222> LOCATION: (10)..(10)
<223> OTHER INFORMATION: Xaa = alpha-aminoisobutyric acid
<220> FEATURE:
<221> NAME/KEY: MOD_RES
<222> LOCATION: (16)..(16)
<223> OTHER INFORMATION: modified by NH-hexyl
<220> FEATURE:
<221> NAME/KEY: MOD_RES
<222> LOCATION: (28)..(28)
<223> OTHER INFORMATION: AMIDATION

<400> SEQUENCE: 146

Gly Xaa Glu Phe Leu Ser Pro Glu His Xaa Arg Val Gln Gln Arg Glu
1               5                   10                  15

Glu Ser Lys Lys Pro Pro Ala Lys Leu Gln Pro Arg
            20                  25

<210> SEQ ID NO 147
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (1)..(1)
<223> OTHER INFORMATION: modified by acyl
<220> FEATURE:
<221> NAME/KEY: MOD_RES
<222> LOCATION: (18)..(18)
<223> OTHER INFORMATION: modified by NH-hexyl
```

```
<220> FEATURE:
<221> NAME/KEY: MOD_RES
<222> LOCATION: (28)..(28)
<223> OTHER INFORMATION: AMIDATION

<400> SEQUENCE: 147

Gly Ser Ser Phe Leu Ser Pro Glu His Gln Arg Val Gln Gln Arg Lys
1               5                   10                  15

Glu Glu Lys Lys Pro Pro Ala Lys Leu Gln Pro Arg
            20                  25

<210> SEQ ID NO 148
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (1)..(1)
<223> OTHER INFORMATION: modified by acyl
<220> FEATURE:
<221> NAME/KEY: MOD_RES
<222> LOCATION: (18)..(18)
<223> OTHER INFORMATION: modified by n-octanoyl
<220> FEATURE:
<221> NAME/KEY: MOD_RES
<222> LOCATION: (28)..(28)
<223> OTHER INFORMATION: AMIDATION

<400> SEQUENCE: 148

Gly Ser Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 149
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (1)..(1)
<223> OTHER INFORMATION: modified by acyl
<220> FEATURE:
<221> NAME/KEY: MOD_RES
<222> LOCATION: (3)..(3)
<223> OTHER INFORMATION: modified by NH-hexyl
<220> FEATURE:
<221> NAME/KEY: MOD_RES
<222> LOCATION: (18)..(18)
<223> OTHER INFORMATION: modified by NH-hexyl
<220> FEATURE:
<221> NAME/KEY: MOD_RES
<222> LOCATION: (28)..(28)
<223> OTHER INFORMATION: AMIDATION

<400> SEQUENCE: 149

Gly Ser Glu Phe Leu Ser Pro Glu His Gln Arg Val Gln Gln Arg Lys
1               5                   10                  15

Glu Glu Lys Lys Pro Pro Ala Lys Leu Gln Pro Arg
            20                  25

<210> SEQ ID NO 150
<211> LENGTH: 28
<212> TYPE: PRT
<213> ORGANISM: Artificial Sequence
<220> FEATURE:
<223> OTHER INFORMATION: Ghrelin Analog
```

```
<220> FEATURE:
<221> NAME/KEY: MOD_RES
<222> LOCATION: (1)..(1)
<223> OTHER INFORMATION: modified with acyl
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (18)..(18)
<223> OTHER INFORMATION: modified with n-octanoyl
<220> FEATURE:
<221> NAME/KEY: MOD_RES
<222> LOCATION: (28)..(28)
<223> OTHER INFORMATION: AMIDATION

<400> SEQUENCE: 150

Gly Ser Glu Phe Leu Ser Pro Glu His Gln Arg Val Gln Gln Arg Lys
1               5                   10                  15
Glu Ser Lys Lys Pro Pro Ala Lys Leu Gln Pro Arg
            20                  25

<210> SEQ ID NO 151
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (1)..(1)
<223> OTHER INFORMATION: modified with acyl
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MOD_RES
<222> LOCATION: (18)..(18)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 151

Gly Xaa Ser Phe Leu Ser Pro Glu His Gln Arg Val Gln Gln Arg Lys
1               5                   10                  15
Glu Glu Lys Lys Pro Pro Ala Lys Leu Gln Pro Arg
            20                  25

<210> SEQ ID NO 152
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (1)..(1)
<223> OTHER INFORMATION: modified with acyl
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (18)..(18)
<223> OTHER INFORMATION: modified with NH-hexyl
```

```
<220> FEATURE:
<221> NAME/KEY: MOD_RES
<222> LOCATION: (28)..(28)
<223> OTHER INFORMATION: AMIDATION

<400> SEQUENCE: 152

Gly Xaa Glu Phe Leu Ser Pro Glu His Gln Arg Val Gln Gln Arg Lys
1               5                   10                  15

Glu Glu Lys Lys Pro Pro Ala Lys Leu Gln Pro Arg
            20                  25

<210> SEQ ID NO 153
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (1)..(1)
<223> OTHER INFORMATION: modified with acyl
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MISC_FEATURE
<222> LOCATION: (8)..(8)
<223> OTHER INFORMATION: Xaa = alpha-aminoisobutyric acid
<220> FEATURE:
<221> NAME/KEY: MOD_RES
<222> LOCATION: (18)..(18)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 153

Gly Xaa Ser Phe Leu Ser Pro Xaa His Gln Arg Val Gln Gln Arg Lys
1               5                   10                  15

Glu Glu Lys Lys Pro Pro Ala Lys Leu Gln Pro Arg
            20                  25

<210> SEQ ID NO 154
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (1)..(1)
<223> OTHER INFORMATION: modified with acyl
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (8)..(8)
<223> OTHER INFORMATION: Xaa = alpha-aminoisobutyric acid
<220> FEATURE:
<221> NAME/KEY: MOD_RES
<222> LOCATION: (18)..(18)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION
```

```
<400> SEQUENCE: 154

Gly Xaa Glu Phe Leu Ser Pro Xaa His Gln Arg Val Gln Gln Arg Lys
1               5                   10                  15

Glu Glu Lys Lys Pro Pro Ala Lys Leu Gln Pro Arg
            20                  25

<210> SEQ ID NO 155
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (1)..(1)
<223> OTHER INFORMATION: modified with acyl
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MISC_FEATURE
<222> LOCATION: (10)..(10)
<223> OTHER INFORMATION: Xaa = alpha-aminoisobutyric acid
<220> FEATURE:
<221> NAME/KEY: MOD_RES
<222> LOCATION: (18)..(18)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 155

Gly Xaa Ser Phe Leu Ser Pro Glu His Xaa Arg Val Gln Gln Arg Lys
1               5                   10                  15

Glu Glu Lys Lys Pro Pro Ala Lys Leu Gln Pro Arg
            20                  25

<210> SEQ ID NO 156
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (1)..(1)
<223> OTHER INFORMATION: modified with acyl
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (10)..(10)
<223> OTHER INFORMATION: Xaa = alpha-aminoisobutyric acid
<220> FEATURE:
<221> NAME/KEY: MOD_RES
<222> LOCATION: (18)..(18)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 156

Gly Xaa Glu Phe Leu Ser Pro Glu His Xaa Arg Val Gln Gln Arg Lys
```

```
                 1               5              10              15

Glu Glu Lys Lys Pro Pro Ala Lys Leu Gln Pro Arg
            20              25

<210> SEQ ID NO 157
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (1)..(1)
<223> OTHER INFORMATION: modified with acyl
<220> FEATURE:
<221> NAME/KEY: MOD_RES
<222> LOCATION: (19)..(19)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 157

Gly Ser Ser Phe Leu Ser Pro Glu His Gln Arg Val Gln Gln Arg Lys
1               5                   10                  15

Glu Ser Glu Lys Pro Pro Ala Lys Leu Gln Pro Arg
            20              25

<210> SEQ ID NO 158
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (1)..(1)
<223> OTHER INFORMATION: modified with acyl
<220> FEATURE:
<221> NAME/KEY: MOD_RES
<222> LOCATION: (19)..(19)
<223> OTHER INFORMATION: modified with n-octanoyl
<220> FEATURE:
<221> NAME/KEY: MOD_RES
<222> LOCATION: (28)..(28)
<223> OTHER INFORMATION: AMIDATION

<400> SEQUENCE: 158

Gly Ser Ser Phe Leu Ser Pro Glu His Gln Arg Val Gln Gln Arg Lys
1               5                   10                  15

Glu Ser Ser Lys Pro Pro Ala Lys Leu Gln Pro Arg
            20              25

<210> SEQ ID NO 159
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (1)..(1)
<223> OTHER INFORMATION: modified with acyl
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (19)..(19)
<223> OTHER INFORMATION: modified with NH-hexyl
```

```
<220> FEATURE:
<221> NAME/KEY: MOD_RES
<222> LOCATION: (28)..(28)
<223> OTHER INFORMATION: AMIDATION

<400> SEQUENCE: 159

Gly Ser Glu Phe Leu Ser Pro Glu His Gln Arg Val Gln Gln Arg Lys
1               5                   10                  15

Glu Ser Glu Lys Pro Pro Ala Lys Leu Gln Pro Arg
            20                  25

<210> SEQ ID NO 160
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (1)..(1)
<223> OTHER INFORMATION: modified with acyl
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (19)..(19)
<223> OTHER INFORMATION: modified with n-octanoyl
<220> FEATURE:
<221> NAME/KEY: MOD_RES
<222> LOCATION: (28)..(28)
<223> OTHER INFORMATION: AMIDATION

<400> SEQUENCE: 160

Gly Ser Glu Phe Leu Ser Pro Glu His Gln Arg Val Gln Gln Arg Lys
1               5                   10                  15

Glu Ser Ser Lys Pro Pro Ala Lys Leu Gln Pro Arg
            20                  25

<210> SEQ ID NO 161
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (1)..(1)
<223> OTHER INFORMATION: modified with acyl
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MOD_RES
<222> LOCATION: (19)..(19)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 161

Gly Xaa Ser Phe Leu Ser Pro Glu His Gln Arg Val Gln Gln Arg Lys
1               5                   10                  15

Glu Ser Glu Lys Pro Pro Ala Lys Leu Gln Pro Arg
            20                  25

<210> SEQ ID NO 162
<211> LENGTH: 28
```

-continued

```
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (1)..(1)
<223> OTHER INFORMATION: modified with acyl
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (19)..(19)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 162

Gly Xaa Glu Phe Leu Ser Pro Glu His Gln Arg Val Gln Gln Arg Lys
1               5                   10                  15

Glu Ser Glu Lys Pro Pro Ala Lys Leu Gln Pro Arg
            20                  25

<210> SEQ ID NO 163
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (1)..(1)
<223> OTHER INFORMATION: modified with acyl
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MISC_FEATURE
<222> LOCATION: (8)..(8)
<223> OTHER INFORMATION: Xaa = alpha-aminoisobutyric acid
<220> FEATURE:
<221> NAME/KEY: MOD_RES
<222> LOCATION: (19)..(19)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 163

Gly Xaa Ser Phe Leu Ser Pro Xaa His Gln Arg Val Gln Gln Arg Lys
1               5                   10                  15

Glu Ser Glu Lys Pro Pro Ala Lys Leu Gln Pro Arg
            20                  25

<210> SEQ ID NO 164
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (1)..(1)
<223> OTHER INFORMATION: modified with acyl
```

```
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (8)..(8)
<223> OTHER INFORMATION: Xaa = alpha-aminoisobutyric acid
<220> FEATURE:
<221> NAME/KEY: MOD_RES
<222> LOCATION: (19)..(19)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 164

Gly Xaa Glu Phe Leu Ser Pro Xaa His Gln Arg Val Gln Gln Arg Lys
1               5                   10                  15

Glu Ser Glu Lys Pro Pro Ala Lys Leu Gln Pro Arg
            20                  25

<210> SEQ ID NO 165
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (1)..(1)
<223> OTHER INFORMATION: modified with acyl
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MISC_FEATURE
<222> LOCATION: (10)..(10)
<223> OTHER INFORMATION: Xaa = alpha-aminoisobutyric acid
<220> FEATURE:
<221> NAME/KEY: MOD_RES
<222> LOCATION: (19)..(19)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 165

Gly Xaa Ser Phe Leu Ser Pro Glu His Xaa Arg Val Gln Gln Arg Lys
1               5                   10                  15

Glu Ser Glu Lys Pro Pro Ala Lys Leu Gln Pro Arg
            20                  25

<210> SEQ ID NO 166
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (1)..(1)
<223> OTHER INFORMATION: modified with acyl
<220> FEATURE:
<221> NAME/KEY: MISC_FEATURE
<222> LOCATION: (2)..(2)
<223> OTHER INFORMATION: Xaa = alpha-aminoisobutyric acid
```

```
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (10)..(10)
<223> OTHER INFORMATION: Xaa = alpha-aminoisobutyric acid
<220> FEATURE:
<221> NAME/KEY: MOD_RES
<222> LOCATION: (19)..(19)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 166

Gly Xaa Glu Phe Leu Ser Pro Glu His Xaa Arg Val Gln Gln Arg Lys
 1               5                  10                  15

Glu Ser Glu Lys Pro Pro Ala Lys Leu Gln Pro Arg
            20                  25

<210> SEQ ID NO 167
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (1)..(1)
<223> OTHER INFORMATION: modified with acyl
<220> FEATURE:
<221> NAME/KEY: MOD_RES
<222> LOCATION: (20)..(20)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 167

Gly Ser Ser Phe Leu Ser Pro Glu His Gln Arg Val Gln Gln Arg Lys
 1               5                  10                  15

Glu Ser Lys Glu Pro Pro Ala Lys Leu Gln Pro Arg
            20                  25

<210> SEQ ID NO 168
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (1)..(1)
<223> OTHER INFORMATION: modified with acyl
<220> FEATURE:
<221> NAME/KEY: MOD_RES
<222> LOCATION: (20)..(20)
<223> OTHER INFORMATION: modified with n-octanoyl
<220> FEATURE:
<221> NAME/KEY: MOD_RES
<222> LOCATION: (28)..(28)
<223> OTHER INFORMATION: AMIDATION

<400> SEQUENCE: 168

Gly Ser Ser Phe Leu Ser Pro Glu His Gln Arg Val Gln Gln Arg Lys
 1               5                  10                  15

Glu Ser Lys Ser Pro Pro Ala Lys Leu Gln Pro Arg
            20                  25
```

```
<210> SEQ ID NO 169
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (1)..(1)
<223> OTHER INFORMATION: modified with acyl
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (20)..(20)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 169

Gly Ser Glu Phe Leu Ser Pro Glu His Gln Arg Val Gln Gln Arg Lys
 1               5                  10                  15

Glu Ser Lys Glu Pro Pro Ala Lys Leu Gln Pro Arg
            20                  25

<210> SEQ ID NO 170
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (1)..(1)
<223> OTHER INFORMATION: modified with acyl
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (20)..(20)
<223> OTHER INFORMATION: modified with n-octanoyl
<220> FEATURE:
<221> NAME/KEY: MOD_RES
<222> LOCATION: (28)..(28)
<223> OTHER INFORMATION: AMIDATION

<400> SEQUENCE: 170

Gly Ser Glu Phe Leu Ser Pro Glu His Gln Arg Val Gln Gln Arg Lys
 1               5                  10                  15

Glu Ser Lys Ser Pro Pro Ala Lys Leu Gln Pro Arg
            20                  25

<210> SEQ ID NO 171
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (1)..(1)
<223> OTHER INFORMATION: modified with acyl
<220> FEATURE:
<221> NAME/KEY: MISC_FEATURE
<222> LOCATION: (2)..(2)
<223> OTHER INFORMATION: Xaa = alpha-aminoisobutyric acid
```

```
<220> FEATURE:
<221> NAME/KEY: MOD_RES
<222> LOCATION: (20)..(20)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 171

Gly Xaa Ser Phe Leu Ser Pro Glu His Gln Arg Val Gln Gln Arg Lys
1               5                   10                  15

Glu Ser Lys Glu Pro Pro Ala Lys Leu Gln Pro Arg
            20                  25

<210> SEQ ID NO 172
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (1)..(1)
<223> OTHER INFORMATION: modified with acyl
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (20)..(20)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 172

Gly Xaa Glu Phe Leu Ser Pro Glu His Gln Arg Val Gln Gln Arg Lys
1               5                   10                  15

Glu Ser Lys Glu Pro Pro Ala Lys Leu Gln Pro Arg
            20                  25

<210> SEQ ID NO 173
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (1)..(1)
<223> OTHER INFORMATION: modified with acyl
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MISC_FEATURE
<222> LOCATION: (8)..(8)
<223> OTHER INFORMATION: Xaa = alpha-aminoisobutyric acid
<220> FEATURE:
<221> NAME/KEY: MOD_RES
<222> LOCATION: (20)..(20)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION
```

<400> SEQUENCE: 173

Gly Xaa Ser Phe Leu Ser Pro Xaa His Gln Arg Val Gln Gln Arg Lys
1               5                   10                  15

Glu Ser Lys Glu Pro Pro Ala Lys Leu Gln Pro Arg
            20                  25

<210> SEQ ID NO 174
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (1)..(1)
<223> OTHER INFORMATION: modified with acyl
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (8)..(8)
<223> OTHER INFORMATION: Xaa = alpha-aminoisobutyric acid
<220> FEATURE:
<221> NAME/KEY: MOD_RES
<222> LOCATION: (20)..(20)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 174

Gly Xaa Glu Phe Leu Ser Pro Xaa His Gln Arg Val Gln Gln Arg Lys
1               5                   10                  15

Glu Ser Lys Glu Pro Pro Ala Lys Leu Gln Pro Arg
            20                  25

<210> SEQ ID NO 175
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (1)..(1)
<223> OTHER INFORMATION: modified with acyl
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MISC_FEATURE
<222> LOCATION: (10)..(10)
<223> OTHER INFORMATION: Xaa = alpha-aminoisobutyric acid
<220> FEATURE:
<221> NAME/KEY: MOD_RES
<222> LOCATION: (20)..(20)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 175

Gly Xaa Ser Phe Leu Ser Pro Glu His Xaa Arg Val Gln Gln Arg Lys

```
                1               5                  10                  15
Glu Ser Lys Glu Pro Pro Ala Lys Leu Gln Pro Arg
            20                  25
```

<210> SEQ ID NO 176
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MOD_RES
<222> LOCATION: (1)..(1)
<223> OTHER INFORMATION: modified with acyl
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (10)..(10)
<223> OTHER INFORMATION: Xaa = alpha-aminoisobutyric acid
<220> FEATURE:
<221> NAME/KEY: MOD_RES
<222> LOCATION: (20)..(20)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 176

```
Gly Xaa Glu Phe Leu Ser Pro Glu His Xaa Arg Val Gln Gln Arg Lys
1               5                   10                  15
Glu Ser Lys Glu Pro Pro Ala Lys Leu Gln Pro Arg
            20                  25
```

<210> SEQ ID NO 177
<211> LENGTH: 28
<212> TYPE: PRT
<213> ORGANISM: Artificial Sequence
<220> FEATURE:
<223> OTHER INFORMATION: Ghrelin Analog
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MOD_RES
<222> LOCATION: (17)..(17)
<223> OTHER INFORMATION: modified with myristyl
<220> FEATURE:
<221> NAME/KEY: MOD_RES
<222> LOCATION: (28)..(28)
<223> OTHER INFORMATION: AMIDATION

<400> SEQUENCE: 177

```
Gly Xaa Ser Phe Leu Ser Pro Glu His Gln Arg Val Gln Gln Arg Lys
1               5                   10                  15
Lys Ser Lys Lys Pro Pro Ala Lys Leu Gln Pro Arg
            20                  25
```

<210> SEQ ID NO 178
<211> LENGTH: 28
<212> TYPE: PRT
<213> ORGANISM: Artificial Sequence
<220> FEATURE:
<223> OTHER INFORMATION: Ghrelin Analog

```
<220> FEATURE:
<221> NAME/KEY: MOD_RES
<222> LOCATION: (1)..(1)
<223> OTHER INFORMATION: modified with myristyl
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MOD_RES
<222> LOCATION: (17)..(17)
<223> OTHER INFORMATION: modified with myristyl
<220> FEATURE:
<221> NAME/KEY: MOD_RES
<222> LOCATION: (28)..(28)
<223> OTHER INFORMATION: AMIDATION

<400> SEQUENCE: 178

Gly Xaa Ser Phe Leu Ser Pro Glu His Gln Arg Val Gln Gln Arg Lys
1               5                   10                  15

Lys Ser Lys Lys Pro Pro Ala Lys Leu Gln Pro Arg
            20                  25

<210> SEQ ID NO 179
<211> LENGTH: 28
<212> TYPE: PRT
<213> ORGANISM: Artificial Sequence
<220> FEATURE:
<223> OTHER INFORMATION: Grehlin Analog
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MISC_FEATURE
<222> LOCATION: (8)..(8)
<223> OTHER INFORMATION: Xaa = alpha-aminoisobutyric acid
<220> FEATURE:
<221> NAME/KEY: MISC_FEATURE
<222> LOCATION: (17)..(17)
<223> OTHER INFORMATION: modified with NH-hexyl

<400> SEQUENCE: 179

Gly Xaa Ser Phe Leu Ser Pro Xaa His Gln Arg Val Gln Gln Arg Lys
1               5                   10                  15

Glu Ser Lys Lys Pro Pro Ala Lys Leu Gln Pro Arg
            20                  25

<210> SEQ ID NO 180
<211> LENGTH: 28
<212> TYPE: PRT
<213> ORGANISM: Homo sapiens

<400> SEQUENCE: 180

Gly Ser Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 181
<211> LENGTH: 28
<212> TYPE: PRT
<213> ORGANISM: Artificial Sequence
<220> FEATURE:
<223> OTHER INFORMATION: synthetic analog of ghrelin
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MOD_RES
```

```
<222> LOCATION: (28)..(28)
<223> OTHER INFORMATION: AMIDATION

<400> SEQUENCE: 181

Gly Xaa Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 182
<211> LENGTH: 18
<212> TYPE: PRT
<213> ORGANISM: Homo sapiens

<400> SEQUENCE: 182

Gly Ser Ser Phe Leu Ser Pro Glu His Gln Arg Val Gln Gln Arg Lys
1               5                   10                  15

Glu Ser

<210> SEQ ID NO 183
<211> LENGTH: 28
<212> TYPE: PRT
<213> ORGANISM: Artificial Sequence
<220> FEATURE:
<223> OTHER INFORMATION: synthetic analog of ghrelin
<220> FEATURE:
<221> NAME/KEY: MISC_FEATURE
<222> LOCATION: (2)..(2)
<223> OTHER INFORMATION: Xaa = alpha-aminoisobutyric acid

<400> SEQUENCE: 183

Gly Xaa Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 184
<211> LENGTH: 27
<212> TYPE: DNA
<213> ORGANISM: Artificial Sequence
<220> FEATURE:
<223> OTHER INFORMATION: synthetic oligonucleotide primer for ghrelin

<400> SEQUENCE: 184
atgtggaacg cgacgcccag cgaagag                                       27

<210> SEQ ID NO 185
<211> LENGTH: 27
<212> TYPE: DNA
<213> ORGANISM: Artificial Sequence
<220> FEATURE:
<223> OTHER INFORMATION: synthetic oligonucleotide primer for ghrelin

<400> SEQUENCE: 185
tcatgtatta atactagatt ctgtcca                                       27
```